US012624010B2

(12) United States Patent
Gabellieri et al.

(10) Patent No.: US 12,624,010 B2
(45) Date of Patent: May 12, 2026

(54) DIHYDROOXAZOLE AND THIOUREA DERIVATIVES MODULATING THE NLRP3 INFLAMMASOME PATHWAY

(71) Applicant: AC IMMUNE SA, Lausanne (CH)

(72) Inventors: Emanuele Gabellieri, Le mont sur Lausanne (CH); Jérôme Molette, Prévessin-Moëns (FR); Véronique Dehlinger, Morges (CH)

(73) Assignee: AC IMMUNE SA, Lausanne (CH)

( * ) Notice: Subject to any disclaimer, the term of this patent is extended or adjusted under 35 U.S.C. 154(b) by 627 days.

(21) Appl. No.: 18/010,032

(22) PCT Filed: Jun. 18, 2021

(86) PCT No.: PCT/EP2021/066695

§ 371 (c)(1),
(2) Date: Dec. 13, 2022

(87) PCT Pub. No.: WO2021/255279

PCT Pub. Date: Dec. 23, 2021

(65) Prior Publication Data

US 2023/0250070 A1 Aug. 10, 2023

(30) Foreign Application Priority Data

Jun. 19, 2020 (EP) .................................... 20181221
Mar. 22, 2021 (EP) .................................... 21164097

(51) Int. Cl.

| | |
|---|---|
| ***C07D 263/28*** | (2006.01) |
| ***C07C 335/16*** | (2006.01) |
| ***C07D 213/55*** | (2006.01) |
| ***C07D 213/64*** | (2006.01) |
| ***C07D 233/58*** | (2006.01) |
| ***C07D 261/08*** | (2006.01) |
| ***C07D 309/06*** | (2006.01) |
| ***C07D 413/04*** | (2006.01) |
| ***C07D 417/04*** | (2006.01) |

(52) U.S. Cl.

CPC .......... *C07D 263/28* (2013.01); *C07C 335/16* (2013.01); *C07D 213/55* (2013.01); *C07D 213/64* (2013.01); *C07D 233/58* (2013.01); *C07D 261/08* (2013.01); *C07D 309/06* (2013.01); *C07D 413/04* (2013.01); *C07D 417/04* (2013.01)

(58) Field of Classification Search

CPC .................................................... C07D 263/28
See application file for complete search history.

(56) References Cited

U.S. PATENT DOCUMENTS

| | | | |
|---|---|---|---|
| 6,433,009 | B1 | 8/2002 | Dombroski et al. |
| 2019/0119224 | A1 | 4/2019 | Glick et al. |
| 2020/0131141 | A1 | 4/2020 | Harrison et al. |
| 2020/0140382 | A1 | 5/2020 | Sharma et al. |
| 2020/0207780 | A1 | 7/2020 | Luke |
| 2020/0299284 | A1 | 9/2020 | Luke |
| 2020/0331886 | A1 | 10/2020 | Miller et al. |
| 2021/0171477 | A1 | 6/2021 | Franchi et al. |
| 2021/0230129 | A1 | 7/2021 | Franchi et al. |
| 2021/0253596 | A1 | 8/2021 | McBride et al. |
| 2021/0261512 | A1 | 8/2021 | Miller et al. |
| 2021/0261568 | A1 | 8/2021 | Stafford et al. |
| 2021/0308140 | A1 | 10/2021 | Farady et al. |
| 2022/0112159 | A1 | 4/2022 | Luke |
| 2022/0194923 | A1 | 6/2022 | Cooper et al. |
| 2022/0289692 | A1 | 9/2022 | Miller et al. |
| 2022/0306649 | A1 | 9/2022 | Stafford et al. |
| 2022/0340591 | A1 | 10/2022 | Venkatraman et al. |

FOREIGN PATENT DOCUMENTS

| | | | |
|---|---|---|---|
| WO | 2018167468 | A1 | 9/2018 |
| WO | 2019211463 | A1 | 11/2019 |
| WO | 2020157069 | A1 | 8/2020 |

OTHER PUBLICATIONS

International Search report PCT/EP2021/066695 dated Oct. 7, 2021 (pp. 1-4).

*Primary Examiner* — Golam M Shameem
(74) *Attorney, Agent, or Firm* — Millen, White, Zelano & Branigan, P.C.; Brion P. Heaney

(57) ABSTRACT

The present invention relates to novel compounds for the treatment, alleviation or prevention of a group of diseases, disorders and abnormalities which are responsive to the modulation or inhibition of the activation of a component of the NLRP3 inflammasome pathway. In particular, the component of the inflammasome pathway is a NOD-like receptor (NLR) family, pyrin domain-containing protein 3 (NLRP3) inflammasome. More particularly, the compounds of the present invention have the capability to modulate the NLRP3 inflammasome pathway. Further, the compounds of the present invention are suitable for the treatment, alleviation or prevention of a group of diseases, disorders and abnormalities which are responsive to the modulation, in particular decrease, IL-1 beta and/or IL-18 levels.

12 Claims, 1 Drawing Sheet

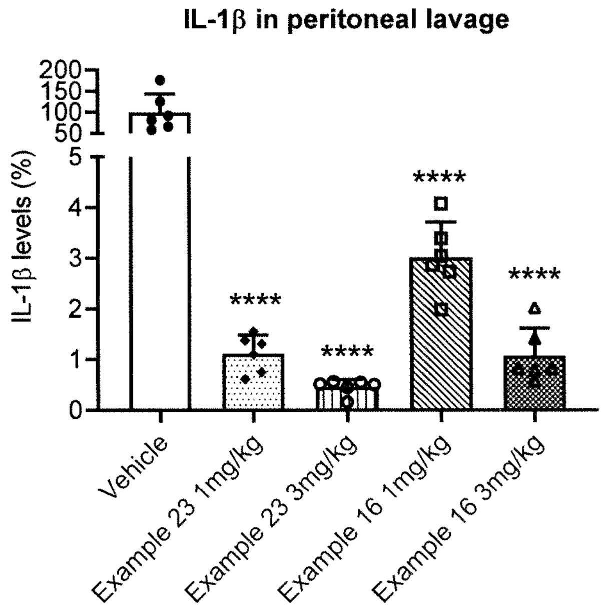
IL-1β in peritoneal lavage
IL-1β levels (%)
200
150
100
50
5
4
3
2
1
0
****
****
****
****
Vehicle
Example 23 1mg/kg
Example 23 3mg/kg
Example 16 1mg/kg
Example 16 3mg/kg
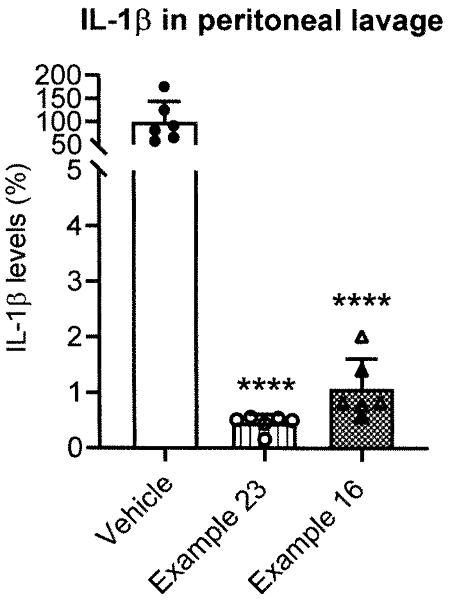
IL-1β in peritoneal lavage
IL-1β levels (%)
200
150
100
50
5
4
3
2
1
0
****
****
Vehicle
Example 23
Example 16

DIHYDROOXAZOLE AND THIOUREA DERIVATIVES MODULATING THE NLRP3 INFLAMMASOME PATHWAY

FIELD OF THE INVENTION

The present invention relates to novel compounds that are useful for the treatment, alleviation or prevention of a disease, disorder or abnormality which is responsive to the modulation, in particular inhibition of the activation, of a component of the NLRP3 inflammasome pathway. In particular, the component of the inflammasome pathway is NOD-like receptor (NLR) family, pyrin domain-containing protein 3 (NLRP3) inflammasome. More particularly, the compounds of the present invention have the capability to modulate, e.g., inhibit the activation of, the NLRP3 inflammasome pathway. Further, the compounds of the present invention have the capability to modulate, in particular decrease, IL-1 beta and/or IL-18 levels. The present invention relates to novel compounds for the treatment, alleviation or prevention of a disease, disorder or abnormality which is responsive to the inhibition of the activation of the NLRP3 inflammasome pathway. The present invention relates to novel compounds for the treatment, alleviation or prevention of a disease, disorder or abnormality which is responsive to the modulation of IL-1 beta and/or IL-18 levels. The present invention relates to pharmaceutical compositions comprising said compounds, methods of using said compounds in the treatment of various diseases, disorders or abnormalities which is responsive to the above-mentioned modulation, medicaments containing them and their uses thereof.

BACKGROUND OF THE INVENTION

Inflammasome protein complexes are the key components of inflammatory signalling. These complexes assemble in response to various danger signals such as molecules from infectious agents (pathogen-associated molecular patterns, PAMPs) as well as altered host molecules, products of sterile tissue damage and environmental factors (danger associated molecular patterns, DAMPs). The inflammasome family consists of NALP1-14, IPAF, and NAIP 1-6, with each family member providing specificity towards different PAMPs/DAMPs including nucleic acids, bacterial proteins, metabolites, protein aggregates and the activity of toxins (Sharma, D. & Kanneganti, T. D. The cell biology of inflammasomes: mechanisms of inflammasome activation and regulation. *J. Cell Biol.* 213, 617-629 (2016)). Inflammasomes are typically composed of a sensor (a cytosolic pattern-recognition receptor, PRR) and an adaptor protein called apoptosis associated speck-like protein containing a caspase-recruitment domain (CARD) (ASC), and an effector such as the protease caspase-1 (Broz, P.; Dixit, V. M. Inflammasomes: Mechanism of Assembly, Regulation and Signalling. *Nat. Rev. Immunol.* 2016, 16, 407-420). NLRP3 (NOD-like receptor (NLR) family, pyrin domain-containing protein 3) inflammasome is one of the best-described family members. It is a tripartite protein of the NLR family and contains an amino-terminal PYRIN (PYD) domain, a nucleotide-binding NACHT domain and a carboxy-terminal leucine-rich repeat (LRR) domain. In response to various agents including aggregated proteins, crystals and altered cellular ion homeostasis, the NLRP3 sensor molecule assembles into a multi-molecular complex with apoptosis-associated speck-like protein containing a caspase activation and recruitment domain (ASC aka PYCARD) adaptor protein. ASC protein polymerization into a large complex (ASC speck) leads to activation of caspase-1 effector protein and subsequent cleavage of pro-IL-1 beta (B) and pro-IL18 into their active secreted forms and mediates pyroptosis (Heneka et al., 2018 *Nat Rev Neurosci*). IL-1 beta (β) acts through IL-1 beta (β) receptors, induces secondary pro-inflammatory signals including IL-6 and TNF alpha secretion, and attracts and activates cells of adaptive immune system at the sites of infection. NLRP3/ASC complexes seems to be released into the extracellular environment where they can propagate inflammation.

Multiple genetic and pharmacological evidence highlight the importance of NLRP3 inflammasome in human disease. NLRP3 gain-of-function mutations lead to the inherited cryopyrin-associated periodic syndromes (CAPS) including Muckle-Wells syndrome (MWS), familial cold auto-inflammatory syndrome (FCAS) and neonatal-onset multisystem inflammatory disease (NOMID).

Accumulation of tissue damage products associated with ageing results in activation of NLRP3 inflammasome in multiple diseases including metabolic disorders, Alzheimer's disease, Parkinson's disease, amyotrophic lateral sclerosis, atherosclerosis, obesity, lung diseases, liver diseases and gout.

Vast experimental evidence from animal models points out the detrimental role of excessive NLRP3 activation in a wide spectrum of diseases. NLRP3-inflammasome genetic or pharmacological downregulation showed protection in models of Alzheimer's disease, Parkinson's disease, amyotrophic lateral sclerosis, demyelination, viral encephalitis, epilepsy, stroke, atherosclerosis, asthma, allergic inflammation, cryopyrin-associated periodic syndromes (CAPS), gout, inflammatory bowel disease, non-alcoholic fatty liver disease (NAFLD), non-alcoholic steatohepatitis (NASH), hypertension, myocardial infarction, oxalate-induced nephropathy, graft-versus host disease, type 1 and type 2 diabetes, rheumatoid arthritis, myelodysplastic syndrome, among others (Heneka et al., *Nat. Rev. Neurosci.* 2018 Oct.; 19 (10): 610-621; Mangan et al., *Nat. Rev. Drug Discov.* 2018 August; 17 (8): 588-606).

For the reasons described above modulation of NLRP3 inflammasome pathway activity represents a promising therapeutic approach.

Current treatments for NLRP3-related diseases include biologics targeting IL-1. These are the recombinant IL-1 receptor antagonist anakinra, the neutralizing IL-1 beta (3) antibody canakinumab and the soluble decoy IL-1 receptor rilonacept. However, their activity is limited to downstream effectors of inflammasome and their bioavailability for central nervous system (CNS) applications is limited.

Several small molecules have been shown to inhibit the NLRP3 inflammasome pathway (Baldwin, A. G., Brough, D. & Freeman, S. Inhibiting the NLRP3 inflammasome pathway: a chemical perspective. *J. Med. Chem.* 59, 1691-1710 (2016); reviewed in Mangan et al., *Nat Rev Drug Discov.* 2018 Aug.; 17 (8): 588-606). These include various chemical classes such as sulfonylurea-based compounds (glyburide, CP-456,773 (aka CRID3 and MCC950) and its derivatives); fenamate classes of non-steroidal anti-inflammatory drugs; hydroxysulfonamide analogue JC-171; novel boron compound series; benzimidazole-containing structure Fc11a-2; polyketide spirodalesol; acrylate and acrylamide derivatives; 3,4-methylenedioxy-β-nitrostyrene; β-sulfonyl nitrile molecule OLT1177; CY-09; BOT-4-one; and Michael acceptors. Most of these compounds have a promiscuous mode of action and limited potency.

WO2016131098, WO2017/140778 and WO2018215818 refer to sulfonylurea and related compounds and their use in treating or identifying a disease or condition responsive to inhibition of NLRP3 or inhibition of the activation of NLRP3 or related components of the inflammatory process.

WO2019008025, WO2019008029, WO2019034686, WO2019034688, WO2019034690, WO2019034692, WO2019034693, WO2019034696, WO2019034697, WO2019068772, WO2019092170, WO2019092171 and WO2019092172 refer to novel compounds (e.g. sulfonylureas, sulfonylthioureas, sulfoximine ureas and sulfoximine thioureas), useful in the treatment and prevention of medical disorders and diseases, most especially by NLRP3 inhibition.

WO2017184604, WO2017184623, WO2017184624, WO2019023145, WO2019023147 and WO2019079119 refer to chemical entities that are useful for treating a condition, disease, or disorder in which a decrease or increase in NLRP3 activity contributes to the pathology and/or symptoms and/or progression of the condition, disease, or disorder in a subject.

WO2019211463, WO2020021447, and WO2021043966 disclose compounds for inhibiting NLRP3 and/or NLRP3 inflammasome pathway.

WO2018136890 refers to sulfonylurea and sulfonyl thiourea compounds and their use in treating a disease or condition responsive to modulation of cytokines such as IL-1 beta (B) and IL-18, modulation of NLRP3 or inhibition of the activation of NLRP3 or related components of the inflammatory process.

WO2018225018 and WO2019043610 refer to NLRP3 modulators as well as to the use of the novel inhibitor compounds in the treatment of diseases or conditions as well as treatment of disease states mediated by NLRP3 as well as treatment of diseases or conditions in which interleukin 1 beta (B) activity and interleukin-18 (IL-18) are implicated.

WO2018015445 refers to sulfonylurea compounds which possess inflammasome inhibitory activity and are accordingly useful in methods of treatment of the human or animal body.

WO2020018975 discloses sulfonimidamide derivatives defined as inhibitors of interleukin-1 activity and NLRP3 modulators in connection with inflammatory processes.

WO9832733 refers to aryl and heteroaryl substituted sulfonyl ureas that are inhibitors of interleukin-1 alpha (a) and interleukin-1 beta (B) processing and release.

WO2020018970 discloses sulfonylureas defined as inhibitors of interleukin-1 activity.

The crosstalk between the NLRP3 inflammasome pathway and Tau pathology has been recently deciphered. Ising et al. (*Nature* 2019 Nov.; 575 (7784): 669-673) investigated the important role of microglia and NLRP3 inflammasome pathway activation in the pathogenesis of tauopathies in the Tau22 mouse model of FrontoTemporal Dementia (FTD). Genetic ablation of components of the NLRP3 inflammasome pathway in Tau22 mice reduced Tau aggregation/phosphorylation as well as improved cognition. Stancu et al. (*Acta Neuropathol.* 2019; 137 (4): 599-617) investigated the role of inflammasome activation in prion-like or templated seeding of Tau pathology. Significant inhibition of exogenously seeded Tau pathology was found in ASC deficient-PS19 Tau transgenic mice. Furthermore, it was demonstrated that chronic intracerebral administration of the NLRP3 inhibitor, MCC950, inhibits exogenously seeded Tau pathology. Finally, ASC deficiency also decreased non-exogenously seeded Tau pathology in PS19 mice.

There is a need to identify and develop specific NLRP3 inflammasome pathway inhibitors and/or modulators of interleukin activity with improved pharmacological and/or physiological and/or physicochemical properties.

The present invention provides compounds of formula (I'), compound of formula (I), compound of formula (II'), or compounds of formula (II) which have surprisingly been found to be capable of modulating a component of the NLRP3 inflammasome pathway, in particular inhibiting the activation, of a component of the NLRP3 inflammasome pathway, such as NLRP3 inflammasome. Thus, such compounds are beneficial in the treatment of a disease, disorder, or abnormality which is responsive to the modulation of a component of the NLRP3 inflammasome pathway and/or which is responsive to the modulation of IL-1 beta and/or IL-18 levels that commonly lead to pathological inflammation.

SUMMARY OF THE INVENTION

Accordingly, the present invention provides compounds of formula (I'), compounds of formula (I), compounds of formula (II'), or compounds of formula (II), or stereoisomers, or racemic mixtures, or tautomers, or polymorphs, or pharmaceutically acceptable salts, or prodrugs, or hydrates, or solvates thereof. Within the present invention any reference to the compounds of formula (I'), (I), (II') or (II), or the preferred embodiments thereof is intended to also refer to the stereoisomers, or racemic mixtures, or tautomers, or polymorphs, or pharmaceutically acceptable salts, or prodrugs, or hydrates, or solvates thereof.

The compounds of formula (I'), (I), (II'), or (II), or a stereoisomer, a racemic mixture, a tautomer, a polymorph, a pharmaceutically acceptable salt, a prodrug, a hydrate, or a solvate thereof, are suitable for the treatment, alleviation or prevention of a disease, disorder or an abnormality which is responsive to the modulation, in particular inhibition, of a component of the NLRP3 inflammasome pathway, or which is responsive to the modulation, in particular decrease, of IL-1 beta and/or IL-18 levels. In particular, the component of the inflammasome pathway is the NLRP3 inflammasome. Activation of the NLRP3 inflammasome pathway can trigger the formation of ASC specks, cleavage and activation of Caspase-1 and Caspase-8 and subsequent activation and release IL-1 beta, IL-18, gasdermin D cleavage and pore formation, pyroptosis, and release of IL-1alpha, IL-33, IL-17 and High-Mobility Group Box (HMGB) protein. The compounds of formula (I'), (I), (II'), or (II), or a stereoisomer, a racemic mixture, a tautomer, a polymorph, a pharmaceutically acceptable salt, a prodrug, a hydrate, or a solvate thereof, have the capability to modulate, in particular decrease, IL-1 beta and/or IL-18 levels.

The compounds of formula (I'), (I), (II'), and (II), or a stereoisomer, a racemic mixture, a tautomer, a polymorph, a pharmaceutically acceptable salt, a prodrug, a hydrate, or a solvate thereof, display high capability in modulating and, in particular inhibiting the activation of, a component of the NLRP3 inflammasome pathway, in particular wherein the component of the inflammasome pathway is the NLRP3 inflammasome. Due to their unique design features, these compounds display properties such as modulating or inhibiting the activation of the NLRP3 inflammasome pathway allowing them to be a successful medicament for the treatment, alleviation or prevention of diseases, disorders and abnormalities responsive to the modulation or inhibition of a component of the NLRP3 inflammasome pathway such as, for example, Alzheimer's disease, Parkinson's disease, CAPS, non-alcoholic fatty liver disease (NAFLD), non-alcoholic steatohepatitis (NASH) and gout.

In a further embodiment, the invention relates to a pharmaceutical composition comprising a compound of formula (I'), (I), (II'), or (II), or a stereoisomer, a racemic mixture, a tautomer, a polymorph, a pharmaceutically acceptable salt, a prodrug, a hydrate, or a solvate thereof, and optionally comprising at least one pharmaceutically acceptable carrier, diluent, adjuvant or excipient.

In another embodiment, the present invention refers to a compound of formula (I'), (I), (II'), or (II), or a stereoisomer, a racemic mixture, a tautomer, a polymorph, a pharmaceutically acceptable salt, a prodrug, a hydrate, or a solvate thereof, for use as a medicament.

Yet another embodiment, the present invention refers to a compound of formula (I'), (I), (II'), or (II), or a stereoisomer, a racemic mixture, a tautomer, a polymorph, a pharmaceutically acceptable salt, a prodrug, a hydrate, or a solvate thereof, for use in the treatment, alleviation or prevention of a disease, disorder, or abnormality which is responsive to the modulation, in particular inhibition of activation, of a component of the NLRP3 inflammasome pathway and/or which is responsive to the modulation, in particular decrease, of IL-1 beta and/or IL-18 levels.

A further embodiment is concerned with the use of the compound of formula (I'), (I), (II'), or (II), or a stereoisomer, a racemic mixture, a tautomer, a polymorph, a pharmaceutically acceptable salt, a prodrug, a hydrate, or a solvate thereof, for the manufacture of a medicament for treating, alleviating or preventing a disease, disorder or abnormality which is responsive to the modulation, in particular inhibition of activation, of a component of the NLRP3 inflammasome pathway and/or which is responsive to the modulation, in particular decrease, of IL-1 beta and/or IL-18 levels.

In yet another embodiment, the present invention is directed to a method of treating, alleviating or preventing a disease, disorder or abnormality which is responsive to the modulation, in particular inhibition of activation, of a component of the NLRP3 inflammasome pathway or which is responsive to the modulation, in particular decrease, of IL-1 beta and/or IL-18 levels, the method comprising administering a therapeutically effective amount of a compound of formula (I'), (I), (II'), or (II), or a stereoisomer, a racemic mixture, a tautomer, a polymorph, a pharmaceutically acceptable salt, a prodrug, a hydrate, or a solvate thereof, to a subject in need thereof (e.g. a patient).

A pharmaceutical composition comprising a combination of a compound of formula (I'), (I), (II'), or (II), or a stereoisomer, a racemic mixture, a tautomer, a polymorph, a pharmaceutically acceptable salt, a prodrug, a hydrate, or a solvate thereof, and at least one further biologically active compound differing from the compound of formula (I'), (I), (II'), or (II), or a stereoisomer, a racemic mixture, a tautomer, a polymorph, a pharmaceutically acceptable salt, a prodrug, a hydrate, or a solvate thereof, and optionally comprising at least one pharmaceutically acceptable carrier, diluent, adjuvant or excipient, is also the subject-matter of the present invention.

In particular, the further biologically active compound can be one which is used for the treatment of a disease, disorder, or abnormality associated with a disease targeting different pathomechanism, e.g. an anti-amyloid beta antibody, anti-Tau antibody, amyloid beta small molecule inhibitor, Tau aggregation small molecule inhibitor, anti-alpha synuclein antibody or alpha-synuclein aggregation small molecule inhibitor, anti-TDP-43 antibody or anti-TDP-43 aggregation small molecule inhibitor, among others. When a compound of the invention is used in combination with a further biologically active compound, the dose of each compound may differ from the dose if the compound is used as monotherapy.

An additional embodiment relates to the use of the compound of formula (I'), (I), (II') or (II), or a stereoisomer, a racemic mixture, a tautomer, a polymorph, a pharmaceutically acceptable salt, a prodrug, a hydrate, or a solvate thereof, as an analytical reference or an in vitro screening tool.

The following clauses are also part of the invention:

A1. A compound of formula (I)

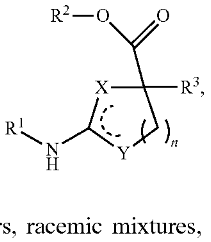

(I)

or stereoisomers, racemic mixtures, tautomers, pharmaceutically acceptable salts, prodrugs, hydrates, or solvates thereof;

wherein

X is independently selected from the group consisting of O, N and S;

Y is independently selected from the group consisting of N and O;

as valency permits, (is a combination of a single bond and a double bond or is two single bonds;

n is 1 or 2;

$R^1$ is

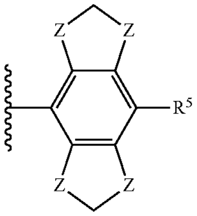

wherein

Z is independently selected from the group consisting of $CH_2$ and O provided that no more than two of Z are O;

$R^5$ is independently selected from the group consisting of hydrogen and halogen;

$R^2$ is independently selected from the group consisting of $C_1$-$C_6$alkyl and $C_3$-$C_6$cycloalkyl;

$R^3$ is independently selected from the group consisting of

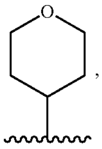,
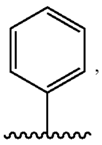,
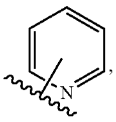,
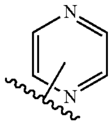,
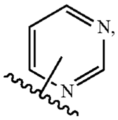,
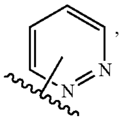,
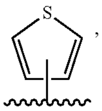,
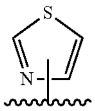, -continued

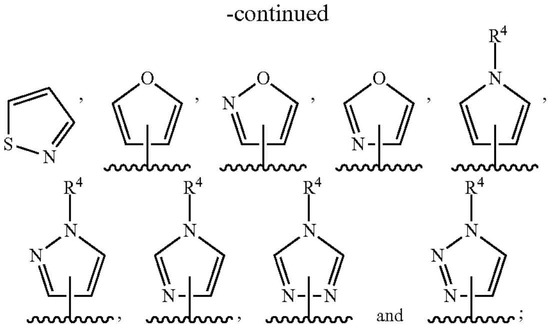

and wherein other than at the position of $R^4$, $R^3$ can be optionally substituted with halogen, $C_1$-$C_6$alkyl or —OMe;

$R^4$ is independently selected from the group consisting of hydrogen, $C_1$-$C_6$alkyl and $C_3$-$C_6$ cycloalkyl;

wherein any mentioned $C_1$-$C_6$alkyl can be optionally substituted with —OH; and $C_3$-$C_6$cycloalkyl can be optionally substituted with —OH.

A2. The compound of formula (I) according to clause A1 which is a compound of formula (Ic) or a compound of formula (Id)

(Ic)

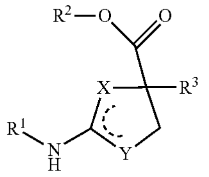

or (Id)

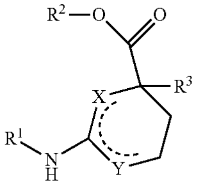

or stereoisomers, racemic mixtures, tautomers, pharmaceutically acceptable salts, prodrugs, hydrates, or solvates thereof wherein (, x, Y, $R^1$, $R^2$ are $R^3$ are as defined in clause 1.

A3. The compound of formula (I) according to clause A2 which is a compound of formula (Ic)

(Ic)

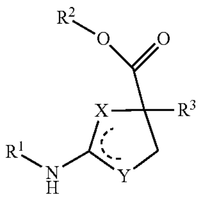

wherein (, X, Y, $R^1$, $R^2$ are $R^3$ are as defined in clause 1.

A4. The compound of formula (I) according to clause A3, wherein

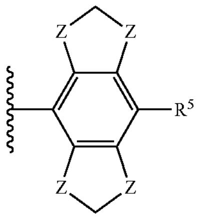

$R^1$ is wherein

Z is $CH_2$;

$R^5$ is hydrogen;

X is O;

Y is N;

as valency permits, (is the combination of a single bond and a double bond;

$R^2$ is ethyl;

$R^3$ is independently selected from the group consisting of

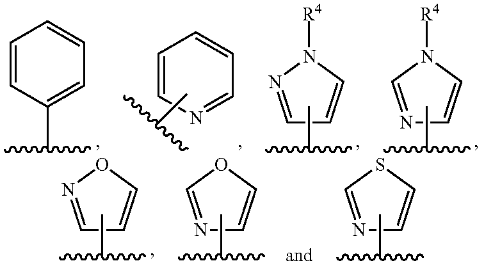

and wherein other than at the position of $R^4$, $R^3$ can be optionally substituted with Cl, isopropyl or —OMe, wherein isopropyl can be optionally substituted with —OH; and $R^4$ is methyl or ethyl.

A5. The compound according to clause A1 to A4 which is selected from

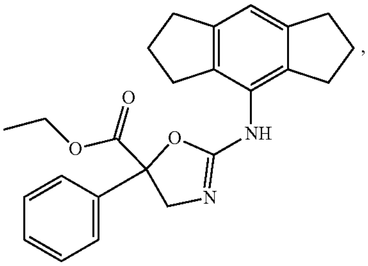

,

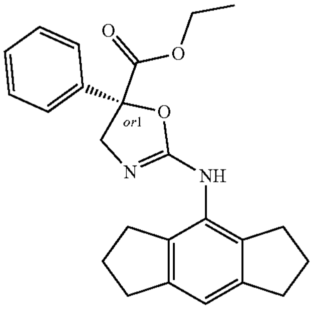

,

-continued
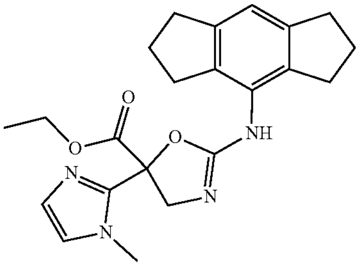
,
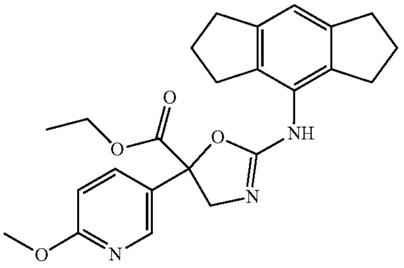
,
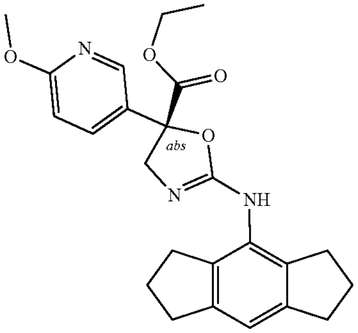
,
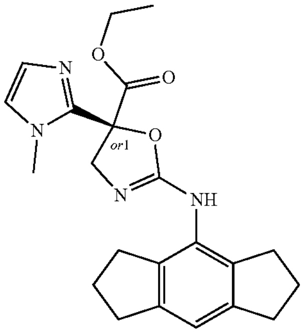
,
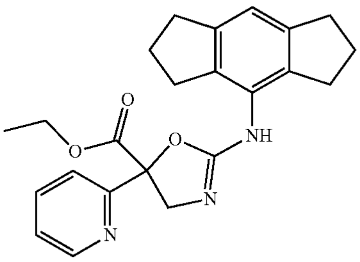
,
-continued
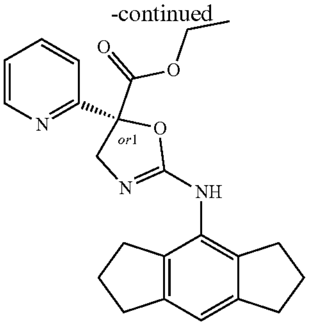
,
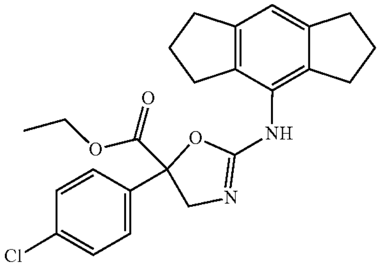
,
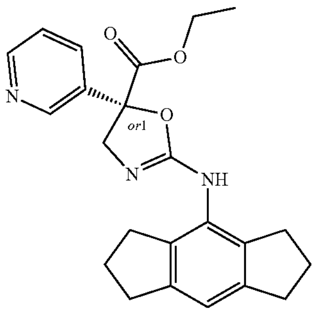
,
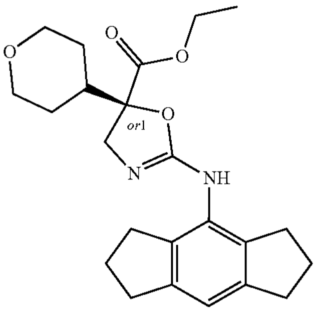
,
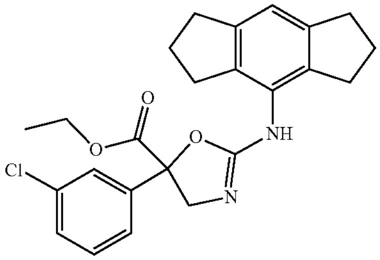
and
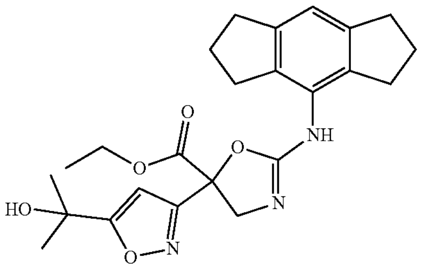
.

A6. A compound of formula (II)

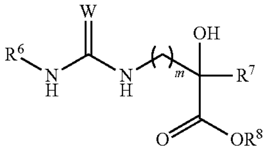

(II)

or stereoisomers, racemic mixtures, tautomers, pharmaceutically acceptable salts, prodrugs, hydrates or solvates thereof;

wherein

W is independently selected from the group consisting of O and S;

m is 1 or 2;

$R^6$ is

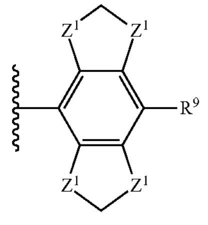

wherein $Z^1$ is independently selected from the group consisting of $CH_2$ and O provided that no more than two of $Z^1$ are O;

$R^9$ is independently selected from the group consisting of hydrogen and halogen;

$R^8$ is independently selected from the group consisting of $C_1$-$C_6$alkyl and $C_3$-$C_6$cycloalkyl;

$R^7$ is independently selected from the group consisting of

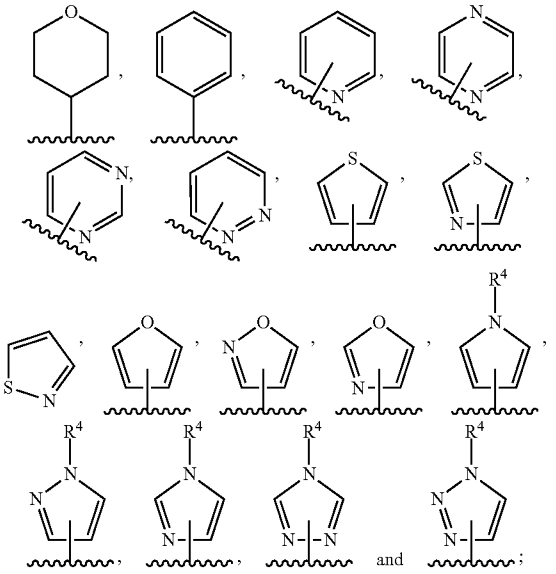

wherein other than at the position of $R^4$, $R^7$ can be optionally substituted with halogen, $C_1$-$C_6$alkyl or —OMe;

$R^4$ is selected from the group consisting of hydrogen, $C_1$-$C_6$alkyl and $C_3$-$C_6$cycloalkyl;

wherein any mentioned $C_1$-$C_6$alkyl can be optionally substituted with —OH; and $C_3$-$C_6$cycloalkyl can be optionally substituted with —OH.

A7. The compound according to clause A6 which is

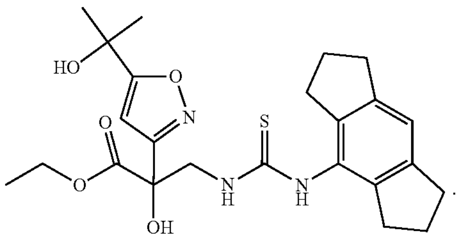 [SMILES: CCOC(=O)C(O)(CNC(=S)Nc1c2c(cc3c1CCC3)CCC2)c1cc(C(C)(C)O)on1]

A8. A pharmaceutical composition comprising a compound of formula (I) or formula (II) as defined in any one of the preceding clauses and optionally comprising at least a pharmaceutically acceptable carrier, diluent, adjuvant or excipient.

A9. The compound of formula (I) or formula (II) according to any one of clauses A1 to A7 for use as a medicament.

A10. The compound of formula (I) or formula (II) according to any one of clauses A1 to A7 for use in the treatment, alleviation or prevention of a disorder or an abnormality associated with the modulation of a component of the inflammasome pathway and/or the modulation of IL-1 beta and/or IL-18 levels.

A11. The compound of formula (I) or formula (II) for use according to clause A10, wherein the component of the inflammasome pathway is NLRP3 inflammasome.

A12. The compound of formula (I) or formula (II) for use according to clause A10 or A11, wherein the component of the inflammasome pathway is inhibited.

A13. The compound of formula (I) or formula (II) for use according to any one of clauses A10 to A12, wherein the disorder or the abnormality is selected from Alzheimer's disease, Parkinson's disease, amyotrophic lateral sclerosis, demyelination, viral encephalitis, epilepsy, stroke, atherosclerosis, asthma, allergic inflammation, cryopyrin-associated periodic syndromes (CAPS), Muckle-Wells syndrome (MWS), familial cold autoinflammatory syndrome (FCAS), neonatal-onset multisystem inflammatory disease (NOMID), gout, pseudo-gout, inflammatory bowel disease, non-alcoholic fatty liver disease, non-alcoholic steatohepatitis, hypertension, myocardial infarction, oxalate-induced nephropathy, graft-versus host disease, type 1 diabetes, type 2 diabetes, rheumatoid arthritis, myelodysplastic syndrome, familial Mediterranean fever (FMF), TNF receptor associated periodic syndrome (TRAPS), mevalonate kinase deficiency (MKD), hyperimmunoglobulinemia D, periodic fever syndrome (HIDS), deficiency of interleukin 1 receptor (DIRA) antagonist, Majeed syndrome, acne, pyogenic arthritis pyoderma gangrenosum and acne (PAPA), haploinsufficiency of A20 (HA20), PLCG2-associated antibody deficiency and immune dysregulation (PLAID), pediatric granulomatous arthritis (PGA), PLCG2-associated autoinflammation, antibody deficiency and immune dysregulation (APLAID), sideroblastic anemia with B-cell immunodeficiency, periodic fevers, developmental delay (SIFD), chronic nonbacterial osteomyelitis (CNO), Sweet's syndrome, chronic recurrent multifocal osteomyelitis (CRMO), synovitis, pustulosis, acne, hyperostosis, osteitis syndrome (SAPHO), multiple sclerosis (MS), psoriasis, Behcet's disease, Sjogren's syndrome, Schnitzler syndrome, chronic obstructive pulmonary disorder (COPD), steroid-resistant asthma, asbestosis, silicosis, cystic fibrosis, motor neuron disease, Huntington's disease, cerebral malaria, brain injury from pneumococcal meningitis, obesity, age-related macular degeneration (AMD), corneal infection, uveitis, dry eye, chronic kidney disease, diabetic nephropathy, alcoholic liver disease, skin contact hypersensitivity, sunburn, osteoarthritis, systemic juvenile idiopathic arthritis, adult-onset Still's disease, relapsing polychondritis, Chikungunya virus, Ross River virus, influenza, HIV, Coronaviruses, Dengue, Zika virus, hidradenitis suppurativa (HS), lung cancer metastasis, pancreatic cancers, gastric cancers, myelodisplastic syndrome, leukemia; polymyositis, colitis, helminth infection, bacterial infection, abdominal aortic aneurism, wound healing, depression, psychological stress, pericarditis including Dressler's syndrome, ischaemia reperfusion injury, frontotemporal dementia, HIV-associated neurocognitive disorder, Coronavirus-associated inflammatory pathologies, and traumatic brain injury; preferably the disorder is selected from Alzheimer's disease, Parkinson's disease, amyotrophic lateral sclerosis, demyelination, viral encephalitis, epilepsy, stroke, atherosclerosis, asthma, allergic inflammation, cryopyrin-associated periodic syndromes (CAPS), gout, inflammatory bowel disease, non-alcoholic fatty liver disease (NAFLD), non-alcoholic steatohepatitis (NASH), hypertension, myocardial infarction, oxalate-induced nephropathy, graft-versus host disease, type 1 diabetes, type 2 diabetes, rheumatoid arthritis, myelodysplastic syndrome, anti-neutrophil cytoplasmic antibody-associated vasculitis (AAV), lupus nephritis, anti-glomerular basement membrane (GMB) disease, IgA nephropathy, glomerulonephritis (GN), systemic lupus erythematosus (SLE), Focal Segmental Glomerulosclerosis, Minimal change disease (MCD), Psoriatic Arthritis, and Hereditary Recurrent Fevers (HRFs).

A14. The compound of formula (I) or formula (II) for use according to clause A13, wherein the disorder or the abnormality is selected from Alzheimer's disease, Parkinson's disease, cryopyrin-associated periodic syndromes (CAPS), nonalcoholic fatty liver disease, NASH and gout.

A15. A pharmaceutical composition comprising a combination of a compound of formula (I) or formula (II) according to any one of clauses A1 to A7 and at least one further biologically active compound differing from the compound of formula (I) or formula (II), and optionally comprising at least a pharmaceutically acceptable carrier, diluent, adjuvant or excipient.

A16. A pharmaceutical mixture comprising a combination of a compound of formula (I) or formula (II) according to any one of clauses A1 to A7.

A17. Use of the compound of formula (I) or formula (II) according to any one of clauses A1 to A7 as an analytical reference or an in vitro screening tool.

A18. A method for producing a compound of formula (Ic) according to clauses A1 to A5 comprising the step of cyclization of a compound of formula (II) in presence of a condensation agent

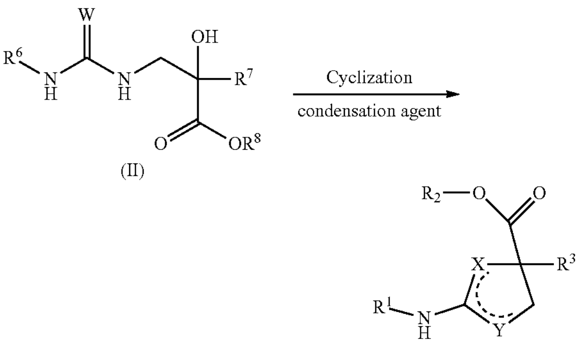

(II)

(Ic)

wherein $R^6$, W, $R^7$, $R^8$, X, Y, $R^1$, $R^2$ and $R^3$ are defined as in any one of clauses A1 to A4 and A6.

A19. A method for producing a compound of formula (II) according to clause A6 or A7 comprising the step of coupling a compound of formula (III) with a urea or thiourea derivative of formula (IV) in the presence of a solvent and a base

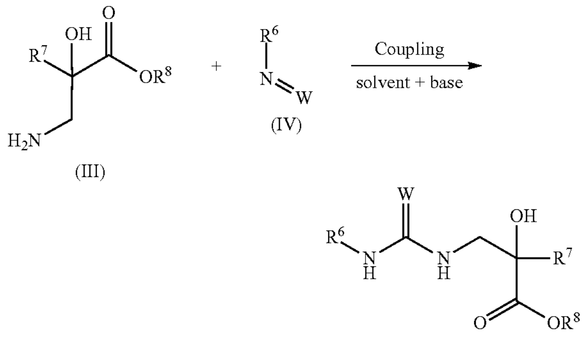

(III)

(IV)

(III)

wherein $R^6$, W, $R^7$ and $R^8$ are defined as in any one of clauses A1 to A4 and A6.

In another aspect, the following clauses are also part of the invention:

B1. A compound of formula (I)

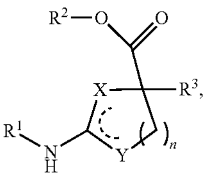

(I)

or a stereoisomer, a racemic mixture, a tautomer, a polymorph, a pharmaceutically acceptable salt, a prodrug, a hydrate, or a solvate thereof;

wherein

X is independently selected from the group consisting of O, N and S;

Y is independently selected from the group consisting of N and O;

as valency permits, ( is a combination of a single bond and a double bond or is two single bonds;

n is 1 or 2;

$R^1$ is

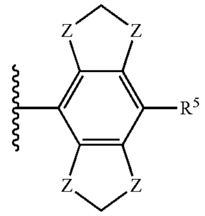

wherein

Z is independently selected from the group consisting of $CH_2$ and O provided that no more than two of Z are O;

$R^5$ is independently selected from the group consisting of hydrogen and halogen;

$R^2$ is independently selected from the group consisting of hydrogen, $C_1$-$C_6$alkyl, $C_3$-$C_6$cycloalkyl; and $R^3$ is independently selected from the group consisting of hetero$C_3$-$C_6$cycloalkyl, aryl or heteroaryl, wherein each of them can be optionally substituted with —$C_1$-$C_6$alkyl, —O—$C_1$-$C_6$alkyl, -Hal, or —$C_1$-$C_6$alkyl-OH.

B2. The compound according to clause B1, which is a compound of formula (Ic) or a compound of formula (Id)

(Ic)

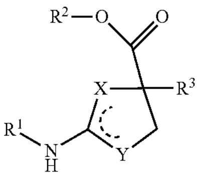

or (Id)

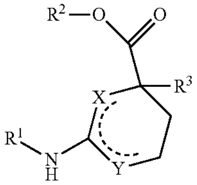

or a stereoisomer, a racemic mixture, a tautomer, a polymorph, a pharmaceutically acceptable salt, a prodrug, a hydrate, or a solvate thereof, wherein (, X, Y, $R^1$, $R^2$ are $R^3$ are as defined in clause B1.

B3. The compound according to clause B2, which is a compound of formula (Ic)

(Ic)

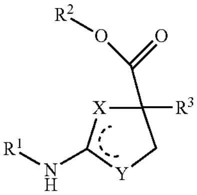

wherein (, X, Y, $R^1$, $R^2$ are $R^3$ are as defined in clause B1.

B4. The compound according to any of the preceding clauses, wherein $R^2$ is hydrogen or ethyl.

B5. The compound according to any of the preceding clauses, wherein

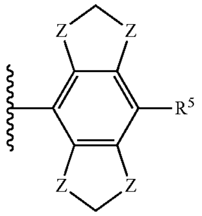

$R^1$ is wherein

Z is $CH_2$;

$R^5$ is hydrogen;

X is O;

Y is N;

as valency permits, ( is the combination of a single bond and a double bond; and $R^3$ is

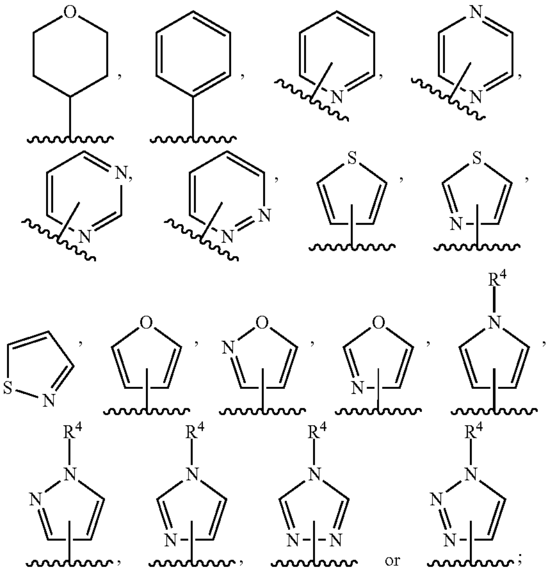

each of them can be optionally substituted, and $R^4$ is independently selected from the group consisting of hydrogen, $C_1$-$C_6$alkyl and $C_3$-$C_6$cycloalkyl.

B6. The compound according to any of the preceding clauses, which is selected from

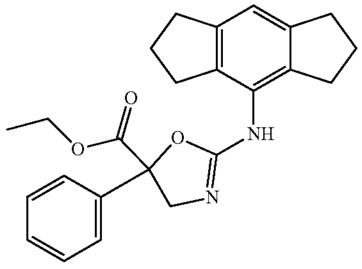

;

-continued
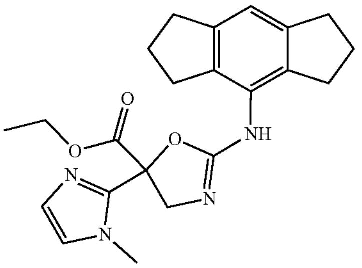
;
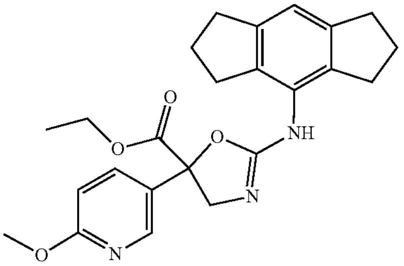
;
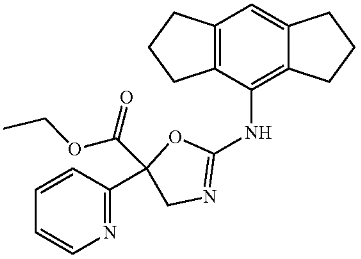
;
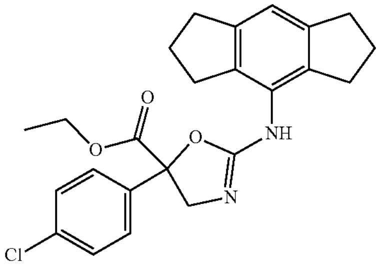
;
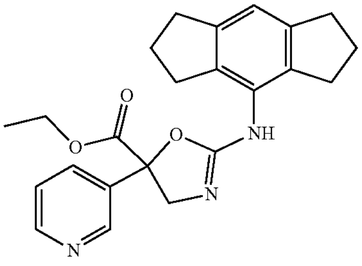
;
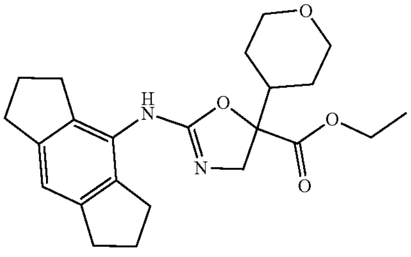
;
-continued
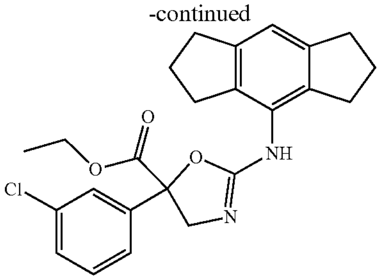
;
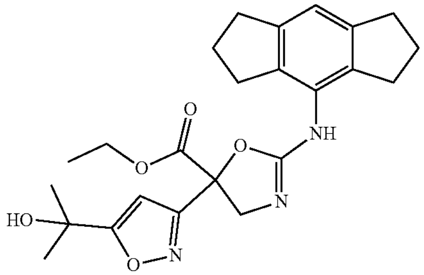
;
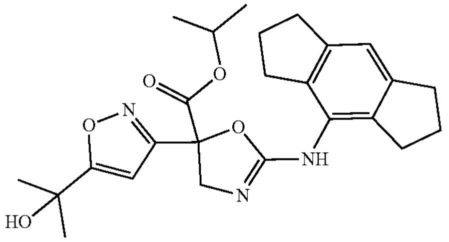
;
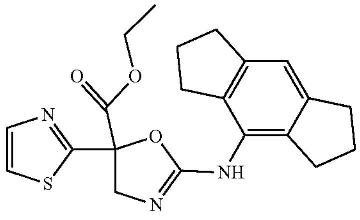
;
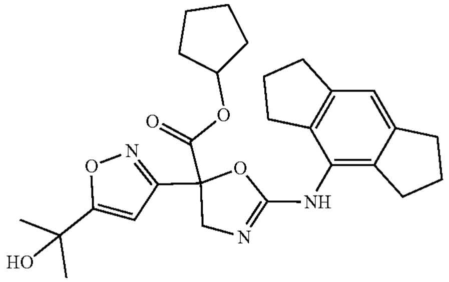
;
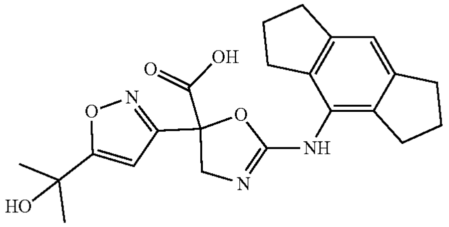
;
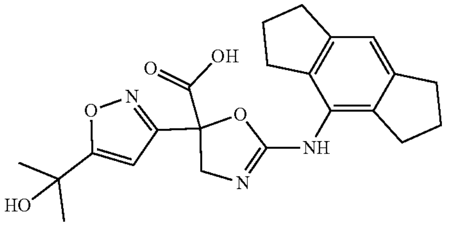
;

-continued

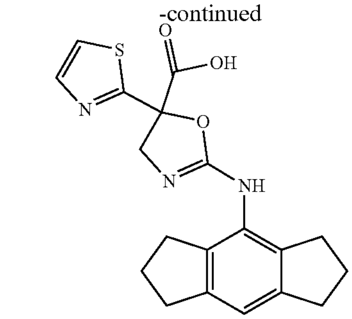

;

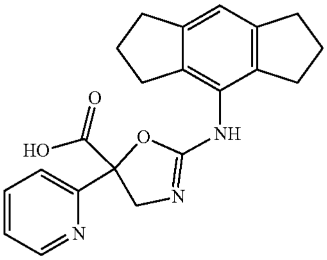

; and

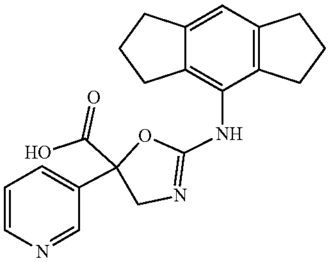

or a stereoisomer, a racemic mixture, a tautomer, a polymorph, a pharmaceutically acceptable salt, a prodrug, a hydrate, or a solvate thereof.

B7. A compound of formula (II)

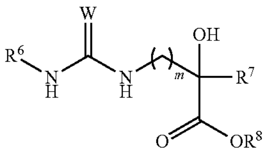

(II)

or a stereoisomer, a racemic mixture, a tautomer, a polymorph, a pharmaceutically acceptable salt, a prodrug, a hydrate, or a solvate thereof, wherein W is independently selected from the group consisting of O and S;

m is 1 or 2;

$R^6$ is

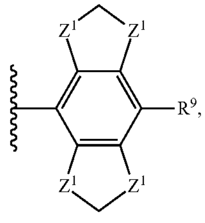

wherein $Z^1$ is independently selected from the group consisting of $CH_2$ and O provided that no more than two of $Z^1$ are O;

$R^9$ is independently selected from the group consisting of hydrogen and halogen;

$R^8$ is independently selected from the group consisting of hydrogen, $C_1$-$C_6$alkyl, $C_3$-$C_6$ cycloalkyl; and $R^7$ is independently selected from the group consisting of hetero$C_3$-$C_6$cycloalkyl, aryl or heteroaryl wherein each of them can be optionally substituted.

B8. The compound according to clause B7, wherein $R^8$ is hydrogen or ethyl.

B9. The compound according to clause B8, wherein $R^7$ is

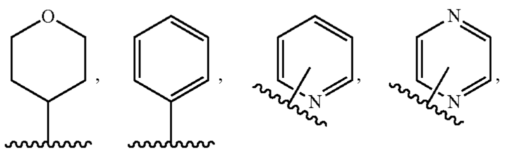

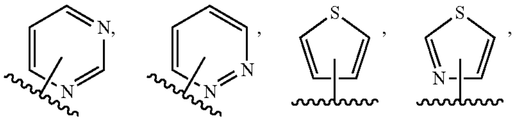

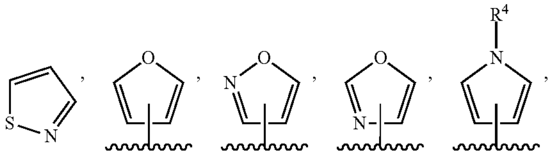

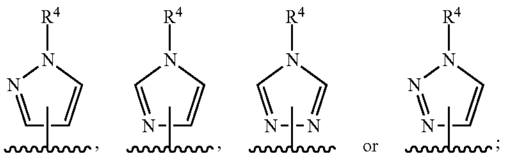

each of them can be optionally substituted and $R^4$ is independently selected from the group consisting of hydrogen, $C_1$-$C_6$alkyl and $C_3$-$C_6$cycloalkyl.

B10. The compound according to clauses B7 to B9, which is

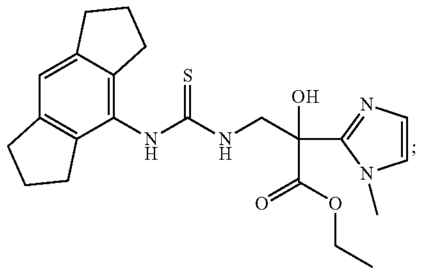

;

-continued

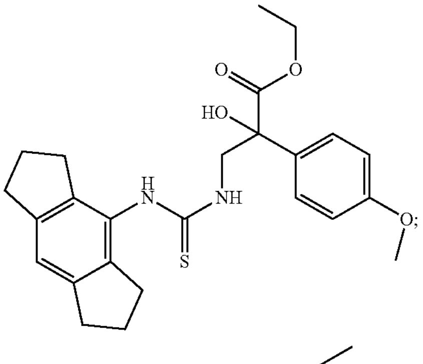

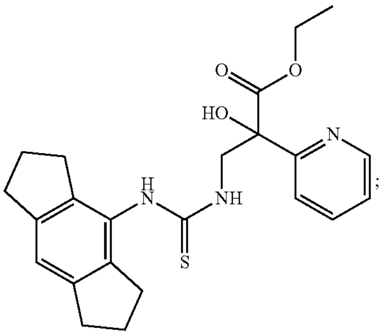

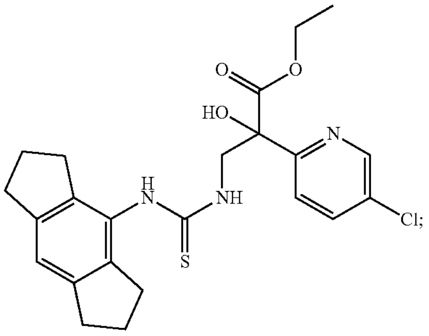

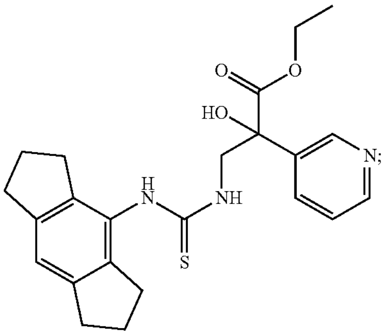

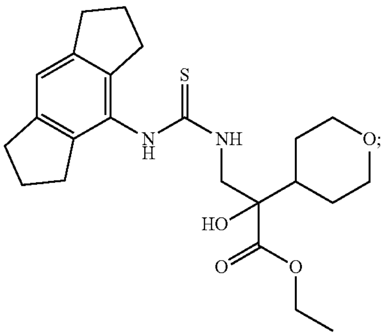

-continued

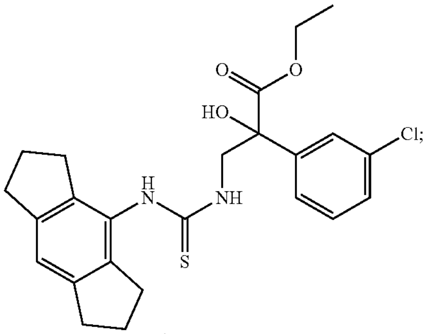

or

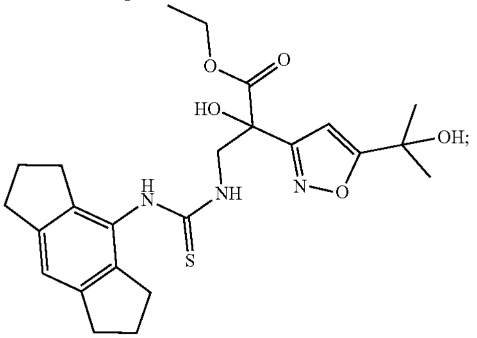

or a stereoisomer, a racemic mixture, a tautomer, a polymorph, a pharmaceutically acceptable salt, a prodrug, a hydrate, or a solvate thereof.

B11. A pharmaceutical composition comprising a compound of formula (I) or a compound of formula (II) as defined in any one of clauses B1 to B10, or a stereoisomer, a racemic mixture, a tautomer, a polymorph, a pharmaceutically acceptable salt, a prodrug, a hydrate, or a solvate thereof, and optionally comprising at least one pharmaceutically acceptable carrier, diluent, adjuvant or excipient.

B12. The compound according to any one of clauses B1 to B10, or a stereoisomer, a racemic mixture, a tautomer, a polymorph, a pharmaceutically acceptable salt, a prodrug, a hydrate, or a solvate thereof, for use as a medicament.

B13. The compound according to any one of clauses B1 to B10, or a stereoisomer, a racemic mixture, a tautomer, a polymorph, a pharmaceutically acceptable salt, a prodrug, a hydrate, or a solvate thereof, for use in the treatment, alleviation or prevention of a disease, or a disorder or an abnormality which is responsive to the modulation of a component of the NLRP3 inflammasome pathway and/or which is responsive to the modulation of IL-1 beta and/or IL-18 levels.

B14. The compound for use according to clause 13, wherein the component of the inflammasome pathway is NLRP3 inflammasome.

B15. The compound for use according to clause B13 or B14, wherein the activation of NLRP3 inflammasome pathway is inhibited.

B16. The compound for use according to any one of clauses B13 to B15, wherein the disease, the disorder or the abnormality is selected from Alzheimer's disease, Parkinson's disease, amyotrophic lateral sclerosis, demyelination, viral encephalitis, epilepsy, stroke, atherosclerosis, asthma, allergic inflammation, cryopyrin-associated periodic syndromes (CAPS), Muckle-Wells syndrome (MWS), familial cold autoinflammatory syndrome (FCAS), neonatal-onset multisystem inflammatory disease (NOMID), gout, pseudo-gout, inflammatory bowel disease, nonalcoholic fatty liver disease, nonalcoholic steatohepatitis, hypertension, myocardial infarction, oxalate-induced nephropathy, graft-versus host disease, type 1 diabetes, type 2 diabetes, rheumatoid arthritis, myelodysplastic syndrome, familial Mediterranean fever (FMF), TNF receptor associated periodic syndrome (TRAPS), mevalonate kinase deficiency (MKD), hyperimmunoglobulinemia D, periodic fever syndrome (HIDS), deficiency of interleukin 1 receptor (DIRA) antagonist, Majeed syndrome, acne, pyogenic arthritis pyoderma gangrenosum and acne (PAPA), haploinsufficiency of A20 (HA20), PLCG2-associated antibody deficiency and immune dysregulation (PLAID), pediatric granulomatous arthritis (PGA), PLCG2-associated autoinflammation, antibody deficiency and immune dysregulation (APLAID), sideroblastic anemia with B-cell immunodeficiency, periodic fevers, developmental delay (SIFD), chronic nonbacterial osteomyelitis (CNO), Sweet's syndrome, chronic recurrent multifocal osteomyelitis (CRMO), synovitis, pustulosis, acne, eczema, alopecia areata, actinic keratosis, hyperostosis, osteitis syndrome (SAPHO), multiple sclerosis (MS), psoriasis, Behcet's disease, Sjogren's syndrome, Schnitzler syndrome, chronic obstructive pulmonary disorder (COPD), steroid-resistant asthma, asbestosis, silicosis, cystic fibrosis, motor neuron disease, Huntington's disease, cerebral malaria, brain injury from pneumococcal meningitis, obesity, age-related macular degeneration (AMD), corneal infection, uveitis, dry eye, chronic kidney disease, diabetic nephropathy, alcoholic liver disease, skin contact hypersensitivity, sunburn, osteoarthritis, systemic juvenile idiopathic arthritis, adult-onset Still's disease, relapsing polychondritis, Chikungunya virus, Ross River virus, influenza, HIV, Coronaviruses, Dengue, Zika virus, hidradenitis suppurativa (HS), lung cancer metastasis, pancreatic cancers, gastric cancers, myelodisplastic syndrome, leukemia; polymyositis, colitis, helminth infection, bacterial infection, abdominal aortic aneurism, wound healing, depression, psychological stress, pericarditis including Dressler's syndrome, ischaemia reperfusion injury, frontotemporal dementia, HIV-associated neurocognitive disorder, Coronavirus-associated inflammatory pathologies, and traumatic brain injury; preferably the disorder is selected from Alzheimer's disease, Parkinson's disease, amyotrophic lateral sclerosis, demyelination, viral encephalitis, epilepsy, stroke, atherosclerosis, asthma, allergic inflammation, cryopyrin-associated periodic syndromes (CAPS), gout, inflammatory bowel disease, nonalcoholic fatty liver disease, nonalcoholic steatohepatitis (NASH), hypertension, myocardial infarction, oxalate-induced nephropathy, graft-versus host disease, type 1 diabetes, type 2 diabetes, rheumatoid arthritis, myelodysplastic syndrome, anti-neutrophil cytoplasmic antibody-associated vasculitis (AAV), lupus nephritis, anti-glomerular basement membrane (GMB) disease, IgA nephropathy, glomerulonephritis (GN), systemic lupus erythematosus (SLE), Focal Segmental Glomerulosclerosis, Minimal change disease (MCD), Psoriatic Arthritis, and Hereditary Recurrent Fevers (HRFs).

B17. The compound for use according to clause B16, wherein the disease, the disorder or the abnormality is selected from Alzheimer's disease, Parkinson's disease, cryopyrin-associated periodic syndromes (CAPS), nonalcoholic fatty liver disease, NASH and gout.

B18. The compound for use according to any one of clauses B13 to B15, wherein the disease, the disorder or the abnormality is a disease, disorder or abnormality of the immune system.

B19. The compound for use according to any one of clauses B13 to B15, wherein the disease, the disorder or the abnormality is an inflammatory disease, disorder or abnormality.

B20. The compound for use according to any one of clauses B13 to B15, wherein the disease, the disorder or the abnormality is an autoimmune disease, disorder or abnormality.

B21. The compound for use according to any one of clauses B13 to B15, wherein the disease, the disorder or the abnormality is a disease, disorder or abnormality of the skin.

B22. The compound for use according to clause B21, wherein the disease, disorder or abnormality of the skin is selected from psoriasis, acne, eczema, alopecia areata, or actinic keratosis.

B23. The compound for use according to any one of clauses B13 to B15, wherein the disease, the disorder or the abnormality is a disease, disorder or abnormality of the cardiovascular system.

B24. The compound for use according to any one of clauses B13 to B15, wherein the disease, the disorder or the abnormality is a cancer, a tumor or a malignancy.

B25. The compound for use according to any one of clauses B13 to B15, wherein the disease, the disorder or the abnormality is a disease, disorder or abnormality of the renal system.

B26. The compound for use according to any one of clauses B13 to B15, wherein the disease, the disorder or the abnormality is a disease, disorder or abnormality of the gastrointestinal tract.

B27. The compound for use according to any one of clauses B13 to B15, wherein the disease, the disorder or the abnormality is a disease, disorder or abnormality of the respiratory system.

B28. The compound for use according to any one of clauses B13 to B15, wherein the disease, the disorder or the abnormality is a disease, disorder or abnormality of the endocrine system.

B29. The compound for use according to any one of clauses B13 to B15, wherein the disease, the disorder or the abnormality is a disease, disorder or abnormality of the central nervous system (CNS).

B30. The compound for use according to any one of clauses B13 to B15, wherein the disease, the disorder or the abnormality is a disease, disorder or abnormality of the liver.

B31. A pharmaceutical composition comprising a combination of a compound according to any one of clauses B1 to B10, or a stereoisomer, a racemic mixture, a tautomer, a polymorph, a pharmaceutically acceptable salt, a prodrug, a hydrate, or a solvate thereof, and at least one further biologically active compound differing from the compound of formula (I) and optionally comprising at least one pharmaceutically acceptable carrier, diluent, adjuvant or excipient.

B32. A combination comprising a therapeutically effective amount of a compound according to any one of clauses B1 to B10, or a stereoisomer, a racemic mixture, a tautomer, a polymorph, a pharmaceutically acceptable salt, a prodrug, a hydrate, or a solvate thereof, and at least one further biologically active compound differing from the compound of formula (I) or the compound of formula (II), and optionally at least one pharmaceutically acceptable carrier, diluent, adjuvant or excipient.

B33. A pharmaceutical composition according to clause B31, or the combination according to clause B32, for use as a medicament.

B34. Use of a compound of formula (I) according to any one of clauses B1 to B10, or a stereoisomer, a racemic mixture, a tautomer, a polymorph, a pharmaceutically acceptable salt, a prodrug, a hydrate, or a solvate thereof, as an analytical reference or an in vitro screening tool.

The present invention is described hereinafter.

BRIEF DESCRIPTION OF THE FIGURE

FIG. 1 shows IL-1β release in peritoneal lavage samples from mice dosed with (1 mg/kg or 3 mg/kg) Example 16 and Example 23 by intraperitoneal injection in an LPS-ATP induced peritonitis model.

DETAILED DESCRIPTION OF THE INVENTION

The present invention relates to compounds of formula (I'), compounds of formula (I), including sub-embodiments (Ia), (Ib), (Ic), (Ic'), (Id), (Id'), (Id''), (Id'''), (Ie) and (If), and to compounds of formula (II'), compounds of formula (II), including sub-embodiments (IIa'), (IIa), (IIb'), and (IIb), including stereoisomers, racemic mixtures, tautomers, polymorphs, pharmaceutically acceptable salts, prodrugs, hydrates, or solvates thereof.

The present invention relates to compounds of formula (I') as defined below (I')

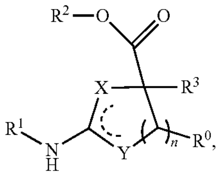

or stereoisomers, racemic mixtures, tautomers, polymorphs, pharmaceutically acceptable salts, prodrugs, hydrates, or solvates thereof;

wherein

X is independently selected from the group consisting of O, N and S;

Y is independently selected from the group consisting of N and O;

as valency permits, is a combination of a single bond and a double bond or is two single bonds;

n is 1 or 2;

$R^0$ is H or $C_1$-$C_3$alkyl;

$R^1$ is

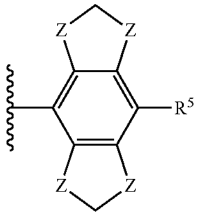

wherein

Z is independently selected from the group consisting of $CH_2$ and O provided that no more than two of Z are O;

$R^5$ is independently selected from the group consisting of hydrogen and halogen;

$R^2$ is independently selected from the group consisting of hydrogen, $C_1$-$C_6$alkyl, $C_3$-$C_6$cycloalkyl; and $R^3$ is independently selected from the group consisting of hetero$C_3$-$C_6$cycloalkyl, aryl or heteroaryl wherein each of them can be optionally substituted with —$C_1$-$C_6$alkyl, —O—$C_1$-$C_6$alkyl, -Hal, or —$C_1$-$C_6$alkyl-OH.

Further, in one embodiment the present invention relates to a compound of formula (I') wherein $R^0$ is H, having formula (I) as defined below (I)

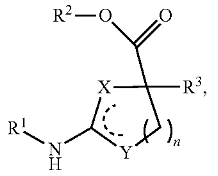

or stereoisomers, racemic mixtures, tautomers, polymorphs, pharmaceutically acceptable salts, prodrugs, hydrates, or solvates thereof;

wherein

X is independently selected from the group consisting of O, N and S;

Y is independently selected from the group consisting of N and O;

as valency permits, is a combination of a single bond and a double bond or is two single bonds;

n is 1 or 2;

$R^1$ is

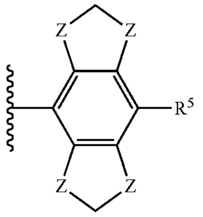

wherein

Z is independently selected from the group consisting of $CH_2$ and O provided that no more than two of Z are O;

$R^5$ is independently selected from the group consisting of hydrogen and halogen;

$R^2$ is independently selected from the group consisting of hydrogen, $C_1$-$C_6$alkyl and $C_3$-$C_6$cycloalkyl;

$R^3$ is independently selected from the group consisting of hetero$C_3$-$C_6$cycloalkyl, aryl or heteroaryl wherein each of them can be optionally substituted with —$C_1$-$C_6$alkyl, —O—$C_1$-$C_6$alkyl, -Hal, or —$C_1$-$C_6$alkyl-OH.

In another embodiment, the invention relates to a compound of formula (I'), in particular it relates to a compound of formula (I), or stereoisomers, or racemic mixtures, or tautomers, or polymorphs, or pharmaceutically acceptable salts, or hydrates, or solvates thereof.

In another embodiment the present invention relates to a compound of formula (I'), in particular it relates to a compound of formula (I), wherein X is independently selected from the group consisting of O and N; and Y is independently selected from the group consisting of N and O.

More preferably, X is independently selected from the group consisting of O and N; and Y is independently selected from the group consisting of N and O; wherein X and Y are never the same.

Even more preferably, X is O; and Y is N.

In another embodiment, the present invention relates to a compound of formula (I'), in particular it relates to a compound of formula (I), wherein as valency permits,  is a combination of a single bond and a double bond. More preferably,  is present as following

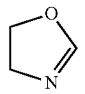

.

In another embodiment, the present invention relates to a compound of formula (I'), in particular it relates to a compound of formula (I), wherein, n is 1.

In one embodiment, the present invention relates to a compound of formula (I'), in particular it relates to a compound of formula (I), wherein $R^0$ is H or $C_1$-$C_3$alkyl. Preferably, $R^0$ is H, methyl or ethyl. More preferably, $R^0$ is H.

In another embodiment, the present invention relates to a compound of formula (I'), in particular it relates to a compound of formula (I), wherein $R^1$ is

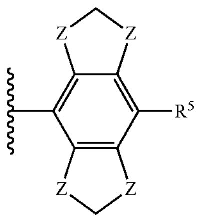

wherein

Z is selected from $CH_2$; and $R^5$ is selected from halogen or hydrogen. Preferably, $R^5$ is halogen, wherein the halogen is, preferably, fluoro. More preferably, $R^5$ is hydrogen.

In another embodiment the present invention relates to a compound of formula (I'), in particular it relates to a compound of formula (I), wherein $R^2$ is independently selected from the group consisting of hydrogen, $C_1$-$C_6$alkyl, and $C_3$-$C_6$cycloalkyl.

Preferably, $R^2$ is independently selected from the group consisting of hydrogen, $C_1$-$C_6$alkyl, and $C_5$-$C_6$cycloalkyl. In one preferred embodiment, $R^2$ is hydrogen. In another preferred embodiment, $R^2$ is $C_1$-$C_6$alkyl, wherein $R^2$ is preferably selected from the group consisting of methyl, ethyl, propyl, isopropyl, butyl, tert-butyl, pentyl, or hexyl. In yet another embodiment, $R^2$ is $C_5$-$C_6$cycloalkyl, more preferably, $R^2$ is cyclopentane.

More preferably, $R^2$ is independently selected from the group consisting of hydrogen, $C_1$-$C_3$alkyl, and $C_5$-$C_6$cycloalkyl. Even more preferably, $R^2$ is independently selected from the group consisting of hydrogen, methyl, ethyl, propyl, isopropyl or cyclopentane. Even more preferably, $R^2$ is independently selected from the group consisting of hydrogen, ethyl, isopropyl or cyclopentane. $R^2$ can be optionally substituted with OH, such as in

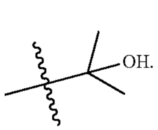 [SMILES: *C(C)(C)O]

In one embodiment, the present invention relates to a compound of formula (I'), in particular it relates to a compound of formula (I), wherein $R^3$ is independently selected from the group consisting of hetero-$C_3$-$C_6$cycloalkyl, aryl or heteroaryl wherein each of them can be optionally substituted with —$C_1$-$C_6$alkyl, —O—$C_1$-$C_6$alkyl, -Hal, or —$C_1$-$C_6$alkyl-OH.

In another embodiment, the present invention relates to a compound of formula (I'), in particular it relates to a compound of formula (I), wherein $R^3$ is independently selected from the group consisting of hetero$C_3$-$C_6$cycloalkyl containing one or two heteroatoms selected from N or O, aryl or $C_5$-$C_6$ heteroaryl containing one, two or three heteroatoms independently from each other selected from S, N and O; wherein each of them can be optionally substituted with—$C_1$-$C_6$alkyl, —O—$C_1$-$C_6$alkyl, -Hal, or —$C_1$-$C_6$alkyl-OH.

In one embodiment, the present invention relates to a compound of formula (I'), in particular it relates to a compound of formula (I), wherein $R^3$ is aryl, optionally substituted with—$C_1$-$C_6$alkyl, —O—$C_1$-$C_6$alkyl, -Hal, or —$C_1$-$C_6$alkyl-OH. In a particular embodiment, the aryl group is optionally substituted with—O—$C_1$-$C_6$alkyl, or -Hal. In a particular embodiment, the aryl group is optionally substituted with —O—$C_1$alkyl, or -Hal, wherein the halogen (-Hal) is, preferably, chloro.

More preferably, $R^3$ is independently selected from the group consisting of hetero$C_3$-$C_6$cycloalkyl containing one or two hetero atoms selected from N or O, $C_5$-$C_6$ aryl, or $C_5$-$C_6$heteroaryl containing one, two or three hetero atoms independently from each other selected from S, N and O; wherein each of them can be optionally substituted with —$C_1$-$C_6$alkyl, —O—$C_1$-$C_6$alkyl, -Hal, or —$C_1$-$C_6$alkyl-OH.

Even more preferably, $R^3$ is hetero$C_3$-$C_6$cycloalkyl containing one heteroatom, wherein the heteroatom is O; and $R^3$ is optionally substituted with—$C_1$-$C_6$alkyl, —O—$C_1$-$C_6$alkyl, -Hal, or —$C_1$-$C_6$alkyl-OH.

Even more preferably, $R^3$ is $C_5$-$C_6$heteroaryl containing one, two or three hetero atoms independently from each other selected from S, N and O; wherein each of them can be optionally substituted with one substituent selected from—$C_1$-$C_6$alkyl, —O—$C_1$-$C_6$alkyl, -Hal, or —$C_1$-$C_6$alkyl-OH.

In another embodiment, the invention provides for a compound of formula (I'), in particular it relates to a compound of formula (I), wherein $R^3$ is selected from the following:

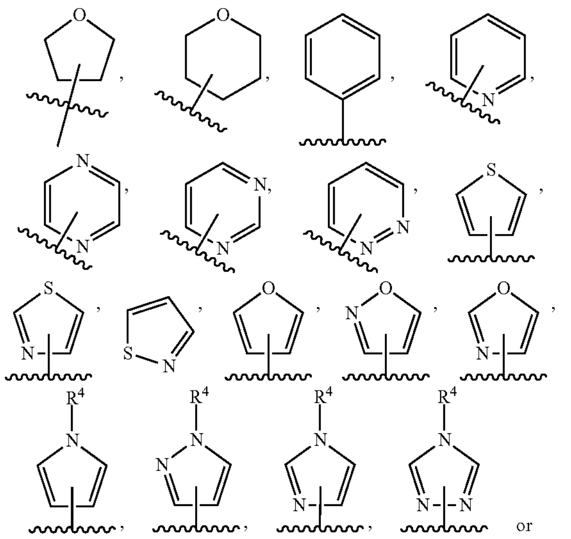

or

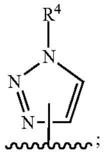

wherein $R^4$ is independently selected from the group consisting of hydrogen, $C_1$-$C_6$alkyl and $C_3$-$C_6$cycloalkyl, and wherein each of them can be optionally substituted with—$C_1$-$C_6$alkyl, —O—$C_1$-$C_6$alkyl, -Hal, or —$C_1$-$C_6$alkyl-OH.

More preferably, $R^3$ is selected from the following:

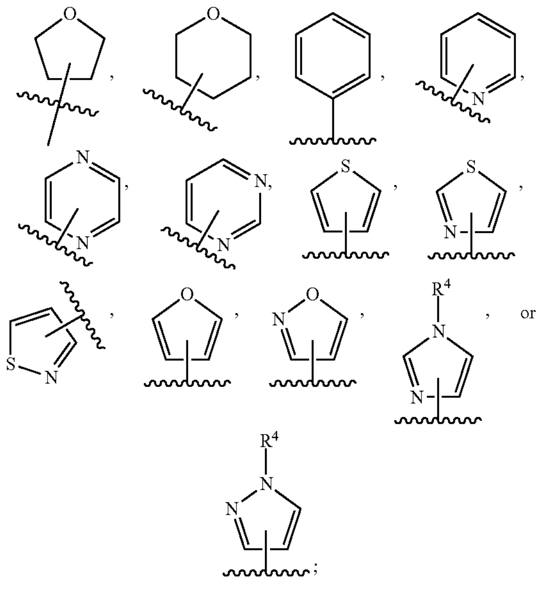

wherein $R^4$ is independently selected from the group consisting of hydrogen, $C_1$-$C_6$alkyl and $C_3$-$C_6$cycloalkyl, and wherein each of them can be optionally substituted with—$C_1$-$C_6$alkyl, —O—$C_1$-$C_6$alkyl, -Hal, or —$C_1$-$C_6$alkyl-OH.

Even more preferably, $R^3$ is selected from the following:

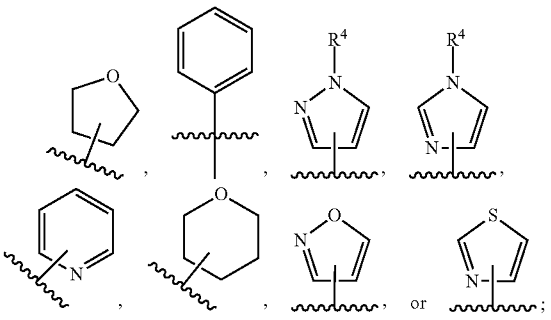

wherein $R^4$ is independently selected from the group consisting of hydrogen, $C_1$-$C_6$alkyl and $C_3$-$C_6$cycloalkyl, and wherein each of them can be optionally substituted with—$C_1$-$C_6$alkyl, —O—$C_1$-$C_6$alkyl, -Hal, or —$C_1$-$C_6$alkyl-OH.

Even more preferably, $R^3$ is

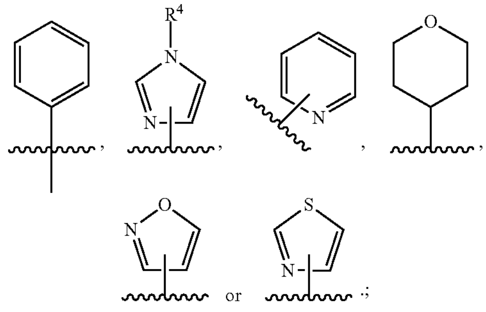

wherein $R^4$ is independently selected from the group consisting of hydrogen, $C_1$-$C_6$alkyl and $C_3$-$C_6$cycloalkyl.

In another preferred embodiment, the invention provides for a compound of formula (I'), in particular it relates to a compound of formula (I), wherein $R^3$ is selected from the following:

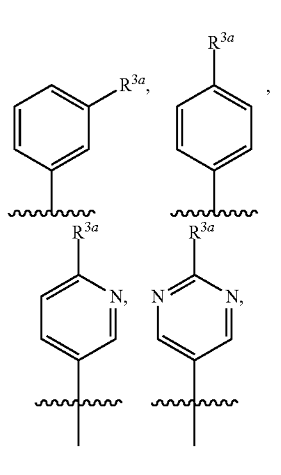

-continued

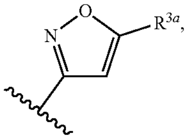

, or

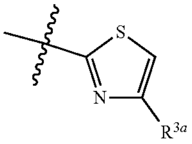

;

wherein $R^3$ is optionally substituted with $R^{3a}$, and wherein $R^{3a}$ is selected from hydrogen, halogen, —O—$C_1$-$C_6$alkyl, —$C_1$-$C_6$ alkyl-OH, or $C_1$-$C_6$alkyl. More preferably, $R^{3a}$ is selected from hydrogen, chloro, methoxy, methyl, isopropyl, or

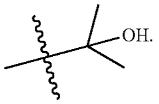 [SMILES: *C(C)(C)O]

In $R^3$, $C_1$-$C_6$alkyl is preferably methyl, ethyl, isopropyl, propyl, isobutyl or butyl and can be optionally substituted with —OH such as

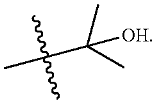 [SMILES: *C(C)(C)O]

In another embodiment the present invention relates to a compound of formula (I'), in particular it relates to a compound of formula (I), wherein $R^4$ is independently selected from the group consisting of hydrogen, methyl, ethyl, isopropyl and propyl. Preferably, $R^4$ is methyl or isopropyl. More preferably, $R^4$ is methyl.

In another embodiment the present invention relates to a compound of formula (I'), in particular it relates to a compound of formula (I), wherein $R^2$ is hydrogen and $R^3$ is a)

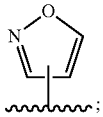

;

preferably

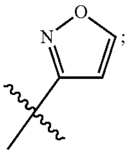 [SMILES: *c1ccon1]

;

b)

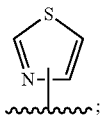

;

preferably

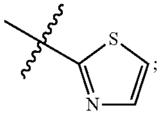 [SMILES: *c1nccs1]

;

c)

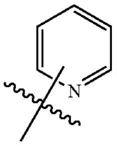

;

preferably

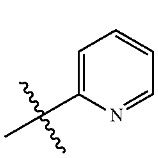

or

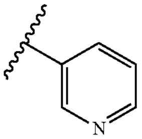

;

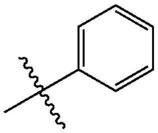

;

d)

e)

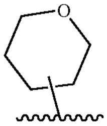

, preferably

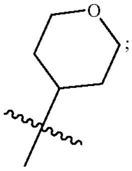

; or f)

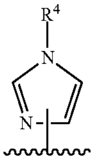

, preferably

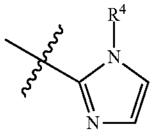

wherein $R^4$ is independently selected from the group consisting of hydrogen, $C_1$-$C_6$alkyl and $C_3$-$C_6$cycloalkyl In another embodiment the present invention relates to a compound of formula (I'), in particular it relates to a compound of formula (I), wherein $R^2$ is hydrogen and $R^3$ is a)

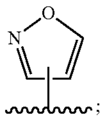
;

preferably

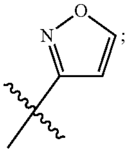 [SMILES: *c1ccon1]
;

b)

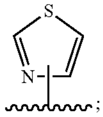
;

preferably

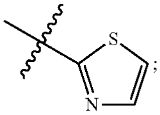
; or c)

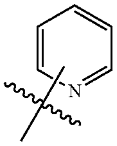
;

preferably

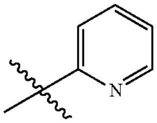
or
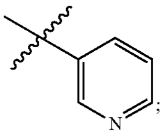
; and wherein each $R^3$ can be optionally substituted with—$C_1$-$C_6$alkyl, —O—$C_1$-$C_6$alkyl, -Hal, or —$C_1$-$C_6$alkyl-OH.

$R^4$ is independently selected from the group consisting of hydrogen, methyl, ethyl, isopropyl and propyl. More preferably, $R^4$ is methyl.

In each of the above embodiments, $R^3$ can be optionally substituted with halogen, —O—$C_1$-$C_6$alkyl, —$C_1$-$C_6$alkyl-OH, or $C_1$-$C_6$alkyl. More preferably, $R^3$ can be optionally substituted with chloro, methoxy, methyl, isopropyl or

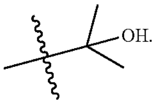 [SMILES: *C(C)(C)O]

In $R^3$, $C_1$-$C_6$alkyl is preferably methyl, ethyl, isopropyl, propyl, isobutyl or butyl and can be optionally substituted with —OH such as in

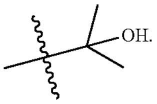 [SMILES: *C(C)(C)O]

In another embodiment the present invention relates to a compound of formula (I'), in particular it relates to a compound of formula (I), wherein $R^2$ is $C_1$-$C_6$alkyl and $R^3$ is a)

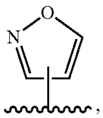
, preferably

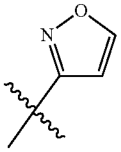
, or
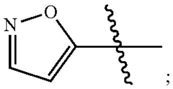
;

b)

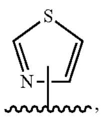
, preferably

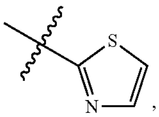
, or
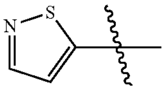
;

c)
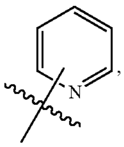,
preferably
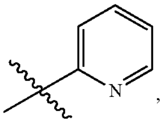, or 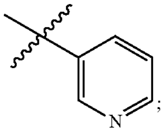;
d)
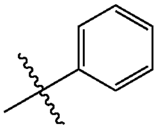;
e)
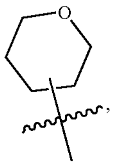,
preferably
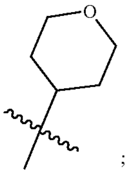 [SMILES: *C1CCOCC1];
f)
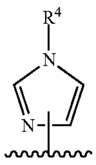,
preferably
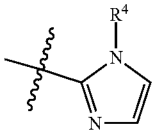, or 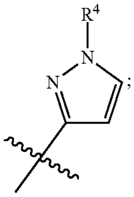;
wherein $R^4$ is independently selected from the group consisting of hydrogen, $C_1$-$C_6$alkyl and $C_3$-$C_6$cycloalkyl;
g)
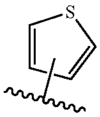,
preferably
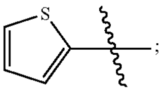 [SMILES: *c1cccs1 ; ";"];
h)
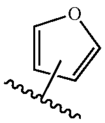,
preferably
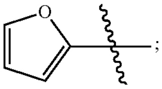 [SMILES: *c1ccco1 ; ";"];
i)
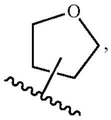,
preferably
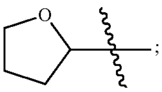 [SMILES: *C1CCCO1 ; ";"];

j)
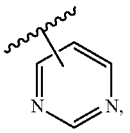
preferably
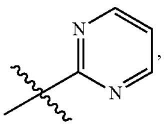
or
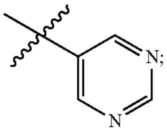
or
k)
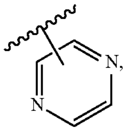
preferably
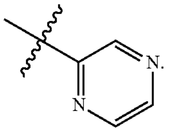 [SMILES: *c1cnccn1]
In another embodiment the present invention relates to a compound of formula (I'), in particular it relates to a compound of formula (I), wherein $R^2$ is $C_1$-$C_6$ alkyl and $R^3$ is
a)
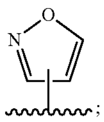
preferably
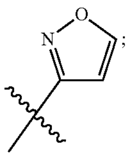 [SMILES: *c1ccon1]
b)
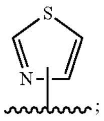
preferably
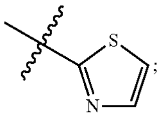 [SMILES: *c1nccs1]
c)
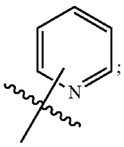
preferably
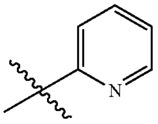
or
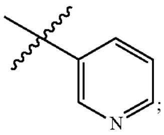
d)
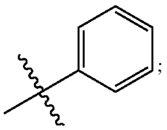 [SMILES: *c1ccccc1]
e)
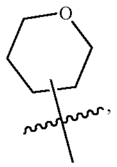
preferably
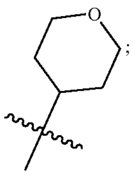
or f)

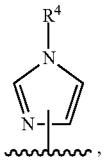

preferably

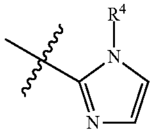

wherein $R^4$ is independently selected from the group consisting of hydrogen, $C_1$-$C_6$ alkyl and $C_3$-$C_6$ cycloalkyl.

In each of the above embodiments, $R^3$ can be optionally substituted with halogen, —O—$C_1$-$C_6$alkyl, —$C_1$-$C_6$alkyl-OH, or $C_1$-$C_6$alkyl. More preferably, $R^3$ can be optionally substituted with chloro, methoxy, methyl or isopropyl or

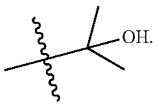 [SMILES: *C(C)(C)O]

In $R^3$, $C_1$-$C_6$alkyl is preferably methyl, ethyl, isopropyl, propyl, isobutyl or butyl and can be optionally substituted with —OH such as in

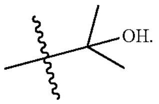 [SMILES: *C(C)(C)O]

Preferably, $R^2$ is $C_1$-$C_6$alkyl, wherein $R^2$ is preferably selected from the group consisting of methyl, ethyl, propyl, isopropyl, butyl, tert-butyl, pentyl, or hexyl. More preferably, $R^2$ is $C_1$-$C_3$alkyl. More preferably, $R^2$ is independently selected from the group consisting of methyl, ethyl, propyl or isopropyl. Even more preferably, $R^2$ is independently selected from the group consisting of ethyl or isopropyl. $R^2$ can be optionally substituted with OH.

In another embodiment the present invention relates to a compound of formula (I'), in particular it relates to a compound of formula (I), wherein $R^2$ is $C_3$-$C_6$cycloalkyl and $R^3$ is a)

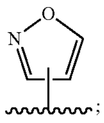

preferably

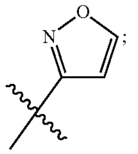 [SMILES: *c1ccon1]

b)

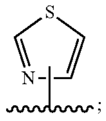

preferably

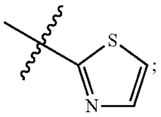 [SMILES: *c1nccs1]

c)

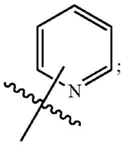

preferably

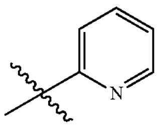

or

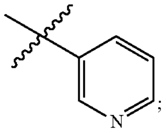

d)

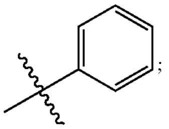 [SMILES: *c1ccccc1]

e)

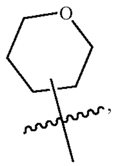

preferably

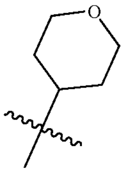

; or f)

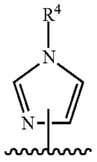

, preferably

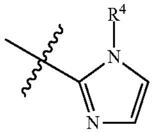

wherein $R^4$ is independently selected from the group consisting of hydrogen, $C_1$-$C_6$alkyl and $C_3$-$C_6$cycloalkyl.

In each of the above embodiments, $R^3$ can be optionally substituted with halogen, —O—$C_1$-$C_6$alkyl, —$C_1$-$C_6$alkyl-OH, or $C_1$-$C_6$alkyl. More preferably, $R^3$ can be optionally substituted with chloro, methoxy, methyl or isopropyl or

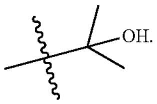 [SMILES: *C(C)(C)O]

In $R^3$, $C_1$-$C_6$alkyl is preferably methyl, ethyl, isopropyl, propyl, isobutyl or butyl and can be optionally substituted with —OH such as in

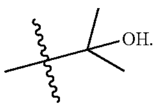 [SMILES: *C(C)(C)O]

Preferably, $R^2$ is $C_5$-$C_6$cycloalkyl. More preferably, $R^2$ is cyclopentane. $R^2$ can be optionally substituted with OH.

Preferably, $R^4$ is independently selected from the group consisting of hydrogen, methyl, ethyl, isopropyl and propyl. More preferably, $R^4$ is methyl.

Further, in one embodiment the present invention relates to compounds of formula (I) as defined below (I)

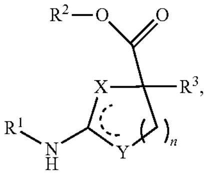

or stereoisomers, racemic mixtures, tautomers, pharmaceutically acceptable salts, prodrugs, hydrates, or solvates thereof;

wherein

X is independently selected from the group consisting of O, N and S;

Y is independently selected from the group consisting of N and O;

as valency permits, ⁝ is a combination of a single bond and a double bond or is two single bonds;

n is 1 or 2;

$R^1$ is

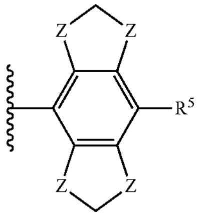

wherein

Z is independently selected from the group consisting of $CH_2$ and O provided that no more than two of Z are O;

$R^5$ is independently selected from the group consisting of hydrogen and halogen;

$R^2$ is independently selected from the group consisting of $C_1$-$C_6$ alkyl and $C_3$-$C_6$ cycloalkyl;

$R^3$ is independently selected from the group consisting of

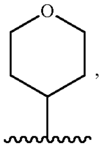 , 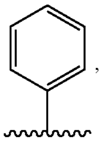 , 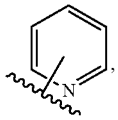 , 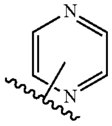 , 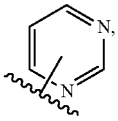 , 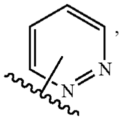 , 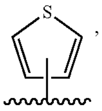 , 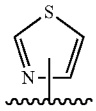 , 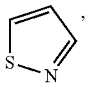 , 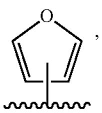 , 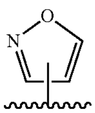 , 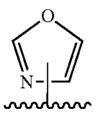 , 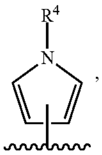 , 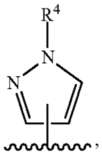 , 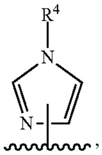 , 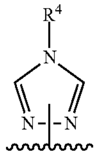 and 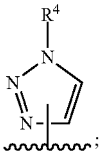 ;

wherein other than at the position of $R^4$, $R^3$ can be optionally substituted with halogen, $C_1$-$C_6$ alkyl or —OMe;

$R^4$ is independently selected from the group consisting of hydrogen, $C_1$-$C_6$ alkyl and $C_3$-$C_6$ cycloalkyl;

wherein any mentioned $C_1$-$C_6$ alkyl can be optionally substituted with —OH; and $C_3$-$C_6$ cycloalkyl can be optionally substituted with —OH.

In one embodiment, the invention is directed to compounds of formula (I), or stereoisomers, or racemic mixtures, or tautomers, or polymorphs, or pharmaceutically acceptable salts, or hydrates, or solvates thereof.

Preferably, $R^1$ is

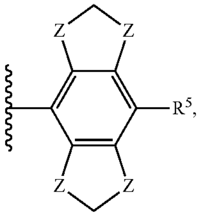

wherein Z is $CH_2$ and $R^5$ is hydrogen or halogen.

More preferably, $R^1$ is

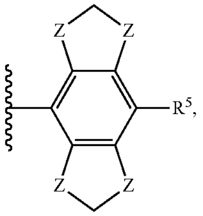

wherein Z is $CH_2$ and $R^5$ is hydrogen or F (fluoro).

Preferably, $R^5$ is hydrogen or a halogen selected from F and Cl. More preferably, $R^5$ is F or Cl, even more preferably, $R^5$ is F (fluoro).

Preferably, X is preferably O.

Preferably, Y is preferably N.

n is preferably 1.

$R^2$ is independently selected from the group consisting of hydrogen, $C_1$-$C_6$alkyl, $C_3$-$C_6$cycloalkyl. Preferably, $R^2$ is independently selected from the group consisting of hydrogen, $C_1$-$C_6$alkyl, and $C_5$-$C_6$cycloalkyl. In one preferred embodiment, $R^2$ is hydrogen. Preferably, $R^2$ $C_1$-$C_6$alkyl, wherein $R^2$ is preferably selected from the group consisting of methyl, ethyl, propyl, isopropyl, butyl, tert-butyl, pentyl, or hexyl. In yet another embodiment, $R^2$ is $C_5$-$C_6$cycloalkyl, more preferably, $R^2$ is cyclopentane. Preferably, $R^2$ is methyl, ethyl, propyl or cyclopropyl. More preferably, $R^2$ is ethyl.

In a preferred embodiment, the invention provides for a compound of formula (I), wherein $R^3$ is selected from the following, $R^3$ is selected from the following:

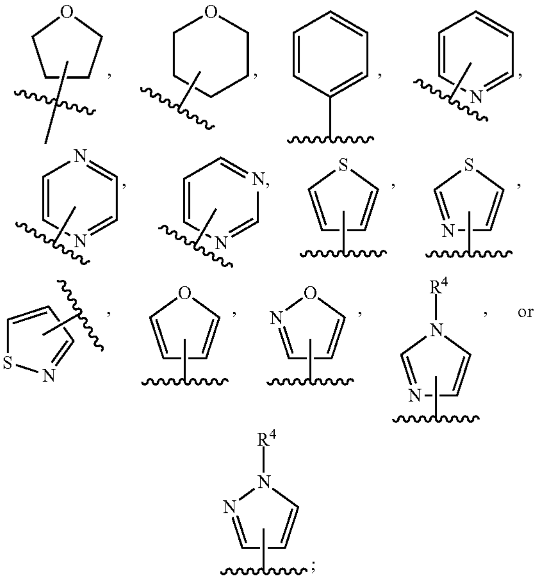

wherein $R^4$ is independently selected from the group consisting of hydrogen, $C_1$-$C_6$alkyl and $C_3$-$C_6$cycloalkyl, and wherein each of them can be optionally substituted with—$C_1$-$C_6$alkyl, —O—$C_1$-$C_6$alkyl, -Hal, or —$C_1$-$C_6$alkyl-OH.

Preferably, $R^3$ is selected from the following:

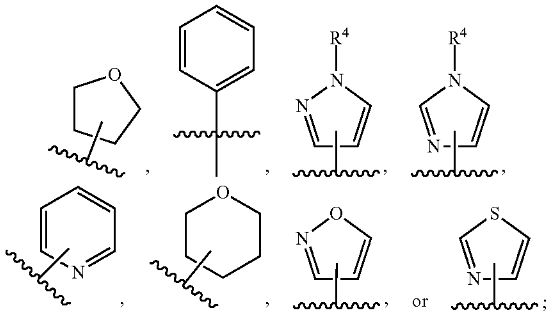

wherein $R^4$ is independently selected from the group consisting of hydrogen, $C_1$-$C_6$alkyl and $C_3$-$C_6$cycloalkyl, and wherein each of them can be optionally substituted with—$C_1$-$C_6$alkyl, —O—$C_1$-$C_6$alkyl, -Hal, or —$C_1$-$C_6$alkyl-OH.

Preferably, $R^3$ is

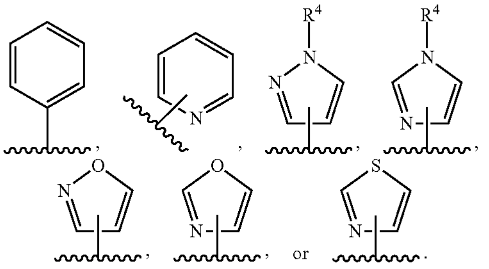

More preferably, $R^3$ is selected from the following:

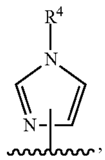, 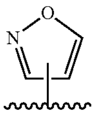 or 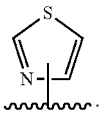.

Preferably, other than at the position of $R^4$, $R^3$ can be optionally substituted with one or two of the group selected from halogen, $C_1$-$C_6$alkyl or —OMe. Preferably $R^3$ can be optionally substituted with one or two $C_1$-$C_6$alkyl which can be further optionally substituted with —OH. More preferably, $R^3$ can be optionally substituted with one or two of the group selected from —Cl, $C_1$-$C_4$alkyl or —OMe, wherein $C_1$-$C_4$alkyl can optionally be substituted with —OH. Even more preferably, $R^3$ can be optionally substituted with one or two of the group selected from —Cl, isopropyl and —OMe, wherein isopropyl can be optionally substituted with —OH.

More preferably, $R^3$ is selected from the following:

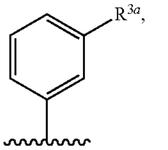, 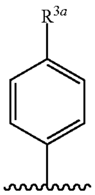, 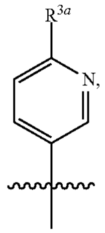, 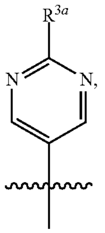

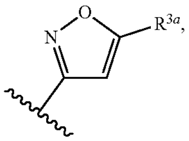, or 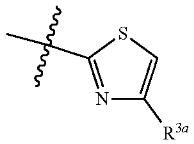;

wherein $R^3$ is optionally substituted with $R^{3a}$, and wherein $R^{3a}$ is selected from hydrogen, halogen, —O—$C_1$-$C_6$alkyl, —$C_1$-$C_6$alkyl-OH, or $C_1$-$C_6$alkyl. More preferably, $R^{3a}$ is selected from hydrogen, chloro, methoxy, methyl, isopropyl, or

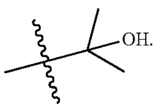 [SMILES: *C(C)(C)O].

Preferably, $R^4$ is selected from the group consisting of hydrogen and $C_1$-$C_6$alkyl. More preferably, $R^4$ is methyl, isopropyl, or ethyl; in particular methyl or isopropyl. More preferably, $R^4$ is methyl or ethyl. Even more preferably, $R^4$ is methyl.

Preferably, in any of the instances of $C_1$-$C_6$alkyl, $C_1$-$C_6$alkyl can be optionally substituted with —OH.

Preferably, in any of the instances of $C_3$-$C_6$cycloalkyl, $C_3$-$C_6$ cycloalkyl can be optionally substituted with —OH.

In a further embodiment, the present invention relates to compounds of formula (I') whereas as valency permits, is the combination of a single bond and a double bond as described in formulae (Ia') or (Ib')

(Ia')

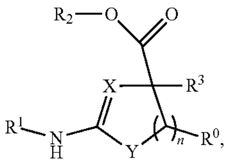, or (Ib')

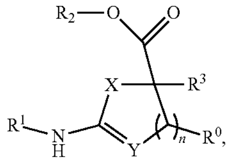, or stereoisomers, or racemic mixtures, or tautomers, or polymorphs, or pharmaceutically acceptable salts, or hydrates, or solvates thereof, wherein X, Y, n, $R^0$, $R^1$, $R^2$ are $R^3$ are as defined above. Embodiments as defined for compounds of formula (I') apply here.

In a further embodiment, the present invention relates to compounds of formula (I'), in particular it relates to a compound of formula (I), whereas as valency permits, is the combination of a single bond and a double bond as described in formula (Ia) or (Ib)

(Ia)

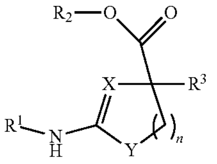 or (Ib)

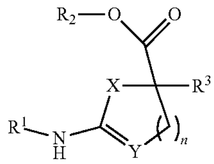

or stereoisomers, or racemic mixtures, or tautomers, or polymorphs, or pharmaceutically acceptable salts, or hydrates, or solvates thereof, wherein X, Y, n, $R^1$, $R^2$ are $R^3$ are as defined above. Embodiments as defined for compounds of formula (I') wherein $R^0$ is H, or of formula (I) apply here.

Preferably, the combination of a single bond and double bond is as described in compounds of formula (Ib') or (Ib)

(Ib')

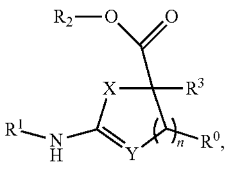, or

-continued (Ib)

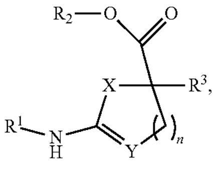

or stereoisomers, or racemic mixtures, or tautomers, or polymorphs, or pharmaceutically acceptable salts, or hydrates, or solvates thereof, wherein X, Y, n, $R^0$, $R^1$, $R^2$ are $R^3$ are as defined above.

In yet another embodiment, the present invention relates to a compound of formula (I') defined as compounds of formula (Ic'), (Id'), (Id'') or (Id''')

(Ic')

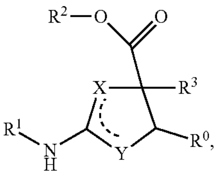

(Id')

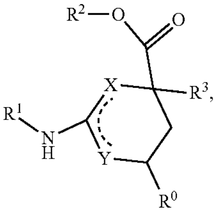

(Id'')

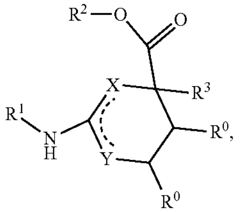

or (Id''')

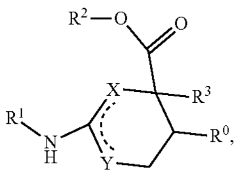

or stereoisomers, or racemic mixtures, or tautomers, or polymorphs, or pharmaceutically acceptable salts, or hydrates, or solvates thereof, wherein X, Y, n, $R^0$, $R^1$, $R^2$ are $R^3$ are as defined above.

In a preferred embodiment, the present invention relates to a compound of formula (I') defined as compounds of formula (Ic), (Ic'), (Id), or (Id')

(Ic)

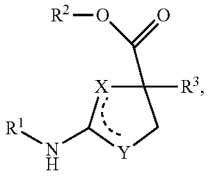

(Ic')

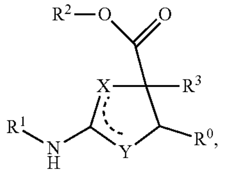

(Id)

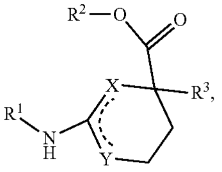

or (Id')

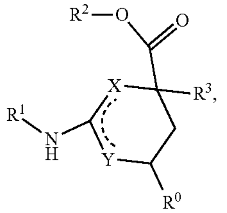

or stereoisomers, or racemic mixtures, or tautomers, or polymorphs, or pharmaceutically acceptable salts, or hydrates, or solvates thereof, wherein X, Y, $R^1$, $R^2$ are $R^3$ are defined as above; and wherein $R^0$ is $C_1$-$C_3$alkyl.

In a more preferred embodiment, the present invention relates to a compound of formula (I'), in particular it relates to a compound of formula (I), defined as compounds of formula (Ic) or (Id)

(Ic)

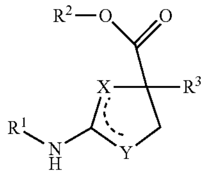

or (Id)

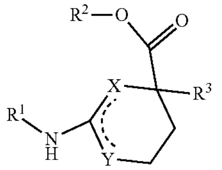

or stereoisomers, or racemic mixtures, or tautomers, or polymorphs, or pharmaceutically acceptable salts, or hydrates, or solvates thereof, wherein X, Y, $R^1$, $R^2$ are $R^3$ are defined as above. Embodiments as defined for compounds of formula (I') or (I) apply here.

The compounds of formula (Ic) or (Ic') correspond to the compound of formula (I') when n is 1. The compounds of formula (Id), (Id'), (Id'') or (Id''') correspond to the compound of formula (I') when n is 2.

Preferably, the compound of formula (I') is a compound of formula (Ic) or (Ic')

(Ic)

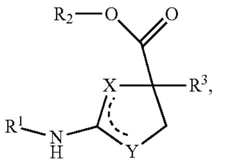

or (Ic')

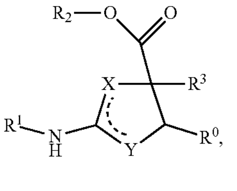

or stereoisomers, or racemic mixtures, or tautomers, or polymorphs, or pharmaceutically acceptable salts, or hydrates, or solvates thereof, wherein $R^0$ is methyl, or ethyl.

More preferably, the compound of formula (I') is a compound of formula (Ic)

(Ic)

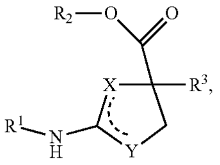

or stereoisomers, or racemic mixtures, or tautomers, or polymorphs, or pharmaceutically acceptable salts, or hydrates, or solvates thereof.

In yet a further embodiment, the present invention relates to stereoisomers of compounds of formula (I') which are defined as compounds of formula (Ie') or (If')

(Ie')

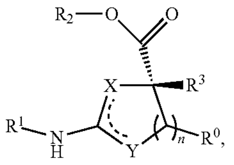

or (If')

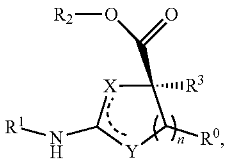

or stereoisomers, or racemic mixtures, or tautomers, or polymorphs, or pharmaceutically acceptable salts, or hydrates, or solvates thereof, wherein X, Y, n, $R^0$, $R^1$, $R^2$ and $R^3$ are defined as above. Embodiments as defined for compounds of formula (I') apply here.

In a preferred embodiment, the present invention relates to stereoisomers of compounds of formula (I) which are defined as compounds of formula (Ie) or (If)

(Ie)

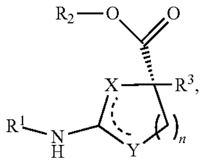

and (If)

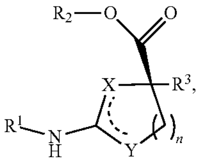

or stereoisomers, or racemic mixtures, or tautomers, or polymorphs, or pharmaceutically acceptable salts, or hydrates, or solvates thereof, wherein X, Y, n, $R^1$, $R^2$ and $R^3$ are defined as above. Embodiments as defined for compounds of formula (I) apply here.

In a further embodiment, the present invention relates to compounds of formula (Ic)

(Ic)

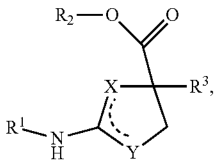

or stereoisomers, racemic mixtures, tautomers, polymorphs, pharmaceutically acceptable salts, prodrugs, hydrates, or solvates thereof;

wherein

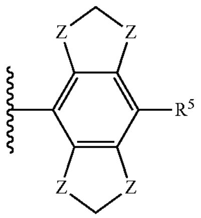

$R^1$ is wherein

Z is $CH_2$;

$R^5$ is independently selected from the group consisting of hydrogen or halogen;

X is O;

Y is N;

as valency permits,  is the combination of a single bond and a double bond; $R^2$ is independently selected from the group consisting of hydrogen, $C_1$-$C_6$alkyl, $C_3$-$C_6$cycloalkyl. In a preferred embodiment, $R^2$ is as defined herein above. In another embodiment $R^2$ is ethyl.

In one embodiment, the present invention relates to a compound of formula (I'), wherein $R^3$ is independently selected from the group consisting of hetero$C_3$-$C_6$cycloalkyl, aryl or heteroaryl wherein each of them can be optionally substituted with—$C_1$-$C_6$alkyl, —O—$C_1$-$C_6$alkyl, -Hal, or —$C_1$-$C_6$alkyl-OH. In a preferred embodiment, $R^3$ is as defined herein above.

In another embodiment, the invention provides for a compound of formula (I'), wherein $R^3$ is selected from the following:

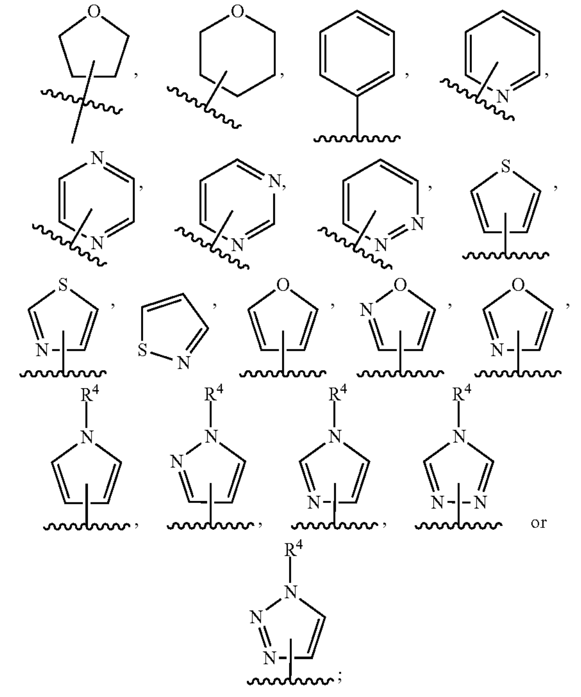

wherein $R^4$ is independently selected from the group consisting of hydrogen, $C_1$-$C_6$alkyl and $C_3$-$C_6$cycloalkyl, and wherein each of them can be optionally substituted with—$C_1$-$C_6$alkyl, —O—$C_1$-$C_6$alkyl, -Hal, or —$C_1$-$C_6$alkyl-OH.

More preferably, $R^3$ is selected from the following:

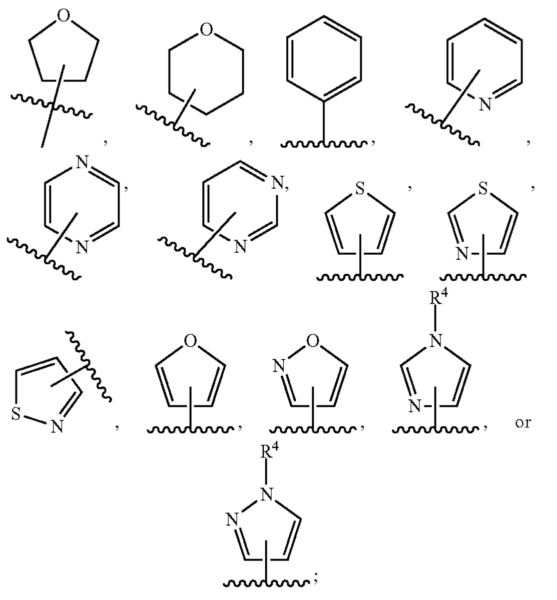

wherein $R^4$ is independently selected from the group consisting of hydrogen, $C_1$-$C_6$alkyl and $C_3$-$C_6$cycloalkyl, and wherein each of them can be optionally substituted with—$C_1$-$C_6$alkyl, —O—$C_1$-$C_6$alkyl, -Hal, or —$C_1$-$C_6$alkyl-OH.

Even more preferably, $R^3$ is selected from the following:

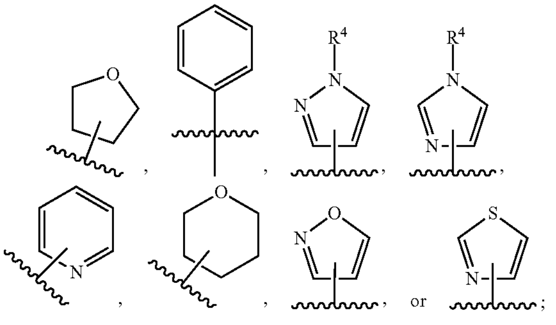

wherein $R^4$ is independently selected from the group consisting of hydrogen, $C_1$-$C_6$alkyl and $C_3$-$C_6$cycloalkyl, and wherein each of them can be optionally substituted with—$C_1$-$C_6$alkyl, —O—$C_1$-$C_6$alkyl, -Hal, or —$C_1$-$C_6$alkyl-OH. Preferably, $R^4$ is methyl, isopropyl or ethyl. More preferably, $R^4$ is methyl, or isopropyl. Even more preferably, $R^4$ is methyl.

In a further embodiment, the present invention relates to compounds of formula (Ic)

(Ic)

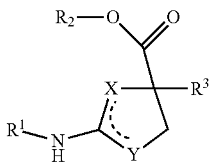

or stereoisomers, racemic mixtures, tautomers, polymorphs, pharmaceutically acceptable salts, prodrugs, hydrates, or solvates thereof;

wherein

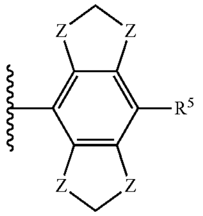

$R^1$ is wherein

Z is $CH_2$;

$R^5$ is hydrogen;

X is O;

Y is N;

as valency permits,  is the combination of a single bond and a double bond;

$R^2$ is ethyl;

$R^3$ is independently selected from

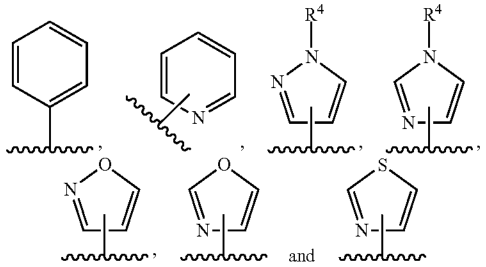

and wherein other than at the position of $R^4$, $R^3$ can be optionally substituted with —Cl, isopropyl or —OMe, wherein isopropyl can be optionally substituted with —OH; and $R^4$ is methyl or ethyl.

Preferably, the compounds of formula (Ic) are:

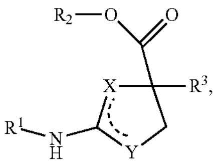

(Ic)

or stereoisomers, racemic mixtures, tautomers, polymorphs, pharmaceutically acceptable salts, prodrugs, hydrates, or solvates thereof; wherein

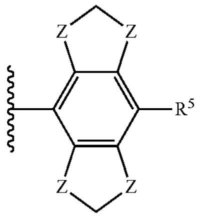

$R^1$ is wherein

Z is $CH_2$;

$R^5$ is hydrogen;

X is O;

Y is N;

as valency permits, is the combination of a single bond and a double bond;

$R^2$ is independently selected from the group consisting of hydrogen, methyl, ethyl, propyl, isopropyl or cyclopentane. Even more preferably, $R^2$ is independently selected from the group consisting of hydrogen, ethyl, isopropyl or cyclopentane. $R^2$ can be optionally substituted with OH, such as in

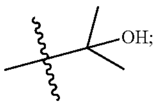 [SMILES: *C(C)(C)O]

$R^3$ is independently selected from:

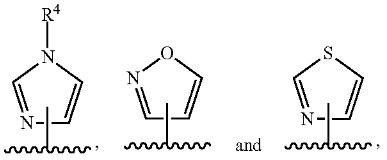

and wherein other than at the position of $R^4$, $R^3$ can be optionally substituted with Cl, isopropyl, or —OMe, wherein isopropyl can be optionally substituted with—OH; and $R^4$ is methyl, isopropyl, or ethyl. More preferably, $R^4$ is methyl, or isopropyl. Even more preferably, $R^4$ is methyl.

Preferably, the compounds of formula (Ic) are

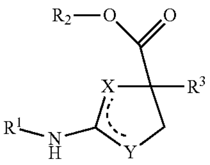

(Ic)

or stereoisomers, racemic mixtures, tautomers, polymorphs, pharmaceutically acceptable salts, prodrugs, hydrates, or solvates thereof;

wherein

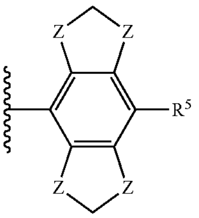

$R^1$ is wherein

Z is $CH_2$;

$R^5$ is hydrogen;

X is O;

Y is N;

as valency permits, is the combination of a single bond and a double bond;

$R^2$ is ethyl;

$R^3$ is independently selected from

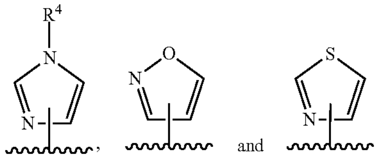

and wherein other than at the position of $R^4$, $R^3$ can be optionally substituted with Cl, isopropyl or —OMe wherein isopropyl can be optionally substituted with —OH; and $R^4$ is methyl or ethyl.

In a further embodiment, the present invention relates to the following compounds of formula (I')
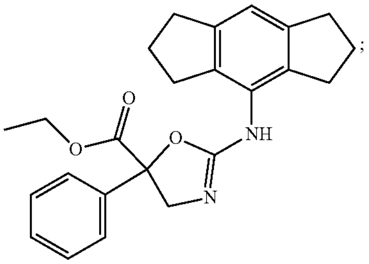 [SMILES: CCOC(=O)C1(c2ccccc2)CN=C(Nc2c3c(cc4c2CCC4)CCC3)O1]
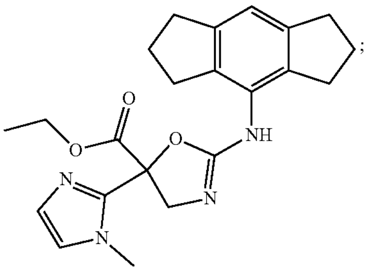 [SMILES: CCOC(=O)C1(c2nccn2C)CN=C(Nc2c3c(cc4c2CCC4)CCC3)O1]
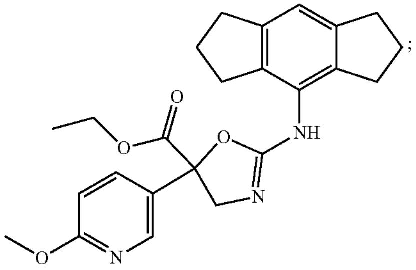 [SMILES: CCOC(=O)C1(c2ccc(OC)nc2)CN=C(Nc2c3c(cc4c2CCC4)CCC3)O1]
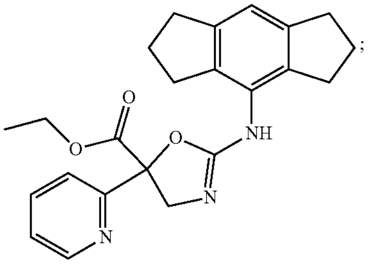 [SMILES: CCOC(=O)C1(c2ccccn2)CN=C(Nc2c3c(cc4c2CCC4)CCC3)O1]
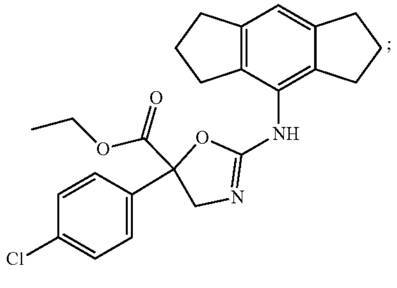 [SMILES: CCOC(=O)C1(c2ccc(Cl)cc2)CN=C(Nc2c3c(cc4c2CCC4)CCC3)O1]
-continued
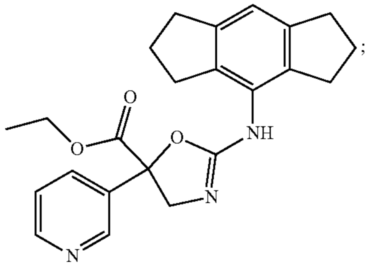 [SMILES: CCOC(=O)C1(c2cccnc2)CN=C(Nc2c3c(cc4c2CCC4)CCC3)O1]
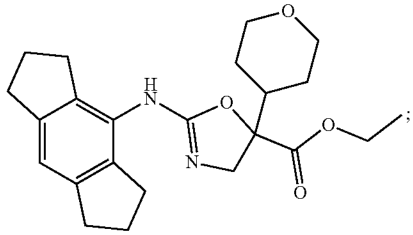 [SMILES: CCOC(=O)C1(C2CCOCC2)CN=C(Nc2c3c(cc4c2CCC4)CCC3)O1]
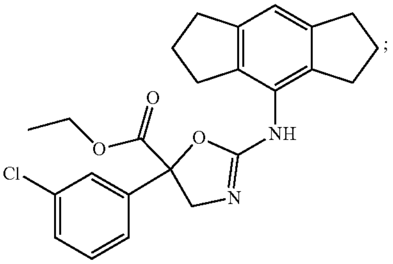 [SMILES: CCOC(=O)C1(c2cccc(Cl)c2)CN=C(Nc2c3c(cc4c2CCC4)CCC3)O1]
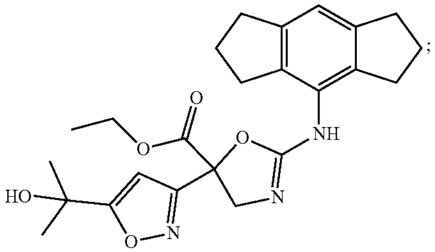 [SMILES: CCOC(=O)C1(c2cc(C(C)(C)O)on2)CN=C(Nc2c3c(cc4c2CCC4)CCC3)O1]
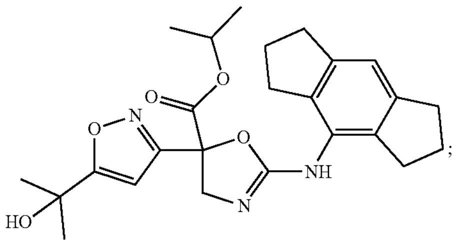 [SMILES: CC(C)OC(=O)C1(c2cc(C(C)(C)O)on2)CN=C(Nc2c3c(cc4c2CCC4)CCC3)O1]
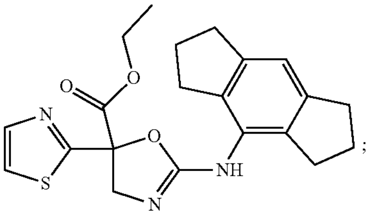 [SMILES: CCOC(=O)C1(c2nccs2)CN=C(Nc2c3c(cc4c2CCC4)CCC3)O1]

-continued
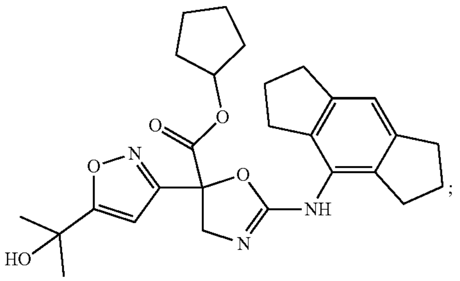 [SMILES: CC(C)(O)c1cc(C2(C(=O)OC3CCCC3)CN=C(Nc3c4c(cc5c3CCC5)CCC4)O2)no1]
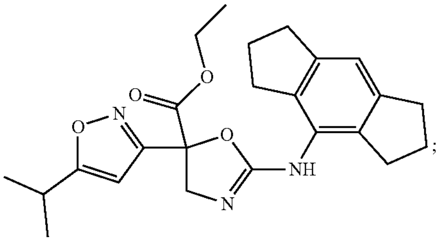 [SMILES: CCOC(=O)C1(c2cc(C(C)C)on2)CN=C(Nc2c3c(cc4c2CCC4)CCC3)O1]
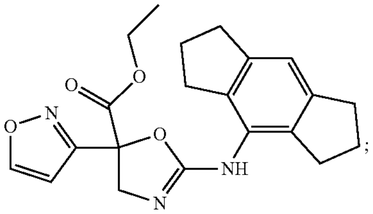 [SMILES: CCOC(=O)C1(c2ccon2)CN=C(Nc2c3c(cc4c2CCC4)CCC3)O1]
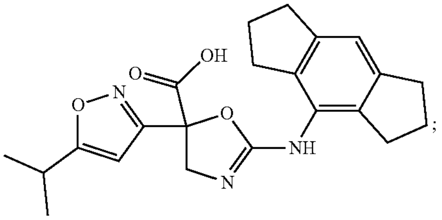 [SMILES: CC(C)c1cc(C2(C(=O)O)CN=C(Nc3c4c(cc5c3CCC5)CCC4)O2)no1]
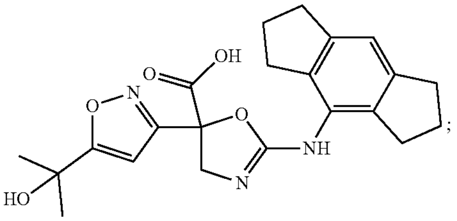 [SMILES: CC(C)(O)c1cc(C2(C(=O)O)CN=C(Nc3c4c(cc5c3CCC5)CCC4)O2)no1]
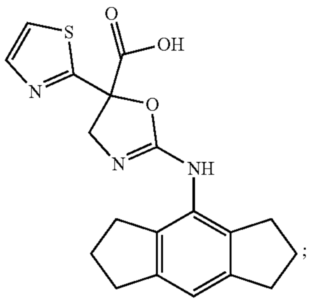
-continued
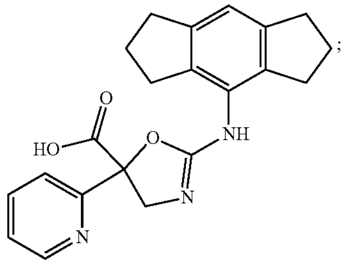 [SMILES: O=C(O)C1(c2ccccn2)CN=C(Nc2c3c(cc4c2CCC4)CCC3)O1]
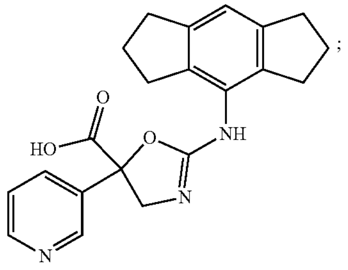 [SMILES: O=C(O)C1(c2cccnc2)CN=C(Nc2c3c(cc4c2CCC4)CCC3)O1]
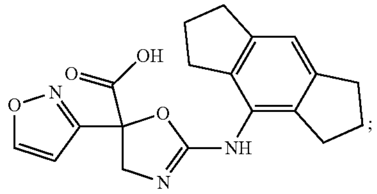 [SMILES: O=C(O)C1(c2ccon2)CN=C(Nc2c3c(cc4c2CCC4)CCC3)O1]
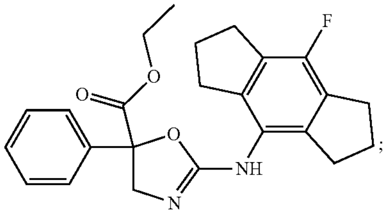 [SMILES: CCOC(=O)C1(c2ccccc2)CN=C(Nc2c3c(c(F)c4c2CCC4)CCC3)O1]
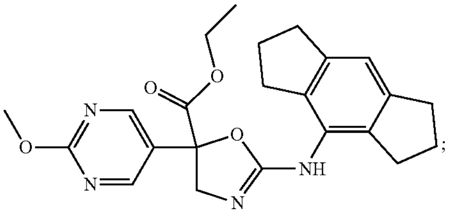 [SMILES: CCOC(=O)C1(c2cnc(OC)nc2)CN=C(Nc2c3c(cc4c2CCC4)CCC3)O1]
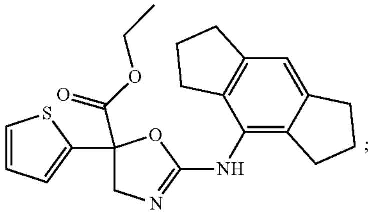 [SMILES: CCOC(=O)C1(c2cccs2)CN=C(Nc2c3c(cc4c2CCC4)CCC3)O1]
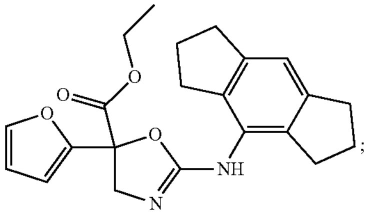 [SMILES: CCOC(=O)C1(c2ccco2)CN=C(Nc2c3c(cc4c2CCC4)CCC3)O1]

-continued
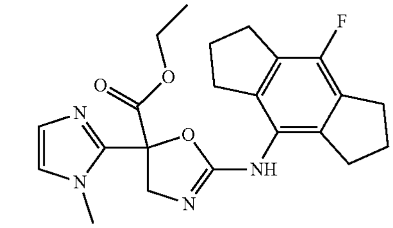
;
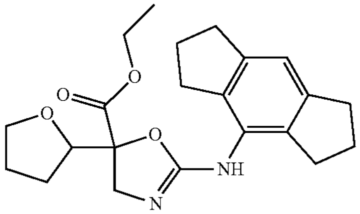
;
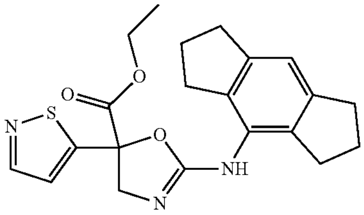
;
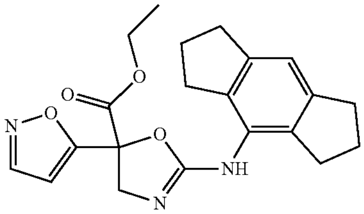
;
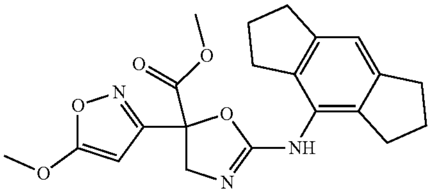
;
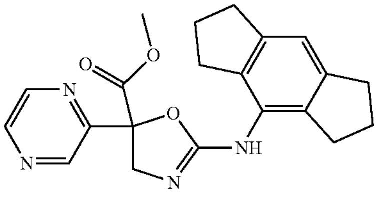
;
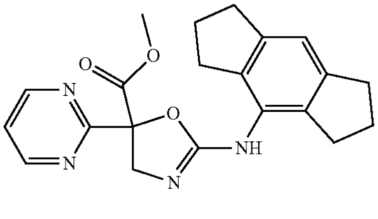
;
-continued
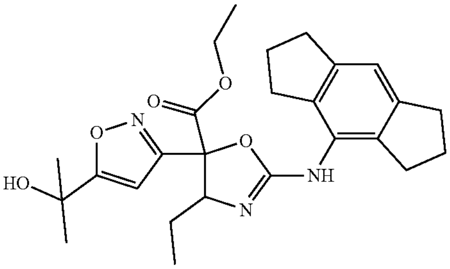
;
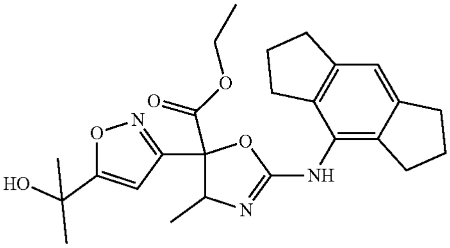
;
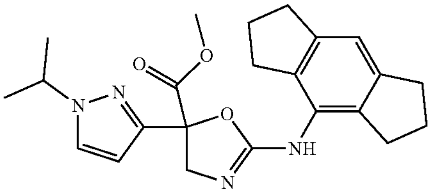
;
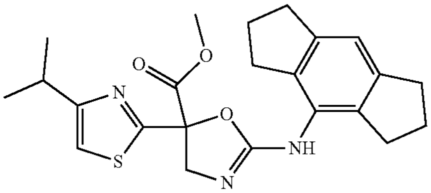
;
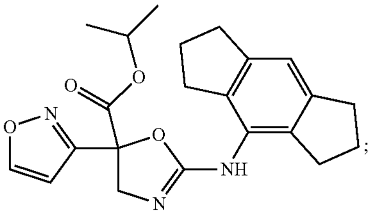 [SMILES: CC(C)OC(=O)C1(c2ccon2)CN=C(Nc2c3c(cc4c2CCC4)CCC3)O1]
;
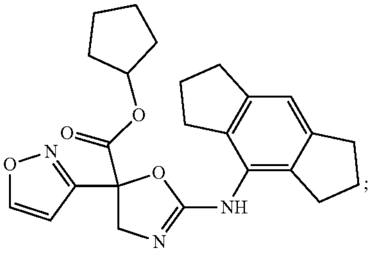 [SMILES: O=C(OC1CCCC1)C1(c2ccon2)CN=C(Nc2c3c(cc4c2CCC4)CCC3)O1]
;

-continued
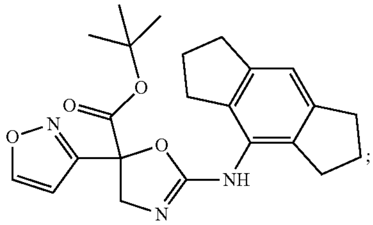 [SMILES: CC(C)(C)OC(=O)C1(c2ccon2)CN=C(Nc2c3c(cc4c2CCC4)CCC3)O1]
;
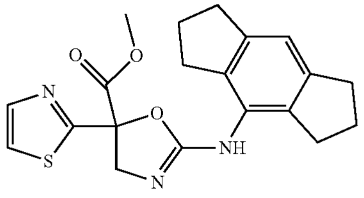
;
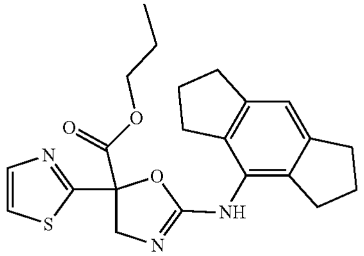
;
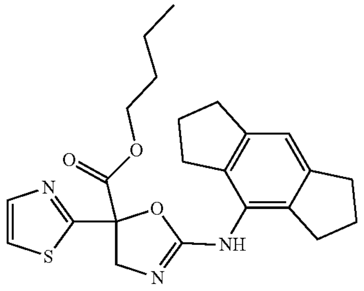
;
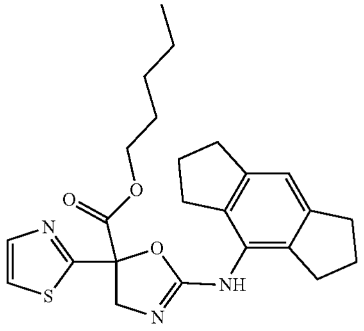
;
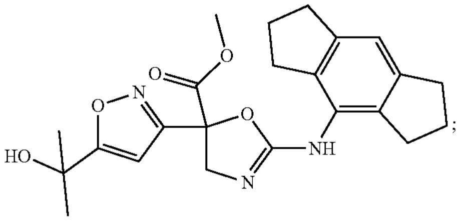 [SMILES: COC(=O)C1(c2cc(C(C)(C)O)on2)CN=C(Nc2c3c(cc4c2CCC4)CCC3)O1]
;
-continued
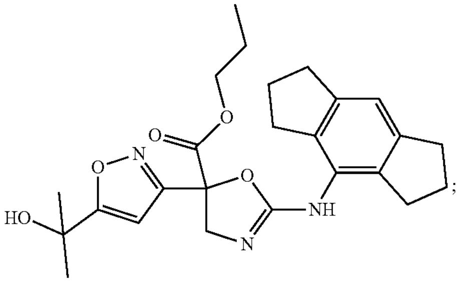 [SMILES: CCCOC(=O)C1(c2cc(C(C)(C)O)on2)CN=C(Nc2c3c(cc4c2CCC4)CCC3)O1]
;
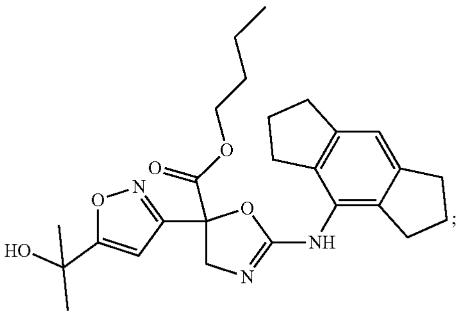 [SMILES: CCCCOC(=O)C1(c2cc(C(C)(C)O)on2)CN=C(Nc2c3c(cc4c2CCC4)CCC3)O1]
;
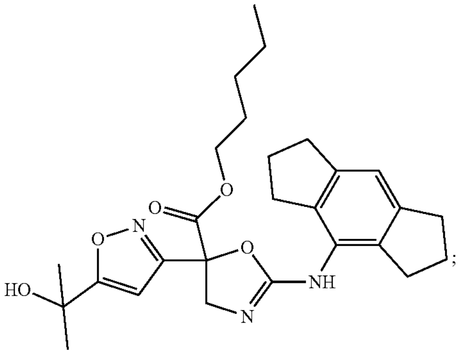 [SMILES: CCCCCOC(=O)C1(c2cc(C(C)(C)O)on2)CN=C(Nc2c3c(cc4c2CCC4)CCC3)O1]
;
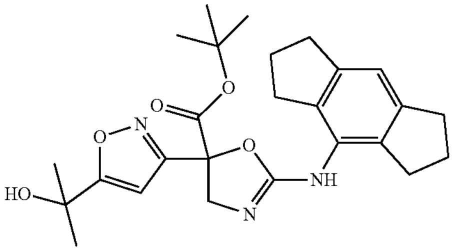
;
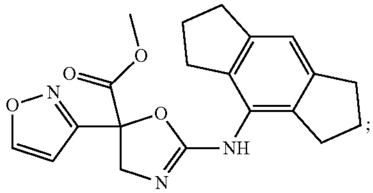 [SMILES: COC(=O)C1(c2ccon2)CN=C(Nc2c3c(cc4c2CCC4)CCC3)O1]
;
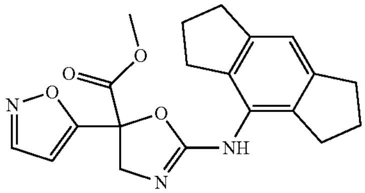
;

-continued
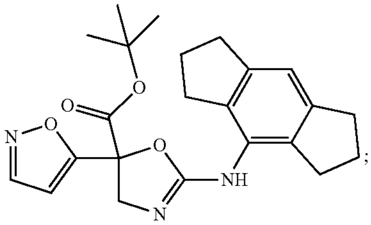 [SMILES: CC(C)(C)OC(=O)C1(c2ccno2)CN=C(Nc2c3c(cc4c2CCC4)CCC3)O1]
;
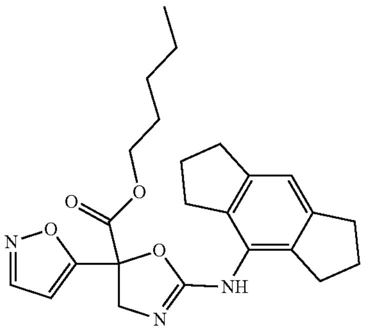
;
or a stereoisomer, a racemic mixture, a tautomer, a polymorph, a pharmaceutically acceptable salt, a prodrug, a hydrate, or a solvate thereof.
In another embodiment the present invention relates to the following compounds of formula (I')
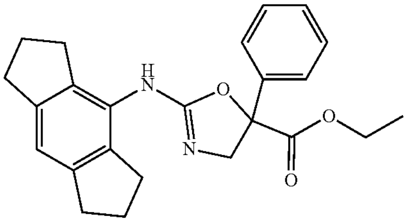
;
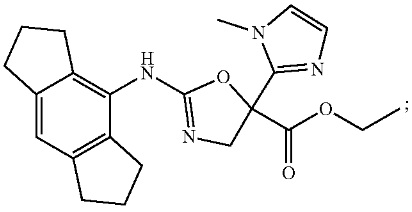 [SMILES: CCOC(=O)C1(c2nccn2C)CN=C(Nc2c3c(cc4c2CCC4)CCC3)O1]
;
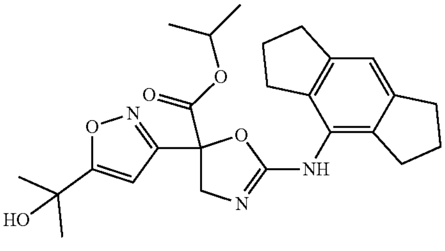
;
-continued
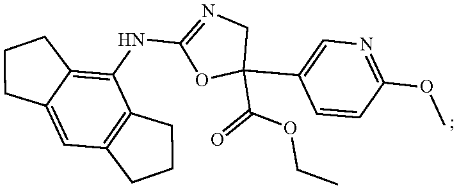 [SMILES: CCOC(=O)C1(c2ccc(OC)nc2)CN=C(Nc2c3c(cc4c2CCC4)CCC3)O1]
;
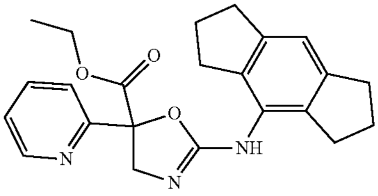
;
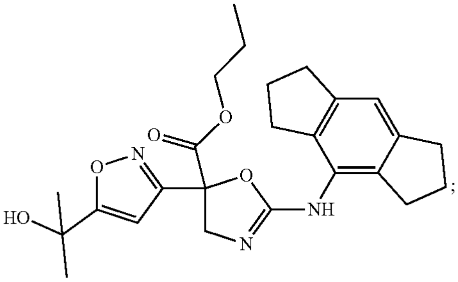 [SMILES: CCCOC(=O)C1(c2cc(C(C)(C)O)on2)CN=C(Nc2c3c(cc4c2CCC4)CCC3)O1]
;
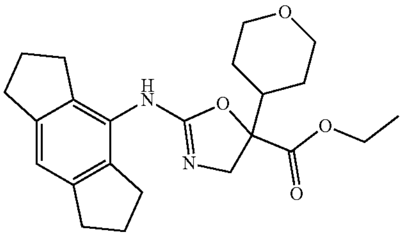
;
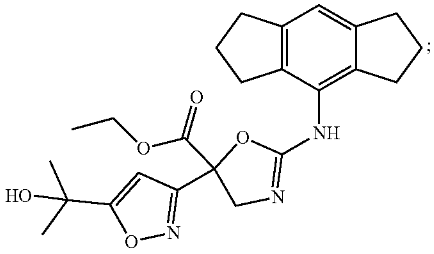 [SMILES: CCOC(=O)C1(c2cc(C(C)(C)O)on2)CN=C(Nc2c3c(cc4c2CCC4)CCC3)O1]
;
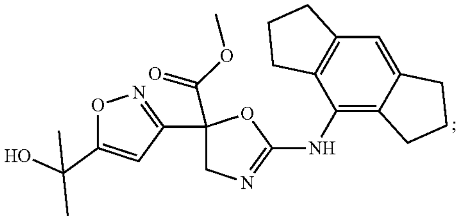 [SMILES: COC(=O)C1(c2cc(C(C)(C)O)on2)CN=C(Nc2c3c(cc4c2CCC4)CCC3)O1]
;

-continued
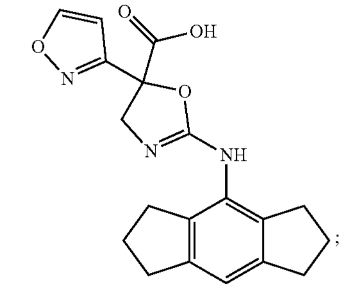
;
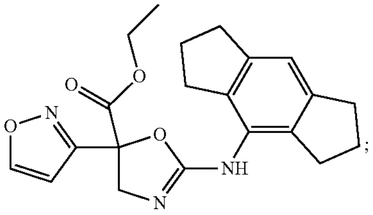 [SMILES: CCOC(=O)C1(c2ccon2)CN=C(Nc2c3c(cc4c2CCC4)CCC3)O1]
;
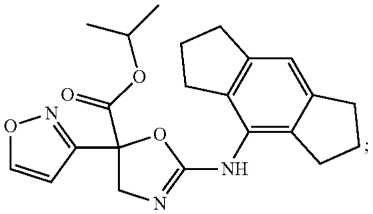 [SMILES: CC(C)OC(=O)C1(c2ccon2)CN=C(Nc2c3c(cc4c2CCC4)CCC3)O1]
;
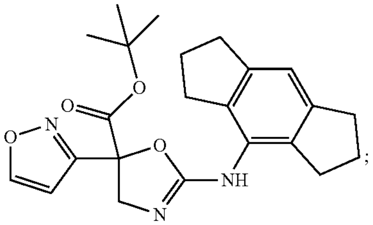 [SMILES: CC(C)(C)OC(=O)C1(c2ccon2)CN=C(Nc2c3c(cc4c2CCC4)CCC3)O1]
;
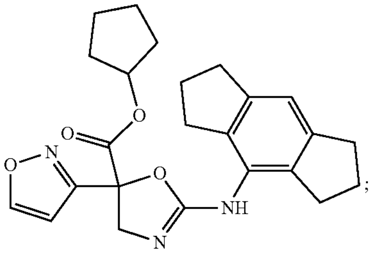 [SMILES: O=C(OC1CCCC1)C1(c2ccon2)CN=C(Nc2c3c(cc4c2CCC4)CCC3)O1]
;
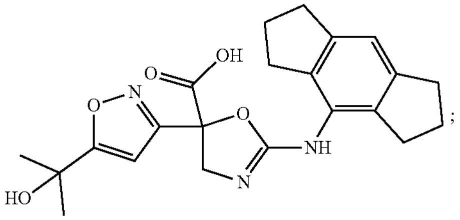 [SMILES: CC(C)(O)c1cc(C2(C(=O)O)CN=C(Nc3c4c(cc5c3CCC5)CCC4)O2)no1]
;
-continued
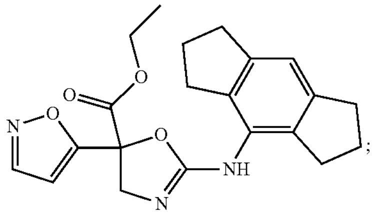
;
or a stereoisomer, a racemic mixture, a tautomer, a polymorph, a pharmaceutically acceptable salt, a prodrug, a hydrate, or a solvate thereof.
In another embodiment the present invention relates to the following compounds of formula (I')
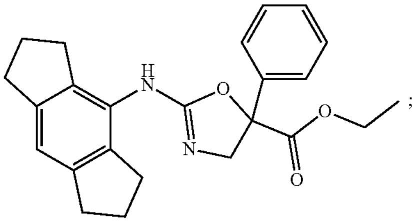 [SMILES: CCOC(=O)C1(c2ccccc2)CN=C(Nc2c3c(cc4c2CCC4)CCC3)O1]
;
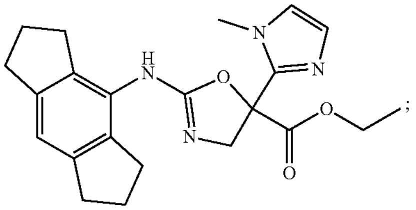 [SMILES: CCOC(=O)C1(c2nccn2C)CN=C(Nc2c3c(cc4c2CCC4)CCC3)O1]
;
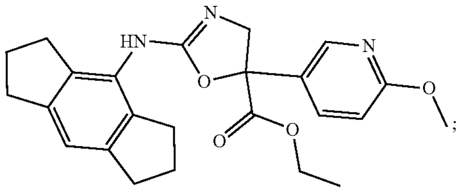 [SMILES: CCOC(=O)C1(c2ccc(OC)nc2)CN=C(Nc2c3c(cc4c2CCC4)CCC3)O1]
;
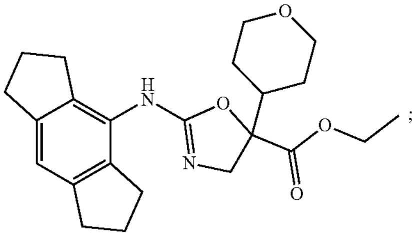 [SMILES: CCOC(=O)C1(C2CCOCC2)CN=C(Nc2c3c(cc4c2CCC4)CCC3)O1]
;
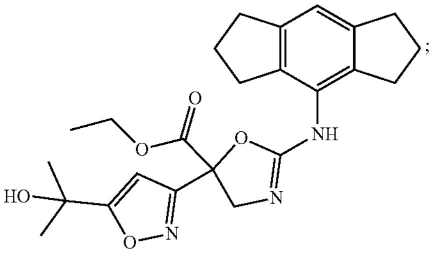 [SMILES: CCOC(=O)C1(c2cc(C(C)(C)O)on2)CN=C(Nc2c3c(cc4c2CCC4)CCC3)O1]
;

-continued
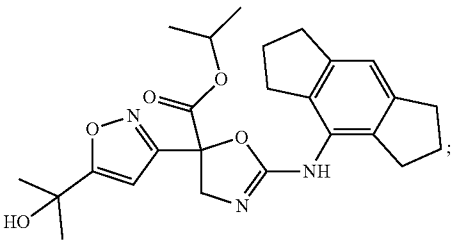 [SMILES: CC(C)OC(=O)C1(c2cc(C(C)(C)O)on2)CN=C(Nc2c3c(cc4c2CCC4)CCC3)O1]
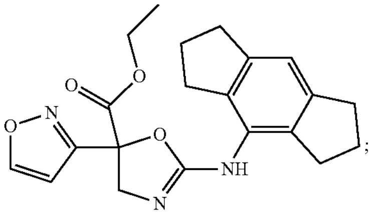 [SMILES: CCOC(=O)C1(c2ccon2)CN=C(Nc2c3c(cc4c2CCC4)CCC3)O1]
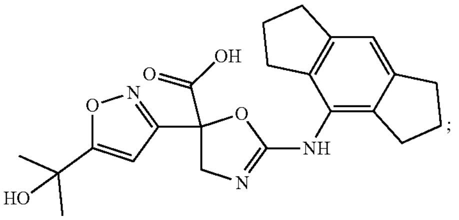 [SMILES: CC(C)(O)c1cc(C2(C(=O)O)CN=C(Nc3c4c(cc5c3CCC5)CCC4)O2)no1]
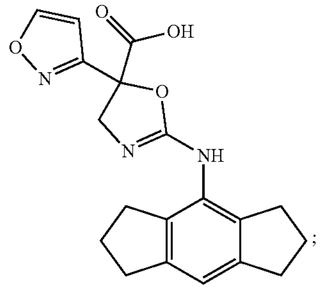
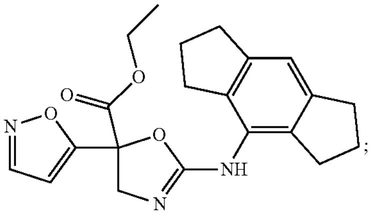
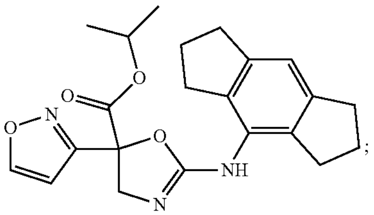 [SMILES: CC(C)OC(=O)C1(c2ccon2)CN=C(Nc2c3c(cc4c2CCC4)CCC3)O1]
-continued
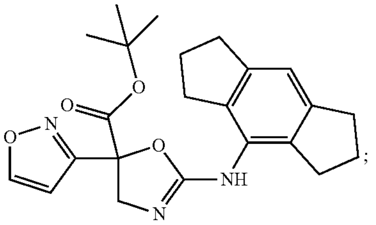 [SMILES: CC(C)(C)OC(=O)C1(c2ccon2)CN=C(Nc2c3c(cc4c2CCC4)CCC3)O1]
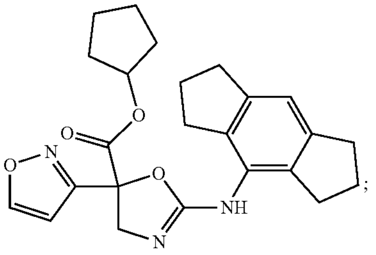 [SMILES: O=C(OC1CCCC1)C1(c2ccon2)CN=C(Nc2c3c(cc4c2CCC4)CCC3)O1]
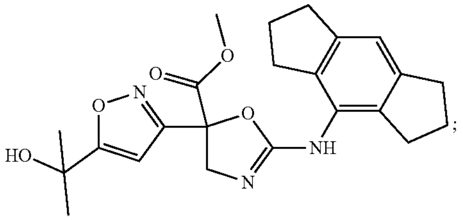 [SMILES: COC(=O)C1(c2cc(C(C)(C)O)on2)CN=C(Nc2c3c(cc4c2CCC4)CCC3)O1]
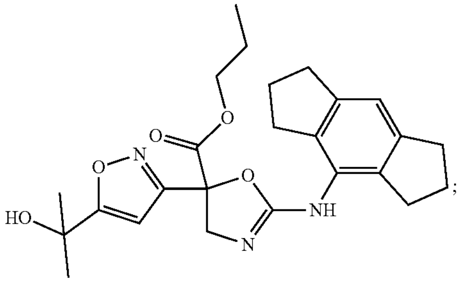 [SMILES: CCCOC(=O)C1(c2cc(C(C)(C)O)on2)CN=C(Nc2c3c(cc4c2CCC4)CCC3)O1]
or a stereoisomer, a racemic mixture, a tautomer, a polymorph, a pharmaceutically acceptable salt, a prodrug, a hydrate, or a solvate thereof.
In a further embodiment, the present invention relates to the following compound of formula (I')
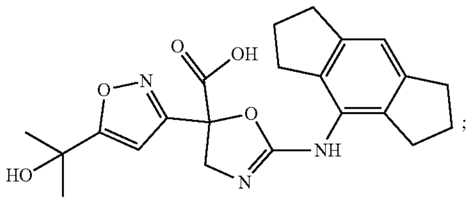
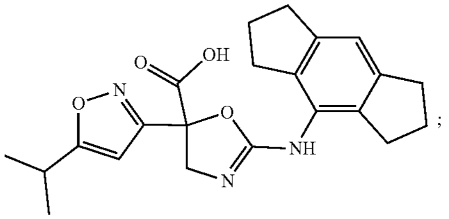

-continued
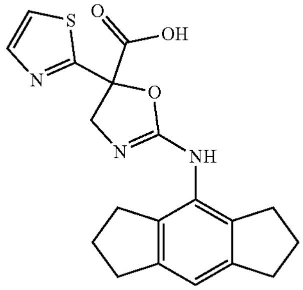
;
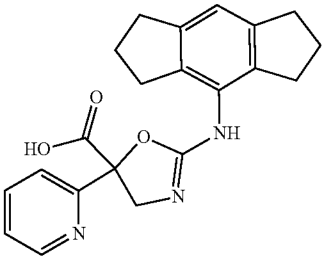
;
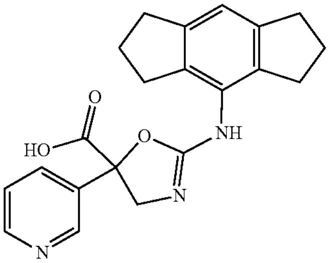
; and
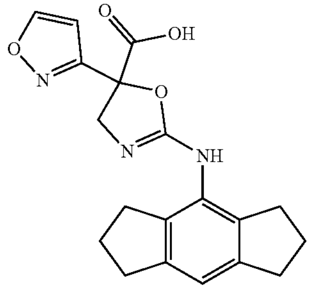
;
or a stereoisomer, a racemic mixture, a tautomer, a polymorph, a pharmaceutically acceptable salt, a prodrug, a hydrate, or a solvate thereof.
In a further embodiment, the present invention relates to the following compounds of formula (I')
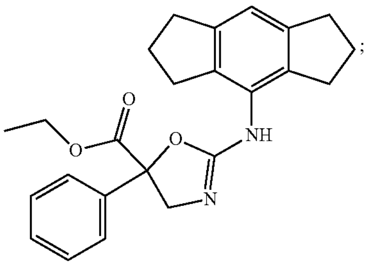 [SMILES: CCOC(=O)C1(c2ccccn2)CN=C(Nc2c3c(cc4c2CCC4)CCC3)O1]
;
-continued
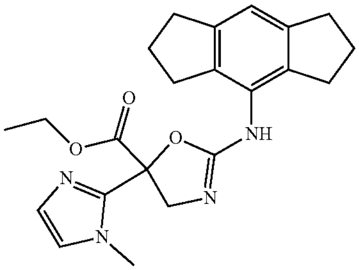
;
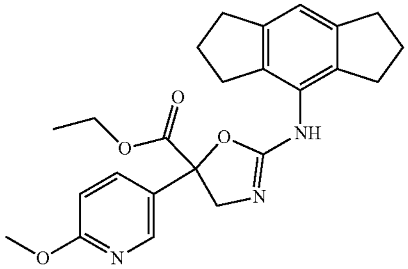
;
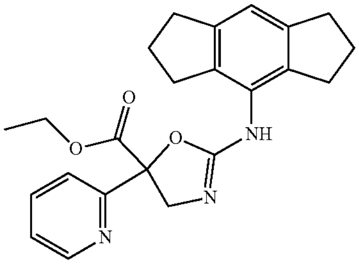
;
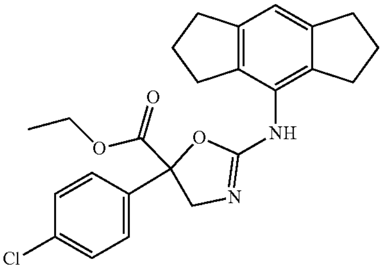
;
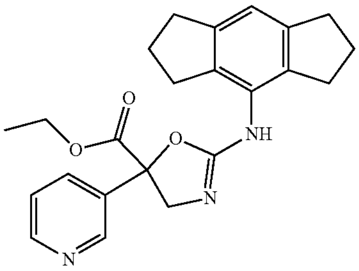
;
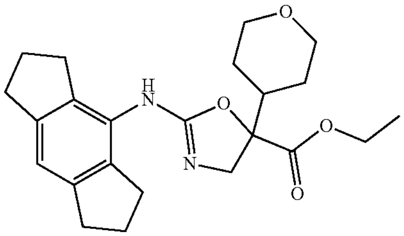
;

-continued
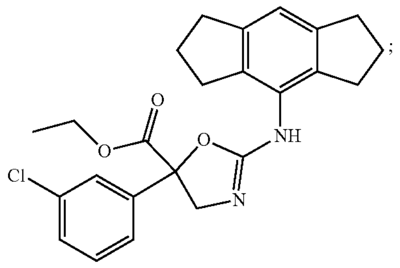 [SMILES: CCOC(=O)C1(c2cccc(Cl)c2)CN=C(Nc2c3c(cc4c2CCC4)CCC3)O1]
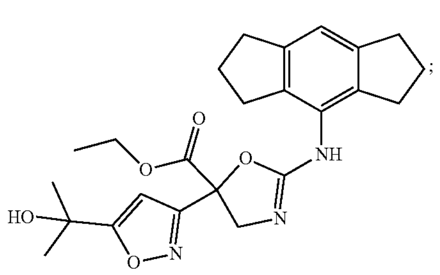 [SMILES: CCOC(=O)C1(c2cc(C(C)(C)O)on2)CN=C(Nc2c3c(cc4c2CCC4)CCC3)O1]
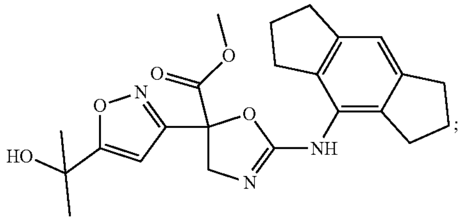 [SMILES: COC(=O)C1(c2cc(C(C)(C)O)on2)CN=C(Nc2c3c(cc4c2CCC4)CCC3)O1]
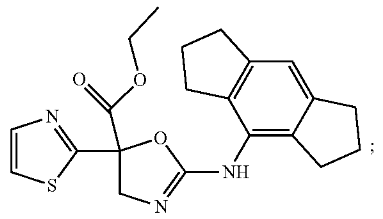 [SMILES: CCOC(=O)C1(c2nccs2)CN=C(Nc2c3c(cc4c2CCC4)CCC3)O1]
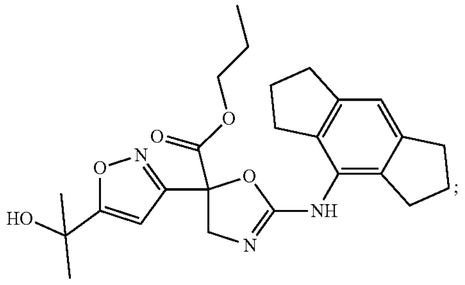 [SMILES: CCCOC(=O)C1(c2cc(C(C)(C)O)on2)CN=C(Nc2c3c(cc4c2CCC4)CCC3)O1]
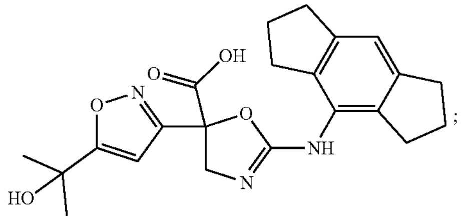 [SMILES: CC(C)(O)c1cc(C2(C(=O)O)CN=C(Nc3c4c(cc5c3CCC5)CCC4)O2)no1]
-continued
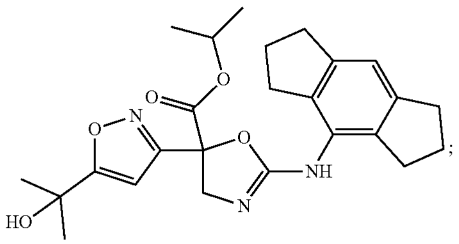 [SMILES: CC(C)OC(=O)C1(c2cc(C(C)(C)O)on2)CN=C(Nc2c3c(cc4c2CCC4)CCC3)O1]
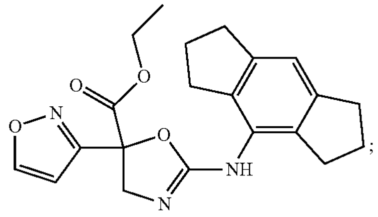 [SMILES: CCOC(=O)C1(c2ccon2)CN=C(Nc2c3c(cc4c2CCC4)CCC3)O1]
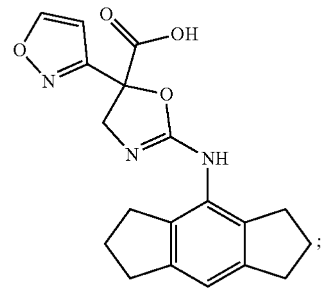
or a stereoisomer, a racemic mixture, a tautomer, a polymorph, a pharmaceutically acceptable salt, a prodrug, a hydrate, or a solvate thereof.
In a further embodiment, the present invention relates to the following the compound of formula (I')
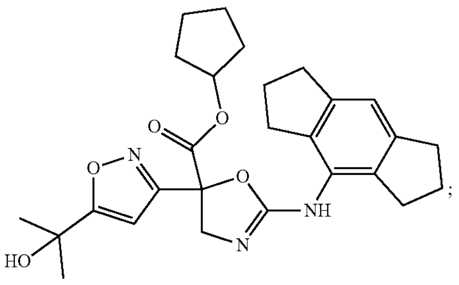 [SMILES: CC(C)(O)c1cc(C2(C(=O)OC3CCCC3)CN=C(Nc3c4c(cc5c3CCC5)CCC4)O2)no1]
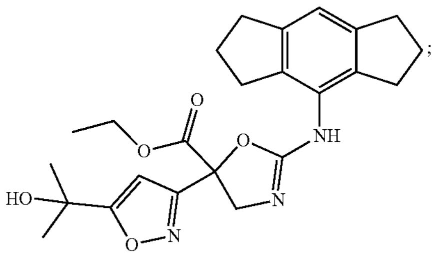 [SMILES: CCOC(=O)C1(c2cc(C(C)(C)O)on2)CN=C(Nc2c3c(cc4c2CCC4)CCC3)O1]

-continued

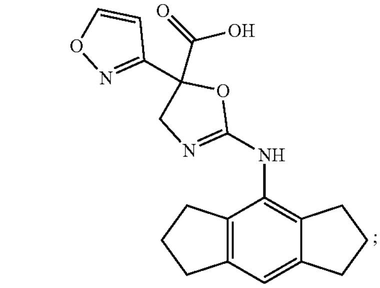
;

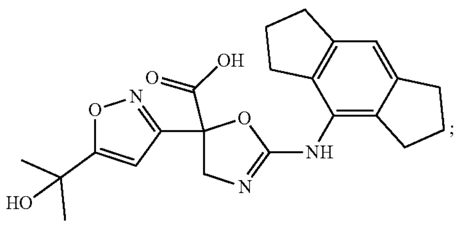 [SMILES: CC(C)(O)c1cc(C2(C(=O)O)CN=C(Nc3c4c(cc5c3CCC5)CCC4)O2)no1]
;

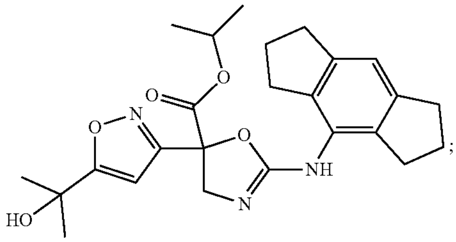 [SMILES: CC(C)OC(=O)C1(c2cc(C(C)(C)O)on2)CN=C(Nc2c3c(cc4c2CCC4)CCC3)O1]
;

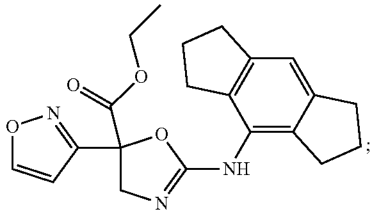 [SMILES: CCOC(=O)C1(c2ccon2)CN=C(Nc2c3c(cc4c2CCC4)CCC3)O1]
;

or a stereoisomer, a racemic mixture, a tautomer, a polymorph, a pharmaceutically acceptable salt, a prodrug, a hydrate, or a solvate thereof.

In one embodiment, the present invention further relates to a compound of formula (II') as defined below (II')

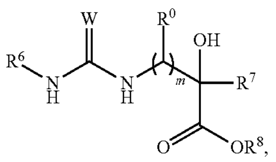

or stereoisomers, racemic mixtures, tautomers, polymorphs, pharmaceutically acceptable salts, prodrugs, hydrates, or solvates thereof;

wherein

W is independently selected from the group consisting of O and S;

m is 1 or 2;

$R^0$ is H, or $C_1$-$C_3$alkyl;

$R^6$ is

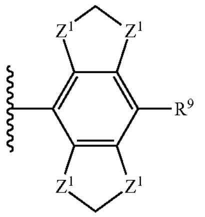

wherein $Z^1$ is independently selected from the group consisting of $CH_2$ and O provided that no more than two of $Z^1$ are O;

$R^9$ is independently selected from the group consisting of hydrogen and halogen;

$R^8$ is independently selected from the group consisting of hydrogen, $C_1$-$C_6$alkyl, and $C_3$-$C_6$cycloalkyl and;

$R^7$ is independently selected from the group consisting of hetero$C_3$-$C_6$cycloalkyl, aryl, or heteroaryl, wherein each of them can be optionally substituted.

Further, in one embodiment the present invention relates to a compound of formula (II') wherein $R^0$ is H, having formula (II) as defined below (II)

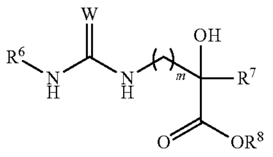

or stereoisomers, racemic mixtures, tautomers, polymorphs, pharmaceutically acceptable salts, prodrugs, hydrates, or solvates thereof;

wherein

W is independently selected from the group consisting of O and S;

m is 1 or 2;

$R^6$ is

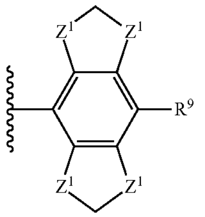

wherein $Z^1$ is independently selected from the group consisting of $CH_2$ and O provided that no more than two of $Z^1$ are O;

$R^9$ is independently selected from the group consisting of hydrogen and halogen;

$R^8$ is independently selected from the group consisting of hydrogen, $C_1$-$C_6$ alkyl, and $C_3$-$C_6$ cycloalkyl and;

$R^7$ is independently selected from the group consisting of hetero $C_3$-$C_6$ cycloalkyl, aryl or heteroaryl, wherein each of them can be optionally substituted.

In another embodiment, the present invention relates to a compound of formula (II'), in particular it relates to a compound of formula (II), wherein W is independently selected from the group consisting of O and S. Preferably, W is O. More preferably, W is S.

In another embodiment, the present invention relates to a compound of formula (II'), in particular it relates to a compound of formula (II), wherein m is 1.

In one embodiment, the present invention relates to a compound of formula (II'), wherein $R^0$ is H or $C_1$-$C_3$alkyl. Preferably, $R^0$ is H, methyl or ethyl. More preferably, $R^0$ is H.

In another embodiment, the present invention relates to a compound of formula (II'), in particular it relates to a compound of formula (II), wherein $R^6$ is

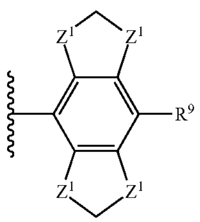

wherein $Z^1$ is $CH_2$; and $R^9$ is hydrogen.

In another embodiment, the present invention relates to a compound of formula (II'), in particular it relates to a compound of formula (II), wherein $R^8$ is independently selected from the group consisting of hydrogen, $C_1$-$C_6$alkyl, and $C_3$-$C_6$cycloalkyl. More preferably, $R^8$ is independently selected from the group consisting of hydrogen, $C_1$-$C_6$alkyl, and $C_5$-$C_6$cycloalkyl. Even more preferably, $R^8$ is independently selected from the group consisting of hydrogen, methyl, ethyl, propyl, isopropyl, butyl, tert-butyl, pentyl, hexyl, or cyclopentane, preferably $R^8$ is independently selected from the group consisting of hydrogen, methyl, ethyl, propyl, isopropyl or cyclopentane. Even more preferably, $R^8$ is independently selected from the group consisting of ethyl, isopropyl or cyclopentane. $R^8$ can be optionally substituted with OH. More preferably, $R^8$ is ethyl.

$R^7$ is independently selected from the group consisting of hetero$C_3$-$C_6$cycloalkyl, aryl or heteroaryl wherein each of them can be optionally substituted with—$C_1$-$C_6$alkyl, —O—$C_1$-$C_6$alkyl, -Hal, or —$C_1$-$C_6$alkyl-OH.

In another embodiment, the present invention relates to a compound of formula (II'), in particular it relates to a compound of formula (II), wherein $R^7$ is independently selected from the group consisting of hetero$C_3$-$C_6$cycloalkyl containing one or two heteroatoms selected from N or O, aryl or $C_5$-$C_6$ heteroaryl containing one, two or three heteroatoms independently from each other selected from S, N and O; wherein each of them can be optionally substituted with—$C_1$-$C_6$alkyl, —O—$C_1$-$C_6$alkyl, -Hal, or —$C_1$-$C_6$alkyl-OH. More preferably, $R^7$ is independently selected from the group consisting of hetero$C_3$-$C_6$cycloalkyl containing one or two heteroatoms selected from N or O, $C_5$-$C_6$aryl or $C_5$-$C_6$heteroaryl containing one, two or three heteroatoms independently from each other selected from S, N and O; wherein each of them can be optionally substituted with—$C_1$-$C_6$alkyl, —O—$C_1$-$C_6$alkyl, -Hal, or —$C_1$-$C_6$alkyl-OH. Even more preferably, $R^7$ is hetero$C_3$-$C_6$cycloalkyl containing one heteroatom, wherein the heteroatom is O; and $R^7$ is optionally substituted with—$C_1$-$C_6$alkyl, —O—$C_1$-$C_6$alkyl, -Hal, or —$C_1$-$C_6$alkyl-OH.

In one embodiment, the present invention relates to a compound of formula (II'), in particular it relates to a compound of formula (II), wherein $R^7$ is aryl, optionally substituted with—$C_1$-$C_6$alkyl, —O—$C_1$-$C_6$alkyl, -Hal, or —$C_1$-$C_6$alkyl-OH. In a particular embodiment, the aryl group is optionally substituted with—O—$C_1$-$C_6$alkyl, or -Hal. In a particular embodiment, the aryl group is optionally substituted with —O—$C_1$alkyl, or -Hal, wherein the halogen (-Hal) is, preferably, Chloro.

In one embodiment, the present invention relates to a compound of formula (II'), in particular it relates to a compound of formula (II), wherein $R^7$ is $C_5$-$C_6$ heteroaryl containing one, two or three hetero atoms independently from each other selected from S, N and O; wherein each of them can be optionally substituted with one substituent selected from—$C_1$-$C_6$alkyl, —O—$C_1$-$C_6$alkyl, -Hal, or —$C_1$-$C_6$alkyl-OH.

Even more preferably, $R^7$ is independently selected from the group consisting of

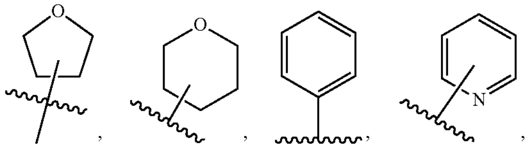

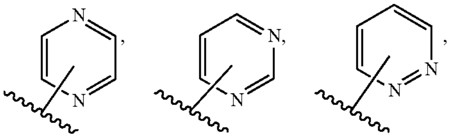

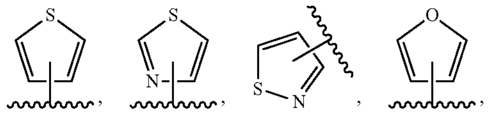

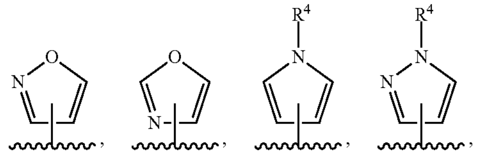

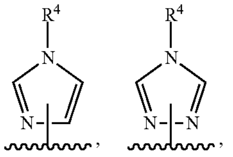

or

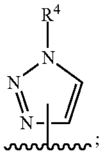

;

wherein $R^4$ is independently selected from the group consisting of hydrogen, $C_1$-$C_6$alkyl and $C_3$-$C_6$cycloalkyl, and wherein each of them can be optionally substituted with—$C_1$-$C_6$alkyl, —O—$C_1$-$C_6$alkyl, -Hal, or —$C_1$-$C_6$alkyl-OH, and wherein any mentioned $C_1$-$C_6$alkyl can be optionally substituted with —OH; and $C_3$-$C_6$cycloalkyl can be optionally substituted with —OH.

Preferably $R^7$ is independently selected from the following:

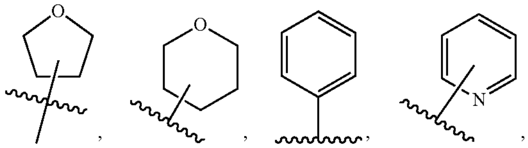

-continued

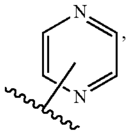, 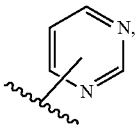 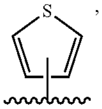, 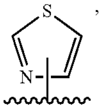,

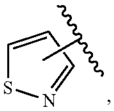, 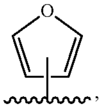, 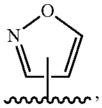, 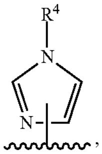, or

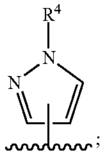;

wherein $R^4$ is independently selected from the group consisting of hydrogen, $C_1$-$C_6$alkyl and $C_3$-$C_6$cycloalkyl, and wherein each of them can be optionally substituted with—$C_1$-$C_6$alkyl, —O—$C_1$-$C_6$alkyl, -Hal, or $C_1$-$C_6$alkyl-OH.

More preferably, $R^7$ is selected from the following

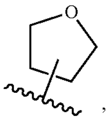, 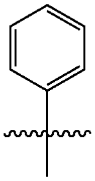, 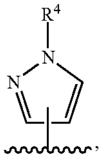, 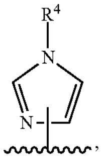,

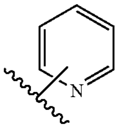, 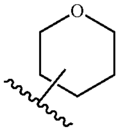, 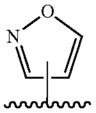, or 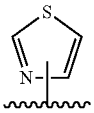;

wherein $R^4$ is independently selected from the group consisting of hydrogen, $C_1$-$C_6$alkyl and $C_3$-$C_6$cycloalkyl, and wherein each of them can be optionally substituted with—$C_1$-$C_6$alkyl, —O—$C_1$-$C_6$alkyl, -Hal, or —$C_1$-$C_6$alkyl-OH.

In each of the above embodiments, $R^7$ can be optionally substituted with halogen, —O—$C_1$-$C_6$alkyl, —$C_1$-$C_6$alkyl-OH, or $C_1$-$C_6$alkyl. More preferably, $R^7$ can be optionally substituted with chloro, methoxy, methyl or isopropyl or

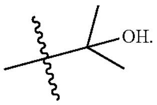 [SMILES: *C(C)(C)O]

In $R^7$, $C_1$-$C_6$alkyl is preferably methyl, ethyl, isopropyl, propyl, isobutyl or butyl and can be optionally substituted with —OH such as in

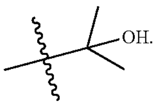 [SMILES: *C(C)(C)O]

In another embodiment, the present invention relates to a compound of formula (II'), in particular it relates to a compound of formula (II), wherein $R^4$ is independently selected from the group consisting of hydrogen, methyl, ethyl, isopropyl and propyl. More preferably, $R^4$ is methyl.

In one embodiment, the present invention relates to a compound of formula (II'), in particular it relates to a compound of formula (II), wherein $R^8$ is hydrogen and $R^7$ is a)

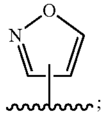;

preferably

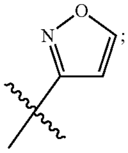 [SMILES: *c1ccon1];

b)

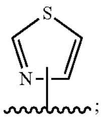;

preferably

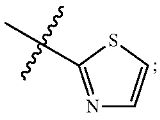 [SMILES: *c1nccs1];

c)

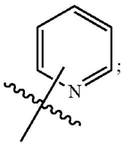;

preferably

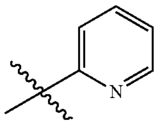 or 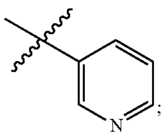;

d)

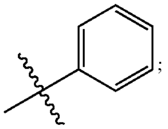 [SMILES: *c1ccccc1]

e)

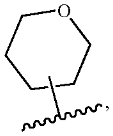

preferably

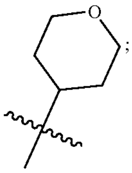

or f)

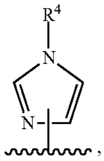

preferably

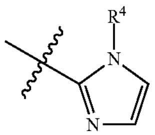

wherein $R^4$ is independently selected from the group consisting of hydrogen, $C_1$-$C_6$alkyl and $C_3$-$C_6$cycloalkyl.

In another embodiment, the present invention relates to a compound of formula (II'), in particular it relates to a compound of formula (II), wherein $R^8$ is hydrogen and $R^7$ is a)

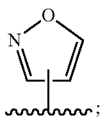

preferably

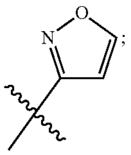 [SMILES: *c1ccon1]

b)

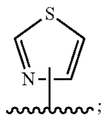

preferably

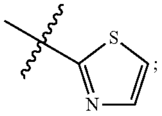

or c)

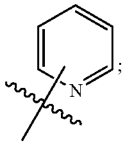

preferably

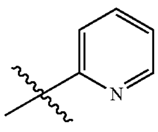

or

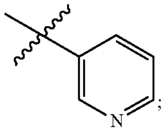

and wherein each $R^7$ can be optionally substituted with—$C_1$-$C_6$alkyl, —O—$C_1$-$C_6$alkyl, -Hal, or —$C_1$-$C_6$alkyl-OH.

In each of the above embodiments, $R^7$ can be optionally substituted with halogen, —O—$C_1$-$C_6$alkyl, —$C_1$-$C_6$alkyl-OH, or $C_1$-$C_6$alkyl. More preferably, $R^7$ can be optionally substituted with chloro, methoxy, methyl or isopropyl or

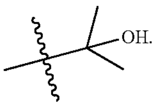 [SMILES: *C(C)(C)O]

In $R^7$, $C_1$-$C_6$alkyl is preferably methyl, ethyl, isopropyl, propyl, isobutyl or butyl and can be optionally substituted with —OH such as in

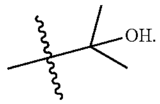 [SMILES: *C(C)(C)O]

Preferably, $R^4$ is independently selected from the group consisting of hydrogen methyl, ethyl, isopropyl and propyl. More preferably, $R^4$ is methyl.

In one embodiment, present invention relates to a compound of formula (II'), in particular it relates to a compound of formula (II), wherein $R^8$ is $C_1$-$C_6$alkyl and $R^7$ is a)

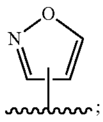

;

preferably

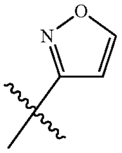

or

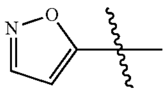

;

b)

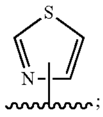

;

preferably

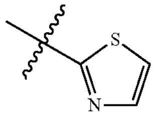

or

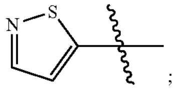

;

c)

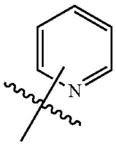

;

preferably

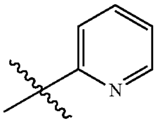

or

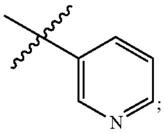

;

d)

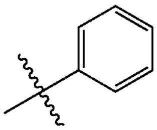

;

e)

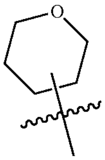

, preferably

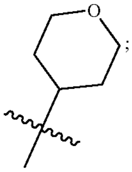

; or f)

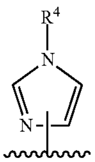

, preferably

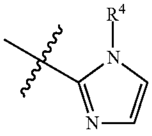

, or

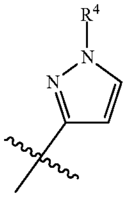

;

wherein $R^4$ is independently selected from the group consisting of hydrogen, $C_1$-$C_6$alkyl and $C_3$-$C_6$cycloalkyl;

g)
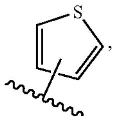,
preferably
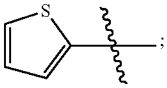;
h)
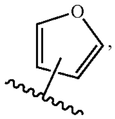,
preferably
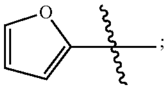 [SMILES: *c1ccco1];
i)
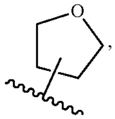,
preferably
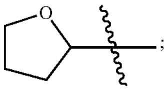 [SMILES: *C1CCCO1];
j)
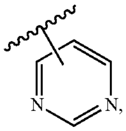,
preferably
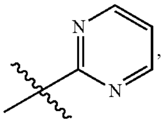, or 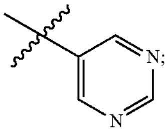; or
k)
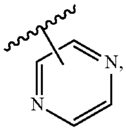,
preferably
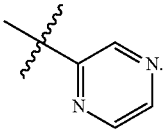 [SMILES: *c1cnccn1].
In one embodiment, present invention relates to a compound of formula (II'), in particular it relates to a compound of formula (II), wherein $R^8$ is $C_1$-$C_6$ alkyl and $R^7$ is
a)
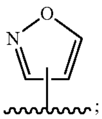;
preferably
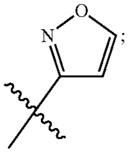 [SMILES: *c1ccon1];
b)
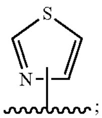;
preferably
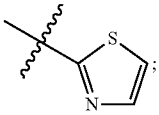 [SMILES: *c1nccs1];

c)

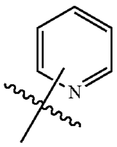;

preferably

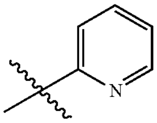 or 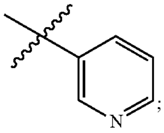;

d)

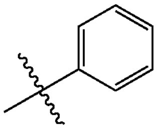;

e)

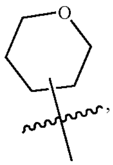, preferably

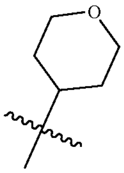; or f)

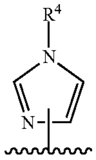, preferably

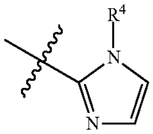

wherein $R^4$ is independently selected from the group consisting of hydrogen, $C_1$-$C_6$ alkyl and $C_3$-$C_6$ cycloalkyl.

In each of the above embodiments, $R^7$ can be optionally substituted with halogen, —O—$C_1$-$C_6$alkyl, —$C_1$-$C_6$alkyl-OH, or $C_1$-$C_6$alkyl. More preferably, $R^7$ can be optionally substituted with chloro, methoxy, methyl or isopropyl or

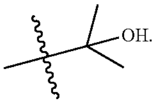 [SMILES: *C(C)(C)O]

In $R^7$, $C_1$-$C_6$alkyl is preferably methyl, ethyl, isopropyl, propyl, isobutyl or butyl and can be optionally substituted with —OH such as in

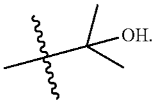 [SMILES: *C(C)(C)O]

Preferably, $R^8$ is $C_1$-$C_6$alkyl, wherein $R^8$ is preferably selected from the group consisting of methyl, ethyl, propyl, isopropyl, butyl, tert-butyl, pentyl, or hexyl. More preferably, $R^8$ is $C_1$-$C_3$alkyl. More preferably, $R^8$ is independently selected from the group consisting of methyl, ethyl, propyl or isopropyl. Even more preferably, $R^8$ is independently selected from the group consisting of ethyl or isopropyl. $R^8$ can be optionally substituted with OH.

In one embodiment, the present invention relates to a compound of formula (II'), in particular it relates to a compound of formula (II), wherein $R^8$ is $C_3$-$C_6$ cycloalkyl and $R^7$ is a)

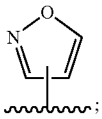;

preferably

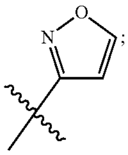 [SMILES: *c1ccon1];

b)

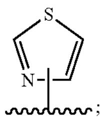

preferably

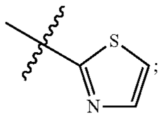 [SMILES: *c1nccs1]

c)

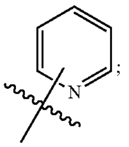

preferably

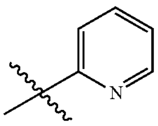

or

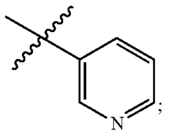

d)

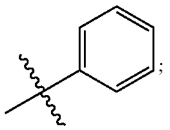 [SMILES: *c1ccccc1]

e)

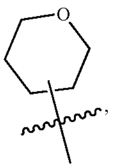

preferably

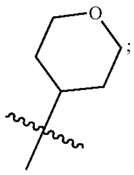

; or f)

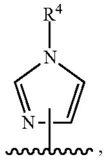

preferably

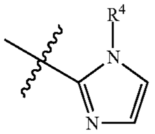

wherein $R^4$ is independently selected from the group consisting of hydrogen, $C_1$-$C_6$alkyl and $C_3$-$C_6$cycloalkyl.

In each of the above embodiments, $R^7$ can be optionally substituted with halogen, —O—$C_1$-$C_6$alkyl, —$C_1$-$C_6$alkyl-OH, or $C_1$-$C_6$alkyl. More preferably, $R^7$ can be optionally substituted with chloro, methoxy, methyl or isopropyl or

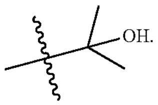 [SMILES: *C(C)(C)O]

In $R^7$, $C_1$-$C_6$alkyl is preferably methyl, ethyl, isopropyl, propyl, isobutyl or butyl and can be optionally substituted with —OH such as in

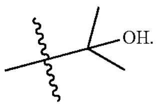 [SMILES: *C(C)(C)O]

Preferably, $R^8$ is $C_1$-$C_6$alkyl, or $C_5$-$C_6$cycloalkyl. More preferably, $R^8$ is ethyl, or cyclopentane. Even more preferably, $R^8$ is ethyl. Preferably, $R^8$ is $C_5$-$C_6$ cycloalkyl. More preferably, $R^8$ is cyclopentane. $R^8$ can be optionally substituted with OH.

Preferably, $R^4$ is independently selected from the group consisting of hydrogen, methyl, ethyl, isopropyl and propyl. More preferably, $R^4$ is methyl.

In a further embodiment, the present invention relates to a compound of formula (II), as defined below (II)

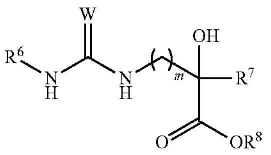

or stereoisomers, racemic mixtures, tautomers, polymorphs, pharmaceutically acceptable salts, prodrugs, hydrates, or solvates thereof; wherein W, m, $R^6$, $Z^1$, $R^9$, $R^8$, and $R^7$ are as defined in compound of formula (II') herein above.

In one embodiment, the present invention relates to a compound of formula (II), or stereoisomers, or racemic mixtures, or tautomers, or polymorph, or pharmaceutically acceptable salts, or hydrates, or solvates thereof.

In a further embodiment, the present invention relates to a compound of formula (II), as defined below (II)

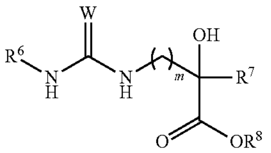

or stereoisomers, racemic mixtures, tautomers, polymorphs, pharmaceutically acceptable salts, prodrugs, hydrates, or solvates thereof;

wherein

W is independently selected from the group consisting of O and S;

m is 1 or 2;

$R^6$ is

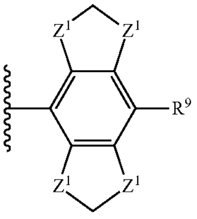

wherein $Z^1$ is independently selected from the group consisting of $CH_2$ and O provided that no more than two of $Z^1$ are O;

$R^9$ is independently selected from the group consisting of hydrogen and halogen;

$R^8$ is independently selected from the group consisting of $C_1$-$C_6$ alkyl and $C_3$-$C_6$ cycloalkyl;

$R^7$ is independently selected from the group consisting of

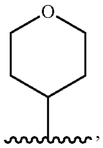, 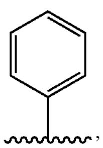, 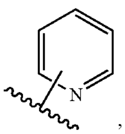, 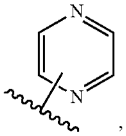,

-continued

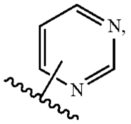 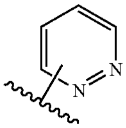, 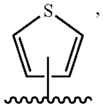, 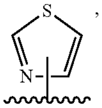,

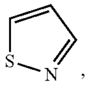, 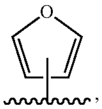, 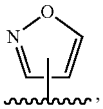, 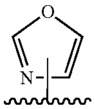, 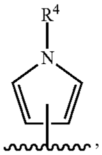,

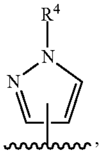, 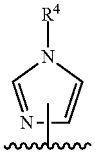, 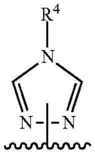 and 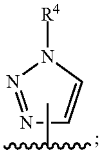;

wherein other than at the position of $R^4$, $R^7$ can be optionally substituted with halogen, $C_1$-$C_6$ alkyl or —OMe; $R^4$ is selected from the group consisting of hydrogen, $C_1$-$C_6$ alkyl and $C_3$-$C_6$ cycloalkyl;

wherein any mentioned $C_1$-$C_6$ alkyl can be optionally substituted with —OH; and $C_3$-$C_6$ cycloalkyl can be optionally substituted with —OH.

Preferably, $R^6$ is

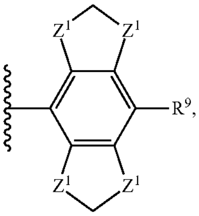

wherein $Z^1$ is $CH_2$ and $R^9$ is hydrogen or halogen.

More preferably, $R^6$ is

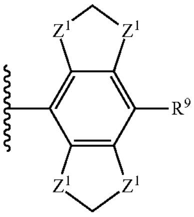

wherein $Z^1$ is $CH_2$ and $R^9$ is hydrogen or F (fluoro).

In another embodiment, the present invention relates to a compound of formula (II), wherein $R^9$ is hydrogen or halogen selected from F and $C_1$. More preferably, $R^9$ is hydrogen.

In one embodiment, the present invention relates to a compound of formula (II), wherein W is O. In one embodiment, W is preferably S.

In one embodiment, the present invention relates to a compound of formula (II), wherein m is 1.

In one embodiment, the present invention relates to a compound of formula (II), wherein $R^8$ is methyl, ethyl, propyl or cyclopropyl. More preferably, $R^8$ is ethyl.

In one embodiment, the present invention relates to a compound of formula (II), wherein $R^7$ is independently selected from the following:

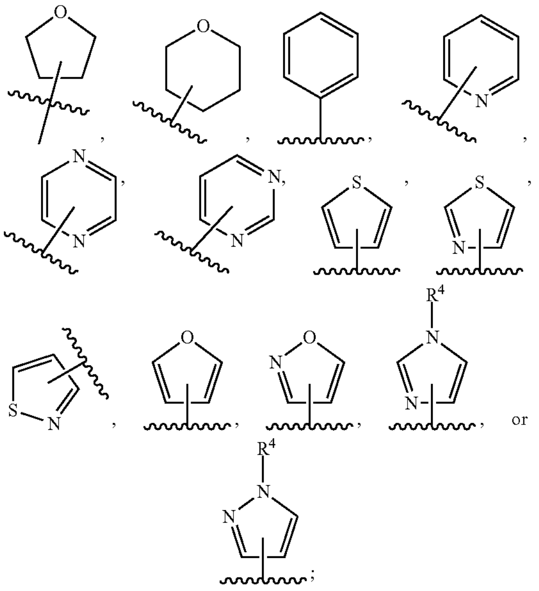

wherein $R^4$ is independently selected from the group consisting of hydrogen, $C_1$-$C_6$alkyl and $C_3$-$C_6$cycloalkyl, and wherein each of them can be optionally substituted with—$C_1$-$C_6$alkyl, —O—$C_1$-$C_6$alkyl, -Hal, or —$C_1$-$C_6$alkyl-OH.

Preferably, $R^7$ is selected from the following:

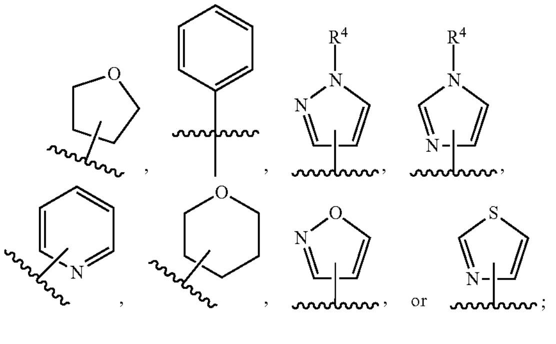

wherein $R^4$ is independently selected from the group consisting of hydrogen, $C_1$-$C_6$alkyl and $C_3$-$C_6$cycloalkyl, and wherein each of them can be optionally substituted with—$C_1$-$C_6$alkyl, —O—$C_1$-$C_6$alkyl, -Hal, or —$C_1$-$C_6$alkyl-OH.

In one embodiment, the present invention relates to a compound of formula (II), wherein $R^7$ is

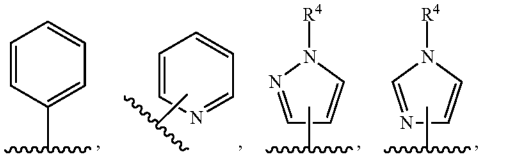

-continued

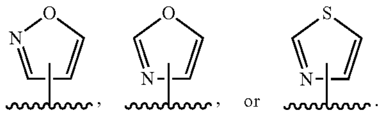

More preferably, $R^7$ is

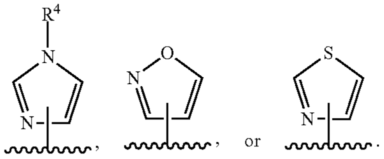

Preferably, other than at the position of $R^4$, $R^7$ can be optionally substituted with one or two of the group selected from halogen, $C_1$-$C_6$alkyl or —OMe. Preferably $R^7$ can be optionally substituted with one or two $C_1$-$C_6$alkyl which can be further optionally substituted with —OH. More preferably, $R^7$ can be optionally substituted with one or two of the group selected from —Cl, $C_1$-$C_4$alkyl or —OMe, wherein $C_1$-$C_4$alkyl can be optionally substituted with —OH. Even more preferably, $R^7$ can be optionally substituted with one or two of the group selected from —Cl, isopropyl and —OMe wherein isopropyl can be optionally substituted with —OH.

Preferably, $R^4$ is selected from the group consisting of hydrogen, and $C_1$-$C_6$alkyl. More preferably, $R^4$ is methyl or ethyl. Even more preferably, $R^4$ is methyl.

Preferably, in any of the instances of $C_1$-$C_6$alkyl, $C_1$-$C_6$alkyl can be optionally substituted with —OH.

Preferably, in any of the instances of $C_3$-$C_6$cycloalkyl, $C_3$-$C_6$cycloalkyl can be optionally substituted with —OH.

In a further embodiment, the present invention relates to stereoisomers of a compound of formula (II') which are defined as compounds of formula (IIa') or (IIb')

(IIa')

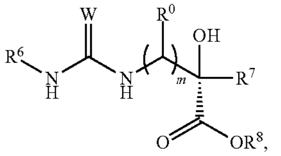

or (IIb')

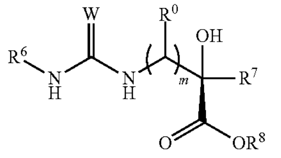

or a stereoisomer, a racemic mixture, a tautomer, a polymorph, a pharmaceutically acceptable salt, a prodrug, a hydrate, or a solvate thereof, wherein W, m, $R^6$, $R^7$, $R^0$, and $R^8$ are defined as above. Embodiments as defined for compounds of formula (II') apply here.

In a preferred embodiment, the present invention relates to stereoisomers of a compound of formula (II) which are defined as compounds of formula (IIa) or (IIb)

(IIa)

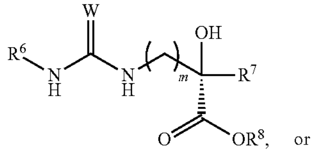

or (IIb)

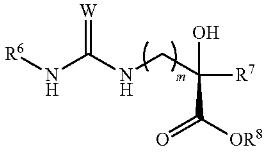

or a stereoisomer, a racemic mixture, a tautomer, a polymorph, a pharmaceutically acceptable salt, a prodrug, a hydrate, or a solvate thereof, wherein W, m, $R^6$, $R^7$ and $R^8$ are defined as above. Embodiments as defined for compounds of formula (II) apply here.

In a further embodiment, the present invention relates to the following compound of formula (II'):

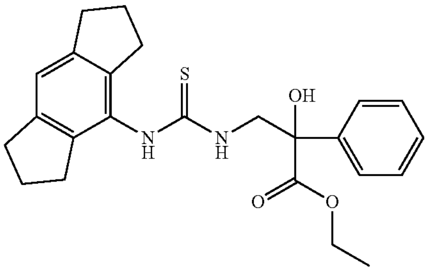

;

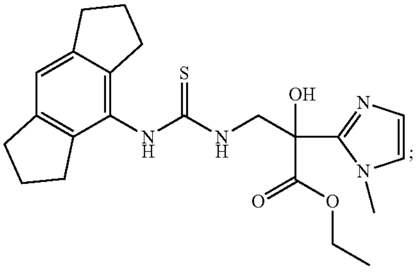 [SMILES: CCOC(=O)C(O)(CNC(=S)Nc1c2c(cc3c1CCC3)CCC2)c1nccn1C]

;

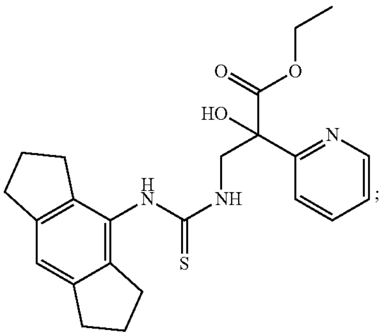 [SMILES: CCOC(=O)C(O)(CNC(=S)Nc1c2c(cc3c1CCC3)CCC2)c1ccccn1]

;

-continued

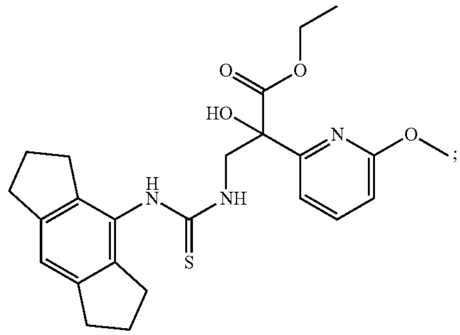 [SMILES: CCOC(=O)C(O)(CNC(=S)Nc1c2c(cc3c1CCC3)CCC2)c1cccc(OC)n1]

;

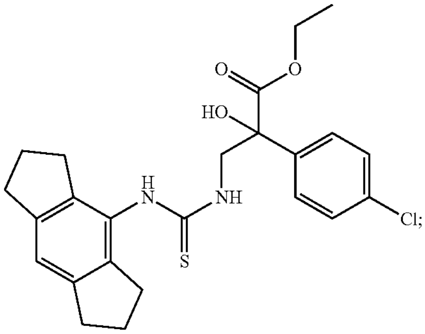 [SMILES: CCOC(=O)C(O)(CNC(=S)Nc1c2c(cc3c1CCC3)CCC2)c1ccc(Cl)cc1]

;

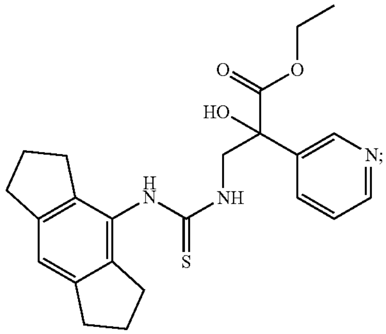 [SMILES: CCOC(=O)C(O)(CNC(=S)Nc1c2c(cc3c1CCC3)CCC2)c1cccnc1]

;

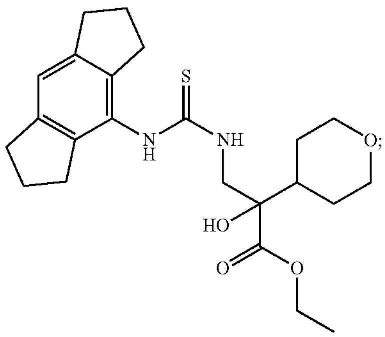 [SMILES: CCOC(=O)C(O)(CNC(=S)Nc1c2c(cc3c1CCC3)CCC2)C1CCOCC1]

;

-continued
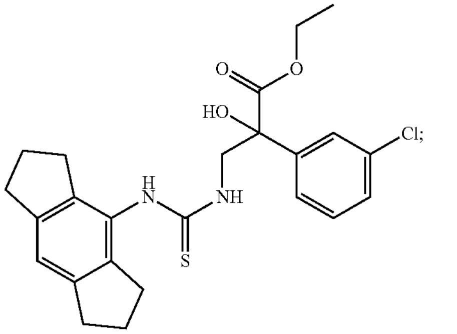 [SMILES: CCOC(=O)C(O)(CNC(=S)Nc1c2c(cc3c1CCC3)CCC2)c1cccc(Cl)c1]
;
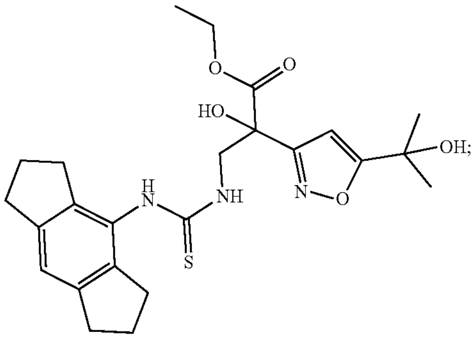 [SMILES: CCOC(=O)C(O)(CNC(=S)Nc1c2c(cc3c1CCC3)CCC2)c1cc(C(C)(C)O)on1]
;
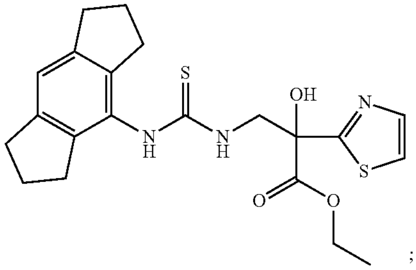 [SMILES: CCOC(=O)C(O)(CNC(=S)Nc1c2c(cc3c1CCC3)CCC2)c1nccs1]
;
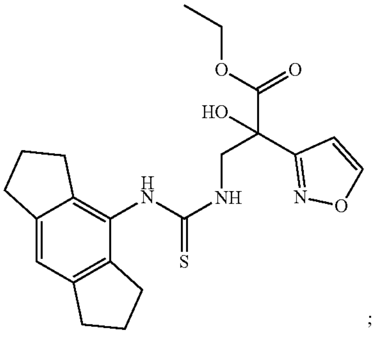 [SMILES: CCOC(=O)C(O)(CNC(=S)Nc1c2c(cc3c1CCC3)CCC2)c1ccon1]
;
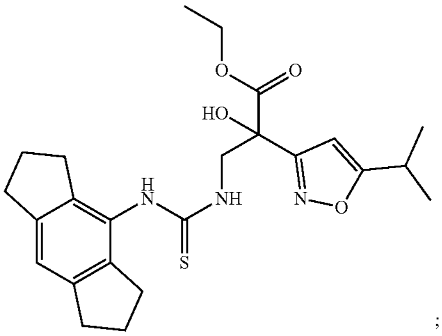 [SMILES: CCOC(=O)C(O)(CNC(=S)Nc1c2c(cc3c1CCC3)CCC2)c1cc(C(C)C)on1]
;
-continued
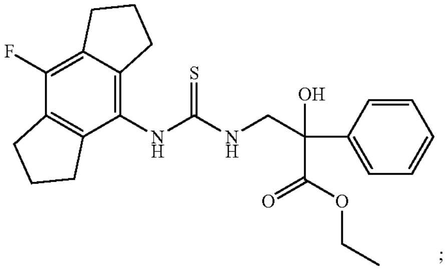 [SMILES: CCOC(=O)C(O)(CNC(=S)Nc1c2c(c(F)c3c1CCC3)CCC2)c1ccccc1]
;
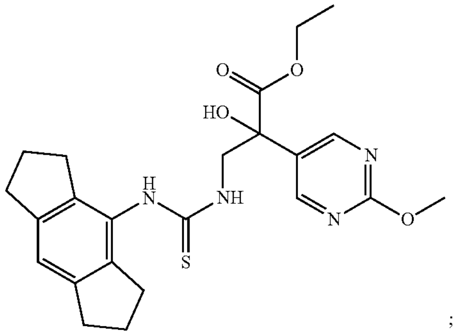 [SMILES: CCOC(=O)C(O)(CNC(=S)Nc1c2c(cc3c1CCC3)CCC2)c1cnc(OC)nc1]
;
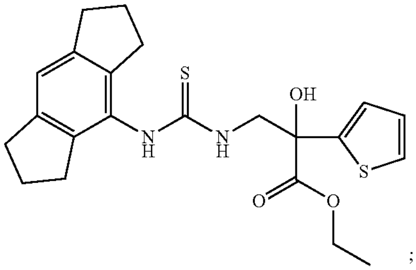
;
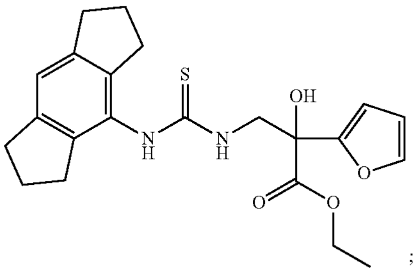 [SMILES: CCOC(=O)C(O)(CNC(=S)Nc1c2c(cc3c1CCC3)CCC2)c1ccco1]
;
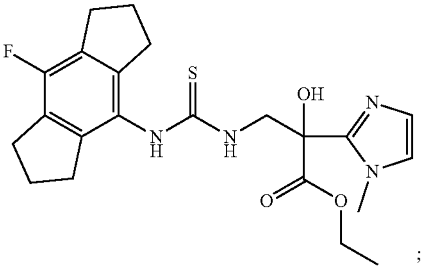 [SMILES: CCOC(=O)C(O)(CNC(=S)Nc1c2c(c(F)c3c1CCC3)CCC2)c1nccn1C]
;

-continued
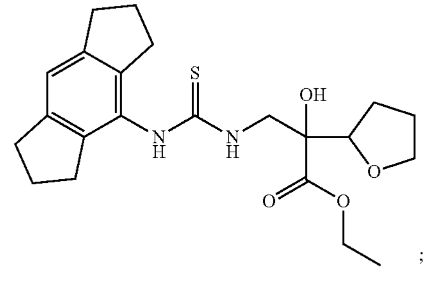 [SMILES: CCOC(=O)C(O)(CNC(=S)Nc1c2c(cc3c1CCC3)CCC2)C1CCCO1]
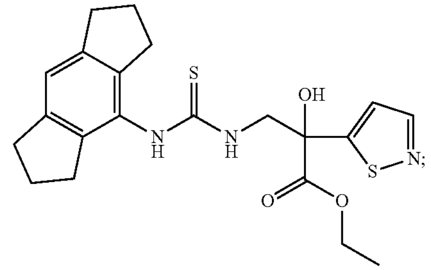 [SMILES: CCOC(=O)C(O)(CNC(=S)Nc1c2c(cc3c1CCC3)CCC2)c1ccns1]
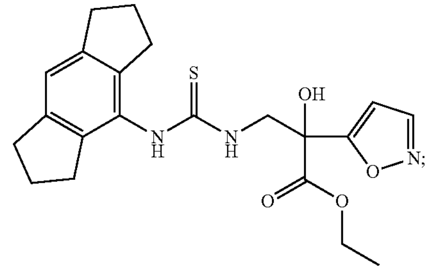 [SMILES: CCOC(=O)C(O)(CNC(=S)Nc1c2c(cc3c1CCC3)CCC2)c1ccno1]
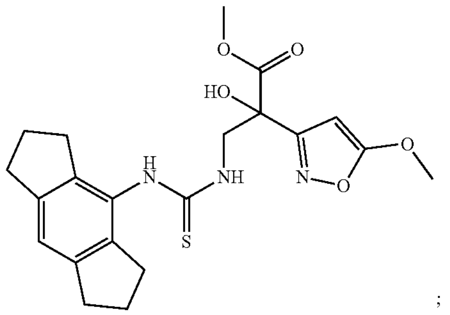 [SMILES: COC(=O)C(O)(CNC(=S)Nc1c2c(cc3c1CCC3)CCC2)c1cc(OC)on1]
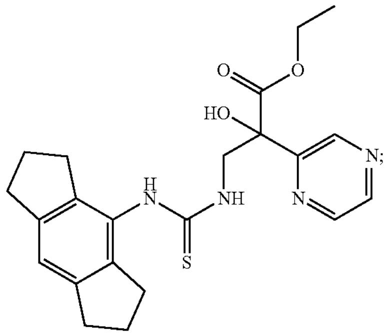 [SMILES: CCOC(=O)C(O)(CNC(=S)Nc1c2c(cc3c1CCC3)CCC2)c1cnccn1]
-continued
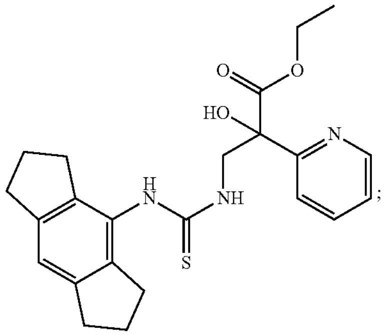 [SMILES: CCOC(=O)C(O)(CNC(=S)Nc1c2c(cc3c1CCC3)CCC2)c1ccccn1]
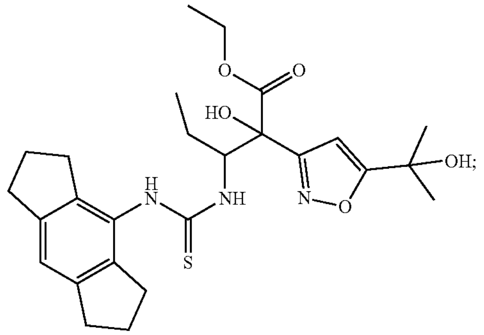 [SMILES: CCOC(=O)C(O)(c1cc(C(C)(C)O)on1)C(CC)NC(=S)Nc1c2c(cc3c1CCC3)CCC2]
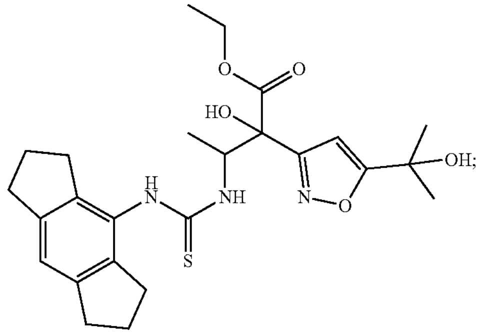 [SMILES: CCOC(=O)C(O)(c1cc(C(C)(C)O)on1)C(C)NC(=S)Nc1c2c(cc3c1CCC3)CCC2]
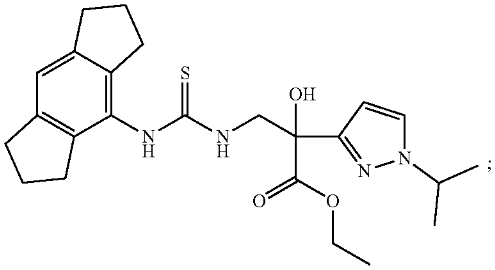 [SMILES: CCOC(=O)C(O)(CNC(=S)Nc1c2c(cc3c1CCC3)CCC2)c1ccn(C(C)C)n1]
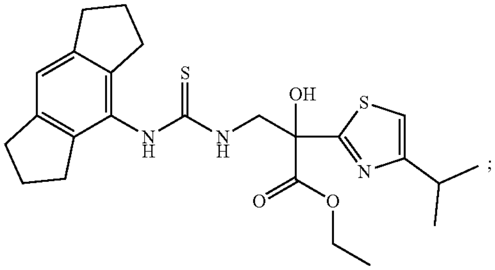 [SMILES: CCOC(=O)C(O)(CNC(=S)Nc1c2c(cc3c1CCC3)CCC2)c1nc(C(C)C)cs1]

or stereoisomers, or racemic mixtures, or tautomers, or polymorph, or pharmaceutically acceptable salts, or hydrates, or solvates thereof.
In a further embodiment, the present invention relates to the following compound of formula (II')
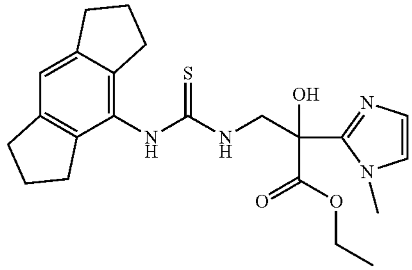
;
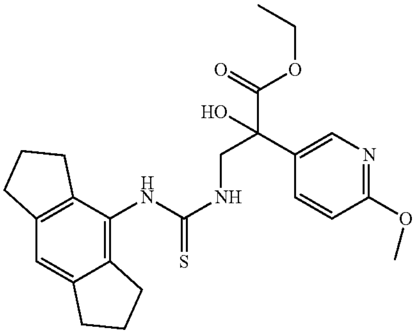
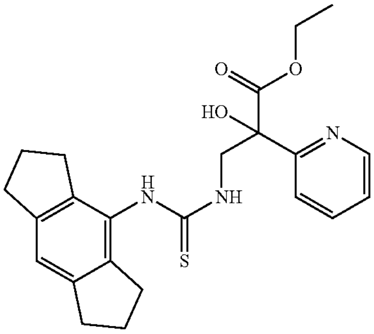
;
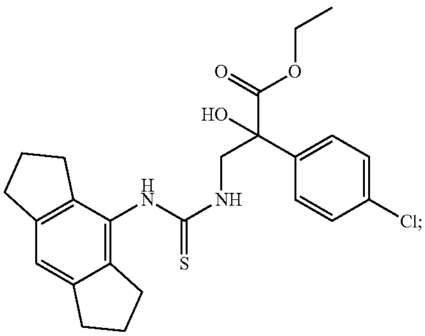
;
-continued
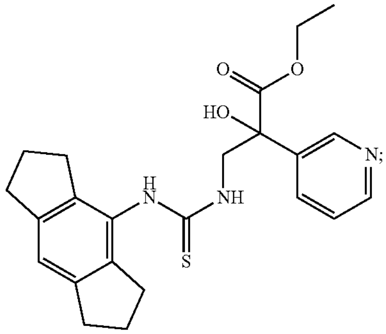
;
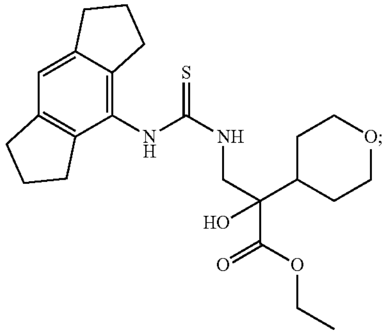
;
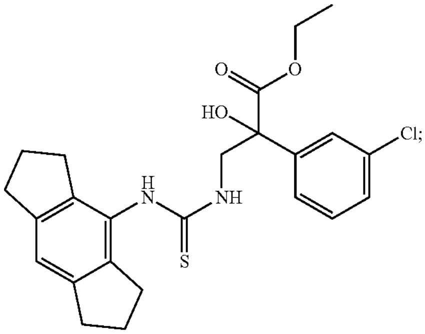
;
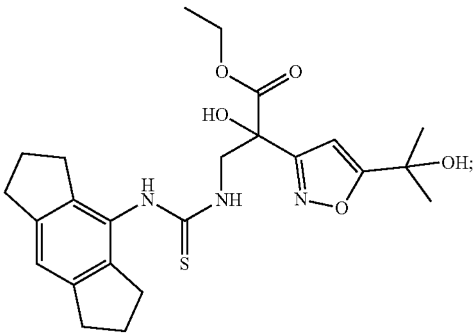
;

-continued
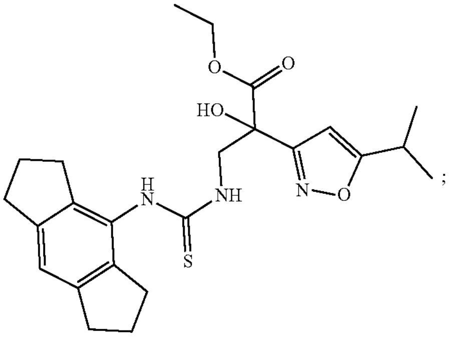
or stereoisomers, or racemic mixtures, or tautomers, or polymorph, or pharmaceutically acceptable salts, or hydrates, or solvates thereof.
In a further embodiment, the present invention relates to the following compound of formula (II')
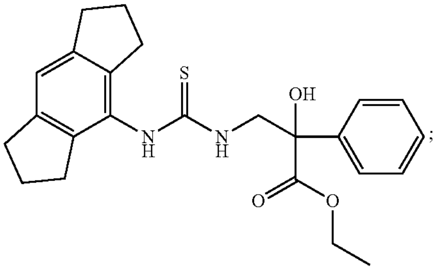
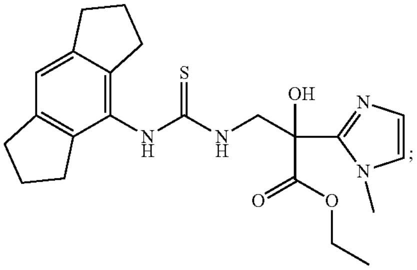
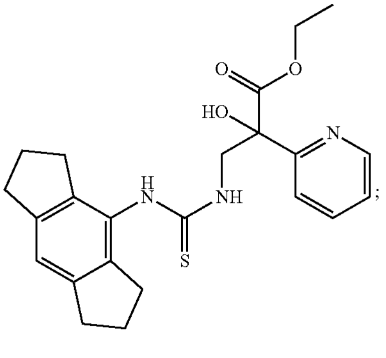
-continued
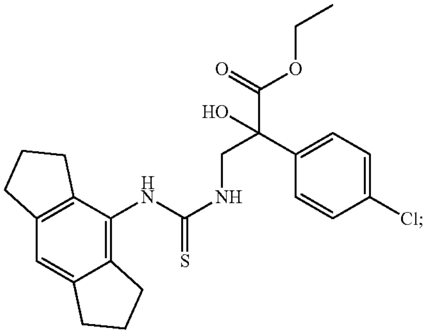 [SMILES: CCOC(=O)C(O)(CNC(=S)Nc1c2c(cc3c1CCC3)CCC2)c1ccc(Cl)cc1]
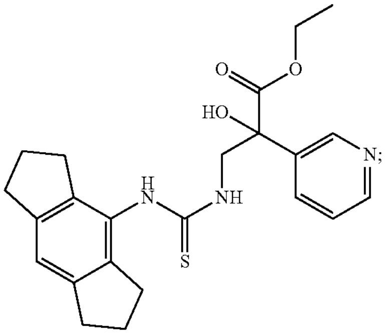 [SMILES: CCOC(=O)C(O)(CNC(=S)Nc1c2c(cc3c1CCC3)CCC2)c1cccnc1]
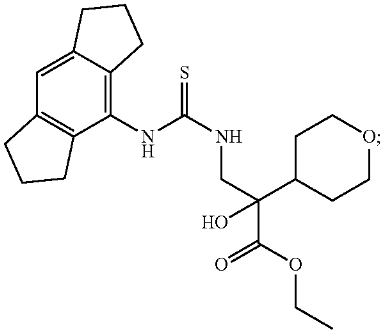 [SMILES: CCOC(=O)C(O)(CNC(=S)Nc1c2c(cc3c1CCC3)CCC2)C1CCOCC1]
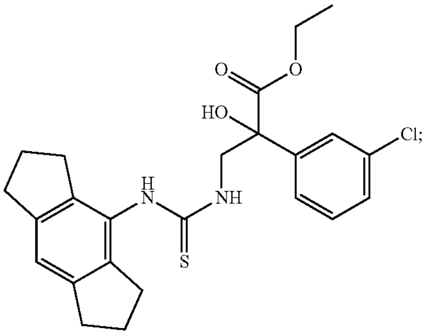 [SMILES: CCOC(=O)C(O)(CNC(=S)Nc1c2c(cc3c1CCC3)CCC2)c1cccc(Cl)c1]
and
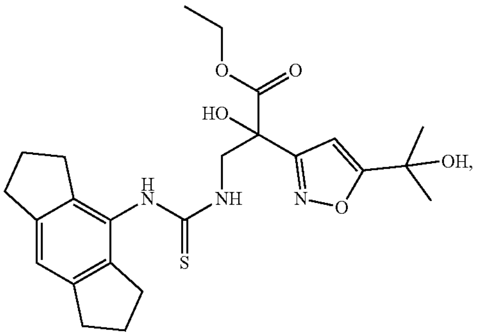 [SMILES: CCOC(=O)C(O)(CNC(=S)Nc1c2c(cc3c1CCC3)CCC2)c1cc(C(C)(C)O)on1]

or stereoisomers, or racemic mixtures, or tautomers, or polymorph, or pharmaceutically acceptable salts, or hydrates, or solvates thereof.

In a further embodiment, the present invention relates to the following compound of formula (II)

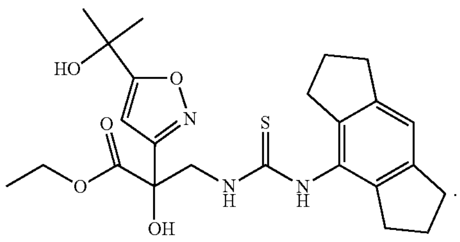 [SMILES: CCOC(=O)C(O)(CNC(=S)Nc1c2c(cc3c1CCC3)CCC2)c1cc(C(C)(C)O)on1]

The present invention relates further to a pharmaceutical composition comprising a compound of formula (I'), (I), (II'), or (II) as defined in the present invention, or a stereoisomer, a racemic mixture, a tautomer, a polymorph, a pharmaceutically acceptable salt, a prodrug, a hydrate, or a solvate thereof, and optionally at least one pharmaceutically acceptable carrier, diluent, adjuvant or excipient.

In one embodiment, the pharmaceutical composition comprises a compound of formula (I') as defined in the present invention, or a stereoisomer, a racemic mixture, a tautomer, a polymorph, a pharmaceutically acceptable salt, a prodrug, a hydrate, or a solvate thereof, and optionally at least one pharmaceutically acceptable carrier, diluent, adjuvant or excipient.

In one embodiment, the pharmaceutical composition comprises a compound of formula (I) as defined in the present invention, or a stereoisomer, a racemic mixture, a tautomer, a polymorph, a pharmaceutically acceptable salt, a prodrug, a hydrate, or a solvate thereof, and optionally at least one pharmaceutically acceptable carrier, diluent, adjuvant or excipient.

In a further embodiment, the pharmaceutical composition comprises a compound of formula (Ia'), (Ia), (Ib'), (Ib), (Ic'), (Ic), (Id'), (Id''), (Id'''), (Id), (Ie'), (Ie), (If') or (If) that are embodiments of formula (I') as defined in the present invention, or a stereoisomer, a racemic mixture, a tautomer, a polymorph, a pharmaceutically acceptable salt, a prodrug, a hydrate, or a solvate thereof, and optionally at least one pharmaceutically acceptable carrier, diluent, adjuvant or excipient.

In one embodiment, the pharmaceutical composition comprises a compound of formula (II') or (II) as defined in the present invention, or a stereoisomer, a racemic mixture, a tautomer, a polymorph, a pharmaceutically acceptable salt, a prodrug, a hydrate, or a solvate thereof, and optionally at least one pharmaceutically acceptable carrier, diluent, adjuvant or excipient.

In a further embodiment, the pharmaceutical composition comprises a compound of formula (IIa'), (IIa), (IIb'), or (IIb) that are embodiments of formula (II') as defined in the present invention, or a stereoisomer, a racemic mixture, a tautomer, a polymorph, a pharmaceutically acceptable salt, a prodrug, a hydrate, or a solvate thereof, and optionally at least one pharmaceutically acceptable carrier, diluent, adjuvant or excipient.

Embodiments as defined above for the compounds of formula (I'), (I), (Ia'), (Ia), (Ib'), (Ib), (Ic'), (Ic), (Id'), (Id'''), (Id''''), (Id), (Ie'), (Ie), (If'), or (If) and (II'), (II), (IIa'), (IIa), (IIb'), or (IIb) apply here as well and can be combined with each other.

Various embodiments of the invention are described herein, it will be recognized that features specified in each embodiment may be combined with other specified features to provide further embodiments of the present invention.

In other words, the present invention relates to a compound of formula (I'), (I), (II'), or (II) as defined in the present invention, or a stereoisomer, a racemic mixture, a tautomer, a polymorph, a pharmaceutically acceptable salt, a prodrug, a hydrate, or a solvate thereof, for use as a medicament.

The present invention relates to a compound of formula (I'), (I), (II'), or (II) as defined in the present invention, or a stereoisomer, a racemic mixture, a tautomer, a polymorph, a pharmaceutically acceptable salt, a prodrug, a hydrate, or a solvate thereof, for use in the treatment, alleviation or prevention of a disease, disorder or abnormality which is responsive to the modulation, in particular inhibition of activation, of a component of the NLRP3 inflammasome pathway and/or which is responsive to the modulation, in particular decrease, of IL-1 beta and/or IL-18 levels. In one embodiment, the modulation is the reduction and/or inhibition of IL-1 beta and/or IL-1 beta levels. Particularly, the modulation is the reduction and/or inhibition of IL-1 beta.

In another embodiment, the present invention relates to a compound of formula (I'), (I), (II'), or (II) as defined in the present invention, or a stereoisomer, a racemic mixture, a tautomer, a polymorph, a pharmaceutically acceptable salt, a prodrug, a hydrate, or a solvate thereof, for use in a method of reducing and/or inhibiting IL-1 beta. In particular, inhibiting IL-1 beta.

The present invention relates to a compound of formula (I'), (I), (II'), or (II) as defined in the present invention, or a stereoisomer, a racemic mixture, a tautomer, a polymorph, a pharmaceutically acceptable salt, a prodrug, a hydrate, or a solvate thereof, for use in the treatment, alleviation or prevention of a disease, disorder or abnormality which is responsive to the modulation, in particular inhibition of activation, of a component of the NLRP3 inflammasome pathway.

The present invention relates to a compound of formula (I'), (I), (II'), or (II) as defined in the present invention, or a stereoisomer, a racemic mixture, a tautomer, a polymorph, a pharmaceutically acceptable salt, a prodrug, a hydrate, or a solvate thereof, for use in the treatment, alleviation or prevention of a disease, disorder or abnormality which is responsive to the modulation, in particular inhibition of activation, of NLRP3 inflammasome pathway.

The present invention relates to a compound of formula (I'), (I), (II'), or (II) as defined in the present invention, or a stereoisomer, a racemic mixture, a tautomer, a polymorph, a pharmaceutically acceptable salt, a prodrug, a hydrate, or a solvate thereof, for use in the treatment, alleviation or prevention of a disease, disorder or abnormality which is responsive to the modulation, in particular decrease, of IL-1 beta and/or IL-18 levels.

In other words, the present invention relates to a method for treating, alleviating or preventing of a disease, disorder or abnormality which is responsive to the modulation, in particular inhibition of activation, of a component of the NLRP3 inflammasome pathway and/or which is responsive to the modulation, in particular decrease, of the IL-1 beta and/or IL-18 levels, wherein the method comprises administering a therapeutically effective amount of a compound of formula (I'), (I), (II'), or (II) as defined in the present invention, or a stereoisomer, a racemic mixture, a tautomer, a polymorph, a pharmaceutically acceptable salt, a prodrug, a hydrate, or a solvate thereof, to a subject in need thereof (e.g. patient).

In one embodiment, the present invention relates to a method for treating, preventing or alleviating a disease, a disorder or abnormality which is responsive to the modulation, in particular inhibition of activation, of a component of the NLRP3 inflammasome pathway, wherein the method comprises administering a therapeutically effective amount of a compound of formula (I'), (I), (II'), or (II) as defined in the present invention, or a stereoisomer, a racemic mixture, a tautomer, a polymorph, a pharmaceutically acceptable salt, a prodrug, a hydrate, or a solvate thereof, to a subject in need thereof (e.g. a patient).

The present invention further relates to a method for treating, preventing or alleviating a disease, a disorder or abnormality which is responsive to the modulation, in particular inhibition of activation, of NLRP3 inflammasome pathway, wherein the method comprises administering a therapeutically effective amount of a compound of formula (I'), (I), (II'), or (II) as defined in the present invention, or a stereoisomer, a racemic mixture, a tautomer, a polymorph, a pharmaceutically acceptable salt, a prodrug, a hydrate, or a solvate thereof, to a subject in need thereof (e.g. a patient).

In one embodiment, the present invention relates to a method for treating, preventing or alleviating a disease, disorder or abnormality responsive to a modulation, in particular a decrease, of IL-1 beta and/or IL-18 levels, wherein the method comprises administering a therapeutically effective amount of a compound of formula (I'), (I), (II'), or (II) as defined in the present invention, or a stereoisomer, a racemic mixture, a tautomer, a polymorph, a pharmaceutically acceptable salt, a prodrug, a hydrate, or a solvate thereof, to a patient in need thereof.

The present invention relates to the use of a compound of formula (I'), (I), (II'), or (II) as defined in the present invention, or a stereoisomer, a racemic mixture, a tautomer, a polymorph, a pharmaceutically acceptable salt, a prodrug, a hydrate, or a solvate thereof, for the manufacture of a medicament. In a further embodiment, the present invention relates to the use of a compound of formula (I'), (I), (II'), or (II) as defined in the present invention, or a stereoisomer, a racemic mixture, a tautomer, a polymorph, a pharmaceutically acceptable salt, a prodrug, a hydrate, or a solvate thereof, for the manufacture of a medicament for treating, alleviating or preventing a disease, disorder or abnormality which is responsive to the modulation, in particular inhibition of activation, of a component of the NLRP3 inflammasome pathway and/or which is responsive to the modulation, in particular decrease, of IL-1 beta and/or IL-18 levels. In one embodiment, the disease, disorder, or abnormality is selected from the list disclosed herein.

The present invention relates to the use of a compound of formula (I'), (I), (II'), or (II) as defined in the present invention, or a stereoisomer, a racemic mixture, a tautomer, a polymorph, a pharmaceutically acceptable salt, a prodrug, a hydrate, or a solvate thereof, for the manufacture of a medicament for treating, alleviating or preventing a disease, disorder or abnormality which is responsive to the modulation, in particular inhibition of activation, of a component of the NLRP3 inflammasome pathway.

The present invention relates to the use of a compound of formula (I'), (I), (II'), or (II) as defined in the present invention, or a stereoisomer, a racemic mixture, a tautomer, a polymorph, a pharmaceutically acceptable salt, a prodrug, a hydrate, or a solvate thereof, for the manufacture of a medicament for treating, alleviating or preventing a disease, disorder or abnormality which is responsive to the modulation, in particular inhibition of activation, of NLRP3 inflammasome pathway.

The present invention relates to the use of a compound of formula (I'), (I), (II'), or (II) as defined in the present invention, or a stereoisomer, a racemic mixture, a tautomer, a polymorph, a pharmaceutically acceptable salt, a prodrug, a hydrate, or a solvate thereof, for the manufacture of a medicament for treating, alleviating or preventing a disease, disorder or abnormality which is responsive to the modulation, in particular decrease, of IL-1 beta and/or IL-18 levels.

The present invention relates to the use of a compound of formula (I'), (I), (II'), or (II) as defined in the present invention, or a stereoisomer, a racemic mixture, a tautomer, a polymorph, a pharmaceutically acceptable salt, a prodrug, a hydrate, or a solvate thereof, for the manufacture of a medicament for reducing and/or inhibiting IL-1 beta and/or IL-1 beta levels. In one embodiment, the present invention relates to the use of a compound of the invention, as defined herein, for the manufacture of a medicament for reducing and/or inhibiting IL-1 beta. In another embodiment, the present invention relates to the use of a compound of the invention, as defined herein, for the manufacture of a medicament for reducing IL-1 beta.

In one embodiment, the present invention relates to a compound of formula (I'), (I), (II'), or (II) as defined in the present invention, or a stereoisomer, a racemic mixture, a tautomer, a polymorph, a pharmaceutically acceptable salt, a prodrug, a hydrate, or a solvate thereof, for use in the treatment, alleviation or prevention of a tauopathy by modulating a component of the inflammasome pathway, in particular, by modulating the NLRP3 inflammasome pathway.

In another embodiment, the disease, the disorder or the abnormality is responsive to modulation of one or more of IL-1β, IL-17, IL-18, IL-1 a, IL-37, IL-33 and Th17 cells, preferably: IL-1 β and IL-18.

In yet another embodiment, the disease, disorder, or abnormality is a disease, disorder, or abnormality selected from Alzheimer's disease, Parkinson's disease, cryopyrin-associated periodic syndromes (CAPS), non-alcoholic fatty liver disease (NAFLD), non-alcoholic steatohepatitis (NASH), and gout.

In a further embodiment, the disease, disorder, or abnormality is a disease, a disorder or an abnormality of the immune system. In an embodiment, the disease, disorder, or abnormality is an inflammatory disease, disorder, or abnormality. In yet another embodiment, the disease, disorder, or abnormality is an autoimmune disease, disorder, or abnormality. In yet another embodiment, the disease, the disorder, or the abnormality is a disease, a disorder, or an abnormality of the central nervous system (CNS). In yet another embodiment, the disease, the disorder, or the abnormality can be a disease, disorder or abnormality or condition of the skin. The disease, the disorder or the abnormality can be a disease, disorder or abnormality or condition of the cardiovascular system. The disease, the disorder or the abnormality or condition can be a cancer, tumor or other malignancy. The disease, the disorder or the abnormality or condition can be a disease, disorder, or abnormality of the renal system. The disease, the disorder or the abnormality or condition can be a disease, disorder, or abnormality of the gastrointestinal tract. The disease, the disorder or the abnormality or condition can be a disease, disorder, or abnormality of the respiratory system. The disease, the disorder or the abnormality or condition can be a disease, disorder, or abnormality of the endocrine system. The disease, the disorder or the abnormality or condition can be liver related disease, disorder, or abnormality.

In one embodiment, the diseases, the disorders or the abnormalities which are responsive to the modulation, in particular inhibition of activation, of a component of the NLRP3 inflammasome pathway can be selected from Alzheimer's disease, Parkinson's disease, amyotrophic lateral sclerosis, demyelination, viral encephalitis, epilepsy, stroke, atherosclerosis, asthma, allergic inflammation, cryopyrin-associated periodic syndromes (CAPS), Muckle-Wells syndrome (MWS), familial cold autoinflammatory syndrome (FCAS), neonatal-onset multisystem inflammatory disease (NOMID), gout, pseudo-gout, inflammatory bowel disease, nonalcoholic fatty liver disease, nonalcoholic steatohepatitis, hypertension, myocardial infarction, oxalate-induced nephropathy, graft-versus host disease, type 1 diabetes, type 2 diabetes, rheumatoid arthritis, myelodysplastic syndrome, familial Mediterranean fever (FMF), TNF receptor associated periodic syndrome (TRAPS), mevalonate kinase deficiency (MKD), hyperimmunoglobulinemia D, periodic fever syndrome (HIDS), deficiency of interleukin 1 receptor (DIRA) antagonist, Majeed syndrome, acne, pyogenic arthritis pyoderma gangrenosum and acne (PAPA), haploinsufficiency of A20 (HA20), PLCG2-associated antibody deficiency and immune dysregulation (PLAID), pediatric granulomatous arthritis (PGA), PLCG2-associated autoinflammation, antibody deficiency and immune dysregulation (APLAID), sideroblastic anemia with B-cell immunodeficiency, periodic fevers, developmental delay (SIFD), chronic nonbacterial osteomyelitis (CNO), Sweet's syndrome, chronic recurrent multifocal osteomyelitis (CRMO), synovitis, pustulosis, acne, eczema, alopecia areata, actinic keratosis, hyperostosis, osteitis syndrome (SAPHO), multiple sclerosis (MS), psoriasis, Behcet's disease, Sjogren's syndrome, Schnitzler syndrome, chronic obstructive pulmonary disorder (COPD), steroid-resistant asthma, asbestosis, silicosis, cystic fibrosis, motor neuron disease, Huntington's disease, cerebral malaria, brain injury from pneumococcal meningitis, obesity, age-related macular degeneration (AMD), corneal infection, uveitis, dry eye, chronic kidney disease, diabetic nephropathy, alcoholic liver disease, skin contact hypersensitivity, sunburn, osteoarthritis, systemic juvenile idiopathic arthritis, adult-onset Still's disease, relapsing polychondritis, Chikungunya virus, Ross River virus, influenza, HIV, Coronaviruses, Dengue, Zika virus, hidradenitis suppurativa (HS), lung cancer metastasis, pancreatic cancers, gastric cancers, myelodisplastic syndrome, leukemia; polymyositis, colitis, helminth infection, bacterial infection, abdominal aortic aneurism, wound healing, depression, psychological stress, pericarditis including Dressler's syndrome, ischaemia reperfusion injury, frontotemporal dementia, HIV-associated neurocognitive disorder, Coronavirus-associated inflammatory pathologies, and traumatic brain injury.

Preferably, the diseases, the disorders or the abnormalities are selected from Alzheimer's disease, Parkinson's disease, amyotrophic lateral sclerosis, demyelination, viral encephalitis, epilepsy, stroke, atherosclerosis, asthma and allergic inflammation, cryopyrin-associated periodic syndromes (CAPS), gout, inflammatory bowel disease, non-alcoholic fatty liver disease (NAFLD), non-alcoholic steatohepatitis (NASH), hypertension, myocardial infarction, oxalate-induced nephropathy, graft-versus host disease, type 1 diabetes, type 2 diabetes, rheumatoid arthritis, myelodysplastic syndrome, anti-neutrophil cytoplasmic antibody-associated vasculitis (AAV), lupus nephritis, anti-glomerular basement membrane (GMB) disease, IgA nephropathy, glomerulonephritis (GN), systemic lupus erythematosus (SLE), Focal Segmental Glomerulosclerosis, Minimal change disease (MCD), Psoriatic Arthritis, and Hereditary Recurrent Fevers (HRFs).

More preferably, the diseases, the disorders or the abnormalities are selected from Alzheimer's disease, Parkinson's disease, amyotrophic lateral sclerosis, demyelination, viral encephalitis, epilepsy, stroke, atherosclerosis, asthma and allergic inflammation, cryopyrin-associated periodic syndromes (CAPS), gout, inflammatory bowel disease, non-alcoholic fatty liver disease (NAFLD), non-alcoholic steatohepatitis (NASH), hypertension, myocardial infarction, oxalate-induced nephropathy, graft-versus host disease, type 1 and type 2 diabetes, rheumatoid arthritis, and myelodysplastic syndrome.

Even more preferably, the diseases, the disorders or the abnormalities are selected from Alzheimer's disease, Parkinson's disease, cryopyrin-associated periodic syndromes (CAPS), non-alcoholic fatty liver disease (NAFLD), non-alcoholic steatohepatitis (NASH), rheumatoid arthritis and gout. Even more preferably, the diseases, the disorders or the abnormalities are selected from Alzheimer's disease, Parkinson's disease, cryopyrin-associated periodic syndromes (CAPS), rheumatoid arthritis and gout.

In one embodiment, the present invention relates to a compound of formula (I'), (I), (II'), or (II) as defined in the present invention, or a stereoisomer, a racemic mixture, a tautomer, a polymorph, a pharmaceutically acceptable salt, a prodrug, a hydrate, or a solvate thereof, for use in the treatment, alleviation or prevention of a IL-18 and/or IL-1 beta related disease by modulating a component of the NLRP3 inflammasome pathway, in particular, by modulating NLRP3 inflammasome pathway. The IL-18 and/or IL-1 beta levels in a subject are decreased as a result of the administration of a compound of formula (I'), (I), (II'), or (II) as defined in the present invention, or a stereoisomer, a racemic mixture, a tautomer, a polymorph, a pharmaceutically acceptable salt, a prodrug, a hydrate, or a solvate thereof.

IL-18 and/or IL-1 beta related diseases, disorders or abnormalities are selected from chronic obstructive pulmonary disease (COPD), transfusion-related lung injury, bronchopulmonary dysplasia (BPD), acute respiratory distress syndrome (ARDS), pediatric autoinflammatory disease or condition, Still's disease, particularly Adult Still's disease or juvenile Still's disease, juvenile rheumatoid arthritis (JRA), juvenile idiopathic arthritis (JIA), systemic juvenile onset idiopathic arthritis (SoJIA), systemic juvenile idiopathic arthritis (sJIA), interstitial lung disease (ILD), macrophage activation syndrome (MAS) including primary, secondary and recurrent MAS, hemophagocytic lymphohistiocytosis (HLH), Familial (hereditary) hemophagocytic lymphohistiocytosis (FHLH) associated with gene defects in perforin, munc 13-4 and 18-2, synthaxin 11, immune deficiencies such as Chediak-Higashi syndrome (CHS), Griscelli syndrome (GS), X-linked lymphoproliferative syndrome (XLP2), X-linked inhibitor of apoptosis protein deficiency (XIAP), acquired hemophagocytic lymphohistiocytosis associated with infectious conditions especially Herpes virus such as EBV and other pathogens, autoinflammatory syndrome associated with NLRC4 mutations, Giant Cell Arteritis (GCA), acne, pyogenic arthritis pyoderma gangrenosum and acne (PAPA), pulmonary sarcoidosis, heart failure, ischemic heart disease, dry eye disease (DED), keratitis, corneal ulcer and abrasion, iritis, glaucoma, Sjogren's syndrome, autoimmune uveitis, Behcet's disease, conjunctivitis, allergic conjunctivitis, diabetes type 2, solid organ and hematologic stem cell transplantation, ischemia reperfusion injury, familial Mediterranean fever (FMF), tumor necrosis factor receptor 1-associated periodic syndromes (TRAPS), hyper-IgD syndromes (mevalonate kinase gene mutation), gout, Schnitzler syndrome, Wegener's granulomatosis also called granulomatosis with polyangitis (GPA), Hashimoto's thyroiditis, Crohn's disease, early onset inflammatory bowel disease (EOIBD), very EOIBD (VEOIBD), infantile IBD, neonatal IBD, ulcerative colitis and Blau syndrome (NOD-2 mutation).

The modulation of NLRP3 inflammasome pathway appears to be beneficial in diseases or disorders or abnormalities with altered IL-18 levels and/or IL-1 beta, which lead to pathological inflammation.

Embodiments as defined above for the compounds of formula (I') such as (Ia'), (Ia), (Ib'), (Ib), (Ic'), (Ic), (Id'), (Id''), (Id'''), (Id), (Ie'), (Ie), (If'), or (If) and for the compounds of formula (II') such (IIa'), (IIa), (IIb'), and (IIb) apply here as well and can be combined with each other.

The present invention relates to compound of formula (I'), (I), (II'), or (II) as defined herewith that are modulators of NLRP3 inflammasome activity and/or modulators of IL-18 and/or IL-1b levels in a subject.

In one embodiment, the invention provides a pharmaceutical composition comprising a compound of formula (I), (I), (II'), or (II) as defined in the present invention, or a stereoisomer, a racemic mixture, a tautomer, a polymorph, a pharmaceutically acceptable salt, a prodrug, a hydrate, or a solvate thereof, and at least one further biologically active compound. Optionally, the pharmaceutical combination may comprise a pharmaceutically acceptable carrier, diluent, adjuvant or excipient as described herein.

In another embodiment, the present invention relates to a pharmaceutical composition comprising a combination of a compound of formula (I'), (I), (II'), or (II) as defined in the present invention, or a stereoisomer, a racemic mixture, a tautomer, a polymorph, a pharmaceutically acceptable salt, a prodrug, a hydrate, or a solvate thereof, and at least one further biologically active compound differing from the compound of formula (I'), (I), (II'), or (II), and optionally comprising at least one pharmaceutically acceptable carrier, diluent, adjuvant or excipient.

In particular the further biologically active compound can be one used for the treatment of a disease, disorder or abnormality which targets a different pathomechanism, e.g. an anti-amyloid beta antibody, anti-Tau antibody, amyloid beta small molecule inhibitor, Tau aggregation small molecule inhibitor, anti-alpha synuclein antibody or alpha-synuclein aggregation small molecule inhibitor, anti-TDP-43 antibody or anti-TDP-43 aggregation small molecule inhibitor, among others. When a compound of the invention is used in combination with a further biologically active compound, the dose of each compound may differ from the dose if the compound is used as a monotherapy. Such biologically active compounds are well known from the literature. Such biological active compound is, for example, a chemical compound, peptide, antibody, antibody fragment, or nucleic acid, which is therapeutically active or enhances the therapeutic activity when administered to a subject (e.g., patient) in combination with a compound of the invention.

In another embodiment, the present invention relates to a pharmaceutical composition comprising a combination comprising a compound of formula (I'), (I), (II'), or (II) as defined in the present invention, or a stereoisomer, a racemic mixture, a tautomer, a polymorph, a pharmaceutically acceptable salt, a prodrug, a hydrate, or a solvate thereof, and at least one further biologically active compound differing from the compound of formula (I'), (I), (II'), or (II), and optionally comprising at least one pharmaceutically acceptable carrier, diluent, adjuvant or excipient, for use as a medicament.

The term "combination" refers to either a fixed combination in one dosage unit form, or a combined administration where a compound of the present invention and a combination partner (e.g. another drug as explained above, also referred to as "therapeutic agent" or "further biologically active compound") may be administered independently at the same time or separately within time intervals.

In another embodiment, the present invention relates to combination, in particular a pharmaceutical combination, comprising a therapeutically effective amount of a compound of formula (I'), (I), (II'), or (II) as defined in the present invention, or a stereoisomer, a racemic mixture, a tautomer, a polymorph, a pharmaceutically acceptable salt, a prodrug, a hydrate, or a solvate thereof, and at least one further biologically active compound, and optionally at least one pharmaceutically acceptable carrier, diluent, adjuvant or excipient. In particular, the at least one further biologically active compound is a compound differing from a compound of formula (I'), (I), (II'), or (II).

In another embodiment, the present invention relates to a combination comprising a therapeutically effective amount of a compound of formula (I'), (I), (II'), or (II) as defined in the present invention, or a stereoisomer, a racemic mixture, a tautomer, a polymorph, a pharmaceutically acceptable salt, a prodrug, a hydrate, or a solvate thereof, and at least one further biologically active compound differing from the compound of formula (I'), (I), (II'), or (II), and optionally comprising at least one pharmaceutically acceptable carrier, diluent, adjuvant or excipient, for use as a medicament.

The present invention relates to the use of a compound of formula (I'), (I), (II'), or (II) as defined in the present invention, or a stereoisomer, a racemic mixture, a tautomer, a polymorph, a pharmaceutically acceptable salt, a prodrug, a hydrate, or a solvate thereof, as an analytical reference or an in vitro screening tool. The compounds of the present invention, or a stereoisomer, a racemic mixture, a tautomer, a polymorph, a pharmaceutically acceptable salt, a prodrug, a hydrate, or a solvate thereof, can be used as an analytical reference or an in vitro screening tool for characterization of cells with activated NLRP3 inflammasome pathway and for testing of compounds targeting the NLRP3 inflammasome pathway.

Accordingly, the invention provides the use of a compound of formula (I'), (I), (II'), or (II) as defined in the present invention, or a stereoisomer, a racemic mixture, a tautomer, a polymorph, a pharmaceutically acceptable salt, a prodrug, a hydrate, or a solvate thereof, for treating, alleviating or preventing a disorder or an abnormality which is responsive to the modulation of a component of the NLRP3 inflammasome pathway or which is responsive to the modulation, in particular decrease, of IL-1 beta and/or IL-18 levels, wherein the medicament is prepared for administration with further biologically active agent. The invention also provides the use of further biologically active agent for treating alleviating or preventing a disorder or an abnormality which is responsive to the modulation of a component of the NLRP3 inflammasome pathway or which is responsive to the modulation, in particular decrease, of IL-1 beta and/or IL-18 levels, wherein the further biologically active agent is administered with a compound of the present invention, or a stereoisomer, a racemic mixture, a tautomer, a polymorph, a pharmaceutically acceptable salt, a prodrug, a hydrate, or a solvate thereof.

In another embodiment, the invention provides the use of a compound of formula (I'), (I), (II'), or (II) as defined in the present invention, or a stereoisomer, a racemic mixture, a tautomer, a polymorph, a pharmaceutically acceptable salt, a prodrug, a hydrate, or a solvate thereof, for treating, alleviating or preventing a disorder or an abnormality which is responsive to the modulation of a component of the NLRP3 inflammasome pathway or which is responsive to the modulation, in particular decrease, of IL-1 beta and/or IL-18 levels, wherein the modulation is the reduction and/or the inhibition of IL-1 beta and/or IL-1 beta levels. Preferably, the modulation is the reduction and/or the inhibition of IL-1 beta. Preferably, the modulation is the inhibition of IL-1 beta. In another embodiment, the invention provides a compound of formula (I'), (I), (II'), or (II) as defined in the present invention, or a stereoisomer, a racemic mixture, a tautomer, a polymorph, a pharmaceutically acceptable salt, a prodrug, a hydrate, or a solvate thereof, for use as a medicament, in particular for inhibiting IL-1_beta.

In another embodiment, the invention also provides a compound of formula (I'), (I), (II'), or (II) as defined in the present invention, or a stereoisomer, a racemic mixture, a tautomer, a polymorph, a pharmaceutically acceptable salt, a prodrug, a hydrate, or a solvate thereof, for use in a method of treating, alleviating or preventing a disease, disorder or abnormality which is responsive to the modulation of a component of the NLRP3 inflammasome pathway or which is responsive to the modulation, in particular decrease, of IL-1 beta and/or IL-18 levels, wherein said compound of formula (I'), (I), (II'), or (II) is prepared for administration with further biologically active compound (as defined herein).

In another embodiment, the present invention also provides a method of treating alleviating or preventing a disease, disorder or abnormality which is responsive to the modulation of a component of the NLRP3 inflammasome pathway or which is responsive to the modulation, in particular decrease, of IL-1 beta and/or IL-18 levels, selected from Alzheimer's disease, Parkinson's disease, amyotrophic lateral sclerosis, demyelination, viral encephalitis, epilepsy, stroke, atherosclerosis, asthma, allergic inflammation, cryopyrin-associated periodic syndromes (CAPS), Muckle-Wells syndrome (MWS), familial cold autoinflammatory syndrome (FCAS), neonatal-onset multisystem inflammatory disease (NOMID), gout, pseudo-gout, inflammatory bowel disease, nonalcoholic fatty liver disease, nonalcoholic steatohepatitis, hypertension, myocardial infarction, oxalate-induced nephropathy, graft-versus host disease, type 1 diabetes, type 2 diabetes, rheumatoid arthritis, myelodysplastic syndrome, familial Mediterranean fever (FMF), TNF receptor associated periodic syndrome (TRAPS), mevalonate kinase deficiency (MKD), hyperimmunoglobulinemia D, periodic fever syndrome (HIDS), deficiency of interleukin 1 receptor (DIRA) antagonist, Majeed syndrome, acne, pyogenic arthritis pyoderma gangrenosum and acne (PAPA), haploinsufficiency of A20 (HA20), PLCG2-associated antibody deficiency and immune dysregulation (PLAID), pediatric granulomatous arthritis (PGA), PLCG2-associated autoinflammation, antibody deficiency and immune dysregulation (APLAID), sideroblastic anemia with B-cell immunodeficiency, periodic fevers, developmental delay (SIFD), chronic nonbacterial osteomyelitis (CNO), Sweet's syndrome, chronic recurrent multifocal osteomyelitis (CRMO), synovitis, pustulosis, acne, eczema, alopecia areata, actinic keratosis, hyperostosis, osteitis syndrome (SAPHO), multiple sclerosis (MS), psoriasis, Behcet's disease, Sjogren's syndrome, Schnitzler syndrome, chronic obstructive pulmonary disorder (COPD), steroid-resistant asthma, asbestosis, silicosis, cystic fibrosis, motor neuron disease, Huntington's disease, cerebral malaria, brain injury from pneumococcal meningitis, obesity, age-related macular degeneration (AMD), corneal infection, uveitis, dry eye, chronic kidney disease, diabetic nephropathy, alcoholic liver disease, skin contact hypersensitivity, sunburn, osteoarthritis, systemic juvenile idiopathic arthritis, adult-onset Still's disease, relapsing polychondritis, Chikungunya virus, Ross River virus, influenza, HIV, Coronaviruses, Dengue, Zika virus, hidradenitis suppurativa (HS), lung cancer metastasis, pancreatic cancers, gastric cancers, myelodisplastic syndrome, leukemia; polymyositis, colitis, helminth infection, bacterial infection, abdominal aortic aneurism, wound healing, depression, psychological stress, pericarditis including Dressler's syndrome, ischaemia reperfusion injury, frontotemporal dementia, HIV-associated neurocognitive disorder, Coronavirus-associated inflammatory pathologies, and traumatic brain injury; preferably the disorder is selected from Alzheimer's disease, Parkinson's disease, amyotrophic lateral sclerosis, demyelination, viral encephalitis, epilepsy, stroke, atherosclerosis, asthma, allergic inflammation, cryopyrin-associated periodic syndromes (CAPS), gout, inflammatory bowel disease, non-alcoholic fatty liver disease (NAFLD), non-alcoholic steatohepatitis (NASH), hypertension, myocardial infarction, oxalate-induced nephropathy, graft-versus host disease, type 1 diabetes, type 2 diabetes, rheumatoid arthritis, myelodysplastic syndrome, anti-neutrophil cytoplasmic antibody-associated vasculitis (AAV), lupus nephritis, anti-glomerular basement membrane (GMB) disease, IgA nephropathy, glomerulonephritis (GN), systemic lupus erythematosus (SLE), Focal Segmental Glomerulosclerosis, Minimal change disease (MCD), Psoriatic Arthritis, and Hereditary Recurrent Fevers (HRFs), comprising administering to the subject a therapeutically effective amount of a compound of formula (I'), (I), (II') or (II), as defined herein, or stereoisomers, or racemic mixtures, or tautomers, or polymorph, or pharmaceutically acceptable salts, or hydrates, or solvates thereof.

In another embodiment, the present invention also provides a method of inhibiting IL-1 beta in a subject in need, the method comprising administering to a subject in need thereof a therapeutically effective amount of a compound of formula (I'), (I), (II') or (II), or a stereoisomer, a racemic mixture, a tautomer, a polymorph, a pharmaceutically acceptable salt, a prodrug, a hydrate, or a solvate thereof.

In particular, the disease, disorder or abnormality is one which is responsive to the inhibition of activation of the NLRP3 inflammasome pathway. More particularly, the disease, disorder or abnormality is responsive to the modulation of one or more of, for example, but not limited to, IL-1 β or IL-18. For example, the disease, disorder, or abnormality is responsive to the modulation of one or more of IL-1β, IL-17, IL-18, IL-1 a, IL-37, IL-33 and Th17 cells, preferably the disease, disorder, or abnormality is responsive to the modulation of IL-1β and/or IL-18.

Method of Synthesizing the Compounds of the Present Invention

The compounds of the present invention can be prepared in accordance with the definition of a compound of formula (I'), (I), (II'), or (II) as disclosed herein, by the synthesis routes described in the following schemes or examples. All methods described herein can be performed in any suitable order unless otherwise indicated herein or otherwise clearly contradicted by the context. The use of any and all examples, or exemplary language (e.g. such as, preferably) provided herein is intended merely to better illustrate the invention and does not pose a limitation on the scope of the invention otherwise claimed.

In the following general methods, $R^0$, $R^1$, $R^2$, $R^3$, $R^4$, $R^5$, $R^6$, $R^7$, $R^8$, X, Y, W, and n are as previously defined in the above embodiments or limited to the designation in the schemes. Unless otherwise stated, starting materials are either commercially available or prepared via know methods.

The present invention relates to a method for preparing a compound of formula (I'), (I), (II'), or (II), as disclosed herein. Preferably, the method is for preparing a compound of formula (I') or any of the sub-embodiments as disclosed above, more preferably a compound of formula (I), even more preferably a compound of formula (Ic). In a further embodiment, the method is preferably for preparing a compound of formula (II'), compound of formula (II), or any of the sub-embodiments as disclosed above.

In one embodiment, the method comprises the step of cyclization of a compound of formula (II') for preparing a compound of formula (I') in the presence of a condensation agent:

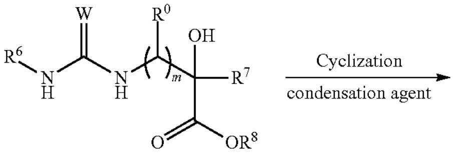

(II')

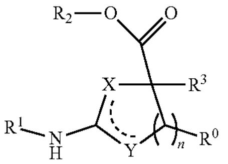

(I')

wherein $R^6$, W, m, n, $R^7$, $R^8$, X, Y, $R^1$, $R^2$, $R^0$, and $R^3$ are as defined above.

In one embodiment, the method comprises the step of cyclization of a compound of formula (II) for preparing a compound of formula (I) in the presence of a condensation agent:

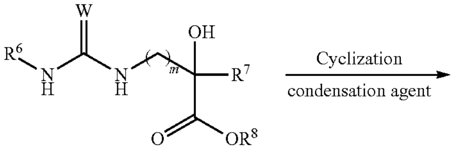

(II)

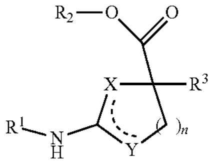

(I)

wherein $R^6$, W, m, n, $R^7$, $R^8$, X, Y, $R^1$, $R^2$ and $R^3$ are as defined above.

Preferably, the present method comprises the step of cyclization of a compound of formula (II) for preparing a compound of formula (I) in the presence of a condensation agent.

The condensation agent is used for cyclization of a compound of formula (II) for preparing a compound of formula (I) in the presence of a base. The base is preferably trimethylamine ($Et_3N$). The condensation agent is preferably N-(3-dimethylaminopropyl)-N'-ethylcarbodiimide (EDC), mukaiyama reagent, iodomethane or TsCl. The cyclization is conducted preferably at room temperature (rt).

In a further embodiment, the method comprises the step of cyclization of a compound of formula (II) for preparing a compound of formula (Ic) in the presence of a condensation agent:

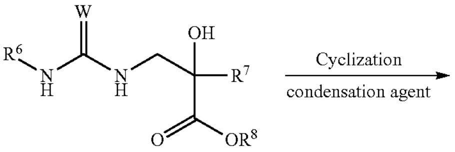

(II)

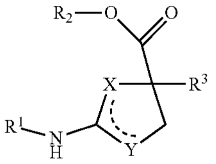

(Ic)

wherein $R^6$, W, $R^7$, $R^8$, X, Y, $R^1$, $R^2$ and $R^3$ are as defined above.

Preferably, the present method comprises a cyclization step of the compound of formula (II') for preparing a compound of formula (I') in the presence of a condensation agent. More preferably, the present method comprises a cyclization step of the compound of formula (II) for preparing a compound of formula (I) in the presence of a condensation agent.

The condensation agent is used for cyclization of a compound of formula (II') for preparing a compound of formula (I') in the presence of a base. The base is preferably trimethylamine ($Et_3N$). The condensation agent is preferably N-(3-dimethylaminopropyl)-N'-ethylcarbodiimide (EDC), mukaiyama reagent, iodomethane or TsCl. The cyclization is conducted preferably at room temperature (rt).

In one embodiment, the method for preparing a compound of formula (II') comprises the step of coupling a compound of formula (III') with a urea or thiourea derivative of formula (IV) in presence of a solvent and a base

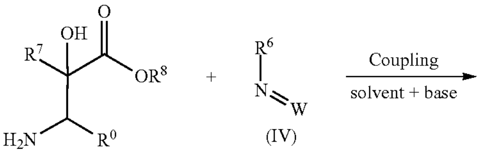

(III') (IV)

-continued

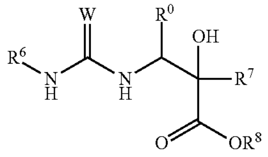

(II')

wherein $R^6$, W, $R^7$, $R^0$, and $R^8$ are as defined above.

In one embodiment, the method for preparing a compound of formula (II) comprises the step of coupling a compound of formula (III) with a urea or thiourea derivative of formula (IV) in presence of a solvent and a base

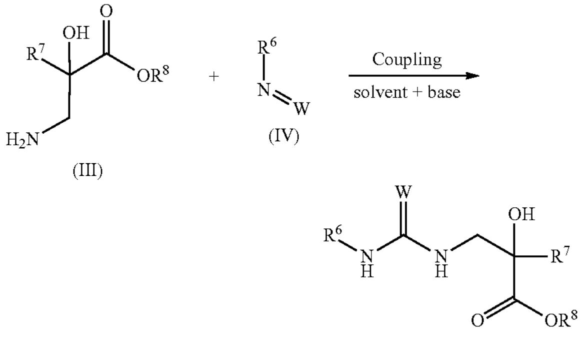

(III) (IV) (II)

wherein $R^6$, W, $R^7$ and $R^8$ are as defined above.

The solvent is preferably dichloromethane (DCM). The base is preferably trimethylamine ($Et_3N$). The coupling reaction is preferably conducted at room temperature (rt).

In one embodiment, the method comprises the step of cyclization of a compound of formula (II') for preparing a compound of formula (I') in the presence of a condensation agent

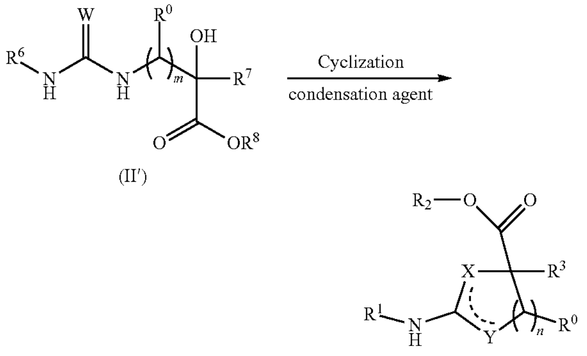

(II') (I')

wherein $R^6$, W, m, n, $R^7$, $R^8$, X, Y, $R^1$, $R^2$, $R^0$ and $R^3$ are as defined above; followed by a step of saponification for preparing a compound of formula (I') wherein X, Y, $R^0$, $R^1$, and $R^3$ are as defined above and $R^2$ is hydrogen in the presence of a saponification agent.

In a preferred embodiment, the method comprises the step of cyclization of a compound of formula (II) for preparing a compound of formula (I) in the presence of a condensation agent

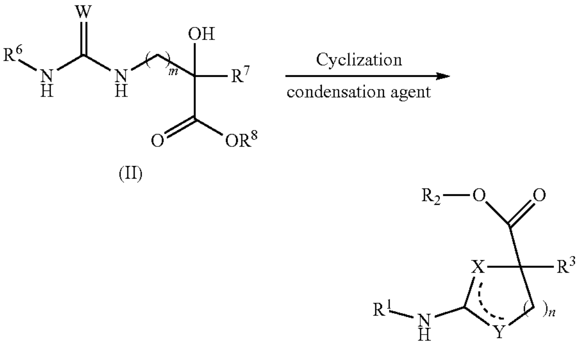

(II) (I)

wherein $R^6$, W, m, n, $R^7$, $R^8$, X, Y, $R^1$, $R^2$ and $R^3$ are as defined above; followed by a step of saponification for preparing a compound of formula (I) wherein X, Y, $R^1$, and $R^3$ are as defined above and $R^2$ is hydrogen in the presence of a saponification agent.

Any combination of the embodiments, preferred embodiments and more preferred embodiments disclosed herein is also envisaged in the present invention.

Pharmaceutical Compositions

While it is possible for the compounds of the present invention, or a stereoisomer, a racemic mixture, a tautomer, a polymorph, a pharmaceutically acceptable salt, a prodrug, a hydrate, or a solvate thereof, to be administered alone, it is preferable to formulate them into a pharmaceutical composition in accordance with standard pharmaceutical practice. Thus, the invention also provides a pharmaceutical composition which comprises a therapeutically effective amount of a compound of formula (I'), (I), (II'), or (II), or a stereoisomer, a racemic mixture, a tautomer, a polymorph, a pharmaceutically acceptable salt, a prodrug, a hydrate, or a solvate thereof, optionally in admixture with a pharmaceutically acceptable carrier, diluent, adjuvant or excipient.

The term "a therapeutically effective amount" of a compound of the present invention refers to an amount of the compound of the present invention (e.g. a compound of formula (I'), (I), (II') or a compound of formula (II), or a stereoisomer, a racemic mixture, a tautomer, a polymorph, a pharmaceutically acceptable salt, a prodrug, a hydrate, or a solvate thereof) that will elicit the biological or medical response of a subject, for example, reduction or inhibition of an enzyme or a protein activity, or ameliorate symptoms, alleviate conditions, slow or delay disease progression, or prevent a disease, a disorder or an abnormality, etc. In one embodiment, the term "a therapeutically effective amount" refers to the amount of the compound of the present invention that, when administered to a subject in need thereof (e.g. a patient), is effective to at least partially alleviate, prevent and/or ameliorate a disease, a disorder, or an abnormality which is responsive to the modulation of a component of the NLRP3 inflammasome pathway or which is responsive to the modulation, in particular decrease, of IL-1 beta and/or IL-18.

Pharmaceutically acceptable carriers, diluents, adjuvants and excipients are well known in the pharmaceutical art and are described, for example, in Remington's Pharmaceutical Sciences, 18th Ed. (Alfonso R. Gennaro, ed.; Mack Publishing Company, Easton, PA, 1990); Remington: the Science and Practice of Pharmacy 19th Ed. (Lippincott, Williams & Wilkins, 1995); Handbook of Pharmaceutical Excipients, $3^{rd}$ Ed. (Arthur H. Kibbe, ed.; Amer. Pharmaceutical Assoc, 1999); Pharmaceutical Codex: Principles and Practice of Pharmaceutics 12th Ed. (Walter Lund ed.; Pharmaceutical Press, London, 1994); The United States Pharmacopeia: The National Formulary (United States Pharmacopeial Convention); Fiedler's "Lexikon der Hilfsstoffe" 5th Ed., Edition Cantor Verlag Aulendorf 2002; "The Handbook of Pharmaceutical Excipients", 4th Ed., American Pharmaceuticals Association, 2003; and Goodman and Gilman's: the Pharmacological Basis of Therapeutics (Louis S. Goodman and Lee E. Limbird, eds.; McGraw Hill, 1992), the disclosures of which are hereby incorporated by reference.

The carriers, diluents, adjuvants and pharmaceutical excipients can be selected with regard to the intended route of administration and standard pharmaceutical practice. These compounds must be acceptable in the sense of being not deleterious to the recipient thereof.

Pharmaceutically useful excipients that may be used in the formulation of the pharmaceutical composition of the present invention may comprise, for example, vehicles, solvents (such as monohydric alcohols such as ethanol, isopropanol and polyhydric alcohols such as glycols), edible oils (such as soybean oil, coconut oil, olive oil, safflower oil, and cottonseed oil), oily esters (such as ethyl oleate and isopropyl myristate), binders (such as hydroxypropylmethyl cellulose (HPMC), hydroxypropyl cellulose (HPC), pregelatinized starch and combinations thereof), solubilizers, thickening agents, stabilizers, disintegrants (such as carboxymethylcellulose calcium (CMC-Ca), carboxymethylcellulose sodium (CMC-Na), crosslinked PVP (e.g., crospovidone, Polyplasdone® or Kollidon® XL), alginic acid, sodium alginate, guar gum, cross-linked CMC (croscarmellose sodium, e.g. Ac-Di-Sol®), carboxymethyl starch-Na (sodium starch glycolate) (e.g., Primojel® or Explotab®), preferably crosslinked PVP and/or croscarmellose sodium), glidants (such as colloidal $SiO_2$ (e.g., Aerosil® 200), magnesium trisilicate, powdered cellulose, talc and combinations thereof), lubricating agents (such as magnesium stearate, aluminium or calcium silicate, stearic acid, hydrogenated castor oil, talc, glyceryl behenate, sodium stearate fumarate and combinations thereof), buffering agents, emulsifiers, wetting agents, suspending agents, sweetening agents, colorants, flavors, coating agents, preservatives, antioxidants, processing agents, drug delivery modifiers and enhancers (such as calcium phosphate), magnesium stearate, talc, monosaccharides, disaccharides, starch, gelatine, cellulose, methylcellulose, sodium carboxymethyl cellulose, dextrose, hydroxypropyl-β-cyclodextrin, polyvinylpyrrolidone, low melting waxes, and ion exchange resins.

The carrier is not particularly limited and will depend on the route of administration as well as the form of the pharmaceutical composition (i.e., solid, liquid, etc.). Suitable carriers include, without limitation, polyols such as mannitol, sorbitol, xylitol; disaccharides such as lactose, sucrose, dextrose and maltose; polysaccharides such as maltodextrine and dextranes; starches such as corn starch; celluloses such as microcrystalline cellulose, sodium carboxy methylcellulose, low-substituted hydroxypropyl cellulose, hydroxyl ethyl cellulose, hydroxypropyl cellulose or mixtures thereof; cylodextrines and inorganic agents such as dicalcium phosphate, calcium hydrogen phosphate; hydroxyapatite, tricalcium phosphate, talcum and silica. Microcrystalline cellulose, sucrose and/or lactose are preferred as carriers. Combinations thereof can also be employed. Carriers can include also protein and cell penetrating peptides which should be selected depending on the route of administration and target.

The diluent is not particularly limited and will depend on the route of administration as well as the form of the pharmaceutical composition (i.e., solid, liquid, etc.). Diluents include, for instance, water, ethanol, propylene glycol and glycerin, and combinations thereof.

An adjuvant is an additive which has few or no pharmacological effects by themselves, but that increases the efficacy or potency of the compounds of the invention if they are administered together.

The routes for administration (delivery) of the compounds of the invention include, but are not limited to, one or more of the following routes of administration: oral (e.g., as a tablet, capsule, or as an ingestible solution), topical, mucosal (e.g. as a nasal spray or aerosol for inhalation), nasal, parenteral (e.g., by an injectable form), gastrointestinal, intraspinal, intraperitoneal, intramuscular, intravenous, intraarterial, intrathecal, intrauterine, intraocular, intradermal, intracranial, intratracheal, intravaginal, intracerebroventricular, intracerebral, subcutaneous, ophthalmic (including intravitreal or intracameral), transdermal, rectal, buccal, epidural and sublingual.

For example, the compounds can be administered orally in the form of tablets, capsules, ovules, elixirs, solutions or suspensions, which may contain flavoring or coloring agents, for immediate-, delayed-, modified-, sustained-, pulsed- or controlled-release applications.

The tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxypropylcellulose (HPC), sucrose, gelatine and acacia. Additionally, lubricating agents such as magnesium stearate, stearic acid, glyceryl behenate and talc may be included. Solid compositions of a similar type may also be employed as fillers in gelatine capsules. Preferred excipients in this regard include starch, cellulose, milk sugar e.g. lactose or high molecular weight polyethylene glycols. For aqueous suspensions and/or elixirs, the agent may be combined with various sweetening or flavoring agents, coloring matter or dyes, with emulsifying and/or suspending agents and with diluents such as water, ethanol, propylene glycol and glycerin, and combinations thereof.

If the compounds of the present invention, as disclosed herein, are administered parenterally, then examples of such administration include one or more of: intravenously, intraarterially, intraperitoneally, intrathecally, intraventricularly, intraurethrally, intrasternally, intracranially, intramuscularly or subcutaneously administering the compounds; and/or by using infusion techniques. For parenteral administration, the compounds can be used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

As indicated, the compounds of the present invention can be administered intranasally or by inhalation and are conveniently delivered in the form of a dry powder inhaler or an aerosol spray presentation from a pressurized container, pump, spray or nebulizer with the use of a suitable propellant, e.g. dichlorodifluoromethane, trichlorofluoromethane, dichlorotetrafluoroethane, a hydrofluoroalkane such as 1,1,1,2-tetrafluoroethane (HFA134AT) or 1,1,1,2,3,3,3-heptafluoropropane (HFA 227EA), carbon dioxide or other suitable gas. In the case of a pressurized aerosol, the dosage unit may be determined by providing a valve to deliver a metered amount. The pressurized container, pump, spray or nebulizer may contain a solution or suspension of the active compound, e. g. using a mixture of ethanol and the propellant as the solvent, which may additionally contain a lubricant, e. g. sorbitan trioleate. Capsules and cartridges (made, for example, from gelatine) for use in an inhaler or insufflator may be formulated to contain a powder mix of the compound and a suitable powder base such as lactose or starch.

Alternatively, the compounds of the present invention, as defined herein, can be administered in the form of a suppository or pessary, or it may be applied topically in the form of a gel, hydrogel, lotion, solution, cream, ointment or dusting powder. The compounds of the present invention, as defined herein, may also be dermally or transdermally administered, for example, by the use of a skin patch.

They may also be administered by the pulmonary or rectal routes. They may also be administered by the ocular route. For ophthalmic use, the compounds can be formulated as micronized suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the compounds of the present invention can be formulated as a suitable ointment containing the active compound suspended or dissolved in, for example, a mixture with one or more of the following: mineral oil, liquid petrolatum, white petrolatum, propylene glycol, emulsifying wax and water. Alternatively, they can be formulated as a suitable lotion or cream, suspended or dissolved in, for example, a mixture of one or more of the following: mineral oil, sorbitan monostearate, polyethylene glycol, liquid paraffin, polysorbate 60, cetyl ester wax, cetearyl alcohol, 2-octyldodecanol, benzyl alcohol and water.

Typically, a physician will determine the actual dosage which will be most suitable for an individual subject. The specific dose level and frequency of dosage for any particular individual may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy.

The claimed compounds, as defined herein, can be used for the treatment, alleviation or prevention of the recited conditions alone or in combination with one or more other biologically active compounds, as defined herein. In particular, the other biologically active compound can be one used for the treatment, alleviation, or prevention of the recited diseases.

The combinations referred to above may conveniently be presented for use in the form of a pharmaceutical formulation. The individual components of such combinations may be administered either sequentially or simultaneously in separate or combined pharmaceutical formulations by any convenient route. When administration is sequential, either the compound of the invention or the other biologically active compound may be administered first. When administration is simultaneous, the combination may be administered either in the same or different pharmaceutical composition. When combined in the same formulation it will be appreciated that the two compounds must be stable and compatible with each other and the other components of the formulation. When formulated separately they may be provided in any convenient formulation, conveniently in such manners as are known for such compounds in the art.

The pharmaceutical compositions of the invention can be produced in a manner known per se to the skilled person as described, for example, in Remington's Pharmaceutical Sciences, 15th Ed., Mack Publishing Co., New Jersey (1975).

The compounds according to the present invention, as disclosed herein, can also be provided in the form of a mixture with at least one further biologically active compound and/or a pharmaceutically acceptable carrier, diluent, adjuvant, or excipient. The compound and/or the further biologically active compound are preferably present in a therapeutically effective amount.

The nature of the further biologically active compound will depend on the intended use of the mixture. The further biologically active substance or compound may exert its biological effect by the same or a similar mechanism as the compound according to the invention or by an unrelated mechanism of action or by a multiplicity of related and/or unrelated mechanisms of action.

The invention also includes all suitable isotopic variations of the compounds of the invention. An isotopic variation of the compound of the invention is defined as one in which at least one atom is replaced by an atom having the same atomic number but an atomic mass different from the atomic mass usually found in nature. Examples of isotopes that can be incorporated into compounds of the invention include isotopes of hydrogen, carbon, nitrogen, oxygen, sulphur, fluorine and chlorine such as $^{2}H$, $^{3}H$, $^{13}C$, $^{14}C$, $^{15}N$, $^{17}O$, $^{18}O$, $^{35}S$, $^{18}F$ and $^{36}Cl$ respectively. Certain isotopic variations of the invention, for example, those in which a radioactive isotope such as $^{3}H$ or $^{14}C$ is incorporated, are useful in drug and/or substrate tissue distribution studies. Tritiated, i.e., $^{3}H$, and carbon-14, i.e., $^{14}C$, isotopes are particularly preferred for their ease of preparation and delectability. $^{18}F$-labeled compounds are particularly suitable for imaging applications such as PET. Further, substitution with isotopes such as deuterium, i.e., $^{2}H$, may afford certain therapeutic advantages resulting from greater metabolic stability, for example, increased in vivo half-life or reduced dosage requirements and hence may be preferred in some circumstances. Isotopic variations of the compounds of the invention can generally be prepared by conventional procedures such as by the illustrative methods or by the preparations described in the Examples and Preparations hereafter using appropriate isotopic variations of suitable reagents.

Method of Use of the Invention

There is evidence for a role of NLRP3-induced IL-1 and IL-18 in the inflammatory responses occurring in connection with, or as a result of, a multitude of different diseases, disorders or abnormalities which is responsive to the modulation of a component of the NLRP3 inflammasome pathway and/or which is responsive to the modulation of IL-1 beta and/or IL-18 levels. (Menu et al., *Clinical and Experimental Immunology,* 2011, 166, 1-15; Strowig et al., *Nature,* 2012, 481, 278-286). The invention provides a compound of formula (I'), (I), (II'), or (II), as defined herein, or a stereoisomer, a racemic mixture, a tautomer, a polymorph, a pharmaceutically acceptable salt, a prodrug, a hydrate, or a solvate thereof, which exhibit valuable pharmacological properties, e.g. NRLP3 inhibiting properties on the NLRP3 inflammasome pathway. Said compounds of the invention may be useful in the treatment, alleviation or prevention of a disease, or a disorder or an abnormality which is responsive to the modulation of a component of the NLRP3 inflammasome pathway and/or which is responsive to the modulation of IL-1 beta and/or IL-18 levels. A number of diseases, disorders or abnormalities have been shown to be involve in NLRP3 including, for example, one of the following:

A. Central nervous system disease (CNS), disorder, or abnormality, such as Alzheimer's disease, Parkinson's disease, dementia, frontotemporal dementia, Huntington's disease, cerebral malaria, brain injury from pneumococcal meningitis, motor neuron disease, traumatic brain injury, amyotrophic lateral sclerosis, or multiple sclerosis (MS);

B. Immune disease, disorder, or abnormality (e.g. autoimmune disease, disorder or abnormality, and disease, disorder, or abnormality, involving the immune system), such as type 1 diabetes, hidradenitis suppurativa (HS), Schnitzler syndrome, multiple sclerosis (MS) including primary progressive multiple sclerosis (PPMS), Sjogren's syndrome, secondary progressive multiple sclerosis (SPMS), TNF receptor associated periodic syndrome (TRAPS), graft-versus host disease or relapsing remitting multiple sclerosis (RRMS);

C. Inflammatory disease, including auto-inflammation and inflammation occurring as a result of an inflammatory disease, disorder, or abnormality, such as mevalonate kinase deficiency (MKD), hyperimmunoglobulinemia D, cryopyrin-associated periodic syndromes (CAPS), Muckle-Wells syndrome (MWS), familial cold autoinflammatory syndrome (FCAS), neonatal-onset multisystem inflammatory disease (NOMID), familial Mediterranean fever (FMF), acne, pyogenic arthritis, pyoderma gangrenosum and acne (PAPA), adult-onset Still's disease (AOSD), Majeed syndrome, PLCG2-associated antibody deficiency and immune dysregulation (PLAID), PLCG2-associated autoinflammation, antibody deficiency and immune dysregulation (APLAID), pyogenic arthritis, haploinsufficiency of A20 (HA20), pediatric granulomatous arthritis (PGA), or sideroblastic anemia with B-cell immunodeficiency, periodic fevers, developmental delay (SIFD);

D. Skin disease, disorder, or abnormality such as hidradenitis suppurativa (HS), dermatitis, psoriasis, skin contact hypersensitivity, acne, periodic fever syndrome (HIDS), Sweet's syndrome, eczema, skin lesions, burn, wound, wound healing, trauma, sunburn, actinic keratosis, deficiency of interleukin 1 receptor (DIRA) antagonist, or alopecia areata;

E. Ocular disease, disorder, or abnormality, such as age-related macular degeneration (AMD), corneal infection, uveitis, glaucoma, dry eye, or demyelination;

F. Cardiovascular disease, disorder, or abnormality (e.g. disease, disorder, or abnormality of the cardiovascular system) such as myocardial infarction, hypertension, ischaemia reperfusion injury, pericarditis including Dressler's syndrome, aneurysms including abdominal aortic aneurism, or stroke;

G. Metabolic disease, disorder, or abnormality, such as type 2 diabetes, obesity, atherosclerosis, gout, or pseudo-gout;

H. Respiratory disease, disorder, or abnormality (e.g. disease, disorder or abnormality of the respiratory system), such as asbestosis, silicosis, cystic fibrosis, allergic inflammation, chronic obstructive pulmonary disorder (COPD), steroid-resistant asthma, or asthma;

I. Liver disease, disorder, or abnormality, (e.g. hepatic disease, disorder or abnormality) such as alcoholic liver disease, alcoholic fatty liver disease (AFLD), alcoholic steatohepatitis (ASH), non-alcoholic fatty liver disease (NAFLD), or non-alcoholic steatohepatitis (NASH) including advanced fibrosis stages F3 and F4;

J. Renal disease, disorder, or abnormality (e.g. disease, disorder or abnormality of the renal system) such as oxalate-induced nephropathy, diabetic nephropathy, chronic kidney disease, or kidney disease;

K. Cancer disease, disorder, or abnormality (e.g. cancer, tumor, or malignancy), such as lung cancer (e.g. lung cancer metastasis), pancreatic cancers, gastric cancers, leukemia, myelodysplastic syndrome (MOS), skin cancer, tumors of the endocrine system, or thyroid cancer;

L. Infections including viral infections, such as helminth infections (e.g. from *schistosoma*, roundworms, tapeworms or flukes), viral encephalitis, bacterial infection, human immunodeficiency virus (HIV), HIV-associated neurocognitive disorder, chronic nonbacterial osteomyelitis (CNO), chronic bacterial osteomyelitis, deficiency of interleukin 1 receptor (DIRA) antagonist, or epilepsy; alphavirus (e.g. Chikungunya virus and Ross River virus), flaviviruses (e.g. Dengue and Zika virus), Coronavirus-associated inflammatory pathologies, Coronaviruses, or influenza virus;

M. Psychological disease, disorder, or abnormality, such as depression, and psychological stress;

N. Inflammation, including inflammation occurring as a result of an inflammatory disease, disorder, or abnormality, such as an autoinflammatory disease, inflammation occurring as a symptom of a non-inflammatory disorder, inflammation occurring as a result of infection, or inflammation secondary to trauma, injury or autoimmunity. Examples of inflammation include inflammatory responses occurring in connection with, or as a result of:

i. A joint disease, disorder, or abnormality, such as periodic fever syndrome (HIDS), rheumatoid arthritis, pustulosis, synovitis, osteoarthritis, chronic recurrent multifocal osteomyelitis (CRMO), systemic juvenile idiopathic arthritis, osteitis syndrome (SAPHO), hyperostosis, relapsing polychondritis, or adult-onset Still's disease;

ii. A gastrointestinal disease, disorder, or abnormality (e.g. disease, disorder or abnormality of the gastrointestinal tract) such as colitis, ulcerative colitis, or inflammatory bowel disease;

iii. A muscular disease, disorder, or abnormality, such as polymyositis, or myasthenia gravis;

iv. A disease, disorder or abnormality of the endocrine system, such as, diabetes, parathyroid disease (e.g. hypothyroidism), tumors of the endocrine system, thyroid cancer, or hypoglycemia; and/or v. A vascular disease, disorder or abnormality, such as Behcet's disease.

In one embodiment, the disease, disorder, or abnormality is selected from Alzheimer's disease, Parkinson's disease, cryopyrin-associated periodic syndromes (CAPS), non-alcoholic fatty liver disease (NAFLD), non-alcoholic steatohepatitis (NASH), and gout.

In particular, the disease, disorder or abnormality is selected from: Alzheimer's disease, Parkinson's disease, amyotrophic lateral sclerosis, demyelination, viral encephalitis, epilepsy, stroke, atherosclerosis, asthma, allergic inflammation, cryopyrin-associated periodic syndromes (CAPS), Muckle-Wells syndrome (MWS), familial cold autoinflammatory syndrome (FCAS), neonatal-onset multisystem inflammatory disease (NOMID), gout, pseudo-gout, inflammatory bowel disease, nonalcoholic fatty liver disease, nonalcoholic steatohepatitis, hypertension, myocardial infarction, oxalate-induced nephropathy, graft-versus host disease, type 1 diabetes, type 2 diabetes, rheumatoid arthritis, myelodysplastic syndrome, familial Mediterranean fever (FMF), TNF receptor associated periodic syndrome (TRAPS), mevalonate kinase deficiency (MKD), hyperimmunoglobulinemia D, periodic fever syndrome (HIDS), deficiency of interleukin 1 receptor (DIRA) antagonist, Majeed syndrome, acne, pyogenic arthritis pyoderma gangrenosum and acne (PAPA), haploinsufficiency of A20 (HA20), PLCG2-associated antibody deficiency and immune dysregulation (PLAID), pediatric granulomatous arthritis (PGA), PLCG2-associated autoinflammation, antibody deficiency and immune dysregulation (APLAID), sideroblastic anemia with B-cell immunodeficiency, periodic fevers, developmental delay (SIFD), chronic nonbacterial osteomyelitis (CNO), Sweet's syndrome, chronic recurrent multifocal osteomyelitis (CRMO), synovitis, pustulosis, acne, eczema, alopecia areata, actinic keratosis, hyperostosis, osteitis syndrome (SAPHO), multiple sclerosis (MS), psoriasis, Behcet's disease, Sjogren's syndrome, Schnitzler syndrome, chronic obstructive pulmonary disorder (COPD), steroid-resistant asthma, asbestosis, silicosis, cystic fibrosis, motor neuron disease, Huntington's disease, cerebral malaria, brain injury from pneumococcal meningitis, obesity, age-related macular degeneration (AMD), corneal infection, uveitis, dry eye, chronic kidney disease, diabetic nephropathy, alcoholic liver disease, skin contact hypersensitivity, sunburn, osteoarthritis, systemic juvenile idiopathic arthritis, adult-onset Still's disease, relapsing polychondritis, Chikungunya virus, Ross River virus, influenza, HIV, Coronaviruses, Dengue, Zika virus, hidradenitis suppurativa (HS), lung cancer metastasis, pancreatic cancers, gastric cancers, myelodisplastic syndrome, leukemia; polymyositis, colitis, helminth infection, bacterial infection, abdominal aortic aneurism, wound healing, depression, psychological stress, pericarditis including Dressler's syndrome, ischaemia reperfusion injury, frontotemporal dementia, HIV-associated neurocognitive disorder, Coronavirus-associated inflammatory pathologies, and traumatic brain injury; preferably the disorder is selected from Alzheimer's disease, Parkinson's disease, amyotrophic lateral sclerosis, demyelination, viral encephalitis, epilepsy, stroke, atherosclerosis, asthma, allergic inflammation, cryopyrin-associated periodic syndromes (CAPS), gout, inflammatory bowel disease, non-alcoholic fatty liver disease (NAFLD), non-alcoholic steatohepatitis (NASH), hypertension, myocardial infarction, oxalate-induced nephropathy, graft-versus host disease, type 1 diabetes, type 2 diabetes, rheumatoid arthritis, myelodysplastic syndrome, anti-neutrophil cytoplasmic antibody-associated vasculitis (AAV), lupus nephritis, anti-glomerular basement membrane (GMB) disease, IgA nephropathy, glomerulonephritis (GN), systemic lupus erythematosus (SLE), Focal Segmental Glomerulosclerosis, Minimal change disease (MCD), Psoriatic Arthritis, and Hereditary Recurrent Fevers (HRFs).

In yet another embodiment, the disease, disorder or abnormality is preferably an inflammatory disease, disorder or abnormality; or an autoimmune disease, disorder or abnormality; or a disease, disorder or abnormality of the skin (such as, for example, but not limited to, psoriasis, acne, eczema, alopecia areata, or actinic keratosis); or a disease, disorder or abnormality of the cardiovascular system; or a disease, disorder, or abnormality such as a cancer, a tumor or a malignancy; or a disease, disorder or abnormality of the renal system; a disease, disorder or abnormality of the gastrointestinal tract; a disease, disorder or abnormality of the respiratory system; or a disease, disorder or abnormality of the endocrine system; or a disease, disorder or abnormality of the central nervous system (CNS); or a disease, disorder or abnormality of the liver.

Definitions

Within the meaning of the present application the following definitions apply unless specified otherwise, and when appropriate, terms used in the singular will also include the plural and vice versa:

"Alkyl" refers to a saturated straight or branched organic moiety consisting of carbon and hydrogen atoms. Examples of suitable alkyl groups have 1 to 6 carbon atoms, preferably 1 to 4 carbon atoms, and include methyl, ethyl, propyl, isopropyl, n-butyl, t-butyl, and isobutyl. Within the present invention any alkyl group can be optionally substituted with one or more (preferably 1 or 2) substituents defined below as "optional substituent". The term "$C_1$-$C_6$alkyl" refers to an alkyl group having 1 to 6 carbon atoms. The terms "$C_1$-$C_4$alkyl", "$C_1$-$C_3$alkyl", or "$C_1$alkyl" are to be construed accordingly.

"Hal" or "halogen" refers to F, Cl, Br, and I. Preferably halogen is F or Cl. More preferably, halogen is Cl. Even more preferably, halogen is F.

"—O—$C_1$-$C_6$alkyl" refers to a radical of the formula —O—$R_a$ where $R_a$ is a "$C_1$-$C_6$alkyl" radical as generally defined above. Examples of "—O—$C_1$-$C_6$alkyl" include, but are not limited to methoxy, ethoxy, propoxy, isopropoxy, pentoxy, and hexoxy.

"$C_1$-$C_6$alkyl-OH" refers to a $C_1$-$C_6$alkyl radical as defined above, wherein one of the hydrogen atoms of the $C_1$-$C_6$alkyl radical is replaced by "OH". Examples of "$C_1$-$C_6$alkyl-OH" include, but not limited to, hydroxy-methyl, 2-hydroxy-ethyl, 2-hydroxy-propyl, 3-hydroxy-ethyl, and 5-hydroxy-pentyl.

"Cycloalkyl" refers to saturated monocyclic, bicyclic or tricyclic hydrocarbyl groups (each cycle having 3 to 6 ring carbon atoms). Preferably, "Cycloalkyl" refers to saturated monocyclic hydrocarbyl groups. The term "$C_3$-$C_6$cycloalkyl" refers to saturated monocyclic hydrocarbyl groups having 3 to 6 carbon atoms. The terms "$C_5$-$C_6$cycloalkyl" is to be construed accordingly. Examples include, but are not limited to cyclopropyl, cyclobutyl, cyclopentyl, and cyclohexyl.

"Hetero$C_3$-$C_6$cycloalkyl" refers to a stable 5- or 6-membered non-aromatic monocyclic ring radical which comprises 1, 2, or 3, heteroatoms individually selected from nitrogen, oxygen and sulfur. Preferably, the 5- or 6-membered non-aromatic monocyclic ring radical comprises 1 heteroatom. More preferably the heteroatom is oxygen. Examples include, but are not limited to, tetrahydropyran, and tetrahydrofuran.

"Aryl" refers to an aromatic hydrocarbon group having 3 to 8 carbon atoms in the ring portion "3- to 8-membered ring" i.e. three-, four-, five-, six-, seven- or eight-membered ring. Preferably, the term "aryl" refers to an aromatic hydrocarbon group having 6 carbon atoms. Preferably, "aryl" is phenyl.

"Heteroaryl" refers to an aromatic "3- to 8-membered ring" i.e. three-, four-, five-, six-, seven- or eight-membered ring, wherein none, one or more of the carbon atoms in the ring have been replaced by 1 or 2 (for the three-membered ring), 1, 2 or 3 (for the four-membered ring), 1, 2, 3, or 4 (for the five-membered ring) or 1, 2, 3, 4, or 5 (for the six-membered ring) 1, 2, 3, 4, 5 or 6 (for the seven-membered ring), or 1, 2, 3, 4, 5, 6 or 7 (for the eight-membered ring) of the same or different heteroatoms, whereby the heteroatoms are selected from O, N and S. Preferably, "Heteroaryl" refers to an aromatic 5- to 10-membered ring. More preferably, "Heteroaryl", e.g. $C_5$-$C_6$heteroaryl, refers to an aromatic 5- to 6-membered aromatic monocyclic ring radical which comprises 1, 2 or 3 heteroatoms individually selected from N, O and S, wherein the heteroaryl radical may be bonded via a carbon atom or heteroatom. Examples of heteroaryl include, but not limited to, furyl, oxazolyl, isoxazolyl, thienyl, isothiazolyl, thiazolyl, pyrazolyl, pyrrolyl, pyridyl, pyrimidyl, pyrazinyl and pyridazinyl.

"Optionally substituted" in reference to a certain group refers to said group as to optionally be substituted with one or more substituents (i.e. the substituent may be present or not). Such "optional substituents" may be selected from the group consisting of optionally substituted $C_1$-$C_{10}$alkyl (e.g., optionally substituted $C_1$-$C_6$alkyl); optionally substituted $C_3$-$C_6$cycloalkyl (e.g., optionally substituted cyclopropyl); optionally substituted hydroxyalkyl; optionally substituted $C_1$-$C_{10}$alkoxy (e.g., optionally substituted $C_1$-$C_6$alkoxy); optionally substituted $C_2$-$C_{10}$alkenyl; optionally substituted $C_2$-$C_{10}$alkynyl;

optionally substituted $C_6$-$C_{12}$ aryl; aryloxy; optionally substituted heteroaryl; optionally substituted heterocyclyl; halo (e.g., F, Cl, Br, and I); hydroxyl; halogenated alkyl (e.g., $CH_2F$, $CHF_2$, $CF_3$, 2-Br-ethyl, $CH_2CF_3$, and $CF_2CF_3$); amino (e.g., $NH_2$, $NR_{30}H$, and $NR_{30}R_{31}$); alkylamino; arylamino; acyl; amido; OH; CN; $N_3$; $NO_2$; $CH_2OH$; $CONH_2$; $CONR_{32}R_{33}$; $CO_2R_{32}$; $CH_2OR_{32}$; $NHCOR_{32}$; $NHCO_2R^{32}$; $C_1$-$C_3$alkylthio; sulfate; sulfonic acid; sulfonate esters such as alkyl or aralkyl sulfonyl; phosphonic acid; phosphate; phosphonate; mono-, di-, or triphosphate esters; trityl or monomethoxytrityl; $R_{32}SO$; $R_{32}SO_2$; $CF_3S$; and $CF_3SO_2$; trialkylsilyl such as dimethyl-t-butylsilyl or diphenylmethylsilyl; wherein $R_{30}$, $R_{31}$, $R_{32}$ and $R_{33}$ are each independently selected from H and optionally substituted $C_1$-$C_{10}$alkyl (e.g. optionally substituted $C_1$-$C_6$alkyl or $C_1$-$C_4$alkyl).

Unless specified otherwise, the term "compound of the present invention" refers to compounds of formula (I'), (I), (II'), or (II), as disclosed herein, or sub-formulae thereof, as disclosed herein, or stereoisomers thereof, or racemic mixtures thereof, or tautomers thereof, or polymorphs thereof, or pharmaceutically acceptable salts thereof, or prodrugs thereof, or hydrates thereof, or solvates thereof. Compounds of the present invention having one or more optically active carbons can exist as racemates and racemic mixtures (including mixtures in all ratios), stereoisomers (including diastereomeric mixtures and individual diastereomers, enantiomeric mixtures and single enantiomers, mixtures of conformers and single conformers), tautomers, atropisomers, and rotamers. All isomeric forms are included in the present invention. Compounds described in this invention containing olefinic double bonds include E and Z geometric isomers. Also included in this invention are all pharmaceutically acceptable salts, prodrugs, hydrates and solvates of compounds of formula (I') or (I).

Tautomers are isomers of a compound which differ only in the position of the protons and electrons. The skeleton of the compound is unchanged. Common tautomeric pairs include: ketone-enol (H—O—C═CH⇆O═C—$CH_2$), enamine-imine ($H_2N$—C═N⇆HN═C—NH).

Solvates, hydrates as well as anhydrous forms of the salt are also encompassed by the invention. The solvent included in the solvates is not particularly limited and can be any pharmaceutically acceptable solvent. Examples include water and $C_{1-4}$ alcohols (such as methanol or ethanol).

"Pharmaceutically acceptable salts" are defined as derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as, but not limited to, hydrochloric, hydrobromic, sulfuric, sulfamic, phosphoric, nitric acid and the like; and the salts prepared from organic acids such as, but not limited to, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic acid, and the like. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Organic solvents include, but are not limited to, nonaqueous media like ethers, ethyl acetate, ethanol, isopropanol, or acetonitrile. Lists of suitable salts can be found in Remington's Pharmaceutical Sciences, $18^{th}$ ed., Mack Publishing Company, Easton, PA, 1990, p. 1445, the disclosure of which is hereby incorporated by reference.

The compounds of the present invention, as defined herein, can also be provided in the form of a prodrug, namely a compound which is metabolized in vivo to the active metabolite. As used hereinafter in the description of the invention and in the claims, the term "prodrug" means any covalently bonded compound which releases the active parent pharmaceutical due to in vivo biotransformation. The reference by Goodman and Gilman (The Pharmacological Basis of Therapeutics, 8 ed, McGraw-Hill, Int. Ed. 1992, "Biotransformation of Drugs", p 13-15) describing prodrugs generally is hereby incorporated herein by reference.

"Pharmaceutically acceptable" is defined as those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

A used herein, the terms "patient" or "subject" mentioned in the present invention typically refer to an animal, particularly a mammal (e.g. rabbits, rats, dogs, mice, guinea pigs, pigs), more particularly primates (e.g. humans, male or female). In certain embodiments, the subject is a human.

"NLRP3" as used herein refers to NOD-like receptor (NLR) family, pyrin-domain containing protein 3 component of inflammasome. Inflammasomes are intracellular supramolecular complexes comprising a sensor molecule, the adaptor apoptosis-associated speck-like protein containing a CARD (ASC) and the effector protease caspase 1. Upon activation of the inflammasome sensor molecule, ASC self-associates into a helical fibrillary assembly resulting in formation of the so-called ASC speck or pyroptosome, which acts as a molecular platform for the activation of pro-caspase 1 via proximity-induced autocatalytic activation. Active caspase 1 triggers the activation and release of interleukin-1 (IL-1) family proteins and enables the non-conventional secretion of numerous cytosolic proteins. Among the pro-inflammatory mediators released upon NLRP3 activation are IL-1 beta (B), IL-18, high-mobility group protein B1 (HMGB1), leukotrienes and prostaglandins. NLRP3 inflammasome pathway activation is an important driver of inflammation interacting with the different cytokine pathways shaping the immune response to infection and injury. Formation of some pro-inflammatory cytokines is triggered by NLRP3 inflammasome pathway activation.

The terms "inhibit", "inhibition" or "inhibiting" refer to the reduction or suppression of a given condition, symptom, or disorder, or disease, or abnormality which is responsive to the modulation of a component of the NLRP3 inflammasome pathway, or a significant decrease in the baseline activity of a biological activity or process.

The terms "treat", "treating" or "treatment" of any disease, disorder or abnormality refer to alleviating or ameliorating or modulating the disease or disorder or abnormality (i.e., slowing or arresting the development of the disease, disorder or abnormality or at least one of the clinical symptoms thereof); or alleviating or ameliorating or modulating at least one physical parameter or biomarker associated with the disease or disorder or abnormality, including those which may not be discernible to the subject (e.g., patient).

The terms "prevent", "preventing" or "prevention" of any disease or disorder or abnormality which is responsive to the modulation of a component of the NLRP3 inflammasome pathway refer to the prophylactic treatment of the disease or disorder or abnormality; or delaying the onset or progression of the disease or disorder.

The term "in need of" a treatment if such subject would benefit biologically, medically or in quality of life from such treatment.

As used herein, "modulation" refers to alteration, e.g., up-regulation, down-regulation, increase or decrease, preferably decrease.

| Abbreviation | Meaning |
|---|---|
| NALP1-14 | NACHT Leucine-rich-repeat Protein 1-14 (it's a synonym of NLRP) |
| IPAF | Ice Protease-Activating Factor |
| NAIP | Neuronal Apoptosis Inhibitory Protein |
| ASC | Apoptosis-associated Speck-like protein containing a CARD |
| nucleotide-binding NACHT domain | NACHT:NAIP (neuronal apoptosis inhibitory protein), CIITA (MHC class II transcription activator), HET-E (incompatibility locus protein from Podospora anserina) and TP1 (telomerase-associated protein) |
| IL | Interleukin |
| TNF-alpha | Tumor Necrosis Factor-alpha |

The definitions and preferred definitions given in the "Definition"-section apply to all of the embodiments described herein unless stated otherwise.

The compounds of the present invention can be synthesized by those skilled in the art by using commonly known preparation steps, for instance those of the general methods shown in the following schemes. These methods are only given for illustrative purposes and should not to be construed as limiting.

General Synthetic Scheme for the Preparation of Compounds of this Invention:

Scheme 1

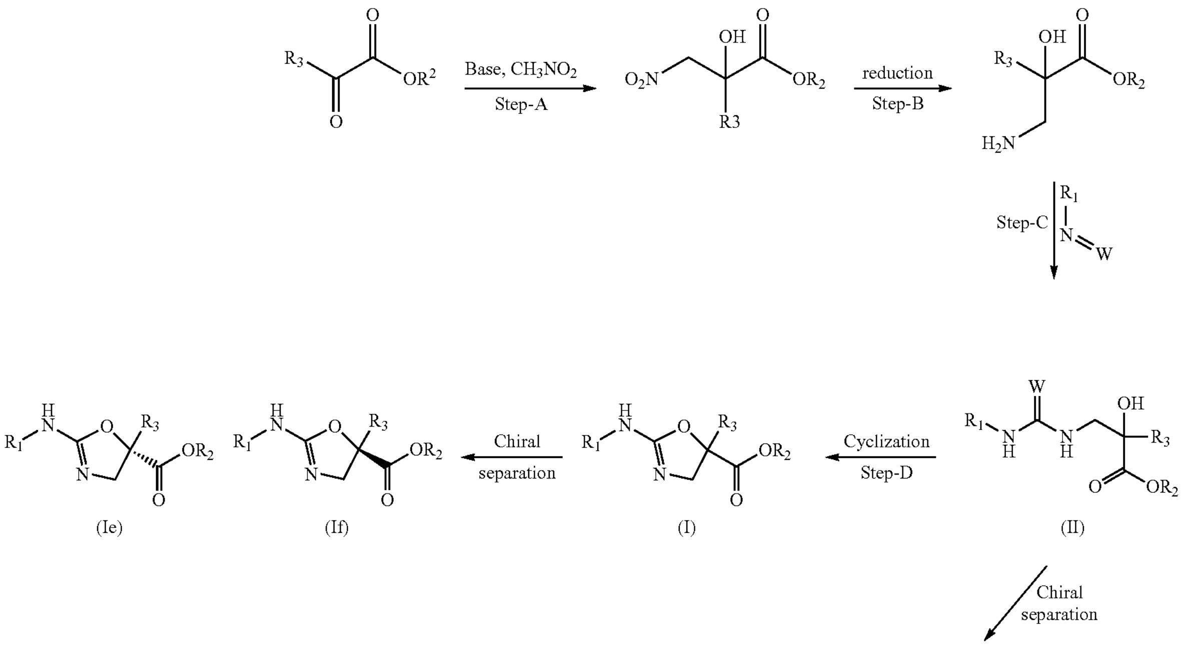

(Ie) (If) (I) (II)

-continued

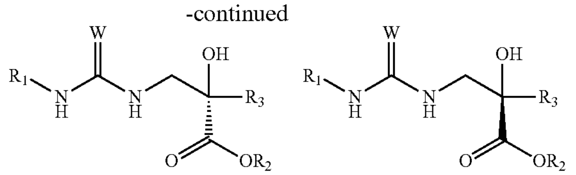

(IIa) (IIb)

Scheme 2

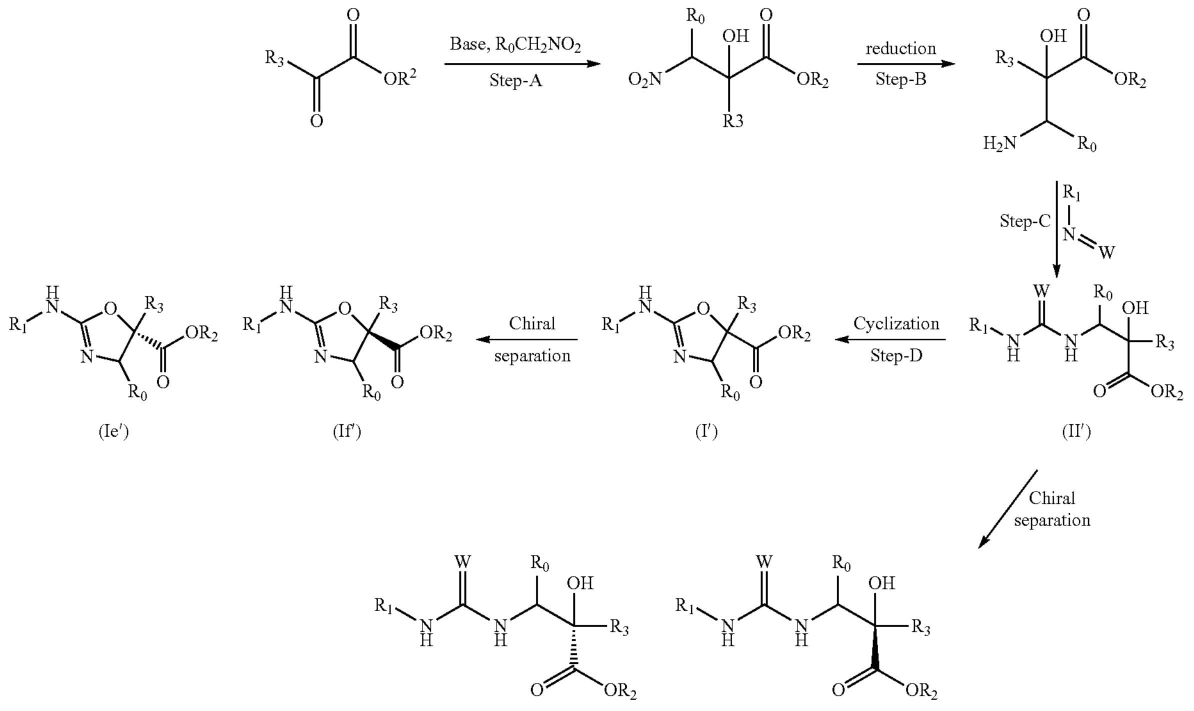

(Ie') (If') (I') (II')

(IIa') (IIb')

From a commercially available arylketoester, a nitro derivative was synthesized using a nitroalkane such as nitromethane with a suitable base and solvent. Reduction of nitro was then achieved either by hydrogen with an appropriate catalyst or by using a metal under acidic conditions such iron or zinc in acetic acid. Subsequently, a thiourea or urea derivative was obtained by treating the amine intermediate with isothiocyanate or isocyanate optionally in the presence of a base. Finally, the cyclization was carried out as known in the art such as, for example, using N-(3-Dimethylaminopropyl)-N'-ethylcarbodiimide (EDC) with a base, mukaiyama reagent with a base, iodomethane with a base or TsCl with a base. Alternatively, $R^2$ functionality could be also introduced at the end of the synthesis by a two-step strategy by saponification/esterification procedures. Ultimately, the enantiomers could be separated by chiral supercritical fluid chromatography (SFC) to obtain the desired single enantiomers.

It is to be noted that in the present invention, the R groups of compounds of formula (I') or (I) and compounds of formula (II') or (II) are similar, in particular $R^2$ and $R^8$ are identical groups and can be used interchangeably throughout the general scheme. In addition, $R^1$ and $R^6$ are identical groups and can be used interchangeably throughout the general scheme. Moreover, $R^3$ and $R^7$ are identical groups and can be used interchangeably throughout the general scheme.

EXAMPLES

The disclosure is further illustrated by the following examples and synthesis schemes, which are not to be construed as limiting the scope of the specific procedures herein described. It is understood that the examples are provided to illustrate certain embodiments and that no limitation to the scope of this disclosure is intended thereby.

All reagents and solvents were obtained from commercial sources and used without further purification. $^1$H-NMR spectra were recorded on Bruker 400 MHz-AVANCE III HD NMR, Bruker 500 MHz-AVANCE III HD NMR spectrometers or Spinsolve 80 Mhz in deuterated solvents. Chemical shifts (δ) are reported in parts per million and coupling constants (J values) in hertz. Spin multiplicities are indicated by the following symbols: s (singlet), d (doublet), t (triplet), q (quartet), m (multiplet), bs (broad singlet). Mass spectra were obtained on a Water ACQUITY SQD2 UPLC/MS system. GC-MS data were collected using an Agilent 7890B gas chromatograph and 5977A mass spectrometer. Chromatography was performed using silica gel (Acme: Silica gel 60, 0.063-0.2 mm) and suitable solvents as indicated in specific examples. Flash purification was conducted with a Biotage Isolera one or Reveleris $X_2$ with KP—NH SNAP cartridges (Biotage) or Reveleris silica cartridges (Grace) and the solvent gradient indicated in specific examples. Thin layer chromatography (TLC) was carried out on silica gel plates (Merck) with UV detection.

Intermediate 1:1-(4-isopropylthiazol-2-yl) ethan-1-one

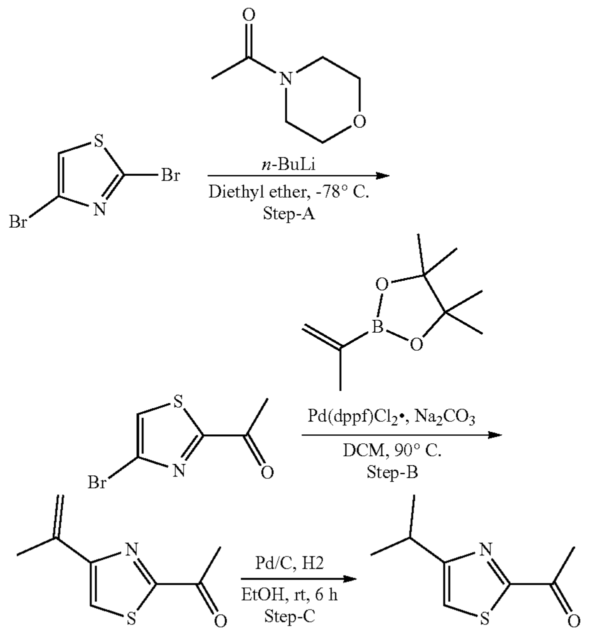

Step A

To a stirred solution of 2,4-dibromothiazole (20 g, 82.833 mmol) in dry diethylether (200 mL), n-BuLi (2.5 M solution in Hexane) (36.2 mL, 90.572 mmol) was added dropwise at −78° C. After 30 minutes, N-acetyl morpholine (14.4 mL, 123.507 mmol) was added dropwise to the reaction mixture and stirring was continued at −78° C. for 1 hour and 30 minutes. The reaction mixture was left to warm up to room temperature and stirred for 16 h. The reaction mixture was quenched with water and extracted with diethylether (2×300 ml). The organic layer was concentrated under reduced pressure. The residue obtained was purified by flash chromatography ($SiO_2$ column, 0-20% ethyl acetate in hexane). to afford 1-(4-bromothiazol-2-yl) ethan-1-one (11.1 g, 65.6%) as an off white solid. $^1$H-NMR (400 MHz $CDCl_3$): δ=7.58 (s, 1H), 2.71 (s, 3H). MS: 205.94 $[(M+H)]^+$.

Step B

To a stirred solution of compound from Step-A (5.0 g of, 24.271 mmol) and isopropenyl boronate ester (8.2 mL of, 43.689 mmol) in 1,4-dioxane (75 mL) was added 2M solution of $Na_2CO_3$ (24 mL, 48.543 mmol); the resulting mixture was degassed for 5 minutes. Pd(dppf)$Cl_2$ DCM (0.99 g of, 1.213 mmol) was added to the reaction mixture, which was further degassed for 10 minutes. After stirring at 90° C. for 16 h, the reaction mixture was cooled to rt and filtered through a bed of celite. The filtrate was diluted with ethyl acetate (50 ml) and washed with water (50 ml). The organic layer was dried and concentrated under reduced pressure. The resulting crude material was purified by flash chromatography ($SiO_2$ column, 0-20% ethyl acetate in hexane to afford 1-(4-(prop-1-en-2-yl) thiazol-2-yl) ethan-1-one (3.1 g, 77.5%) as a pale yellow liquid. $^1$H-NMR (400 MHz, $CDCl_3$): δ=7.45 (s, 1H), 6.00 (d, 1H), 5.26 (m, 1H), 2.73 (s, 3H), 2.17 (m, 3H). MS: 167.99 $[(M+H)]^+$.

Step-C:

To a stirred solution of compound from Step-B (3.1 g, 18.562 mmol) in ethanol (31 ml) was added 10% Pd/C (1.5 g) at rt. The resulting reaction mixture was stirred under at 10 psi hydrogen atmosphere for 3 h, following progress by TLC. After complete consumption of starting material, the reaction mixture was filtered through celite, washed with EtOH and the resulting filtrate was concentrated under vacuum to afford 1-(4-isopropylthiazol-2-yl) ethan-1-one (2.8 g, 90.3%) as of colorless liquid. $^1$H-NMR (400 MHz, $CDCl_3$): δ=7.23 (s, 1H), 3.2-3.13 (m, 1H), 2.70 (s, 3H), 1.34 (d, 6H). MS: 170.03 $(M+H)^+$.

Intermediate 2:1-(1-isopropyl-1H-pyrazol-3-yl) ethan-1-one

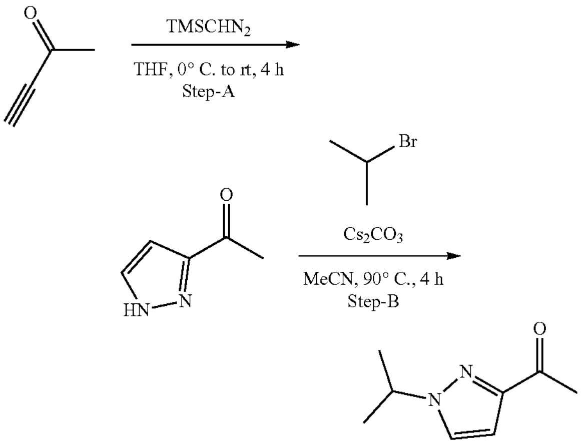

Step A

To a stirred solution of but-3-yn-2-one (15 g, 0.2203 mol) in dry THF (150 ml) was added $TMSCHN_2$ (110 ml, 0.2203 mol) dropwise at 0° C. The reaction was left to warm up to room temperature then was stirred for an additional 4 h. The reaction mixture was diluted with water (500 ml) and extracted with EtOAc (2×250 ml). The organic layer was dried and concentrated under reduced pressure. The resulting crude residue was purified by flash chromatography ($SiO_2$ column, 0-30% ethyl acetate in hexane). to afford 1-(1H-pyrazol-3-yl) ethan-1-one (4.6 g, 19%) as an off white solid. $^1$H-NMR (400 MHz, $CDCl_3$): δ=9.5 to 8.0 (bs, 1H), 7.66 (d, 1H), 6.85 (d, 1H), 2.6 (s, 3H). MS: 111.03 $(M+H)^+$.

Step B

To a stirred solution of compound from Step-A (4.6 g, 0.0417 mol) in acetonitrile (50 ml) was added 2-bromopropane (5.13 g, 0.0417 mol) followed by $CS_2CO_3$ (13.6 g, 0.0417 mol) at room temperature and allowed to stir at 90° C. under $N_2$ atmosphere for 4 h. The reaction mixture was filtered through celite and the filtrate was concentrated under reduced pressure. The resulting crude residue was purified by flash chromatography ($SiO_2$ column, 0-10% ethyl acetate in hexane). to afford 4.0 g of 1-(1-isopropyl-1H-pyrazol-3-yl) ethan-1-one (4 g, 62%) as a colorless liquid. $^1$H-NMR (400 MHz, $CDCl_3$): δ=7.42 (d, 1H), 6.77 (d, 1H), 4.60-4.51 (m, 1H), 2.57 (s, 3H), 1.53 (d, 6H). MS: 153.05 $[(M+H)]^+$.

Example 1: ethyl 2-((1,2,3,5,6,7-hexahydro-s-indacen-4-yl)amino)-5-phenyl-4,5-dihydrooxazole-5-carboxylate

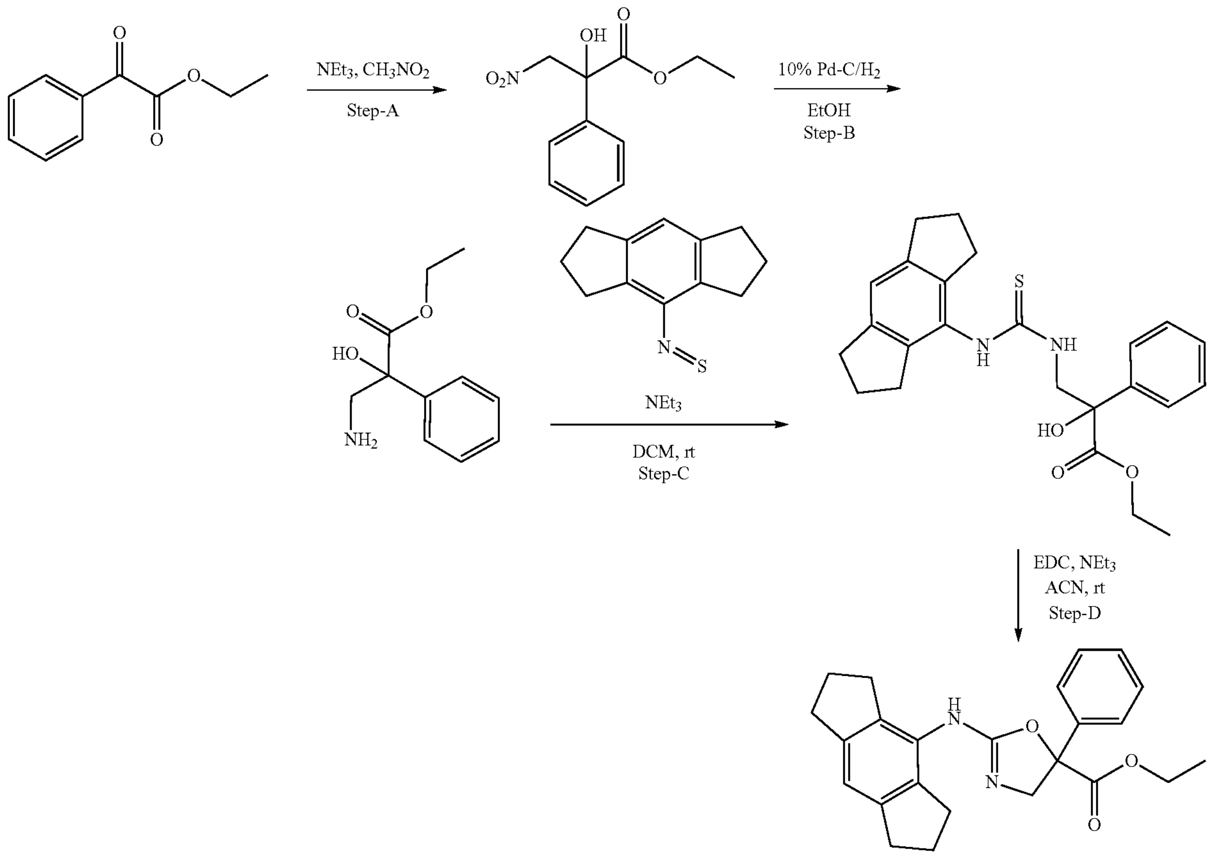

Step-A:

To a stirred solution of ethyl 2-oxo-2-phenylacetate (1.0 g, 5.612 mmol) in nitromethane (0.601 mL, 11.224 mmol) was added triethylamine (0.156 mL, 1.122 mmol). After being stirred at room temperature for 48 h, the reaction mixture was concentrated under reduced pressure to dryness. The crude compound was purified by flash chromatography (Silica, 80 g Reveleris column; 0-50% ethyl acetate in hexane) to afford ethyl 2-hydroxy-3-nitro-2-phenylpropanoate as an off white solid (900 mg, 67%). $^1$H-NMR (500 MHz, DMSO-d6) δ=7.55-7.54 (d, 2H), 7.41-7.34 (m, 3H), 6.80 (s, 1H), 5.59-5.57 (d, 1H), 4.83-4.80 (d, 1H), 4.21-4.15 (m, 2H), 1.19-1.17 (t, 3H).

Step B:

To a stirred solution of the compound from step-A (500 mg, 2.090 mmol) in ethanol (20 mL) was added 10% Pd/C (250 mg) at room temperature. The reaction mixture was stirred under hydrogen atmosphere (~15 psi pressure) for 16 h. Then, the crude mixture was filtered through celite pad and the residue was washed with ethanol. The filtrate was evaporated under reduced pressure to afford ethyl 3-amino-2-hydroxy-2-phenylpropanoate as a colorless gum (420 mg).

$^1$H-NMR (400 MHz, DMSO-d6) δ=7.53-7.48 (m, 2H), 7.39-7.32 (m, 2H), 7.29-7.25 (m, 1H), 5.84 (brs, 1H), 4.13-4.08 (m, 2H), 3.24-3.21 (d, 1H), 2.78-2.75 (d, 1H), 1.18-1.14 (t, 3H). MS: 210.31 $[M+H]^+$ Step C:

To a stirred solution of the compound from step-B (420 mg, 2.0071 mmol) and triethylamine (0.84 ml, 6.021 mmol) in dichloromethane (10 mL) was added 4-isothiocyanato-1,2,3,5,6,7-hexahydro-s-indacene (432.16 mg, 2.0071 mmol). After being stirred at room temperature for 16 h, the reaction mixture was concentrated under reduced pressure to dryness. The crude compound was purified by flash chromatography (Silica, 80 g Reveleris column; 0-50% ethyl acetate in hexane) to afford ethyl 3-(3-(1,2,3,5,6,7-hexahydro-s-indacen-4-yl)thioureido)-2-hydroxy-2-phenylpropanoate as a colorless gum (520 mg). $^1$H-NMR (500 MHz, DMSO-d6) δ=9.27 (brs, 1H), 7.48-7.29 (m, 5H), 6.99 (s, 1H), 6.45 (brs, 1H), 4.19-4.03 (m, 4H), 2.80-2.78 (t, 4H), 2.55-2.49 (m, 4H), 1.91 (brs, 4H), 1.17-1.13 (t, 3H). MS: 425.49 $[M+H]^+$ Step D:

To a stirred solution of the compound from step-C (420 mg, 0.989 mmol) in acetonitrile (20 mL) was added triethylamine (0.414 ml, 1.22 mmol) followed by EDC.HCl (379.2 mg, 1.978 mmol) at 0° C. Then, the reaction mixture was allowed to warm to room temperature. After 48 h, the reaction mixture was diluted with ice water (30 mL) and the crude product was stirred for 30 min. The solid was collected by filtration and dried under reduced pressure to get the crude compound. This crude compound was triturated with diethylether (10 mL), filtered and dried under reduced pressure to afford ethyl 2-((1,2,3,5,6,7-hexahydro-s-indacen-4-yl)amino)-5-phenyl-4,5-dihydrooxazole-5-carboxylate as a white solid (320 mg, 83%). $^1$H-NMR (400 MHz, DMSO-d6) δ=8.60 (brs, 1H), 7.43-7.38 (m, 5H), 6.83 (brs, 1H), 4.21-4.19 (brs, 1H), 4.19-4.15 (m, 2H), 3.83 (brs, 1H), 2.80-2.76 (t, 4H), 2.66 (brs, 4H), 1.97-1.90 (m, 4H), 1.18-1.15 (t, 3H). MS: 391.52 $[M+H]^+$ Example 2: enantiopure ethyl 2-((1,2,3,5,6,7-hexahydro-s-indacen-4-yl)amino)-5-phenyl-4,5-dihydrooxazole-5-carboxylate The enantiopure compound was obtained as an off white solid by chiral SFC separation starting from the racemic mixture of Example 1. (Chiralpak IG (4.6*250) mm, 5μ; Co-Solvent: 50% (0.5% isopropyl amine in 2-propanol), Total flow: 70 mg/ml; Outlet Pressure: 120 bar; Temperature: 30° C.); Second eluting peak. $^1$H-NMR (500 MHz, $CDCl_3$) δ=7.58 (brs, 1H), 7.49-7.46 (d, 2H), 7.40-7.33 (m, 3H), 6.96 (s, 1H), 4.55-4.52 (d, 1H), 4.26-4.22 (q, 2H), 4.09-4.06 (d, 1H), 2.89-2.79 (m, 8H), 2.08-2.00 (m, 4H), 1.28-1.25 (t, 3H). MS: 391.48 $[M+H]^+$. 99.4% ee Example 3: ethyl 2-((1,2,3,5,6,7-hexahydro-s-indacen-4-yl)amino)-5-(1-methyl-1H-imidazol-2-yl)-4,5-dihydrooxazole-5-carboxylate 5.59-5.56 (d, 1H), 5.12-5.09 (d, 1H), 4.26-4.14 (m, 2H), 3.67 (s, 3H), 1.19-1.15 (t, 3H). MS: 244.26 $[M+H]^+$ Step-B:

To a stirred solution of the compound from step-A (400 mg, 1.639 mmol) in ethanol (10 mL) was added 10% Pd/C (220 mg) at room temperature. The reaction mixture was stirred under hydrogen atmosphere (~15 psi pressure) for 12 h. Then, the crude mixture was filtered through a celite pad and the residue was washed with ethanol. The filtrate was evaporated under reduced pressure to afford ethyl 3-amino-2-hydroxy-2-(1-methyl-1H-imidazol-2-yl) propanoate as a colorless gum (200 mg). MS: 214.15 $[M+H]^+$ Step-C:

To a stirred solution of the compound from step-B (450 mg, 2.10 mmol) and triethylamine (637.14 mg, 6.30 mmol) in dichloromethane (DCM) (10 mL) was added 4-isothiocyanato-1,2,3,5,6,7-hexahydro-s-indacene (452.10 mg, 2.10 mmol). After being stirred at room temperature for 12 h, the reaction mixture was concentrated under reduced pressure to dryness. The crude compound was purified by flash chromatography (Silica, Silica 25 g column; 0-50% ethyl acetate hexane) to afford ethyl 3-(3-(1,2,3,5,6,7-hexahydro-s-indacen-4-yl)thioureido)-2-hydroxy-2-(1-methyl-1H-imidazol-2-yl) propanoate as an off-white solid (370 mg). MS: 429.61 [M+H]+

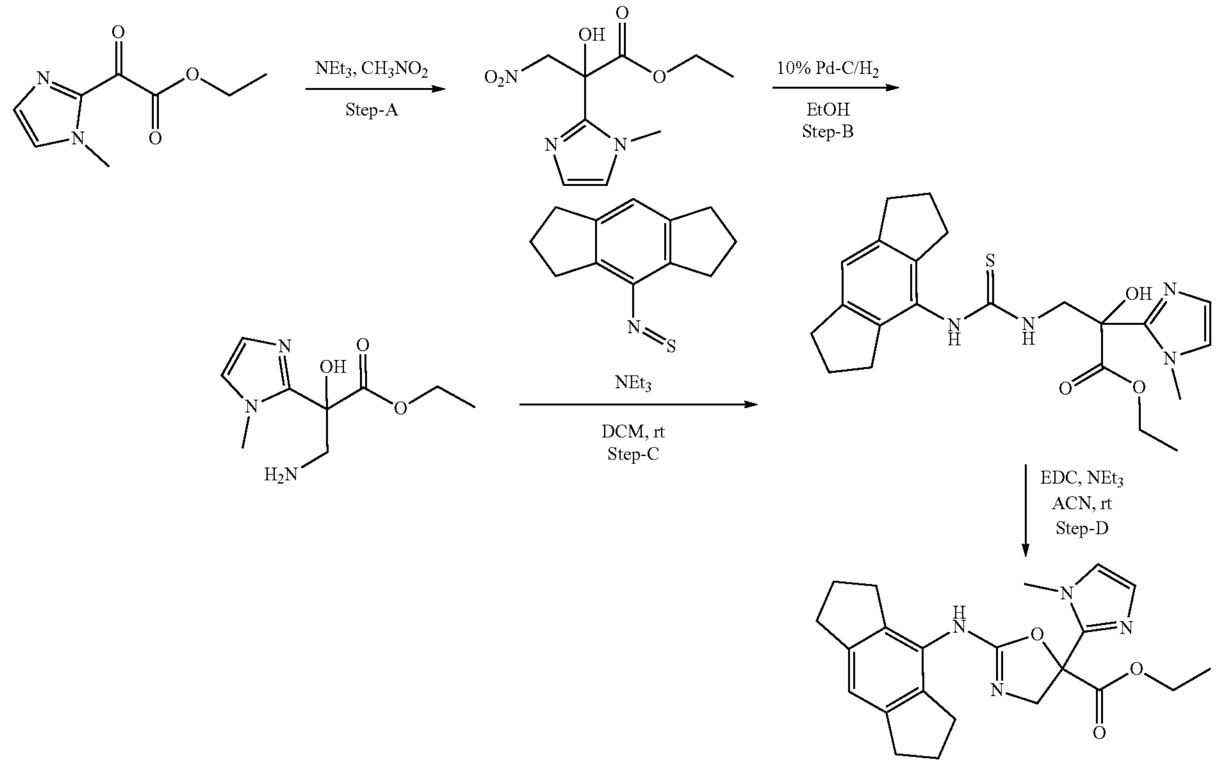

Step-A:

To a stirred solution of ethyl 2-(1-methyl-1H-imidazol-2-yl)-2-oxoacetate (0.9 g, 4.945 mmol) in nitromethane (2.5 mL) was added triethylamine (0.142 mL, 0.989 mmol). After being stirred at room temperature for 16 h, the reaction mixture was concentrated under reduced pressure to afford ethyl 2-hydroxy-2-(1-methyl-1H-imidazol-2-yl)-3-nitropropanoate as an off-white solid (900 mg, 82%). $^1$H-NMR (400 MHz, $CDCl_3$) δ=7.17 (s, 1H), 7.04 (s, 1H), 6.81 (d, 1H), Step-D:

To a stirred solution compound from step-C (350 mg, 0.81 mmol) in acetonitrile (5 mL) was added triethylamine (123.59 mg, 1.22 mmol) followed by EDC.HCl (467.72 mg, 2.447 mmol). Then, the reaction mixture was allowed to warm to room temperature. After 48 h, the reaction mixture was diluted with ice water (30 mL) and the crude product was stirred for 30 min. The solid was collected by filtration and dried under reduced pressure to get a crude compound.

This crude compound was triturated with n-pentane (10 mL), filtered and dried under reduced pressure to afford ethyl 2-((1,2,3,5,6,7-hexahydro-s-indacen-4-yl)amino)-5-(1-methyl-1H-imidazol-2-yl)-4,5-dihydrooxazole-5-carboxylate as a white solid (123 mg, 38%). $^1$H-NMR (500 MHz, DMSO-d6) δ=8.42 (s, 1H), 7.26 (s, 1H), 6.88 (m, 2H), 4.88 (brs, 1H), 4.25-4.21 (m, 2H), 3.39 (brs, 1H), 3.54 (s, 3H), 2.79-2.55 (m, 8H), 1.94-1.91 (m, 4H), 1.20-1.17 (t, 3H). MS: 395.61 [M+H]$^+$ Example 4: enantiopure ethyl 2-((1,2,3,5,6,7-hexahydro-s-indacen-4-yl)amino)-5-(1-methyl-1H-imidazol-2-yl)-4,5-dihydrooxazole-5-carboxylate The enantiopure compound was obtained as an off-white solid by chiral SFC separation starting from the racemic mixture of Example 3. (Chiralpak IG (4.6*250) mm, 5μ; Co-Solvent: 50% (100% Ethanol), Outlet Pressure: 100 bar; Temperature: 30° C.); First eluting peak. $^1$H-NMR (500 MHz, DMSO-d6) δ=8.44 (s, 1H), 7.26 (s, 1H), 6.88 (s, 2H), 4.88 (brs, 1H), 4.25-4.21 (m, 2H), 3.96 (s, 1H), 3.55 (s, 3H), 2.79-2.55 (m, 8H), 1.95-1.90 (m, 4H) 1.20-1.17 (t, 3H). MS: 395.61 [M+H]$^+$. 97.54% ee Example 5: enantiopure ethyl 2-((1,2,3,5,6,7-hexahydro-s-indacen-4-yl)amino)-5-(1-methyl-1H-imidazol-2-yl)-4,5-dihydrooxazole-5-carboxylate The enantiopure compound was obtained as an off white solid by chiral SFC separation starting from the racemic mixture of Example 3. (Chiralpak IG (4.6*250) mm, 5μ; Co-Solvent: 50% (100% Ethanol), Outlet Pressure: 100 bar; Temperature: 30° C.); Second eluting peak. $^1$H-NMR, (500 MHz, DMSO-d6) δ=8.43 (s, 1H), 7.26 (s, 1H), 6.88 (s, 2H), 4.88 (brs, 1H), 4.25-4.21 (m, 2H), 3.96 (s, 1H), 3.55 (s, 3H), 2.79-2.55 (m, 8H), 1.94-1.91 (t, 4H) 1.20-1.17 (t, 3H). MS: 395.61 [M+H]$^+$. 96.56% ee Example 6: ethyl 2-((1,2,3,5,6,7-hexahydro-s-indacen-4-yl)amino)-5-(6-methoxypyridin-3-yl)-4,5-dihydrooxazole-5-carboxylate

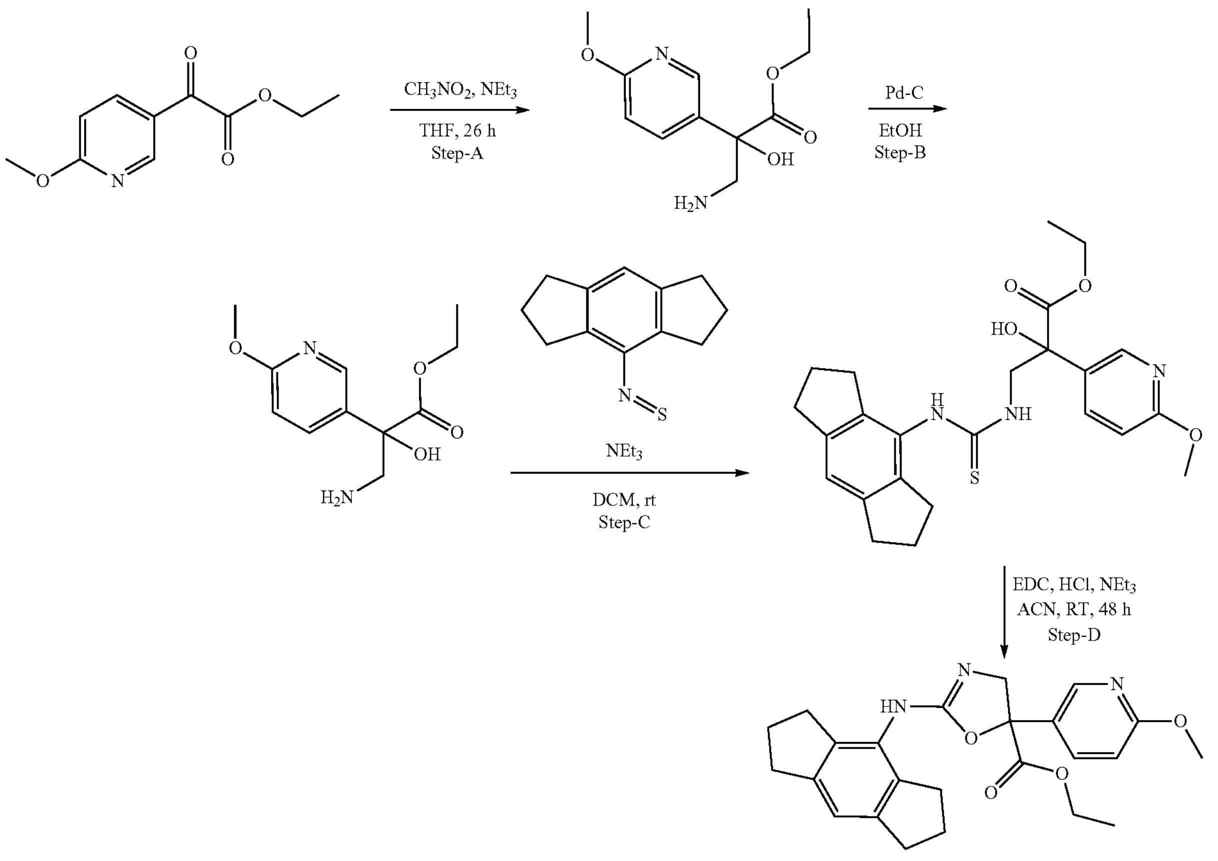

Step-A:

To a stirred solution of ethyl 2-(6-methoxypyridin-3-yl)-2-oxoacetate (1 g, 4.78 mmol) in nitromethane (10 mL) was added triethylamine (0.67 ml, 4.78 mmol). After being stirred at room temperature for 16 h, the reaction mixture was concentrated under reduced pressure. The crude compound was purified by flash chromatography (Silica, 80 g Reveleris column; 0-50% ethyl acetate in hexane) to afford ethyl 2-hydroxy-2-(6-methoxypyridin-3-yl)-3-nitropropanoate as a pale yellow liquid (0.85 g, 66%). $^1$H-NMR (400 MHz, $CDCl_3$) δ=8.38-8.37 (m, 1H), 7.82-7.79 (dd, 1H), 6.78-6.76 (d, 1H), 5.23-5.17 (d, 1H), 4.68-4.65 (d, 1H), 4.44-4.33 (m, 2H), 4.22 (s, 1H), 3.94 (s, 3H), 1.37-1.33 (t, 3H). MS: 371.12 [M+H]$^+$ Step-B:

To a stirred solution of the compound from step-A (0.75 g, 2.77 mmol) in ethanol (15 mL) was added 10% Pd/C (0.38 g) at room temperature. The reaction mixture was stirred under hydrogen atmosphere (~15 psi pressure) for 16 h. Then, the crude mixture was filtered through a celite pad and the residue was washed with ethanol. The filtrate was evaporated under reduced pressure to afford ethyl 3-amino-2-hydroxy-2-(6-methoxypyridin-3-yl) propanoate as a pale yellow gum (345 mg, 52%). MS: 214.13 [M+H]$^+$ Step-C:

To a stirred solution of the compound from step-B (0.34 g, 1.41 mmol) and triethylamine (0.6 mL, 4.249 mmol) in dichloromethane (20 mL) was added 4-isothiocyanato-1,2,3,5,6,7-hexahydro-s-indacene (0.335 g, 1.558 mmol). After being stirred at room temperature for 16 h, the reaction mixture was concentrated under reduced pressure to dryness. The crude compound was purified by flash chromatography (Silica 12 g, Reveleris column; 0-70% ethyl acetate in hexane) to afford ethyl 3-(3-(1,2,3,5,6,7-hexahydro-s-indacen-4-yl)thioureido)-2-hydroxy-2-(6-methoxypyridin-3-yl) propanoate as an off-white solid (0.26 g, 40%). $^{1}$H-NMR, (400 MHz, $CDCl_3$) δ=8.32 (d, 1H), 7.81-7.78 (dd, 1H), 7.29 (s, 1H), 7.09 (s, 1H), 6.74-6.71 (d, 1H), 5.95 (s, 1H), 4.52-4.50 (m, 1H), 4.31-4.20 (m, 3H), 4.19-4.08 (m, 1H), 3.94 (s, 3H), 3.49 (d, 1H), 2.88 (t, 4H), 2.70-2.58 (m, 4H), 2.07-2.00 (m, 4H), 1.31-1.26 (m, 3H). MS: 456.55 [M+H]+

Step-D:

To a stirred solution of the compound from step-C (0.26 g, 0.57 mmol) in acetonitrile (5 mL) was added triethylamine (0.24 mL, 1.71 mmol) followed by EDC.HCl (0.218 g, 1.14 mmol). Then, the reaction mixture was allowed to warm to room temperature. After 48 h, the reaction mixture was diluted with ice water (10 mL) and the crude product was stirred for 30 min. The solid was collected by filtration and dried under reduced pressure to get a crude compound. The crude compound was purified by flash chromatography (Silica, 12 g Reveleris column; 0-70% ethyl acetate in hexane) to afford ethyl 2-((1,2,3,5,6,7-hexahydro-s-indacen-4-yl)amino)-5-(6-methoxypyridin-3-yl)-4,5-dihydrooxazole-5-carboxylate as an off white solid (0.12 g, 52%). $^{1}$H-NMR (500 MHz, $CDCl_3$) δ=8.27 (d, 1H), 7.65 (dd, 1H), 6.97 (s, 1H), 6.77 (d, 1H), 4.50-4.47 (d, 1H), 4.28-4.23 (m, 2H), 4.07 (d, 1H), 3.95 (s, 3H), 2.89-2.80 (m, 8H), 2.07-2.05 (m, 4H), 1.28 (t, 3H). MS: 422.58 $[M+H]^+$ Example 7: enantiopure ethyl 2-((1,2,3,5,6,7-hexahydro-s-indacen-4-yl)amino)-5-(6-methoxypyridin-3-yl)-4,5-dihydrooxazole-5-carboxylate The enantiopure compound was obtained as an off white solid by chiral SFC separation starting from the racemic mixture of Example 6. (Chiralpak IG (4.6*250) mm, 5μ; Co-Solvent: 50% (0.5% triethylamine in ethanol), Outlet Pressure: 100 bar; Temperature: 30° C.); Second eluting peak.

$^{1}$H-NMR, (500 MHz, $CDCl_3$) δ=8.27 (d, 1H), 7.65 (dd, 1H), 6.97 (s, 1H), 6.77 (d, 1H), 4.48 (d, 1H), 4.28-4.24 (m, 2H), 4.06 (d, 1H), 3.95 (s, 3H), 2.89-2.77 (m, 8H), 2.09-2.00 (m, 4H), 1.28 (t, 3H). MS: 422.55 $[M+H]^+$. 99.79% ee

Example 8: ethyl 2-((1,2,3,5,6,7-hexahydro-s-indacen-4-yl)amino)-5-(pyridin-2-yl)-4,5-dihydrooxazole-5-carboxylate

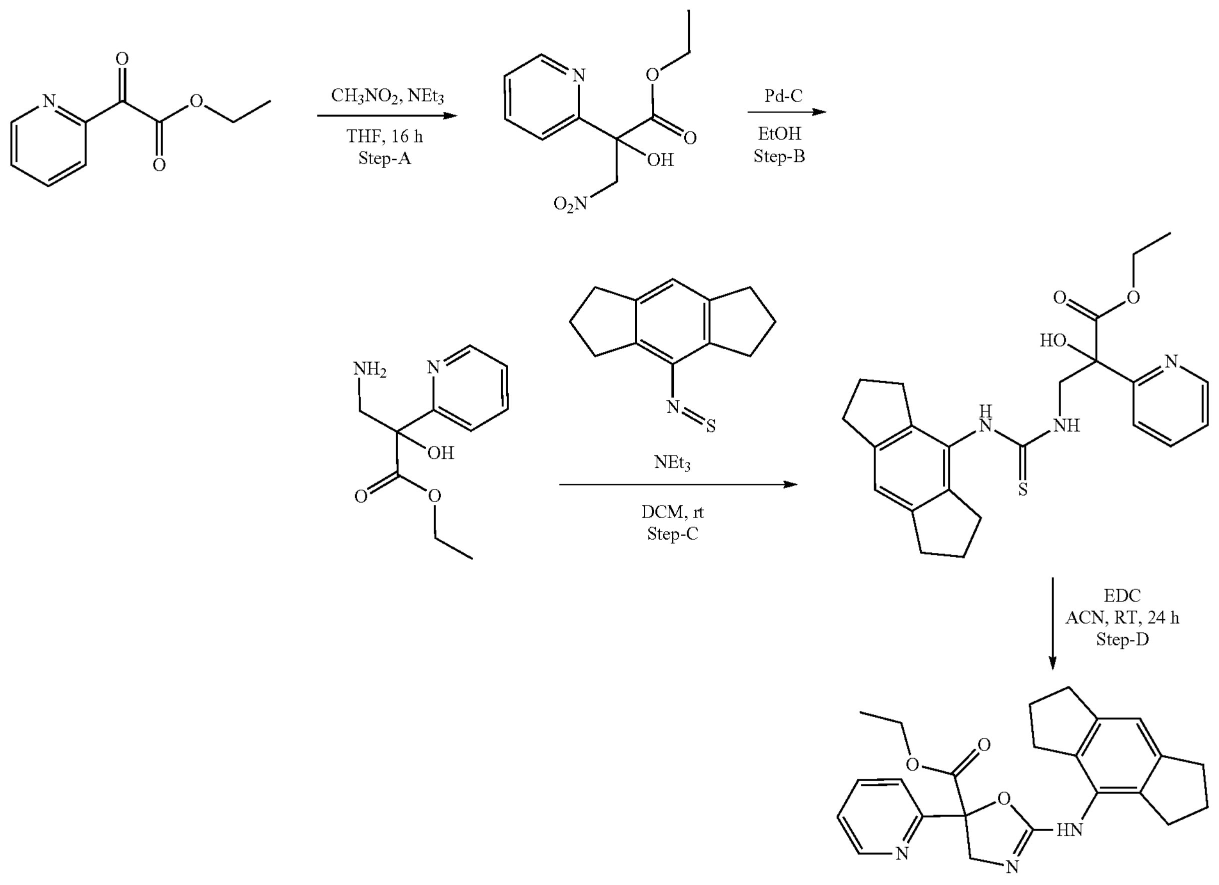

Step-A:

To a stirred solution of ethyl 2-oxo-2-(pyridine-2-yl) acetate (0.9 g, 5.02 mmol) in nitromethane (10 mL) was added triethylamine (0.7 ml, 5.02 mmol). After being stirred at room temperature for 16 h, the reaction mixture was concentrated under reduced pressure. The crude compound was purified by flash chromatography (Silica 25 g column, 0-50% ethyl acetate in hexane) to afford ethyl 2-hydroxy-3-nitro-2-(pyridin-2-yl) propanoate as a colorless liquid (1 g, 83%). MS: 241.32 $[M+H]^+$ Step-B:

To a stirred solution of the compound from step-A (1 g, 4.16 mmol) in ethanol (20 mL) was added 10% Pd/C (0.6 g) at room temperature. The reaction mixture was stirred under hydrogen atmosphere (~15 psi pressure) for 16 h. Then, the crude mixture was filtered through a celite pad and the residue was washed with ethanol. The filtrate was evaporated under reduced pressure to afford ethyl 3-amino-2-hydroxy-2-(pyridin-2-yl) propanoate as a colorless gum (0.6 g, 69%). $^1$H-NMR (400 MHz, $CDCl_3$) δ=8.57 (d, 1H), 7.78-7.74 (m, 1H), 7.63 (d, 1H), 7.30-7.26 (m, 1H), 4.23 (q, 2H), 3.49 (d, 1H), 3.18 (d, 1H), 1.26-1.22 (m, 3H). MS: 211.33 $[M+H]^+$ Step-C:

To a stirred solution of the compound from step-B (0.6 g, 2.85 mmol) and triethylamine (1.19 mL, 8.56 mmol) in dichloromethane (4 mL) was added a solution of 4-isothiocyanato-1,2,3,5,6,7-hexahydro-s-indacene (0.613 g, 2.85 mmol) in dichloromethane (4 mL). After being stirred at room temperature for 16 h, the reaction mixture was concentrated under reduced pressure to dryness. The crude compound was purified by flash chromatography (Silica 12 g, Reveleris column; 0-50% ethyl acetate in hexane) to afford ethyl 3-(3-(1,2,3,5,6,7-hexahydro-s-indacen-4-yl) thioureido)-2-hydroxy-2-(pyridin-2-yl) propanoate as an off-white solid (0.48 g, 40%). $^1$H-NMR, (400 MHz, DMSO-d6) δ=9.27 (s, 1H), 8.40 (s, 1H), 7.84-7.79 (m, 1H), 7.54-7.52 (d, 1H), 7.34-7.31 (m, 1H), 7.00 (s, 1H), 6.62 (s, 1H), 4.17-4.04 (m, 4H), 2.82-2.78 (m, 4H), 2.55-2.49 (m, 4H), 1.94-1.89 (m, 4H), 1.09 (t, 3H). MS: 426.28 [M+H]+

Step-D:

To a stirred solution of the compound from step-C (0.480 g, 1.12 mmol) in acetonitrile (5 mL) was added triethylamine (0.47 ml, 3.38 mmol) followed by EDC.HCl (0.432 g, 2.25 mmol). Then, the reaction mixture was allowed to warm to room temperature. After 24 h, the reaction mixture was diluted with ice water (10 mL) and the crude product was stirred for 30 min. The solid was collected by filtration and dried under reduced pressure to get a crude compound. The crude compound was purified by flash chromatography (Silica, 12 g Reveleris column; 0-70% ethyl acetate in hexane) to afford ethyl 2-((1,2,3,5,6,7-hexahydro-s-indacen-4-yl)amino)-5-(pyridin-2-yl)-4,5-dihydrooxazole-5-carboxylate as an off white solid (0.28 g, 63%). $^1$H-NMR (400 MHz, DMSO-d6) δ=8.59 (d, 1H), 7.94-7.91 (m, 1H), 7.50 (s, 1H), 7.44-7.41 (m, 1H), 6.81 (s, 1H), 4.21-4.16 (m, 4H), 2.79-2.75 (m, 4H), 2.67-2.66 (m, 4H), 1.96-1.89 (m, 4H), 1.15 (t, 3H). MS: 392.57 [M+H]+

Example 9: enantiopure ethyl 2-((1,2,3,5,6,7-hexahydro-s-indacen-4-yl)amino)-5-(pyridin-2-yl)-4,5-dihydrooxazole-5-carboxylate The enantiopure compound was obtained as an off white solid by chiral SFC separation starting from the racemic mixture of Example 8. (Chiralpak IG (4.6*250) mm, 5μ; Co-Solvent: 30% (ethanol), Outlet Pressure: 100 bar; Temperature: 30° C.); Second eluting peak. $^1$H-NMR (400 MHz, DMSO-d6) δ=8.59 (d, 1H), 7.94-7.91 (m, 1H), 7.50 (s, 1H), 7.44-7.41 (m, 1H), 6.81 (s, 1H), 4.21-4.16 (m, 4H), 2.79-2.75 (m, 4H), 2.67-2.66 (m, 4H), 1.96-1.90 (m, 4H), 1.15 (t, 3H). MS: 392.57 $[M+H]^+$. 99.76% ee Example 10: ethyl 5-(4-chlorophenyl)-2-((1,2,3,5,6,7-hexahydro-s-indacene-4-yl)amino)-4,5-dihydrooxazole-5-carboxylate

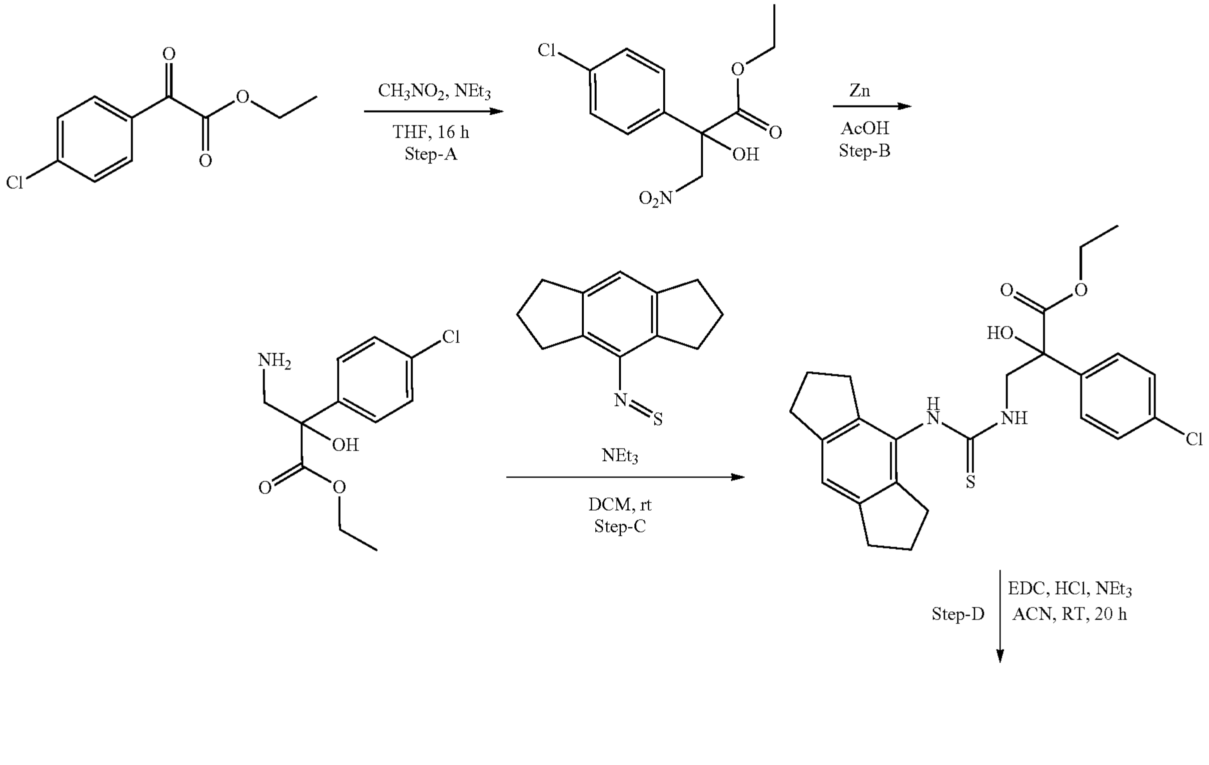

-continued

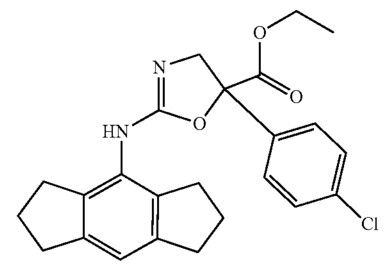

Step-A:

To a stirred solution of ethyl 2-(4-chlorophenyl)-2-oxoacetate (2 g, 9.4 mmol) in nitromethane (10 mL) was added triethylamine (1.31 ml, 9.4 mmol). After being stirred at room temperature for 16 h, the reaction mixture was concentrated under reduced pressure. The crude compound was purified by flash chromatography (Silica, 80 g column; 0-50% EtOAc in hexane) to afford ethyl 2-(4-chlorophenyl)-2-hydroxyl-3-nitropropanate as a colorless liquid (2.4 g, 94%). MS 272.11 $[M+H]^+$ Step-B:

To a stirred solution of the compound from step-A (0.2 g, 0.73 mmol) in acetic acid (5 ml) was added zinc dust (0.2 g, 7.32 mmol) at 0° C. Then, the reaction mixture was allowed to warm to room temperature. After 16 h, the crude mixture was filtered through a celite pad and the residue was washed with ethyl acetate. The filtrate was evaporated under reduced pressure to afford ethyl 3-amino-2-(4-chlorophenyl)-2-hydroxypropanate as a colorless gum (0.16 g, 90%). $^1$H-NMR (500 MHz, Chloroform-d) δ=7.51 (d, 2H), 7.34 (d, 2H), 4.31-4.22 (m, 2H), 3.44 (d, 1H), 3.12 (d, 1H), 1.27 (t, 3H). MS: 244.10 $[M+H]^+$ Step-C:

To a stirred solution of the compound from step-B (0.160 g, 0.65 mmol) and triethylamine (0.27 ml, 1.97 mmol) in dichloromethane (2 mL) was added a solution of 4-isothiocyanato-1,2,3,5,6,7-hexahydro-s-indacene (0.613 g, 2.85 mmol) in dichloromethane (4 mL). After being stirred at room temperature for 16 h, the reaction mixture was concentrated under reduced pressure to dryness. The crude compound was purified by flash chromatography (Silica 12 g, Reveleris column; 0-50% ethyl acetate in hexane) to afford ethyl 2-(4-chlorophenyl)-3-(3-(1,2,3,5,6,7-hexahydro-s-indacen-4-yl)thioureido)-2-hydroxypropanate as an off-white solid (0.2 g, 66%). $^1$H-NMR (400 MHz, DMSO-d6) δ=9.23 (brs, 1H), 7.49 (d, 2H), 7.41 (d, 2H), 6.98 (s, 1H) 6.58 (s, 1H), 4.17-4.02 (m, 4H), 2.86-2.67 (m, 8H), 1.97-1.90 (m, 4H), 1.17-1.14 (m, 3H). MS: 459.33 [M+H]+

Step-D:

To a stirred solution of the compound from step-C (0.20 g, 0.43 mmol) in acetonitrile (4 mL) was added triethylamine (0.18 ml, 1.3 mmol), followed by EDC.HCl (0.167 g, 0.87 mmol). Then, the reaction mixture was allowed to warm to room temperature. After 20 h, the reaction mixture was diluted with ice water (30 mL) and the crude product was stirred for 30 min. The solid was collected by filtration and dried under reduced pressure to get a crude compound. This crude compound was triturated with diethyl ether (10 mL), filtered and dried under reduced pressure to afford ethyl 5-(4-chlorophenyl)-2-((1,2,3,5,6,7-hexahydro-s-indacene-4-yl)amino)-4,5-dihydrooxazole-5-carboxylate as a white solid (70 mg, 38%). $^1$H-NMR (500 MHz, DMSO-d6) δ=8.66 (s, 1H), 7.53-7.45 (m, 4H), 6.85-6.75 (m, 1H), 4.27-3.86 (m, 4H), 2.8-2.63 (m, 8H), 1.97-1.91 (m, 4H), 1.17 (t, 3H). MS: 425.55 $[M+H]^+$ Example 10a: enantiopure ethyl 5-(4-chlorophenyl)-2-((1,2,3,5,6,7-hexahydro-s-indacene-4-yl)amino)-4,5-dihydrooxazole-5-carboxylate The enantiopure compound was obtained as an off-white solid by chiral SFC separation starting from the racemic mixture of Example 10. (Lux Amylose-3 (30*250) mm, 5μ; Co-Solvent: 35% (ethanol), Outlet Pressure: 100 bar; Temperature: 30° C.); Second eluting peak. $^1$H-NMR (500 MHz, DMSO-d6) δ 8.67 (br s, 1H), 7.59-7.38 (m, 4H), 6.85 (s, 1H), 4.36-4.08 (m, 3H), 3.95-3.62 (m, 1H), 2.88-2.57 (m, 8H), 2.03-1.86 (m, 4H), 1.17 (t, 3H). MS: 425.52 $[M+H]^+$ Example 11a: ethyl 2-((1,2,3,5,6,7-hexahydro-s-indacen-4-yl)amino)-5-(pyridin-3-yl)-4,5-dihydrooxazole-5-carboxylate

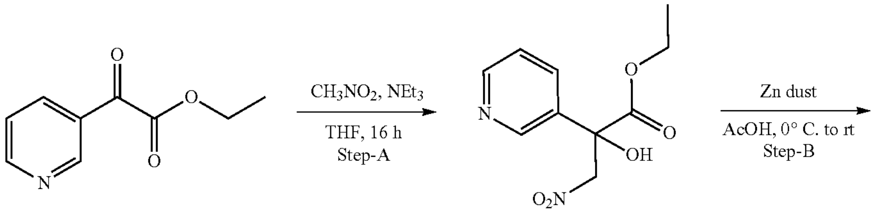

-continued

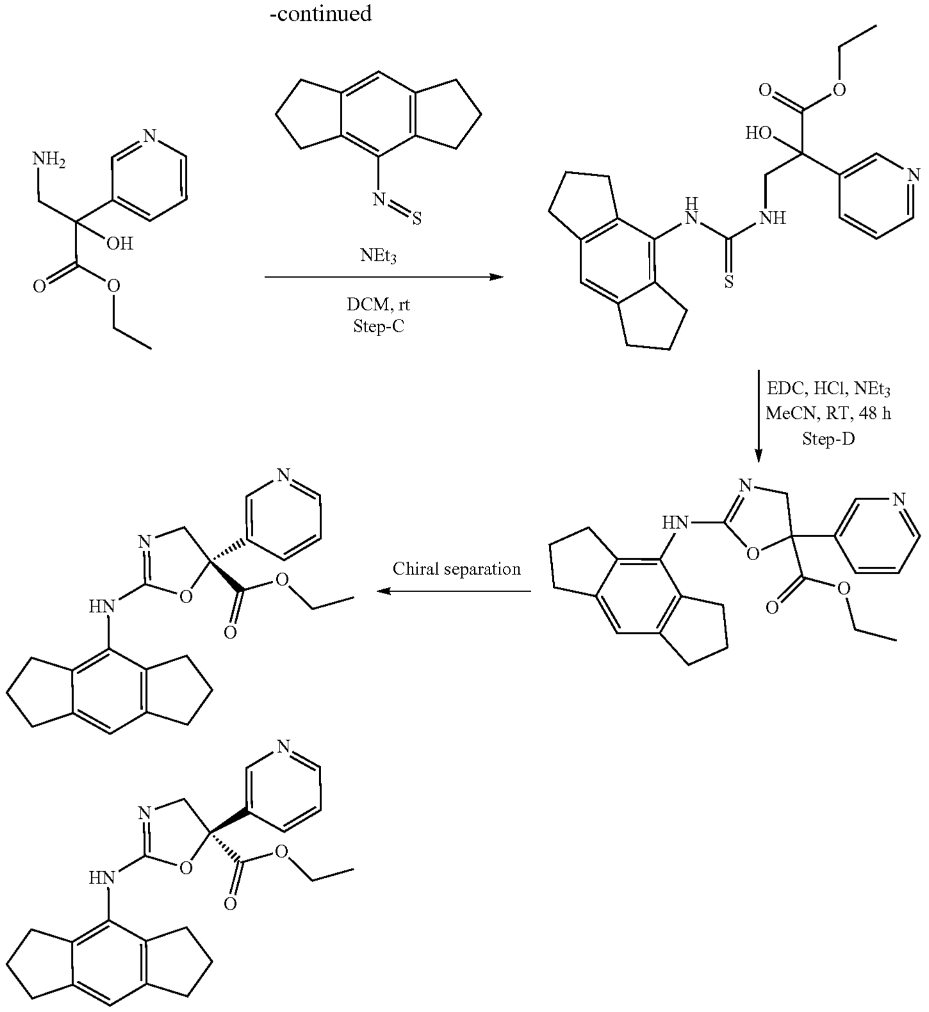

Step-A:

To a stirred solution of ethyl 2-oxo-2-(pyridine-3-yl) acetate (0.5 g, 2.79 mmol) in nitromethane (5 mL) was added triethylamine (0.38 ml, 2.79 mmol). After being stirred at room temperature for 16 h, the reaction mixture was concentrated under reduced pressure. The crude compound was purified by flash chromatography (Silica, 12 g column; 0-50% EtOAc in hexane) to afford ethyl 2-hydroxy-3-nitro-2-(pyridin-3-yl) propanoate as a colorless liquid (0.580 g, 87%). $^1$H-NMR (500 MHz, $CDCl_3$) δ=8.87 (d, 1H), 8.64 (dd, 1H), 7.99-7.97 (m, 1H), 7.37-7.35 (m, 1H), 5.26 (d, 1H), 4.70 (d, 1H), 4.45-4.35 (m, 2H), 1.36 (t, 3H). MS 241.28 $[M+H]^+$ Step-B:

To a stirred solution of the compound from step-A (0.450 g, 1.87 mmol) in acetic acid (5 ml) was added zinc dust (1.21 g, 18.75 mmol) at 0° C. Then, the reaction mixture was allowed to warm to room temperature. After 16 h, the crude mixture was filtered through a celite pad and the residue was washed with ethyl acetate. The filtrate was evaporated under reduced pressure to afford ethyl 3-amino-2-hydroxy-2-(pyridin-3-yl) propanoate as a colorless gum. MS: 211.2 $[M+H]^+$ Step-C:

To a stirred solution of the compound from step-B (0.360 g, 1.71 mmol) and triethylamine (0.71 ml, 5.13 mmol) in dichloromethane (5 mL) was added a solution of 4-isothiocyanato-1,2,3,5,6,7-hexahydro-s-indacene (0.368 g, 1.71 mmol) in dichloromethane (3 mL). After being stirred at room temperature for 16 h, the reaction mixture was concentrated under reduced pressure to dryness. The crude compound was purified by flash chromatography (Silica 12 g, Reveleris column; 0-50% ethyl acetate in hexane) to afford ethyl 3-(3-(1,2,3,5,6,7-hexahydro-s-indacen-4-yl) thioureido)-2-hydroxy-2-(pyridin-3-yl) propanoate as an off-white solid (0.450 g, 61%). $^1$H-NMR (500 MHz, $CDCl_3$) δ=8.80 (d, 1H), 8.57 (dd, 1H), 7.98-7.95 (m, 1H), 7.38-7.29 (m, 2H), 7.10 (s, 1H), 4.54-4.53 (m, 1H), 4.32-4.09 (m, 4H), 2.90-2.86 (m, 4H), 2.71-2.56 (m, 4H), 2.10-2.01 (m, 4H), 1.30-1.22 (m, 3H). MS: 426.3 [M+H]+

Step-D:

To a stirred solution of the compound from step-C (0.4 g, 0.93 mmol) in acetonitrile (5 mL) was added triethylamine (0.39 ml, 2.81 mmol) followed by EDC.HCl (0.54 g, 2.81 mmol). Then, the reaction mixture was allowed to warm to room temperature. After 20 h, the reaction mixture was diluted with ice water (30 mL) and the crude product was stirred for 30 min. The solid was collected by filtration and dried under reduced pressure to get a crude compound. This crude compound was triturated with diethyl ether (20 mL), filtered and dried under reduced pressure to afford ethyl 2-((1,2,3,5,6,7-hexahydro-s-indacen-4-yl)amino)-5-(pyridin-3-yl)-4,5-dihydrooxazole-5-carboxylate as a white solid (207 mg, 56%). $^1$H-NMR (500 MHz, $CDCl_3$) δ 8.82-8.72 (m, 1H), 8.61 (dd, 1H), 7.81 (dt, 1H), 7.33 (ddd, 1H), 6.98

(s, 1H), 4.54 (d, 1H), 4.27 (q, 2H), 4.09 (d, 1H), 2.95-2.77 (m, 8H), 2.16-1.99 (m, 4H), 1.29 (t, 3H). MS: 392.54 [M+H]+.

Example 11: enantiopure ethyl 2-((1,2,3,5,6,7-hexahydro-s-indacen-4-yl)amino)-5-(pyridin-3-yl)-4,5-dihydrooxazole-5-carboxylate The enantiopure compound was obtained as an off white solid by chiral SFC separation starting from the racemic mixture of Example 11a. (Chiralpak IG (4.6*250) mm, 5μ; Co-Solvent: 30% (ethanol), Outlet Pressure: 100 bar; Temperature: 30° C.); Second eluting peak. $^{1}$H-NMR (500 MHz, $CDCl_3$) δ=8.77 (d, 1H), 8.61 (dd, 2H), 7.80 (d, 1H), 7.34-7.32 (m, 1H), 6.97 (s, 1H), 4.54 (d, 1H), 4.29-4.24 (m, 2H), 4.09 (d, 1H), 2.89-2.78 (m, 8H), 2.09-2.03 (m, 4H), 1.29 (t, 3H). MS: 392.57 [M+H]+. 99.91% ee Example 12: enantiopure ethyl 2-((1,2,3,5,6,7-hexahydro-s-indacen-4-yl)amino)-5-(tetrahydro-2H-pyran-4-yl)-4,5-dihydrooxazole-5-carboxylate Step-A:

To a stirred solution of ethyl 2-oxo-2-(tetrahydro-2H-pyran-4-yl)acetate (0.5 g, 2.69 mmol) in nitromethane (5 mL) was added triethylamine (0.075 mL, 0.537 mmol). After being stirred at room temperature for 48 h, the reaction mixture was concentrated under reduced pressure. The crude compound was purified by flash chromatography (Silica, 40 g column; 0-50% EtOAc in hexane) to afford 2-hydroxy-3-nitro-2-(tetrahydro-2H-pyran-4-yl) propanoate as a colorless gum (0.620 g, 93%). $^{1}$H-NMR (400 MHz, $CDCl_3$) δ=4.83 (d, 1H), 4.66 (d, 1H), 4.39-4.33 (m, 2H), 4.05-3.98 (m, 2H), 3.68 (s, 1H), 3.38-3.32 (m, 2H), 1.91-1.88 (m, 1H), 1.70-1.58 (m, 3H), 1.35 (t, 3H), 1.26-1.23 (m, 1H). MS 248.31 $[M+H]^+$ Step-B:

To a stirred solution of the compound from step-A (500 mg, 2.022 mmol) in ethanol (15 mL) was added 10% Pd/C (0.25 g) at room temperature. The reaction mixture was stirred under hydrogen atmosphere (~15 psi pressure) for 16 h. Then, the crude mixture was filtered through a celite pad and the residue was washed with ethanol. The filtrate was

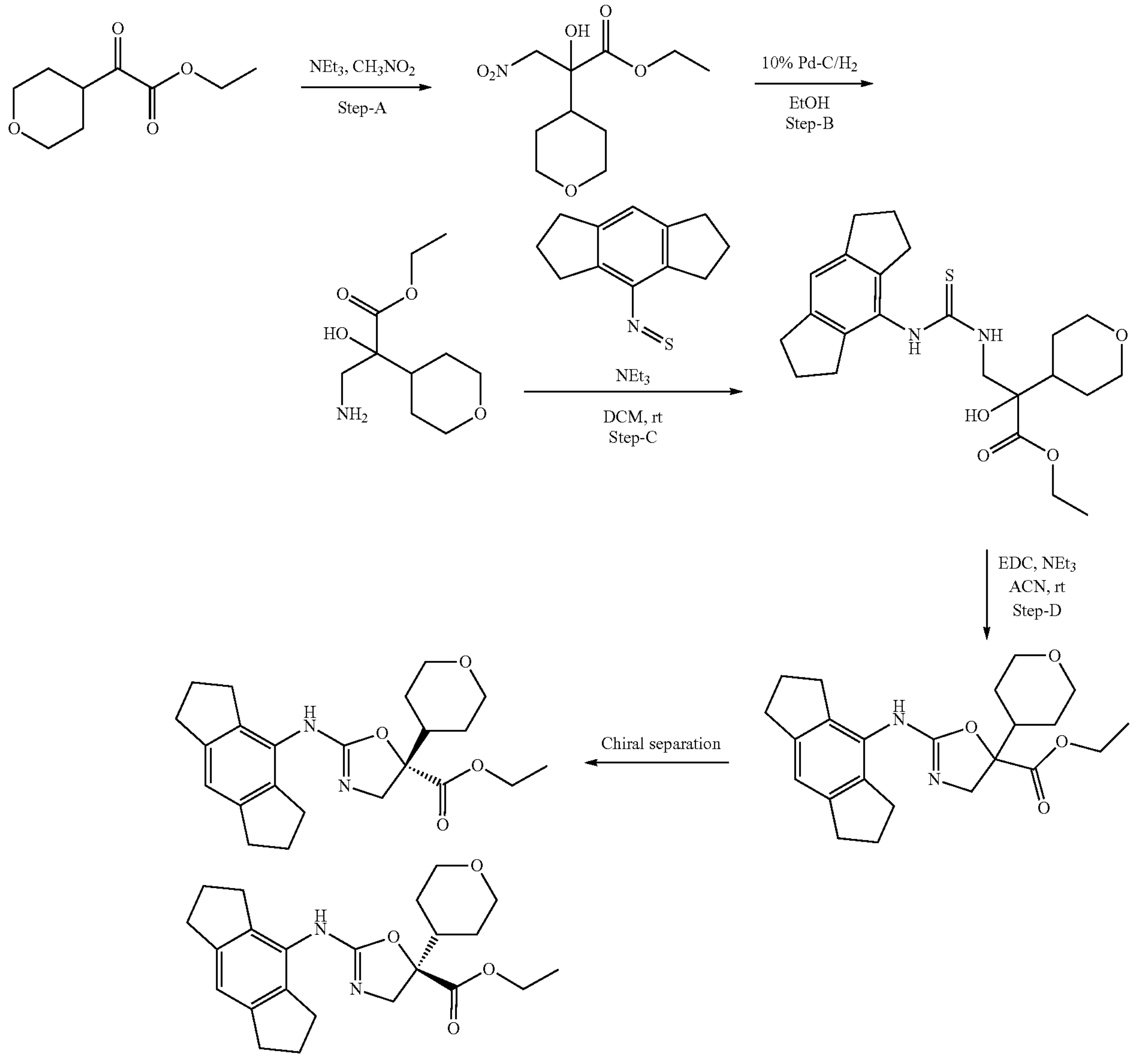

evaporated under reduced pressure to afford ethyl 3-amino-2-hydroxy-2-(tetrahydro-2H-pyran-4-yl) propanoate as a colorless gum.

Step-C:

To a stirred solution of the compound from step-B (260 mg, 1.196 mmol) and triethylamine (0.5 ml, 3.590 mmol) in dichloromethane (5 mL) was added a solution of 4-isothiocyanato-1,2,3,5,6,7-hexahydro-s-indacene (257.6 mg, 1.196 mmol). After being stirred at room temperature for 16 h, the reaction mixture was concentrated under reduced pressure to dryness. The crude compound was purified by flash chromatography (Silica 24 g, Reveleris column; 0-50% ethyl acetate in hexane) to afford ethyl 3-(3-(1,2,3,5,6,7-hexahydro-s-indacen-4-yl)thioureido)-2-hydroxy-2-(tetrahydro-2H-pyran-4-yl) propanoate (0.270 g, 52%) MS: 433.3 $[M+H]^+$.

Step-D:

To a stirred solution of the compound from step-C (270 mg, 0.624 mmol) in acetonitrile (12 mL) was added triethylamine (0.261 ml, 1.872 mmol) followed by EDC.HCl (299 mg, 1.560 mmol). Then, the reaction mixture was allowed to warm to room temperature. After 20 h, the reaction mixture was diluted with ice water (30 mL) and the crude product was stirred for 30 min. The solid was collected by filtration and dried under reduced pressure to get a crude compound. This crude compound was triturated with diethyl ether in pentane (20 mL), filtered and dried under reduced pressure to afford ethyl 2-((1,2,3,5,6,7-hexahydro-s-indacen-4-yl)amino)-5-(tetrahydro-2H-pyran-4-yl)-4,5-dihydrooxazole-5-carboxylate as a white solid (220 mg, 89%). The enantiopure compound was obtained as an off white solid by chiral SFC separation starting from the racemic mixture of Example 8. (Lux Cellulose-4 (30*250) mm, 5μ; Co-Solvent: 45% (ethanol), Outlet Pressure: 120 bar; Temperature: 30° C.); First eluting peak. $^1$H-NMR (500 MHz, $CDCl_3$) δ=6.95 (s, 1H), 4.29-4.25 (m, 2H), 4.05 (m, 2H), 3.95 (d, 1H), 3.84 (d, 1H), 3.41-3.37 (m, 2H), 2.88-2.79 (m, 8H), 2.12-2.03 (m, 5H) 1.68-1.62 (m, 2H), 1.51-1.46 (m, 2H), 1.32 (t, 3H). MS: 399.60 $[M+H]^+$. 99.94% ee Example 13: ethyl 5-(3-chlorophenyl)-2-((1,2,3,5,6,7-hexahydro-s-indacene-4-yl)amino)-4,5-dihydrooxazole-5-carboxylate

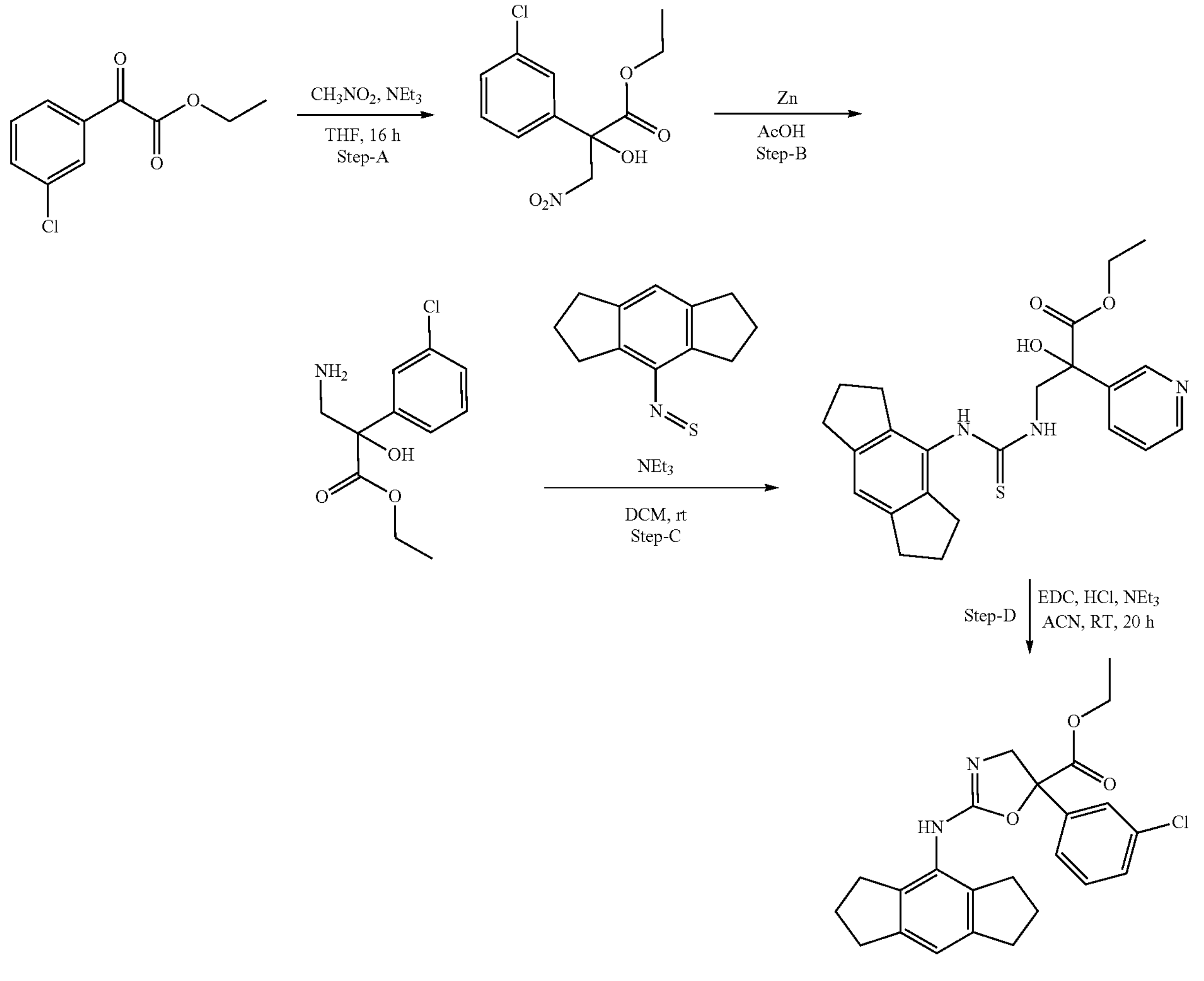

Step-A:

To a stirred solution of ethyl 2-(3-chlorophenyl)-2-oxoacetate (0.50 g, 2.35 mmol) in nitromethane (5 mL) was added triethylamine (0.32 ml, 2.35 mmol). After being stirred at room temperature for 16 h, the reaction mixture was concentrated under reduced pressure. The crude compound was purified by flash chromatography (Silica, 25 g column;

0-50% EtOAc in hexane) to afford 2-hydroxy-3-nitro-2-(tetrahydro-2H-pyran-4-yl) propanoate as a colorless gum (0.62 g, 68%). $^1$H-NMR (400 MHz, $CDCl_3$) δ=7.67-7.63 (m, 1H), 7.52-7.48 (m, 1H), 7.38-7.33 (m, 2H), 5.22 (dd, 1H), 4.65 (d, 1H), 4.47-4.32 (m, 2H), 4.26 (d, 1H), 1.36 (t, 3H).

Step-B:

To a stirred solution of the compound from step-A (0.6 g, 2.19 mmol) in acetic acid (7 ml) was added zinc dust (1.41 g, 21.9 mmol) at 5° C. Then, the reaction mixture was allowed to warm to room temperature. After 16 h, the crude mixture was filtered through a celite pad and the residue was washed with ethyl acetate. The filtrate was evaporated under reduced pressure to afford ethyl 3-amino-2-(3-chlorophenyl)-2-hydroxypropanate as a colorless gum. MS: 244.10 $[M+H]^+$ Step-C:

To a stirred solution of the compound from step-B (0.5 g, 2.05 mmol) and triethylamine (0.85 ml, 6.15 mmol) in dichloromethane (7 mL) was added a solution of 4-isothiocyanato-1,2,3,5,6,7-hexahydro-s-indacene (0.441 g, 2.05 mmol) in dichloromethane (3 mL). After being stirred at room temperature for 16 h, the reaction mixture was concentrated under reduced pressure to dryness. The crude compound was purified by flash chromatography (Silica 12 g, Reveleris column; 0-50% ethyl acetate in hexane) to afford ethyl 2-(3-chlorophenyl)-3-(3-(1,2,3,5,6,7-hexahydro-s-indacen-4-yl)thioureido)-2-hydroxypropanate as an off white solid (0.6 g, 82%). $^1$H-NMR (400 MHz, $CDCl_3$) δ=7.57 (s, 1H), 7.47-7.46 (m, 1H), 7.29-7.26 (m, 2H), 7.09 (s, 1H), 5.92 (s, 1H), 4.52-4.47 (m, 1H), 4.28-4.20 (m, 2H), 4.14-4.09 (m, 1H), 2.89-2.86 (m, 4H), 2.68-2.57 (m, 4H), 2.10-1.99 (m, 4H), 1.28 (t, 3H). MS: 459.27 $[M+H]^+$.

Step-D:

To a stirred solution of the compound from step-C (0.60 g, 1.3 mmol) in acetonitrile (10 mL) was added triethylamine (0.54 ml, 3.92 mmol), followed by EDC.HCl (0.751 g, 3.92 mmol). Then, the reaction mixture was allowed to warm to room temperature. After 20 h, the reaction mixture was diluted with ice water (20 mL) and the crude product was stirred for 30 min. The solid was collected by filtration and dried under reduced pressure to get a crude compound. This crude compound was triturated with diethyl ether (20 mL), filtered and dried under reduced pressure to afford ethyl 5-(3-chlorophenyl)-2-((1,2,3,5,6,7-hexahydro-s-indacene-4-yl)amino)-4,5-dihydrooxazole-5-carboxylate as a white solid (340 mg, 61%). $^1$H-NMR (500 MHz, DMSO-d6) δ=8.69 (s, 1H), 7.48-7.41 (m, 4H), 7.00-6.62 (m, 1H), 4.27-3.88 (m, 4H), 2.80-2.63 (m, 8H), 1.96-1.93 (m, 4H), 1.18 (t, 3H). MS: 425.52 $[M+H]_+$.

Example 13a: enantiopure ethyl 5-(3-chlorophenyl)-2-((1,2,3,5,6,7-hexahydro-s-indacen-4-yl)amino)-4,5-dihydrooxazole-5-carboxylate The enantiopure compound was obtained as an off white solid by chiral SFC separation starting from the racemic mixture of Example 13. (ChiralpakAD-H (30*250) mm, 5μ; Co-Solvent: 20% (ethanol), Outlet Pressure: 120 bar; Temperature: 30° C.); First eluting peak. $^1$H-NMR (500 MHz, $CDCl_3$) δ 7.50 (s, 1H), 7.39-7.31 (m, 3H), 6.97 (s, 1H), 4.52 (d, 1H), 4.25 (q, 2H), 4.04 (d, 1H), 2.93-2.80 (m, 8H), 2.13-2.00 (m, 4H), 1.28 (t, 3H). MS: 425.2 [M+H]+.

Example 14: ethyl 3-(3-(1,2,3,5,6,7-hexahydro-s-indacen-4-yl)thioureido)-2-hydroxy-2-(5-(2-hydroxypropan-2-yl) isoxazol-3-yl) propanoate

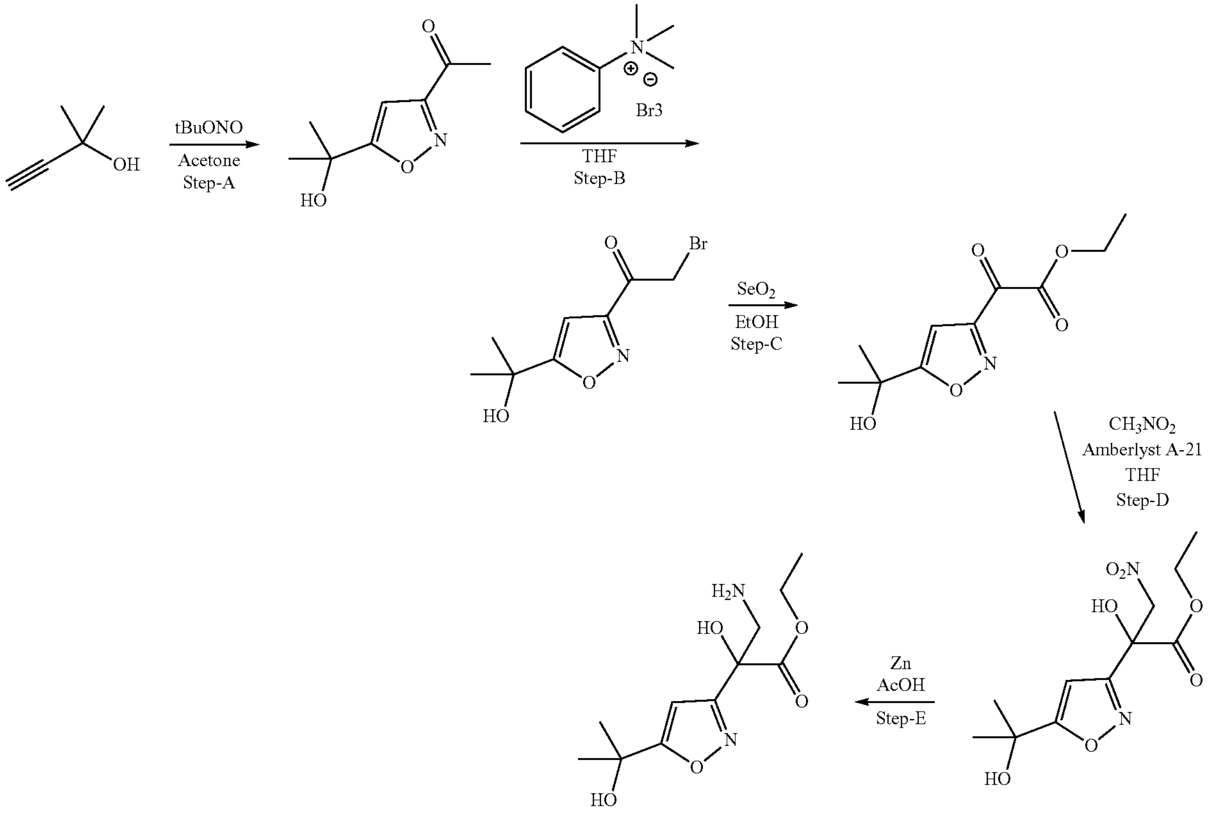

-continued

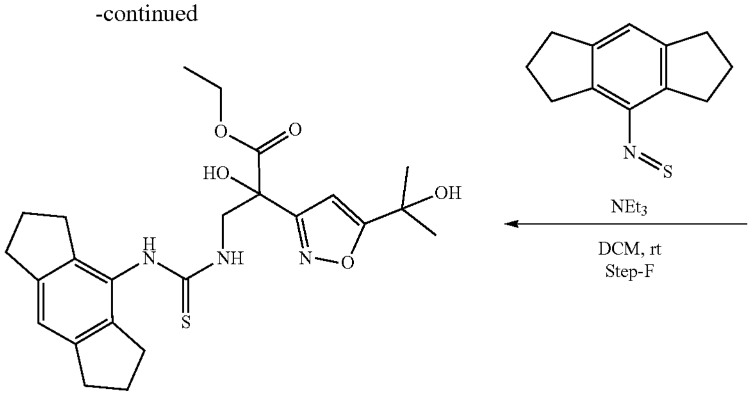

Step-A:

A round-bottom flask was charged with acetone (52.3 ml, 706 mmol), 2-methylbut-3-yn-2-ol (2.304 ml, 23.30 mmol) and tert-butyl nitrite (3.39 ml, 25.6 mmol) at room temperature. The solution was stirred at 60° C. overnight under argon. The reaction mixture was then evaporated under reduced pressure. The crude compound was purified by flash chromatography (Silica, 50 g column; 0-40% ethyl acetate in hexane) to afford 1-(5-(2-hydroxypropan-2-yl) isoxazol-3-yl) ethanone as a yellow oil (1.44 g, 37%). $^1$H-NMR (80 MHz, DMSO-d6) δ 6.59 (s, 1H), 5.73 (s, 1H), 2.56 (s, 3H), 1.49 (s, 6H).

Step-B:

To a stirred solution of the compound from step-A (50 mg, 0.296 mmol) in THF (1 ml) was added phenyltrimethylammonium tribromide (89 mg, 0.236 mmol) at room temperature. The reaction mixture was stirred at 70° C. for 3 h. Water and ethyl acetate were added and the layers were separated. The aqueous layer was extracted with EtOAc (3×). The combined organic layers were washed with water and brine, dried over sodium sulfate, filtered and concentrated under reduced pressure. The crude compound was purified by flash chromatography (Silica, 12 g column; 0-40% ethyl acetate in hexane) to afford 2-bromo-1-(5-(2-hydroxypropan-2-yl) isoxazol-3-yl) ethanone as an orange oil (80 mg, 87%). $^1$H-NMR (80 MHz, DMSO-d6) δ 6.72 (s, 1H), 4.83 (s, 2H), 1.50 (s, 6H).

Step-C:

To a solution of the compound from step-B (1 g, 3.39 mmol) in ethanol (10 mL) was added selenium dioxide (0.751 g, 6.77 mmol). The reaction mixture was heated for 18 h. The crude mixture was cooled to room temperature and concentrated under reduced pressure to dryness. The oil compound was purified by flash chromatography (Silica, 0-40% ethyl acetate in heptane) to afford ethyl 2-(5-(2-hydroxypropan-2-yl) isoxazol-3-yl)-2-oxoacetate as an orange oil (680 mg. 74%). $^1$H-NMR (80 MHz, DMSO-d6) δ 6.87 (s, 1H), 4.40 (q, 2H), 1.54 (s, 6H), 1.34 (t, 3H).

Step-D:

To a stirred solution of the compound from step-C (600 mg, 2.64 mmol) in nitromethane (5 ml, 93 mmol) was added Amberlyst A-21 (500 mg) at room temperature. After being stirred for 5 h, the reaction mixture was filtered and rinsed (3×) with ethyl acetate and the resulting filtrate was evaporated under reduced pressure. The crude compound was purified by flash chromatography (Silica, 25 g column; 0-40% ethyl acetate in hexane) to afford ethyl 2-hydroxy-2-(5-(2-hydroxypropan-2-yl) isoxazol-3-yl)-3-nitropropanoate (663 mg, 83%). $^1$H-NMR (80 MHz, DMSO-d6) δ 7.23 (d, 1H), 6.42 (s, 1H), 5.68 (s, 1H), 5.49 (dd, 1H), 5.04 (d, 1H), 4.23 (q, 2H), 1.45 (s, 6H), 1.20 (t, 3H). MS: 289.04 $[M+H]^+$ Step-E:

Zinc (1.266 g, 19.36 mmol) was added to a cooled solution of the compound from step-D (558 mg, 1.936 mmol) in acetic acid (11 mL). The reaction mixture was allowed to warm up slowly to room temperature. After being stirred 1 h 30 min, the mixture was filtered through celite. The celite pad was washed with ethyl acetate (3×) and the resulting filtrate was evaporated under reduced pressure to get ethyl 3-amino-2-hydroxy-2-(5-(2-hydroxypropan-2-yl) isoxazol-3-yl) propanoate as a yellow oil. The crude compound was directly used to the next step without further purification. MS: 259.07 $[M+H]^+$ Step-F:

To a stirred solution of the compound from step-E (500 mg, 1.936 mmol) and triethylamine (0.837 ml, 6.01 mmol) in THF (11 mL) was added 4-isothiocyanato-1,2,3,5,6,7-hexahydro-s-indacene (453 mg, 2.103 mmol) at room temperature. After 1 h 30 min, the reaction mixture was concentrated under reduced pressure. The crude compound was purified by flash chromatography (Silica, 25 g column; 0-80% ethyl acetate in hexane) to afford ethyl 3-(3-(1,2,3,5,6,7-hexahydro-s-indacen-4-yl)thioureido)-2-hydroxy-2-(5-(2-hydroxypropan-2-yl) isoxazol-3-yl) propanoate as a white foam (570 mg, 56%). 1H-NMR (80 MHz, DMSO-d6) δ 9.34 (s, 1H), 7.00 (s, 1H), 6.80 (s, 1H), 6.32 (s, 1H), 5.63 (s, 1H), 4.22-3.96 (m, 4H), 2.94-2.60 (m, 8H), 1.96 (d, 4H), 1.45 (s, 6H), 1.16 (t, 3H). MS: 474.07 $[M+H]^+$ Example 14a: enantiopure ethyl 3-(3-(1,2,3,5,6,7-hexahydro-s-indacen-4-yl)thioureido)-2-hydroxy-2-(5-(2-hydroxypropan-2-yl) isoxazol-3-yl) propanoate The enantiopure compound was obtained as an off white solid by chiral SFC separation starting from the racemic mixture of Example 14 (Lux Amylose IG (30*250) mm, 5μ; Mobile phase: 30n-hexane: ethanol (90:10), Temperature: 30° C.); First eluting peak. $^1$H-NMR, (400 MHz, DMSO-d6 δ 9.35 (s, 1H), 7.00 (s, 1H), 6.81 (s, 1H), 6.32 (s, 1H), 5.64 (s, 1H), 4.42 (s, 1H), 4.24-4.07 (m, 2H), 4.05-3.89 (m, 1H), 2.89-2.58 (m, 8H), 2.04-1.89 (m, 4H), 1.45 (s, 6H), 1.17 (t, 3H). MS: 474.45 [M+H]+

Example 15: ethyl 2-((1,2,3,5,6,7-hexahydro-s-indacen-4-yl)amino)-5-(5-(2-hydroxypropan-2-yl) isoxazol-3-yl)-4,5-dihydrooxazole-5-carboxylate

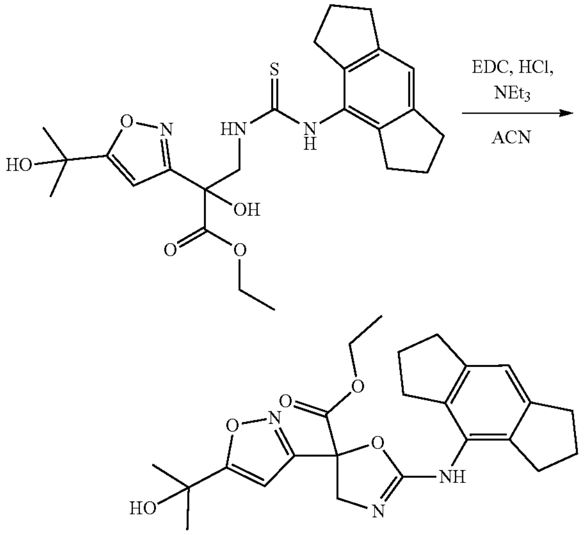

To a stirred cooled (0° C.) solution of the compound of Example 14 (100 mg, 0.211 mmol) in acetonitrile (3.5 ml) was added triethylamine (0.088 ml, 0.633 mmol), followed by N-(3-dimethylaminopropyl)-N'-ethylcarbodiimide hydrochloride (81 mg, 0.422 mmol). The reaction mixture was allowed to warm up slowly to room temperature. After being stirred at room temperature for 48 h, ice was added to the reaction mixture and it was stirred for 30 minutes. The acetonitrile was concentrated under reduced pressure and the resulting solid was filtered off. The solid was rinsed with water and with diethyl ether twice and it was dried in vacuo to afford ethyl 2-((1,2,3,5,6,7-hexahydro-s-indacen-4-yl) amino)-5-(5-(2-hydroxypropan-2-yl) isoxazol-3-yl)-4,5-dihydrooxazole-5-carboxylate as an off white solid (42 mg, 45%). $^1$H-NMR (80 MHz, DMSO-d6) δ 6.86 (s, 1H), 6.42 (s, 1H), 5.71 (s, 1H), 4.44-4.10 (m, 4H), 2.91-2.62 (m, 8H), 2.14-1.80 (m, 4H), 1.48 (s, 6H), 1.22 (t, 3H). MS: 440.12 $[M+H]^+$ Example 16: enantiopure ethyl 2-((1,2,3,5,6,7-hexahydro-s-indacen-4-yl)amino)-5-(5-(2-hydroxypropan-2-yl) isoxazol-3-yl)-4,5-dihydrooxazole-5-carboxylate The enantiopure compound was obtained as an off white solid by chiral SFC separation starting from the racemic mixture of Example 15. (Chiralpak IG (4.6*250) mm, 5μ; Co-Solvent: 50% (0.5% triethylamine in ethanol), Outlet Pressure: 100 bar; Temperature: 30° C.); Second eluting peak. 1H-NMR, (400 MHz, DMSO-d6) δ 8.64 (s, 1H), 6.86 (s, 1H), 6.40 (s, 1H), 5.71 (s, 1H), 4.27-4.00 (m, 4H), 2.80-2.55 (m, 8H), 1.98-1.93 (m, 4H), 1.47 (s, 6H), 1.22 (t, 3H). MS: 440.43 $[M+H]^+$. 99.52% ee Following the above procedures, the following preparative examples were prepared.

| Example | Structure | 1. $^1$H-NMR<br>2. $MH^+$ (ESI) |
|---|---|---|
| Example 17 isopropyl 2-((1,2,3,5,6,7-hexahydro-s-indacen-4-yl)amino)-5-(5-(2-hydroxypropan-2-yl)isoxazol-3-yl)-4,5-dihydrooxazole-5-carboxylate Racemic | 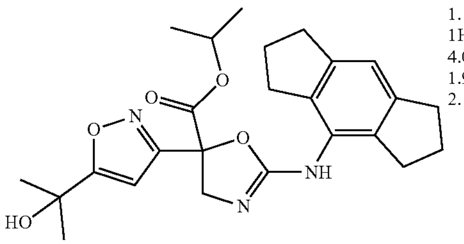 | 1. $^1$H-NMR (400 MHz, DMSO-d6) δ 6.84 (s, 1H), 6.38 (s, 1H), 5.07-5.02 (m, 1H),, 4.25-4.00 (m, 2H), 2.80-2.51 (m, 8H), 1.98-1.90 (m, 4H), 1.48 (s, 6H), 1.22 (t, 6H).<br>2. 454.2 |
| Example 17a Enantiopure 17 (first eluting peak) | | 1. $^1$H-NMR (400 MHz, DMSO-d6) δ 8.63 (s, 1H), 6.86 (s, 1H), 6.38 (s, 1H), 5.70 (s, 1H), 5.17-4.96 (m, 1H), 4.30-3.97 (m, 2H), 2.88-2.58 (m, 8H), 2.07-1.83 (m, 4H), 1.47 (s, 6H), 1.30-1.13 (m, 6H).<br>2. 454.5 |
| Example 18 Enantiopure 17 (second eluting peak) | | 1. $^1$H-NMR (400 MHz, DMSO-d6) δ 6.86 (s, 1H), 6.38 (s, 1H), 5.71 (s, 1H), 5.09-5.02 (m, 1H), 4.25-4.00 (m, 2H), 2.80-2.51 (m, 8H), 1.98-1.90 (m, 4H), 1.48 (s, 6H), 1.22 (t, 6H).<br>2. 454.2 |
| Example 19 cyclopentyl 2-((1,2,3,5,6,7-hexahydro-s-indacen-4-yl)amino)-5-(5-(2-hydroxypropan-2-yl)isoxazol-3-yl)-4,5-dihydrooxazole-5-carboxylate Racemic | 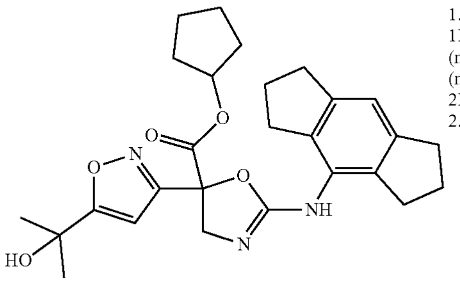 | 1. $^1$H-NMR (400 MHz, DMSO-d6) δ 6.86 (s, 1H), 6.38 (s, 1H), 5.71 (s, 1H), 5.25-5.21 (m, 1H), 4.25-4.00 (m, 2H), 2.80-2.51 (m, 8H), 1.98-1.91 (m, 4H), 1.86-1.81 (m, 2H), 1.72-1.50 (m, 6H), 1.48 (s, 6H).<br>2. 480.2 |

-continued

| Example | Structure | 1. $^1$H-NMR<br>2. MH$^+$ (ESI) |
|---|---|---|
| Example 20<br>Enantiopure 19<br>(second eluting peak) | | 1. $^1$H-NMR (400 MHz, DMSO-d6) δ 6.86 (s, 1H), 6.38 (s, 1H), 5.70 (s, 1H), 5.25-5.21 (m, 1H), 4.25-4.00 (m, 2H), 2.80-2.51 (m, 8H), 1.98-1.91 (m, 4H), 1.86-1.81 (m, 2H), 1.72-1.50 (m, 6H), 1.48 (s, 6H).<br>2. 480.4 |
| Example 21<br>Enantiopure ethyl 2-((1,2,3,5,6,7-hexahydro-s-indacen-4-yl)amino)-5-(thiazol-2-yl)-4,5-dihydrooxazole-5-carboxylate<br>(second eluting peak) | 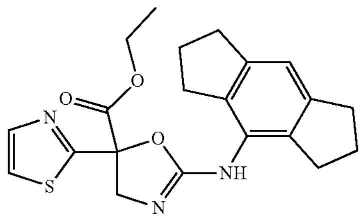 [SMILES: CCOC(=O)C1(c2nccs2)CN=C(Nc2c3c(cc4c2CCC4)CCC3)O1] | 1. $^1$H-NMR (400 MHz, DMSO-d6) δ 8.74 (s, 7.88 (s, 1H), 6.89 (s, 1H), 4.26-4.00 (m, 2H), 2.79-2.58 (m, 8H), 1.97-1.93 (m, 4H), 1.19 (t, 3H).<br>2. 398.3 |
| Example 21A<br>ethyl 2-((1,2,3,5,6,7-hexahydro-s-indacen-4-yl)amino)-5-(5-isopropylisoxazol-3-yl)-4,5-dihydrooxazole-5-carboxylate<br>Racemic | 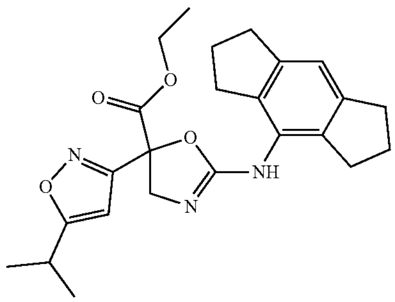 [SMILES: CCOC(=O)C1(c2cc(C(C)C)on2)CN=C(Nc2c3c(cc4c2CCC4)CCC3)O1] | 1. $^1$H-NMR (500 MHz, DMSO-d6) δ 8.62 (br s, 1H), 6.85 (br s, 1H), 6.36 (s, 1H), 4.27-4.10 (m, 4H), 3.19-3.10 (m, 1H), 2.79-2.66 (m, 8H), 1.97-1.90 (m, 4H), 1.26-1.23 (d, 6H), 1.21-1.19 (t, 3H).<br>2. 424.2 |
| Example 21Aa<br>Enantiopure 21A<br>(second eluting peak) | | 1. $^1$H-NMR (500 MHz, DMSO-d6) δ 8.53 (br s, 1H), 6.84 (s, 1H), 6.37 (s, 1H), 4.24 (q, 4H), 3.18-3.04 (m, 1H), 2.78 (t, 9H), 1.94 (p, 4H), 1.26 (d, 6H), 1.21 (t, 4H).<br>2. 424.2 |
| Example 21B<br>ethyl 2-((1,2,3,5,6,7-hexahydro-s-indacen-4-yl)amino)-5-(isoxazol-3-yl)-4,5-dihydrooxazole-5-carboxylate<br>Racemic | 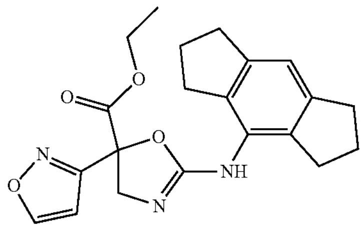 [SMILES: CCOC(=O)C1(c2ccon2)CN=C(Nc2c3c(cc4c2CCC4)CCC3)O1] | 1. $^1$H-NMR (500 MHz, DMSO-d6) δ 9.04 (d, 1H), 8.63 (s, 1H), 6.85 (s, 1H), 6.73 (s, 1H), 4.34-4.00 (m, 4H), 2.88-2.56 (m, 8H), 2.03-1.83 (m, 4H), 1.21 (t, 3H).<br>2. 382.4 |
| Example 21Ba<br>Enantiopure 21B<br>(first eluting peak) | | 1. $^1$H-NMR (500 MHz, DMSO-d6) δ 9.05 (d, 1H), 8.64 (s, 1H), 6.85 (s, 1H), 6.73 (s, 1H), 4.33-4.00 (m, 4H), 2.86-2.56 (m, 8H), 2.03-1.83 (m, 4H), 1.21 (t, 3H).<br>2. 382.2 |
| Example 21Bb<br>Enantiopure 21B<br>(second eluting peak) | | 1. $^1$H-NMR (500 MHz, DMSO-d6) δ 9.05 (d, 1H), 8.63 (s, 1H), 6.85 (s, 1H), 6.73 (s, 1H), 4.33-4.04 (m, 4H), 2.86-2.56 (m, 8H), 2.01-1.87 (m, 4H), 1.21 (t, 3H).<br>2. 382.1 |

Example 22:2-((1,2,3,5,6,7-hexahydro-s-indacen-4-yl)amino)-5-(5-(2-hydroxypropan-2-yl) isoxazol-3-yl)-4,5-dihydrooxazole-5-carboxylic acid

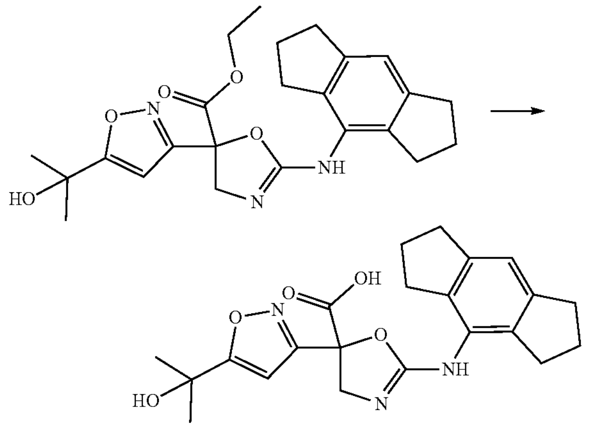

To a stirred solution of the ester of Example 15 (20 mg, 0.0455 mmol) in THF (1 ml) was added sodium trimethylsilanolate (6.125 mg, 0.0546 mmol) in one portion at 0° C. and the reaction mixture was stirred at room temperature under nitrogen atmosphere for 1 h. The reaction mixture was concentrated and triturated in diethyl ether. The resulting solid was dried under reduced pressure to afford 2-((1,2,3,5,6,7-hexahydro-s-indacen-4-yl)amino)-5-(5-(2-hydroxypropan-2-yl) isoxazol-3-yl)-4,5-dihydrooxazole-5-carboxylic acid as an off white solid (20 mg, 99%). $^1$H-NMR (400 MHz, DMSO-d6) δ 6.67 (s, 1H), 6.11 (s, 1H), 5.57 (s, 1H), 4.00-3.70 (m, 2H), 2.77-2.50 (m, 8H), 1,93-1,85 (m, 4H), 1.44 (s, 6H). MS: 412.3 $[M+H]^+$ Following the saponification procedure as described in Example 22, the following preparative examples were synthesized.

| Ester (starting material) | Example | 1. $^1$H-NMR<br>2. Yield<br>3. $MH^+$ (ESI) |
|---|---|---|
| 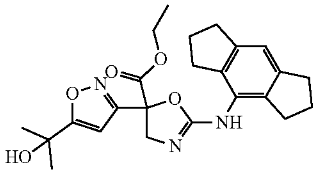 [SMILES: CCOC(=O)C1(c2cc(C(C)(C)O)on2)CN=C(Nc2c3c(cc4c2CCC4)CCC3)O1]<br>Example 16<br>Enantiopure<br>(second eluting peak) | 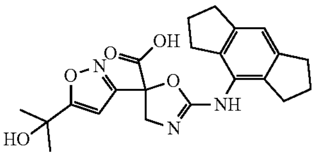 [SMILES: CC(C)(O)c1cc(C2(C(=O)O)CN=C(Nc3c4c(cc5c3CCC5)CCC4)O2)no1]<br>Example 23<br>Enantiopure 2-((1,2,3,5,6,7-hexahydro-s-indacen-4-yl)amino)-5-(5-(2-hydroxypropan-2-yl)isoxazol-3-yl)-4,5-dihydrooxazole-5-carboxylic acid | 1. $^1$H-NMR (400 MHz, DMSO-d6) δ 6.84 (s, 1H), 6.38 (s, 1H), 5.07-5.02 (m, 1H), 4.25-4.00 (m, 2H), 2.80-2.51 (m, 8H), 1.98-1.90 (m, 4H), 1.48 (s, 6H), 1.22 (t, 6H).<br>2. 74%<br>3. 412.16 |
| 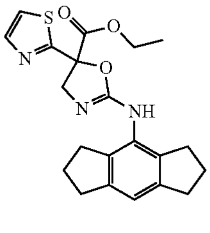<br>Example 21<br>Enantiopure<br>(second eluting peak) | 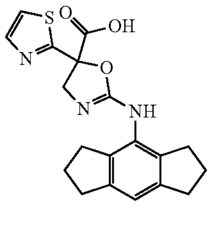<br>Example 24<br>Enantiopure 2-((1,2,3,5,6,7-hexahydro-s-indacen-4-yl)amino)-5-(thiazol-2-yl)-4,5-dihydrooxazole-5-carboxylic acid | 1. $^1$H NMR (80 MHz, DMSO-d6) δ 7.69 (d, 1H), 7.58 (d, 1H), 6.68 (s, 1H), 3.98 (s, 2H), 2.88-2.62 (m, 8H), 2.11-1.72 (m, 4H).<br>2. 94%<br>3. 370.06 |

-continued

| Ester (starting material) | Example | 1. ¹H-NMR<br>2. Yield<br>3. $MH^+$ (ESI) |
| --- | --- | --- |
| 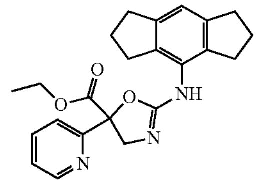<br>Example 9<br>Enantiopure<br>(second eluting peak) | 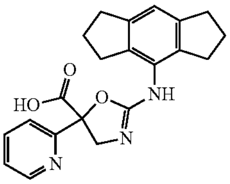 [SMILES: O=C(O)C1(c2ccccn2)CN=C(Nc2c3c(cc4c2CCC4)CCC3)O1]<br>Example 25<br>Enantiopure 2-((1,2,3,5,6,7-hexahydro-s-indacen-4-yl)amino)-5-(pyridin-2-yl)-4,5-dihydrooxazole-5-carboxylic acid | 1. ¹H-NMR (80 MHz, DMSO-d6) δ 8.45 (d, 1H), 7.88-7.56 (m, 1H), 7.51-7.08 (m, 2H), 6.64 (s, 1H), 4.12 (d, 1H), 3.87 (d, 1H), 2.92-2.62 (m, 8H), 2.12-1.73 (m, 4H).<br>2. 86%<br>3. 362.35 (ESI negative) |
| 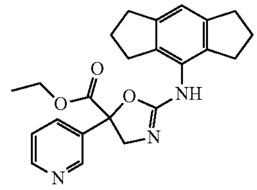<br>Example 11<br>Enantiopure<br>(first eluting peak) | 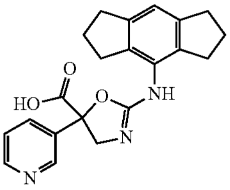 [SMILES: O=C(O)C1(c2cccnc2)CN=C(Nc2c3c(cc4c2CCC4)CCC3)O1]<br>Example 26<br>Enantiopure 2-((1,2,3,5,6,7-hexahydro-s-indacen-4-yl)amino)-5-(pyridin-3-yl)-4,5-dihydrooxazole-5-carboxylic acid | 1. ¹H-NMR (80 MHz, DMSO-d6) δ 8.62 (d, 1H), 8.41 (dd, 1H), 7.79 (dt, 1H), 7.30 (dd, 1H), 6.70 (s, 1H), 4.04 (d, 1H), 3.61-3.41 (m, 1H), 2.94-2.60 (m, 8H), 2.13-1.75 (m, 4H).<br>2. 99%<br>3. 362.32 (ESI negative) |
| 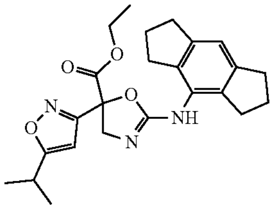 [SMILES: CCOC(=O)C1(c2cc(C(C)C)on2)CN=C(Nc2c3c(cc4c2CCC4)CCC3)O1]<br>Example 21A<br>Racemic | 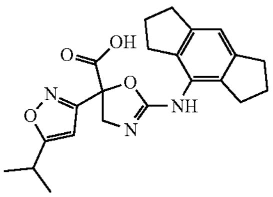 [SMILES: CC(C)c1cc(C2(C(=O)O)CN=C(Nc3c4c(cc5c3CCC5)CCC4)O2)no1]<br>Example 27<br>2-((1,2,3,5,6,7-hexahydro-s-indacen-4-yl)amino)-5-(5-isopropylisoxazol-3-yl)-4,5-dihydrooxazole-5-carboxylate<br>Racemic | 1. ¹H-NMR (80 MHz, DMSO-d6) δ 6.67 (s, 1H), 6.01 (s, 1H), 4.00-3.70 (m, 2H), 3.11-2.97 (m, 1H), 2.85-2.70 (m, 4H), 2.65-2.53 (m, 4H), 1.97-1.78 (m, 4H), 1.22 (d, 6H).<br>2. 66%<br>3. 396.26 |
| Example 21Aa<br>Enantiopure 21A<br>(second eluting peak) | Example 28<br>Enantiopure 2-((1,2,3,5,6,7-hexahydro-s-indacen-4-yl)amino)-5-(5-isopropylisoxazol-3-yl)-4,5-dihydrooxazole-5-carboxylate | 1. ¹H-NMR (80 MHz, DMSO-d6) δ 6.67 (s, 1H), 6.01 (s, 1H), 4.01-3.68 (m, 2H), 3.10-2.93 (m, 1H), 2.75 (t, 4H), 2.65-2.52 (m, 4H), 1.97-1.80 (m, 4H), 1.22 (d, 6H).<br>2. 94%<br>3. 396.33 |
| 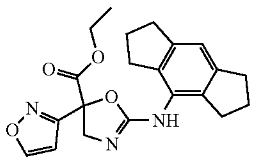 [SMILES: CCOC(=O)C1(c2ccon2)CN=C(Nc2c3c(cc4c2CCC4)CCC3)O1]<br>Example 21Bb<br>Enantiopure 21B<br>(second eluting peak) | 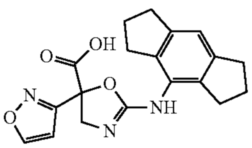 [SMILES: O=C(O)C1(c2ccon2)CN=C(Nc2c3c(cc4c2CCC4)CCC3)O1]<br>Example 29<br>Enantiopure 2-((1,2,3,5,6,7-hexahydro-s-indacen-4-yl)amino)-5-(isoxazol-3-yl)-4,5-dihydrooxazole-5-carboxylate | 1. ¹H-NMR (80 MHz, DMSO-d6) δ 8.98 (d, 1H), 7.00 (s, 1H), 6.64 (s, 1H), 4.32-4.07 (m, 2H), 2.93-2.58 (m, 8H), 2.06-1.90 (m, 4H).<br>2. 93.4%<br>3. 354.11 |

Following the above procedures, the following preparative examples were also prepared.

| Example | Structure | 1. $^1$H-NMR<br>2. MH$^+$ (ESI) |
|---|---|---|
| Example 30<br>ethyl 2-((8-fluoro-1,2,3,5,6,7-hexahydro-s-indacen-4-yl)amino)-5-phenyl-4,5-dihydrooxazole-5-carboxylate<br>Racemic | 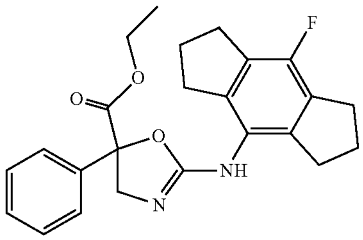 [SMILES: CCOC(=O)C1(c2ccccc2)CN=C(Nc2c3c(c(F)c4c2CCC4)CCC3)O1] | 1. $^1$H-NMR (500 MHz, Chloroform-d) δ 7.52-7.32 (m, 5H), 4.51 (d, 1H), 4.24 (q, 2H), 4.07 (d, 1H), 2.97-2.81 (m, 8H), 2.16-2.05 (m, 4H), 1.26 (t, 3H).<br>2. 409.5 |
| Example 31<br>Enantiopure 30<br>(first eluting peak) | | 1. $^1$H-NMR (500 MHz, Chloroform-d) δ 7.51-7.32 (m, 5H), 4.51 (d, 1H), 4.24 (q, 2H), 4.07 (d, 1H), 3.00-2.80 (m, 8H), 2.21-2.03 (m, 4H), 1.26 (t, 3H).<br>2. 409.5 |
| Example 32<br>ethyl 2-((1,2,3,5,6,7-hexahydro-s-indacen-4-yl)amino)-5-(2-methoxypyrimidin-5-yl)-4,5-dihydrooxazole-5-carboxylate<br>Racemic | 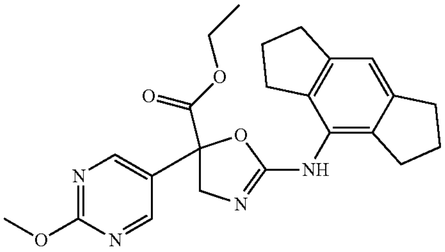 [SMILES: CCOC(=O)C1(c2cnc(OC)nc2)CN=C(Nc2c3c(cc4c2CCC4)CCC3)O1] | 1. $^1$H-NMR (500 MHz, DMSO-d6) δ 8.79-8.57 (m, 2H), 6.87 (s, 1H), 4.29-4.00 (m, 4H), 3.95 (s, 3H), 2.83-2.59 (m, 8H), 2.01-1.87 (m, 4H), 1.20 (t, 3H)<br>2. 423.5 |
| Example 33<br>Enantiopure 32<br>(second eluting peak) | | 1. $^1$H-NMR (500 MHz, DMSO-d6) δ 8.80-8.59 (m, 2H), 6.86 (s, 1H), 4.32-3.99 (m, 4H), 2.92-2.58 (m, 8H), 2.04-1.83 (m, 4H), 1.20 (t, 3H).<br>2. 423.6 |
| Example 34<br>ethyl 2-((1,2,3,5,6,7-hexahydro-s-indacen-4-yl)amino)-5-(thiophen-2-yl)-4,5-dihydrooxazole-5-carboxylate<br>Racemic | 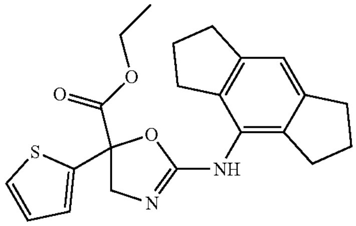 [SMILES: CCOC(=O)C1(c2cccs2)CN=C(Nc2c3c(cc4c2CCC4)CCC3)O1] | 1. $^1$H-NMR (500 MHz, Chloroform-d) δ 7.32 (dd, 1H), 7.16 (dd, 1H), 7.02 (dd, 1H), 6.96 (s, 1H), 4.44 (d, 1H), 4.31 (q, 2H), 4.19 (d, 1H), 2.92-2.81 (m, 8H), 2.11-2.01 (m, 4H), 1.32 (t, 3H).<br>2. 397.2 |
| Example 35<br>Enantiopure 34<br>(first eluting peak) | | 1. $^1$H-NMR (500 MHz, Chloroform-d) δ 7.32 (dd, 1H), 7.16 (dd, 1H), 7.02 (dd, 1H), 6.96 (s, 1H), 4.43 (d, 1H), 4.31 (q, 2H), 4.19 (d, 1H), 2.94-2.78 (m, 8H), 2.14-1.99 (m, 4H), 1.32 (t, 3H).<br>2. 397.2 |
| Example 36<br>ethyl 5-(furan-2-yl)-2-((1,2,3,5,6,7-hexahydro-s-indacen-4-yl)amino)-4,5-dihydrooxazole-5-carboxylate<br>Racemic | 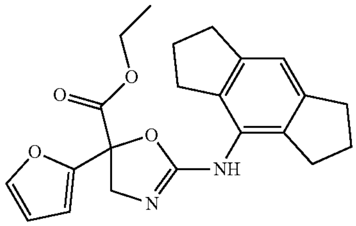 [SMILES: CCOC(=O)C1(c2ccco2)CN=C(Nc2c3c(cc4c2CCC4)CCC3)O1] | 1. $^1$H-NMR (500 MHz, Chloroform-d) δ 7.47 (dd, 1H), 6.96 (s, 1H), 6.50 (d, 1H), 6.41 (dd, 1H), 4.42-4.19 (m, 4H), 2.83 (ddd, 9H), 2.05 (dtd, 5H), 1.31 (t, 4H).<br>2. 381.3 |

-continued

| Example | Structure | 1. ¹H-NMR<br>2. MH⁺ (ESI) |
|---|---|---|
| Example 37<br>ethyl 2-((8-fluoro-1,2,3,5,6,7-hexahydro-s-indacen-4-yl)amino)-5-(1-methyl-1H-imidazol-2-yl)-4,5-dihydrooxazole-5-carboxylate<br>Racemic | 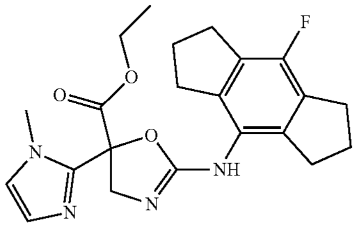 [SMILES: CCOC(=O)C1(c2nccn2C)CN=C(Nc2c3c(c(F)c4c2CCC4)CCC3)O1] | 1. ¹H-NMR (500 MHz, DMSO-d6) δ 8.44 (s, 1H), 7.26 (s, 1H), 6.89 (s, 1H), 4.72 (br s, 1H), 4.23 (q, 2H), 3.95 (br s, 1H), 3.54 (s, 3H), 2.93-2.57 (m, 8H), 2.09-1.88 (m, 4H), 1.18 (t, 3H).<br>2. 413.4 |
| Example 38<br>Enantiopure 37<br>(first eluting peak) | | 1. ¹H-NMR (500 MHz, DMSO-d6) δ 8.43 (s, 1H), 7.26 (s, 1H), 6.89 (s, 1H), 5.00-4.74 (m, 1H), 4.23 (d, 2H), 4.04-3.89 (m, 1H), 3.54 (s, 3H), 2.87-2.59 (m, 8H), 2.12-1.90 (m, 4H), 1.18 (t, 3H).<br>2. 413.4 |
| Example 39<br>Enantiopure 37<br>(second eluting peak) | | 1. ¹H-NMR (500 MHz, DMSO-d6) δ 8.44 (s, 1H), 7.27 (s, 1H), 6.89 (s, 1H), 5.01-4.52 (m, 1H), 4.24 (q, 2H), 4.08-3.87 (m, 1H), 3.54 (s, 3H), 2.94-2.58 (m, 8H), 2.08-1.92 (m, 4H), 1.19 (t, 3H).<br>2. 413.4 |
| Example 40<br>ethyl 2-((1,2,3,5,6,7-hexahydro-s-indacen-4-yl)amino)-5-(tetrahydrofuran-2-yl)-4,5-dihydrooxazole-5-carboxylate<br>Racemic | 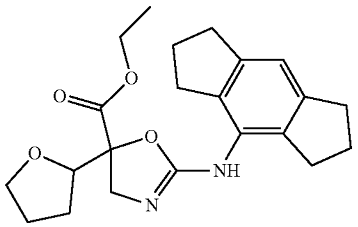 [SMILES: CCOC(=O)C1(C2CCCO2)CN=C(Nc2c3c(cc4c2CCC4)CCC3)O1] | 1. ¹H-NMR (500 MHz, DMSO-d6) δ 8.48 (br s, 1H), 6.82 (s, 1H), 4.34-4.11 (m, 3H), 3.69 (d, 4H), 2.85-2.56 (m, 8H), 2.04-1.60 (m, 8H), 1.21 (t, 3H).<br>2. 385.3 |
| Example 41<br>Enantiopure 40<br>(first eluting peak) | | 1. ¹H-NMR (500 MHz, DMSO-d6) δ 7.64 (1H, br s), 6.01 (s, 1H), 3.48 (t, 1H), 3.42-3.26 (m, 2H), 3.01-2.67 (m, 4H), 2.09-1.75 (m, 8H), 1.30-0.76 (m, 8H), 0.40 (t, 3H).<br>2. 385.2 |
| Example 42<br>Enantiopure 40<br>(third eluting peak) | | 1. ¹H-NMR (500 MHz, DMSO-d6) δ 7.47 (s, 1H), 5.97 (s, 1H), 3.54-3.28 (m, 3H), 3.15-2.71 (m, 4H), 2.13-1.75 (m, 8H), 1.29-0.78 (m, 8H), 0.40 (t, 3H)<br>2. 385.2 |
| Example 43<br>Enantiopure ethyl 2-((1,2,3,5,6,7-hexahydro-s-indacen-4-yl)amino)-5-(isothiazol-5-yl)-4,5-dihydrooxazole-5-carboxylate<br>(second eluting peak) | 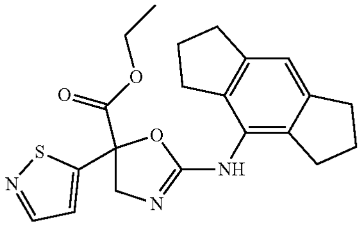 [SMILES: CCOC(=O)C1(c2ccns2)CN=C(Nc2c3c(cc4c2CCC4)CCC3)O1] | 1. ¹H-NMR (500 MHz, DMSO-d6) δ 8.80 (s, 1H), 8.57 (s, 1H), 7.46 (s, 1H), 6.90 (s, 1H), 4.38-3.86 (m, 4H), 2.91-2.67 (m, 8H), 2.04-1.88 (m, 4H), 1.25 (t, 3H).<br>2. 398.4 |
| Example 44<br>ethyl 2-((1,2,3,5,6,7-hexahydro-s-indacen-4-yl)amino)-5-(isoxazol-5-yl)-4,5-dihydrooxazole-5-carboxylate<br>Racemic | 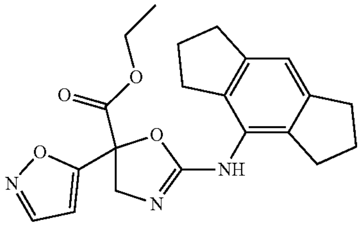 [SMILES: CCOC(=O)C1(c2ccno2)CN=C(Nc2c3c(cc4c2CCC4)CCC3)O1] | 1. ¹H-NMR (500 MHz, DMSO-d6) δ 8.83-8.56 (m, 2H), 6.91 (s, 1H), 6.84 (s, 1H), 4.37-4.22 (m, 4H), 2.86-2.67 (m, 8H), 2.03-1.86 (m, 4H), 1.21 (t, 3H).<br>2. 382.2 |
| Example 45<br>Enantiopure 44<br>(second eluting peak) | | 1. ¹H-NMR (500 MHz, DMSO-d6) δ 8.68 (d, 1H), 6.96-6.77 (m, 2H), 4.34-4.08 (m, 4H), 2.87-2.56 (m, 8H), 2.04-1.82 (m, 4H), 1.21 (t, 3H).<br>2. 382.0 |

-continued

| Example | Structure | 1. $^1$H-NMR<br>2. $MH^+$ (ESI) |
|---|---|---|
| Example 46<br>ethyl 3-(3-(1,2,3,5,6,7-hexahydro-s-indacen-4-yl)thioureido)-2-hydroxy-2-(5-isopropylisoxazol-3-yl)propanoate<br>Racemic | 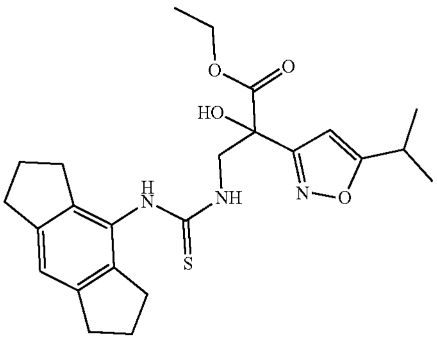 [SMILES: CCOC(=O)C(O)(CNC(=S)Nc1c2c(cc3c1CCC3)CCC2)c1cc(C(C)C)on1] | 1. $^1$H-NMR (500 MHz, DMSO-d6) δ 9.33 (s, 1H), 7.00 (s, 1H), 6.77 (s, 1H), 6.26 (s, 1H), 4.47-4.28 (m, 1H), 4.21-4.05 (m, 2H), 3.99 (dd, 1H), 3.14-2.97 (m, 1H), 2.81 (t, 4H), 2.74-2.58 (m, 4H), 2.01-1.88 (m, 4H), 1.23 (d, 6H), 1.16 (t, 3H).<br>2. 458.2 |
| Example 47<br>Enantiopure 46<br>(second eluting peak) | | 1. $^1$H-NMR (500 MHz, DMSO-d6) δ 9.33 (s, 1H), 7.00 (s, 1H), 6.77 (s, 1H), 6.26 (s, 1H), 4.47-4.28 (m, 1H), 4.21-4.05 (m, 2H), 3.99 (dd, 1H), 3.14-2.97 (m, 1H), 2.81 (t, 4H), 2.74-2.58 (m, 4H), 2.01-1.88 (m, 4H), 1.23 (d, 6H), 1.16 (t, 3H).<br>2. 458.2 |
| Example 48<br>methyl 2-((1,2,3,5,6,7-hexahydro-s-indacen-4-yl)amino)-5-(5-methoxyisoxazol-3-yl)-4,5-dihydrooxazole-5-carboxylate<br>Racemic | 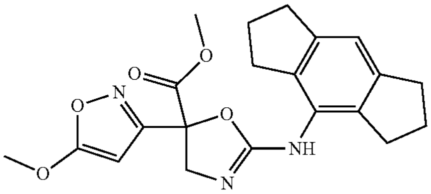 [SMILES: COC(=O)C1(c2cc(OC)on2)CN=C(Nc2c3c(cc4c2CCC4)CCC3)O1] | 1. $^1$H-NMR (400 MHz, DMSO-d6) δ 8.63 (s, 1H), 6.88 (s, 1H), 5.77 (s, 1H), 4.30-4.05 (m, 2H), 4.02 (s, 3H), 3.77 (s, 3H), 2.86-2.56 (m, 8H), 2.05-1.77 (m, 4H).<br>2. 398.0 |
| Example 49<br>ethyl 2-((1,2,3,5,6,7-hexahydro-s-indacen-4-yl)amino)-5-(pyrazin-2-yl)-4,5-dihydrooxazole-5-carboxylate<br>Racemic | 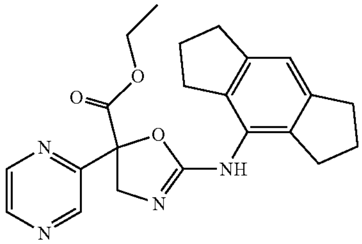 [SMILES: CCOC(=O)C1(c2cnccn2)CN=C(Nc2c3c(cc4c2CCC4)CCC3)O1] | 1. $^1$H-NMR (500 MHz, DMSO-d6) δ 8.91-8.61 (m, 3H), 6.85 (s, 1H), 4.39-4.04 (m, 4H), 2.87-2.57 (m, 8H), 2.07-1.86 (m, 4H), 1.16 (t, 3H).<br>2. 393.0 |
| Example 50<br>ethyl 2-((1,2,3,5,6,7-hexahydro-s-indacen-4-yl)amino)-5-(pyrimidin-2-yl)-4,5-dihydrooxazole-5-carboxylate<br>Racemic | 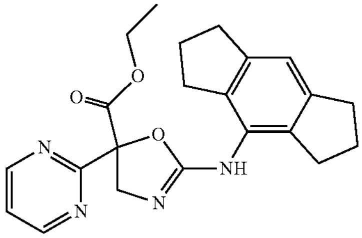 [SMILES: CCOC(=O)C1(c2ncccn2)CN=C(Nc2c3c(cc4c2CCC4)CCC3)O1] | 1. $^1$H-NMR (500 MHz, DMSO-d6) δ 9.01-8.84 (m, 2H), 8.53 (s, 1H), 7.59 (s, 1H), 6.84 (s, 1H), 4.64-3.97 (m, 4H), 2.88-2.58 (m, 8H), 2.03-1.81 (m, 4H), 1.17 (t, 3H).<br>2. 393.2 |
| Example 51<br>Enantiopure trans<br>ethyl 4-ethyl-2-((1,2,3,5,6,7-hexahydro-s-indacen-4-yl)amino)-5-(5-(2-hydroxypropan-2-yl)isoxazol-3-yl)-4,5-dihydrooxazole-5-carboxylate | 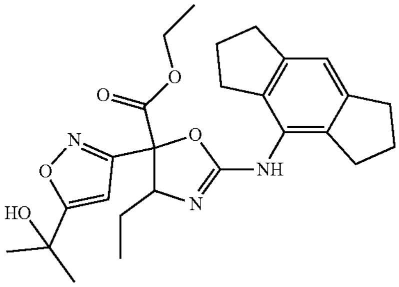 [SMILES: CCOC(=O)C1(c2cc(C(C)(C)O)on2)OC(Nc2c3c(cc4c2CCC4)CCC3)=NC1CC] | 1. $^1$H-NMR (500 MHz, DMSO-d6) δ 6.84 (s, 1H), 6.24 (s, 1H), 5.75 (s, 1H), 4.41-4.10 (m, 3H), 2.79 (t, 8H), 1.96 (p, 4H), 1.46 (s, 6H), 1.41-1.28 (m, 1H), 1.23 (t, 3H), 1.05 (t, 1H), 0.84 (s, 3H).<br>2. 468.3 |

-continued

| Example | Structure | 1. $^1$H-NMR<br>2. $MH^+$ (ESI) |
|---|---|---|
| Example 52<br>ethyl 2-((1,2,3,5,6,7-hexahydro-s-indacen-4-yl)amino)-5-(5-(2-hydroxypropan-2-yl)isoxazol-3-yl)-4-methyl-4,5-dihydrooxazole-5-carboxylate<br>Racemic | 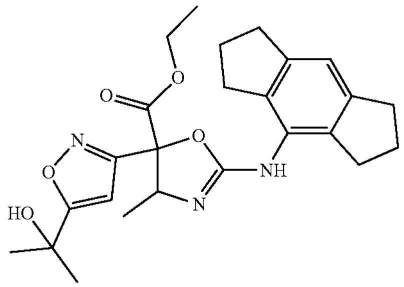 [SMILES: CCOC(=O)C1(c2cc(C(C)(C)O)on2)OC(Nc2c3c(cc4c2CCC4)CCC3)=NC1C] | 1. $^1$H-NMR (500 MHz, DMSO-d6) δ 8.6 (s, 1H), 6.96-6.70 (m, 1H), 6.42-6.21 (m, 1H), 5.76-5.63 (m, 1H), 4.65-4.36 (m, 1H), 4.36-4.19 (m, 2H), 2.89-2.56 (m, 8H), 2.04-1.89 (m, 4H), 1.47 (s, 6H), 1.28-1.20 (m, 3H), 1.19-0.88 (m, 3H).<br>2. 454.3 |
| Example 53<br>Enantiopure 52<br>(fourth eluting peak) | | 1. $^1$H-NMR (500 MHz, DMSO-d6) δ 8.68 (s, 1H), 7.02-6.66 (m, 1H), 6.26 (s, 1H), 5.71 (s, 1H), 4.50-4.36 (m, 1H), 4.27 (q, 2H), 2.86-2.60 (m, 8H), 2.04-1.86 (m, 4H), 1.47 (s, 6H), 1.24 (t, 3H), 0.93 (s, 3H).<br>2. 454.2 |
| Example 54<br>ethyl 2-((1,2,3,5,6,7-hexahydro-s-indacen-4-yl)amino)-5-(1-isopropyl-1H-pyrazol-3-yl)-4,5-dihydrooxazole-5-carboxylate<br>Racemic | 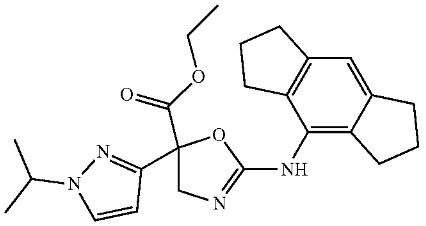 [SMILES: CCOC(=O)C1(c2ccn(C(C)C)n2)CN=C(Nc2c3c(cc4c2CCC4)CCC3)O1] | 1. $^1$H-NMR (500 MHz, DMSO-d6) δ 7.79 (d, 1H), 6.77 (s, 1H), 6.29 (s, 1H), 4.61-4.39 (m, 1H), 4.34-3.92 (m, 4H), 2.83-2.55 (m, 8H), 2.04-1.82 (m, 4H), 1.39 (d, 6H), 1.19 (t, 3H).<br>2. 423.1 |
| Example 55<br>ethyl 2-((1,2,3,5,6,7-hexahydro-s-indacen-4-yl)amino)-5-(4-isopropylthiazol-2-yl)-4,5-dihydrooxazole-5-carboxylate<br>Racemic | 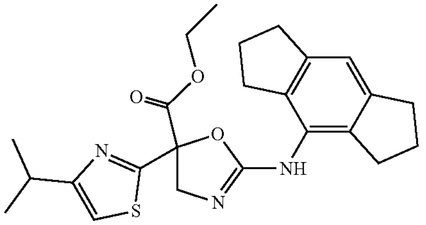 [SMILES: CCOC(=O)C1(c2nc(C(C)C)cs2)CN=C(Nc2c3c(cc4c2CCC4)CCC3)O1] | 1. $^1$H-NMR (500 MHz, DMSO-d6) δ 7.40 (s, 1H), 6.84 (s, 1H), 4.32-4.11 (m, 4H), 3.09-2.96 (m, 1H), 2.85-2.59 (m, 8H), 2.04-1.83 (m, 4H), 1.23 (d, 6H), 1.19 (t, 3H).<br>2. 440.3 |

Example 56: isopropyl 2-((1,2,3,5,6,7-hexahydro-s-indacen-4-yl)amino)-5-(isoxazol-3-yl)-4,5-dihydrooxazole-5-carboxylate

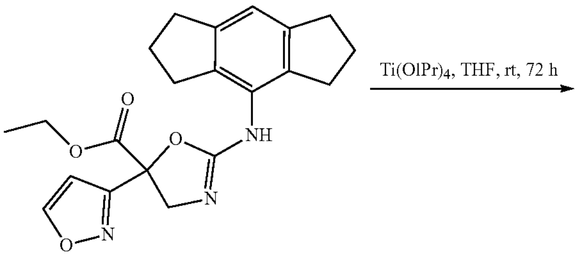

-continued

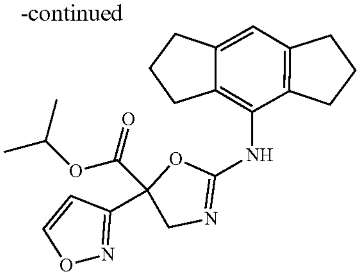

To a stirred solution of the ethyl ester Example 49 (0.200 g, 0.524 mmol) in THF (5 mL) was added Titaniumtetraisopropoxide (0.447 g, 1.573 mmol). After stirring at room temperature for 72 h, the reaction mixture was diluted with water and filtered through a pad of celite. The filtrate was extracted with ethyl acetate (2×10 ml), dried over anhydrous $Na_2SO_4$, filtered and concentrated under reduced pressure. The resulting crude residue was triturated with n-Pentane, filtered and dried under reduced pressure to afford isopropyl 2-((1,2,3,5,6,7-hexahydro-s-indacen-4-yl)amino)-5-(isoxazol-3-yl)-4,5-dihydrooxazole-5-carboxylate as an off white solid (190 mg, 91%). $^1$H-NMR (400 MHz DMSO-D6 δ 9.04 (d, 1H), 8.65 (s, 1H), 6.87 (s, 1H), 6.72 (s, 1H), 5.14-4.94 (m, 1H), 4.32-4.01 (m, 2H), 2.89-2.59 (m, 8H), 2.03-1.82 (m, 4H), 1.26-1.16 (m, 6H). MS: 396.06 $(M+H)^+$.

Example 57: cyclopentyl 2-((1,2,3,5,6,7-hexahydro-s-indacen-4-yl)amino)-5-(isoxazol-3-yl)-4,5-dihydrooxazole-5-carboxylate

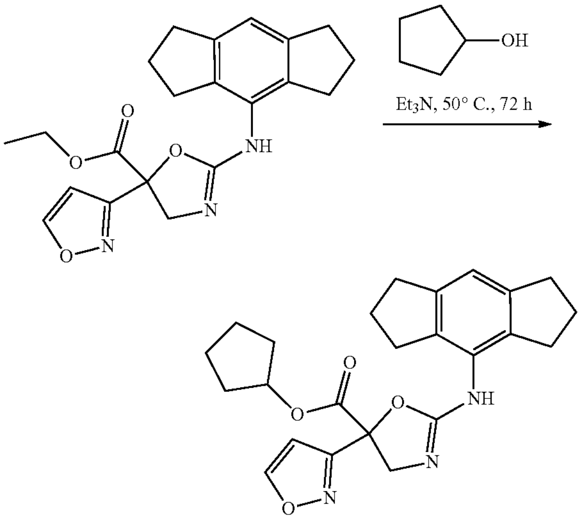

To a stirred solution of the ethyl ester Example 21B (0.5 g, 1.3108 mmol) in cyclopentanol (5 ml) was added $Et_3N$ (0.091 ml, 0.655 mmol) at room temperature and allowed to stir at 80° C. for 72 h. The reaction mixture was concentrated under reduced pressure. The crude compound thus obtained was purified by prep HPLC. (XSELECT PHENYL-HEXYL (150*19) mm 5μ; mobile phase A: 10 mM Ammonium Bicarbonate (Aq) Mobile phase B: 100% Acetonitrile; Flow: 19 mL/min) to afford cyclopentyl 2-((1,2,3,5,6,7-hexahydro-s-indacen-4-yl)amino)-5-(isoxazol-3-yl)-4,5-dihydrooxazole-5-carboxylate (0.19 g, 34%) as a white solid. $^1$H-NMR (400 MHz, DMSO-d6) δ 9.04 (d, 1H), 8.64 (s, 1H), 6.86 (s, 1H), 6.71 (s, 1H), 5.33-5.16 (m, 1H), 4.34-4.03 (m, 2H), 2.89-2.58 (m, 8H), 2.00-1.89 (m, 4H), 1.88-1.77 (m, 2H), 1.69-1.48 (m, 6H). MS: 422.17 $[M+H]^+$

Example 58: enantiopure cyclopentyl 2-((1,2,3,5,6,7-hexahydro-s-indacen-4-yl)amino)-5-(isoxazol-3-yl)-4,5-dihydrooxazole-5-carboxylate The enantiopure compound was obtained as an off white solid by chiral SFC separation starting from the racemic mixture of Example 61. (Chiralpak IG (30*250) mm, 5μ; Co-Solvent: 30% (100% isopropanol), Outlet Pressure: 100 bar; Temperature: 30° C.); Second eluting peak. $^1$H-NMR (400 MHz, DMSO-d6) δ 9.04 (s, 1H), 6.84 (s, 1H), 6.72 (s, 1H), 5.30-5.17 (m, 1H), 4.31-4.01 (m, 2H), 2.88-2.61 (m, 8H), 2.02-1.79 (m, 6H), 1.78-1.50 (m, 6H). MS: 422.06 $[M+H]^+$ Following the above procedures, the following preparative examples were prepared

| | | |
|---|---|---|
| Example 59 Enantiopure isopropyl 2-((1,2,3,5,6,7-hexahydro-s-indacen-4-yl)amino)-5-(isoxazol-3-yl)-4,5-dihydrooxazole-5-carboxylate (second eluting peak) | 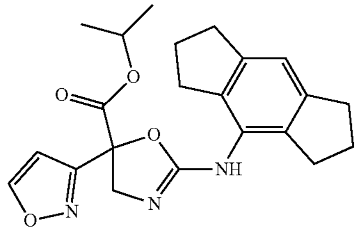 [SMILES: CC(C)OC(=O)C1(c2ccon2)CN=C(Nc2c3c(cc4c2CCC4)CCC3)O1] | 1. $^1$H-NMR (400 MHz, DMSO-d6) δ 9.04 (d, 1H), 8.66 (s, 1H), 7.04-6.60 (m, 2H), 5.05 (hept, 1H), 4.50-3.87 (m, 2H), 2.94-2.59 (m, 8H), 1.94 (p, 4H), 1.21 (dd, 6H). 2. 396.1 |
| Example 60 tert-butyl 2-((1,2,3,5,6,7-hexahydro-s-indacen-4-yl)amino)-5-(isoxazol-3-yl)-4,5-dihydrooxazole-5-carboxylate Racemic | 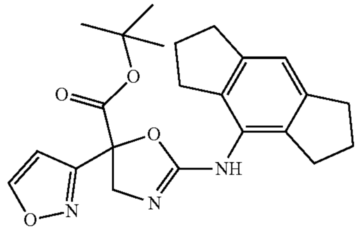 [SMILES: CC(C)(C)OC(=O)C1(c2ccon2)CN=C(Nc2c3c(cc4c2CCC4)CCC3)O1] | 1. $^1$H-NMR (400 MHz, DMSO-d6) δ 9.03 (s, 1H), 8.61 (s, 1H), 7.11-6.49 (m, 2H), 4.34-3.90 (m, 2H), 2.89-2.59 (m, 8H), 1.94 (p, 4H), 1.43 (s, 9H). 2. 410.2 |
| Example 61 Enantiopure 60 (second eluting peak) | | 1. $^1$H-NMR (400 MHz, DMSO-d6) δ 9.04 (d, 1H), 8.62 (s, 1H), 6.86 (s, 1H), 6.69 (s, 1H), 4.33-3.96 (m, 2H), 2.90-2.57 (m, 8H), 2.03-1.87 (m, 4H), 1.44 (s, 9H). 2. 410.0 |

-continued

| | | |
|---|---|---|
| Example 62<br>methyl 2-<br>((1,2,3,5,6,7-<br>hexahydro-s-<br>indacen-4-yl)amino)-<br>5-(thiazol-2-yl)-4,5-<br>dihydrooxazole-5-<br>carboxylate<br>Racemic | 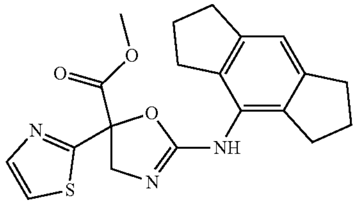 [SMILES: COC(=O)C1(c2nccs2)CN=C(Nc2c3c(cc4c2CCC4)CCC3)O1] | 1. $^1$H-NMR (400 MHz, DMSO-d6) δ 8.73 (s, 1H), 7.99-7.78 (m, 2H), 6.87 (s, 1H), 4.38-4.11 (m, 2H), 3.77 (s, 3H), 2.87-2.55 (m, 8H), 2.03-1.85 (m, 4H).<br>2. 384.2 |
| Example 63<br>Enantiopure 62<br>(first eluting peak) | | 1. $^1$H-NMR (400 MHz, DMSO-d6) δ 8.74 (s, 1H), 7.89 (s, 2H), 6.89 (s, 1H), 4.44-3.99 (m, 2H), 3.77 (s, 3H), 2.92-2.55 (m, 8H), 1.94 (p, 4H).<br>2. 384.2 |
| Example 64<br>Enantiopure 62<br>(second eluting peak) | | 1. $^1$H-NMR (400 MHz, DMSO-d6) δ 8.73 (s, 1H), 7.97-7.82 (m, 2H), 6.88 (s, 1H), 4.42-4.15 (m, 2H), 3.77 (s, 3H), 2.87-2.58 (m, 8H), 2.04-1.86 (m, 4H).<br>2. 384.2 |
| Example 65<br>propyl 2-<br>((1,2,3,5,6,7-<br>hexahydro-s-<br>indacen-4-yl)amino)-<br>5-(thiazol-2-yl)-4,5-<br>dihydrooxazole-5-<br>carboxylate<br>Racemic | 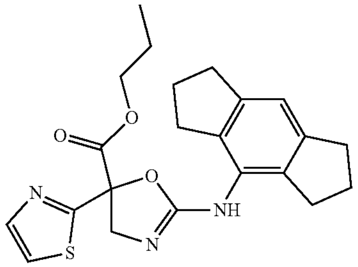 [SMILES: CCCOC(=O)C1(c2nccs2)CN=C(Nc2c3c(cc4c2CCC4)CCC3)O1] | 1. $^1$H-NMR (400 MHz, DMSO-d6) δ 8.74 (s, 1H), 8.01-7.83 (m, 2H), 6.87 (s, 1H), 4.38-4.21 (m, 2H), 4.21-4.11 (m, 2H), 2.87-2.58 (m, 8H), 2.04-1.86 (m, 4H), 1.58 (h, 2H), 0.81 (t, 3H).<br>2. 412.2 |
| Example 66<br>Enantiopure 65<br>(second eluting peak) | | 1. $^1$H-NMR (400 MHz, DMSO-d6) δ 8.74 (s, 1H), 7.97-7.78 (m, 2H), 6.88 (s, 1H), 4.40-4.23 (m, 2H), 4.21-4.10 (m, 2H), 2.87-2.56 (m, 8H), 2.04-1.88 (m, 4H), 1.58 (h, 2H), 0.81 (t, 3H).<br>2. 412.2 |
| Example 67<br>butyl 2-((1,2,3,5,6,7-<br>hexahydro-s-<br>indacen-4-yl)amino)-<br>5-(thiazol-2-yl)-4,5-<br>dihydrooxazole-5-<br>carboxylate<br>Racemic | 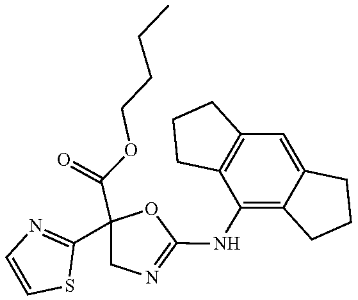 [SMILES: CCCCOC(=O)C1(c2nccs2)CN=C(Nc2c3c(cc4c2CCC4)CCC3)O1] | 1. $^1$H-NMR (400 MHz, DMSO-d6) δ 8.66 (br s, 1H), 7.89 (s, 2H), 6.86 (s, 1H), 4.35-4.11 (m, 4H), 2.86-2.59 (m, 8H), 2.02-1.86 (m, 4H), 1.55 (p, 2H), 1.36-1.14 (m, 2H), 0.84 (t, 3H).<br>2. 426.3 |
| Example 68<br>Enantiopure 67<br>(first eluting peak) | | 1. $^1$H-NMR (400 MHz, DMSO-d6) δ 8.66 (br s, 1H), 7.89 (s, 2H), 6.86 (s, 1H), 4.35-4.11 (m, 4H), 2.86-2.59 (m, 8H), 2.02-1.86 (m, 4H), 1.55 (p, 2H), 1.36-1.14 (m, 2H), 0.84 (t, 3H).<br>2. 426.3 |

-continued

| | | |
|---|---|---|
| Example 69<br>Enantiopure 67<br>(second eluting peak) | | 1. $^{1}$H-NMR (400 MHz, DMSO-d6) d 8.69 (s, 1H), 7.89 (s, 2H), 6.86 (s, 1H), 4.38-4.13 (m, 4H), 2.86-2.58 (m, 8H), 2.02-1.87 (m, 4H), 1.55 (p, 2H), 1.25 (h, 2H), 0.84 (t, 3H).<br>2. 426.3 |
| Example 70<br>butyl 2-((1,2,3,5,6,7-hexahydro-s-indacen-4-yl)amino)-5-(thiazol-2-yl)-4,5-dihydrooxazole-5-carboxylate<br>Racemic | 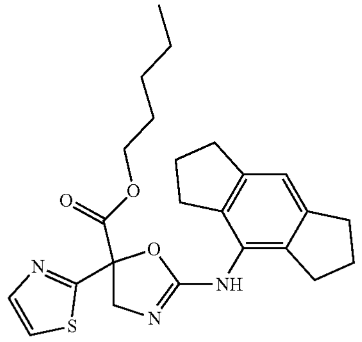 [SMILES: CCCCCOC(=O)C1(c2nccs2)CN=C(Nc2c3c(cc4c2CCC4)CCC3)O1] | 1. $^{1}$H-NMR (400 MHz, DMSO-d6) δ 8,73 (s, 1H), 7.89 (s, 2H), 6.88 (s, 1H), 4.38-4.07 (m, 4H), 2.86-2.58 (m, 8H), 1.95 (m, 4H), 1.64-1.51 (m, 2H), 1.30-1.15 (m, 4H), 0.82 (t, 3H).<br>2. 440.2 |
| Example 71<br>Enantiopure 70<br>(first eluting peak) | | 1. $^{1}$H-NMR (400 MHz, DMSO-d6) δ 7.89 (s, 2H), 6.86 (s, 1H), 4.43-3.94 (m, 4H), 2.93-2.57 (m, 8H), 1.94 (p, 4H), 1.70-1.46 (m, 2H), 1.22 (tq, 4H), 0.82 (t, 3H).<br>2. 440.2 |
| Example 72<br>Enantiopure methyl 2-((1,2,3,5,6,7-hexahydro-s-indacen-4-yl)amino)-5-(5-(2-hydroxypropan-2-yl)isoxazol-3-yl)-4,5-dihydrooxazole-5-carboxylate<br>(first eluting peak) | 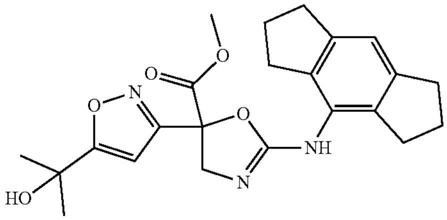 [SMILES: COC(=O)C1(c2cc(C(C)(C)O)on2)CN=C(Nc2c3c(cc4c2CCC4)CCC3)O1] | 1. $^{1}$H-NMR (400 MHz, DMSO-d6) δ 8.61 (s, 1H), 6.85 (s, 1H), 6.41 (s, 1H), 5.71 (s, 1H), 4.30-4.04 (m, 2H), 3.78 (s, 3H), 2.88-2.57 (m, 8H), 1.94 (p, 4H), 1.48 (s, 6H).<br>2. 426.2 |
| Example 73<br>Enantiopure 72<br>(second eluting peak) | | 1. $^{1}$H-NMR (400 MHz, DMSO-d6) δ 8.61 (s, 1H), 6.85 (s, 1H), 6.41 (s, 1H), 5.70 (s, 1H), 4.32-4.02 (m, 2H), 3.77 (s, 3H), 2.86-2.54 (m, 8H), 2.01-1.81 (m, 4H), 1.47 (s, 6H).<br>2. 426.2 |
| Example 74<br>propyl 2-((1,2,3,5,6,7-hexahydro-s-indacen-4-yl)amino)-5-(5-(2-hydroxypropan-2-yl)isoxazol-3-yl)-4,5-dihydrooxazole-5-carboxylate<br>Racemic | 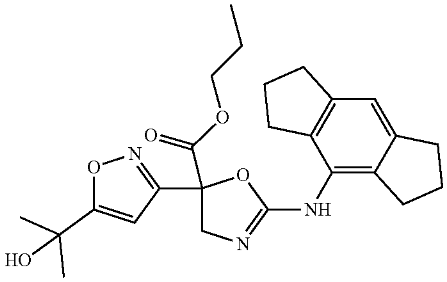 [SMILES: CCCOC(=O)C1(c2cc(C(C)(C)O)on2)CN=C(Nc2c3c(cc4c2CCC4)CCC3)O1] | 1. $^{1}$H-NMR (400 MHz, DMSO-d6) δ 7.15-6.54 (m, 1H), 6.37 (s, 1H), 4.33-3.90 (m, 4H), 3.00-2.53 (m, 10H), 2.01-1.80 (m, 4H), 1.58 (h, 2H), 1.45 (s, 6H), 0.82 (t, 3H).<br>2. 454.2 |
| Example 75<br>Enantiopure 74<br>(second eluting peak) | | 1. $^{1}$H-NMR (400 MHz, DMSO-d6) δ 8.64 (s, 1H), 6.88 (s, 1H), 6.40 (s, 1H), 5.71 (s, 1H), 4.40-3.81 (m, 4H), 2.97-2.57 (m, 8H), 1.95 (q, |

-continued

| | | |
|---|---|---|
| | | 4H), 1.61 (h, 2H), 1.47 (s, 6H), 0.85 (t, 3H).<br>2. 454.3 |
| Example 76<br>butyl 2-((1,2,3,5,6,7-hexahydro-s-indacen-4-yl)amino)-5-(5-(2-hydroxypropan-2-yl)isoxazol-3-yl)-4,5-dihydrooxazole-5-carboxylate<br>Racemic | 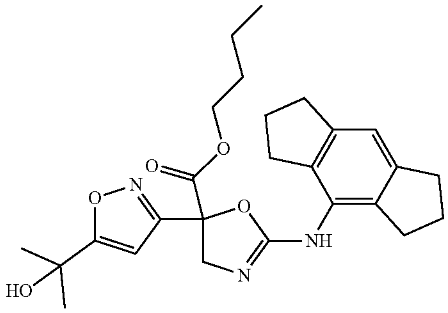 [SMILES: CCCCOC(=O)C1(c2cc(C(C)(C)O)on2)CN=C(Nc2c3c(cc4c2CCC4)CCC3)O1] | 1. $^{1}$H-NMR (400 MHz, DMSO-d6) δ 8.62 (s, 1H), 6.85 (s, 1H), 6.39 (s, 1H), 5.71 (s, 1H), 4.34-3.99 (m, 4H), 2.93-2.56 (m, 8H), 2.06-1.88 (m, 4H), 1.57 (dq, 2H), 1.47 (s, 6H), 1.37-1.23 (m, 2H), 0.86 (t, 3H).<br>2. 468.2 |
| Example 77<br>Enantiopure 76<br>(first eluting peak) | | 1. $^{1}$H-NMR (400 MHz, DMSO-d6) δ 8.63 (s, 1H), 6.89 (s, 1H), 6.39 (s, 1H), 5.71 (s, 1H), 4.40-3.86 (m, 4H), 2.93-2.56 (m, 8H), 2.03-1.83 (m, 4H), 1.71-1.52 (m, 2H), 1.47 (s, 6H), 1.41-1.15 (m, 2H), 0.86 (t, 3H).<br>2. 468.3 |
| Example 78<br>Enantiopure 76<br>(second eluting peak) | | 1. $^{1}$H-NMR (400 MHz, DMSO-d6) δ 8.63 (s, 1H), 6.88 (s, 1H), 6.39 (s, 1H), 5.71 (s, 1H), 4.32-4.01 (m, 4H), 2.89-2.57 (m, 8H), 2.02-1.86 (m, 4H), 1.69-1.52 (m, 2H), 1.47 (s, 6H), 1.38-1.22 (m, 2H), 0.86 (t, 3H)<br>2. 468.3 |
| Example 79<br>pentyl 2-((1,2,3,5,6,7-hexahydro-s-indacen-4-yl)amino)-5-(5-(2-hydroxypropan-2-yl)isoxazol-3-yl)-4,5-dihydrooxazole-5-carboxylate<br>Racemic | 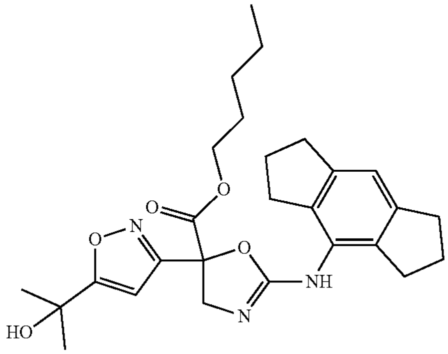 [SMILES: CCCCCOC(=O)C1(c2cc(C(C)(C)O)on2)CN=C(Nc2c3c(cc4c2CCC4)CCC3)O1] | 1. $^{1}$H-NMR (400 MHz, DMSO-d6) δ 8.62 (s, 1H), 6.85 (s, 1H), 6.39 (s, 1H), 5.71 (s, 1H), 4.29-4.01 (m, 4H), 2.89-2.55 (m, 8H), 2.03-1.83 (m, 4H), 1.59 (p, 2H), 1.47 (s, 6H), 1.33-1.18 (m, 4H), 0.85 (t, 3H).<br>2. 482.5 |
| Example 80<br>Enantiopure 79<br>(first eluting peak) | | 1. $^{1}$H-NMR (400 MHz, DMSO-d6 δ 8.63 (s, 1H), 6.85 (s, 1H), 6.39 (s, 1H), 5.70 (s, 1H), 4.31-4.03 (m, 4H), 2.92-2.59 (m, 8H), 2.01-1.83 (m, 4H), 1.64-1.54 (m, 2H), 1.47 (s, 6H), 1.33-1.18 (m, 4H), 0.84 (t, 3H).<br>2. 482.3 |
| Example 81<br>Enantiopure 79<br>(second eluting peak) | | 1. $^{1}$H-NMR (400 MHz, DMSO-d6) δ 8.66 (s, 1H), 6.85 (s, 1H), 6.40 (s, 1H), 5.71 (s, 1H), 4.29-4.01 (m, 4H), 2.87-2.58 (m, 8H), 2.05-1.83 (m, 4H), 1.69-1.56 (m, 2H), 1.47 (s, 6H), 1.33- |

-continued

| | | |
|---|---|---|
| | | 1.16 (m, 4H), 0.85 (t, 3H)<br>2. 482.3 |
| Example 82<br>tert-butyl 2-((1,2,3,5,6,7-hexahydro-s-indacen-4-yl)amino)-5-(5-(2-hydroxypropan-2-yl)isoxazol-3-yl)-4,5-dihydrooxazole-5-carboxylate<br>Racemic | 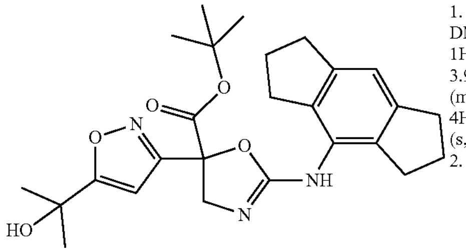 | 1. $^{1}$H-NMR (400 MHz, DMSO-d6) δ 6.83 (s, 1H), 6.34 (s, 1H), 4.22-3.95 (m, 2H), 2.90-2.59 (m, 8H), 2.04-1.84 (m, 4H), 1.47 (s, 6H), 1.44 (s, 9H).<br>2. 468.2 |
| Example 83<br>Enantiopure 82<br>(second eluting peak) | | 1. $^{1}$H-NMR (400 MHz, DMSO-d6) δ 6.84 (s, 1H), 6.34 (s, 1H), 4.22-3.98 (m, 2H), 2.85-2.56 (m, 8H), 2.04-1.88 (m, 4H), 1.47 (s, 6H), 1.44 (s, 9H).<br>2. 468.1 |
| Example 84<br>methyl 2-((1,2,3,5,6,7-hexahydro-s-indacen-4-yl)amino)-5-(isoxazol-3-yl)-4,5-dihydrooxazole-5-carboxylate<br>Racemic | 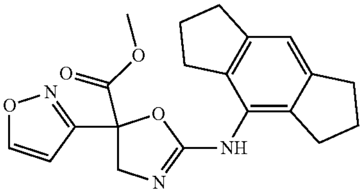 [SMILES: COC(=O)C1(c2ccon2)CN=C(Nc2c3c(cc4c2CCC4)CCC3)O1] | 1. $^{1}$H-NMR (400 MHz, DMSO-d6) δ 9.05 (d, 1H), 8.64 (s, 1H), 6.88 (s, 1H), 6.74 (s, 1H), 4.36-4.06 (m, 2H), 3.77 (s, 3H), 2.85-2.58 (m, 8H), 2.02-1.80 (m, 4H).<br>2. 368.2 |
| Example 85<br>Enantiopure 84<br>(first eluting peak) | | 1. $^{1}$H-NMR (400 MHz, DMSO-d6) δ 9.05 (d, 1H), 8.61 (s, 1H), 6.85 (s, 1H), 6.74 (s, 1H), 4.34-4.01 (m, 2H), 3.77 (s, 3H), 2.90-2.56 (m, 8H), 2.03-1.84 (m, 4H).<br>2. 368.1 |
| Example 86<br>Enantiopure 84<br>(second eluting peak) | | 1. $^{1}$H-NMR (400 MHz, DMSO-d6) δ 9.05 (d, 1H), 8.62 (s, 1H), 6.85 (s, 1H), 6.74 (s, 1H), 4.36-4.00 (m, 2H), 3.77 (s, 3H), 2.90-2.56 (m, 8H), 2.05-1.80 (m, 4H).<br>2. 368.2 |
| Example 87<br>methyl 2-((1,2,3,5,6,7-hexahydro-s-indacen-4-yl)amino)-5-(isoxazol-5-yl)-4,5-dihydrooxazole-5-carboxylate<br>Racemic | 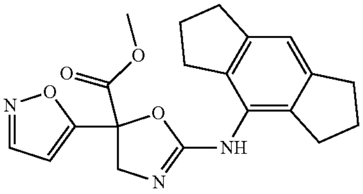 [SMILES: COC(=O)C1(c2ccno2)CN=C(Nc2c3c(cc4c2CCC4)CCC3)O1] | 1. $^{1}$H-NMR (400 MHz, DMSO-d6) δ 8.69 (d, 1H), 6.93-6.79 (m, 2H), 4.37-4.09 (m, 2H), 3.79 (s, 3H), 2.89-2.56 (m, 8H), 2.07-1.85 (m, 4H).<br>2. 368.2 |
| Example 88<br>Enantiopure 87<br>(first eluting peak) | | 1. $^{1}$H-NMR (400 MHz, DMSO-d6) δ 8.69 (m, 2H), 6.96-6.76 (m, 2H), 4.40-4.08 (m, 2H), 3.79 (s, 3H), 2.87-2.55 (m, 8H), 2.04-1.83 (m, 4H).<br>2. 368.2 |
| Example 89<br>Enantiopure 87<br>(second eluting peak) | | 1. $^{1}$H-NMR (400 MHz, DMSO-d6) δ 8.76-8.63 (m, 2H), 6.96-6.82 (m, 2H), 4.38-4.13 (m, 2H), 3.80 (s, 3H), 2.87-2.62 (m, 8H), 2.03-1.86 (m, 4H).<br>2. 368.2 |

-continued

| | | |
|---|---|---|
| Example 90<br>tert-butyl 2-((1,2,3,5,6,7-hexahydro-s-indacen-4-yl)amino)-5-(isoxazol-5-yl)-4,5-dihydrooxazole-5-carboxylate<br>Racemic | 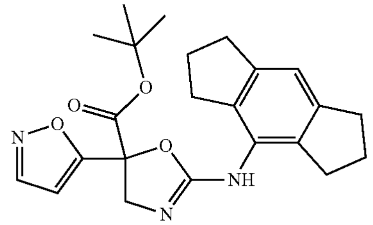 [SMILES: CC(C)(C)OC(=O)C1(c2ccno2)CN=C(Nc2c3c(cc4c2CCC4)CCC3)O1] | 1. $^1$H-NMR (400 MHz, DMSO-d6) δ 8.67 (d, 1H), 6.86 (s, 1H), 6.79 (d, 1H), 4.33-3.97 (m, 2H), 2.87-2.58 (m, 8H), 2.01-1.84 (m, 4H), 1.44 (s, 9H).<br>2. 410.2 |
| Example 91<br>Enantiopure 90<br>(second eluting peak) | | 1. $^1$H-NMR (400 MHz, DMSO-d6) δ 8.67 (d, 1H), 6.86 (s, 1H), 6.78 (d, 1H), 4.33-4.02 (m, 2H), 2.85-2.57 (m, 8H), 2.03-1.84 (m, 4H), 1.44 (s, 9H).<br>2. 410.2 |
| Example 92<br>pentyl 2-((1,2,3,5,6,7-hexahydro-s-indacen-4-yl)amino)-5-(isoxazol-5-yl)-4,5-dihydrooxazole-5-carboxylate<br>Racemic | 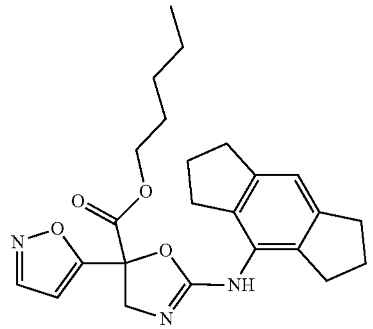 [SMILES: CCCCCOC(=O)C1(c2ccno2)CN=C(Nc2c3c(cc4c2CCC4)CCC3)O1] | 1. $^1$H-NMR (400 MHz, DMSO-d6) δ 8.69 (s, 1H), 6.96-6.79 (m, 2H), 4.36-4.05 (m, 4H), 2.86-2.57 (m, 8H), 1.94 (p, 4H), 1.66-1.52 (m, 2H), 1.33-1.18 (m, 4H), 0.84 (t, 3H).<br>2. 424.2 |
| Example 93<br>Enantiopure 92<br>(second eluting peak) | | 1. $^1$H-NMR (400 MHz, DMSO-d6) δ 8.69 (d, 1H), 6.94-6.76 (m, 2H), 4.34-4.07 (m, 4H), 2.85-2.56 (m, 8H), 2.03-1.85 (m, 4H), 1.64-1.53 (m, 2H), 1.33-1.17 (m, 4H), 0.84 (t, 3H).<br>2. 424.2 |

Biological Assay Description

NLRP3 Inhibition Assay

The following assays were used to determine the inhibitory activity of test compounds on the NLRP3 inflammasome pathway using common stimuli Nigericin (Invivogen) or monosodium urate crystals (MSU) (Invivogen).

Cell Culture

Human monocyte-like cells were cultured in RPMI-1640 Glutamax medium supplemented with 10% heat inactivated FCS and 50 U/ml penicillin-streptomycin (Life Technologies).

NLRP3 Inflammasome Pathway Activation Assay

Human monocyte-like cells were seeded at 75000 per well in a 96-well plate and were differentiated overnight into macrophages with 10 ng/ml PMA (Phorbol Myristate Acetate). The following day, medium containing 10 ng/ml LPS (Lipopolysaccharide) were added. After 3 hours of LPS priming, concentrations of test compound in the range from 100 μM to 6 nM were added 30 min prior to NLRP3 inflammasome pathway stimulation with Nigericin 3.75 μM or MSU 150 μg/ml for 3 h.

Human Whole Blood Assay

Culture Setup Procedure

Preliminary blood hemolysis assessment was performed before running the assay. Blood samples were centrifuged at 1000 g for 10 min. Then, 50 to 100 μL of blood were transferred into Corning™ 96-Well Clear flat bottom plate. Hemolysis was assessed via Tecan at 414 nm wavelength. Hemolysis O.D. values should be lower than 1.

Add 10 μL LPS 9× or CTRL following plate layout.

Add 80 μL of each whole blood/well in PP low-bind 96-well plate.

Incubate for 2 h30 to 3 h at 37° C. and 5% $CO_2$.

Add 10 μL of compounds 10× or control in wells following plate layout.

Incubate for 30 min at 37° C. and 5% $CO_2$.

Add 11 μL ATP 10× or control in all wells following plate layout.

Incubate for 1 h at 37° C. and 5% $CO_2$.

Collect 1 h timepoint→Centrifuge the plate 1000 g 10 min, collect the plasma (40 to 50 μL) and store at −20° C.

Measure IL-1β levels by AlphaLISA

LPS-ATP Induced Peritonitis Mouse Model

C57BL/6 female mice aged 6 to 8 weeks were randomized into experimental groups. Mice were challenged intraperitoneally with 50 μg/kg LPS. Two hours later, mice received i.p. 200 μL of ATP (Adenosine TriPhosphate) 50 mM, pH 7.2. Compounds were administered intraperitoneally at 1 mg/kg or 3 mg/kg, 15 minutes before ATP injection. Thirty minutes after ATP injection, animals were sacrificed by $CO_2$. Cardiac blood was collected through heart puncture. Peritoneal lavage was performed with a total volume of 4 mL of sterile saline solution with intact peritoneum. IL-1b levels were assessed in peritoneal lavage samples via AlphaLisa. Results were expressed as % reduction compared to vehicle-treated group.

Measurement of IL-1β

For IL-1β quantification, supernatants were analyzed using AlphaLISA kits according to the manufacturer's instructions (Perkin Elmer AlphaLISA AL220F). Briefly, in a 384-well OptiPlate™ microplate, 5 μl of sample was mixed, with 20 μl of AlphaLISA Anti-Analyte Acceptor beads (10 μg/mL final) and Biotinylated Antibody Anti-Analyte (1 nM final). Then, incubated 60 minutes at RT, then 25 μL of 2× SA-Donor beads (40 μg/mL final) were added and incubated 30 minutes at RT in the dark. Reading was done using an EnVision-Alpha Reader (PerkinElmer).

$IC_{50}$ (concentration corresponding to 50% inhibition) were determined using GraphPad Prism 8.

The following example compounds were measured:

TABLE 1

| Examples | $IC_{50}$ Human monocyte-like cells MSU (μM) | $IC_{50}$ Human monocyte-like cells Nigericin (μM) | $IC_{50}$ Human whole blood assay (LPS-ATP) | % IL-1beta inhibition vs vehicle (peritoneal lavage samples) |
|---|---|---|---|---|
| 1 | +++ | +++ | | |
| 2 | ++ | ++ | | |
| 3 | +++ | +++ | | |
| 4 | +++ | +++ | | |
| 5 | +++ | +++ | | |
| 6 | +++ | +++ | | |
| 7 | +++ | +++ | | |
| 8 | +++ | +++ | | |
| 9 | +++ | +++ | | |
| 10 | ++ | ++ | | |
| 10a | +++ | + | | |
| 11 | +++ | +++ | | |
| 11a | +++ | +++ | | |
| 12 | ++ | ++ | | |
| 13 | +++ | +++ | | |
| 13a | +++ | +++ | | |
| 14 | +++ | +++ | | |
| 14a | +++ | +++ | | |
| 15 | +++ | +++ | | |
| 16 | +++ | +++ | +++ | 99% |
| 17 | +++ | +++ | | |
| 17a | +++ | +++ | | |
| 18 | +++ | +++ | +++ | |
| 19 | +++ | +++ | | |
| 20 | +++ | +++ | ++ | |
| 21 | +++ | +++ | | |
| 21A | +++ | +++ | | |
| 21Aa | +++ | +++ | | |
| 21B | +++ | +++ | | |
| 21Ba | +++ | +++ | | |
| 21Bb | +++ | +++ | +++ | 73% |
| 22 | +++ | ++ | | |
| 23 | +++ | +++ | ++ | >99% |
| 24 | ++ | ++ | ++ | |
| 25 | ++ | ++ | | |
| 26 | ++ | ++ | | |
| 27 | ++ | ++ | | |
| 28 | +++ | ++ | | |
| 29 | +++ | +++ | ++ | |
| 30 | +++ | ++ | | |
| 31 | +++ | +++ | | |
| 32 | +++ | +++ | | |
| 33 | +++ | +++ | | |
| 34 | ++ | ++ | | |
| 35 | ++ | ++ | | |
| 36 | ++ | ++ | | |
| 37 | +++ | +++ | | |
| 38 | +++ | +++ | | |
| 39 | +++ | +++ | | |
| 40 | +++ | +++ | | |
| 41 | +++ | +++ | | |
| 42 | ++ | +++ | | |
| 43 | +++ | +++ | | |
| 44 | +++ | +++ | | |
| 45 | +++ | +++ | | |
| 46 | ++ | +++ | | |
| 47 | ++ | ++ | | |
| 48 | +++ | +++ | | |
| 49 | +++ | +++ | | |
| 50 | ++ | +++ | | |
| 51 | ++ | ++ | | |
| 52 | ++ | +++ | | |
| 53 | +++ | +++ | | |
| 54 | +++ | +++ | | |
| 55 | +++ | +++ | | |
| 56 | +++ | +++ | | |
| 57 | +++ | +++ | | |
| 58 | +++ | +++ | ++ | |
| 59 | +++ | +++ | ++ | |
| 60 | +++ | +++ | | |
| 61 | +++ | +++ | | |
| 62 | +++ | +++ | | |
| 63 | ++ | ++ | | |
| 64 | +++ | +++ | | |
| 65 | +++ | +++ | | |
| 66 | +++ | +++ | | |
| 67 | +++ | +++ | | |
| 68 | +++ | +++ | | |
| 69 | ++ | ++ | | |
| 70 | +++ | +++ | | |
| 71 | +++ | +++ | | |
| 72 | +++ | +++ | | |
| 73 | +++ | +++ | | |
| 74 | +++ | +++ | | |
| 75 | +++ | +++ | | |
| 76 | +++ | +++ | | |
| 77 | +++ | +++ | | |
| 78 | +++ | +++ | | |
| 79 | +++ | +++ | | |
| 80 | +++ | +++ | | |
| 81 | +++ | +++ | | |
| 82 | +++ | +++ | | |
| 83 | +++ | +++ | | |
| 84 | +++ | +++ | | |
| 85 | ++ | +++ | | |
| 86 | +++ | +++ | | |
| 87 | +++ | +++ | | |
| 88 | ++ | ++ | | |
| 89 | +++ | +++ | | |
| 90 | ++ | +++ | | |
| 91 | +++ | +++ | | |
| 92 | +++ | +++ | | |
| 93 | +++ | +++ | | |

Legend:
+++ $IC_{50}$ < 1 μM;
++ $IC_{50}$ 1 < x < 10 μM;
+ $IC_{50}$ 10 < x < 30 μM.

The tested compounds showed inhibition of IL-1beta release in human monocyte-like cells: (A) using MSU or Nigericin as activators; (B) in human whole blood assay using ATP as activator, see Table 1; and (C) by peritoneal lavage from LPS-ATP induced peritonitis mouse model, see Table 1 and FIG. 1 (as depicted herein below).

In particular, FIG. 1 shows significant inhibition of IL-1ß release in peritoneal lavage samples from mice dosed with (1 mg/kg or 3 mg/kg) Example 16 and Example 23 by intraperitoneal injection in an LPS-ATP induced peritonitis model. Data are expressed as % of cytokine release as compared to vehicle-treated group representing 100% of secretion capacity. n=6 mice per group. **** p<0.0001 vs vehicle-treated group; One-Way ANOVA followed by Dunnett's post-hoc test.

The invention claimed is:

1. A compound of formula (I')

(I')

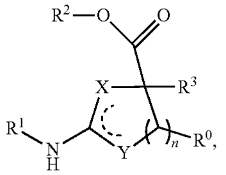

or a stereoisomer, a racemic mixture, a tautomer, a polymorph, a pharmaceutically acceptable salt, a prodrug, a hydrate, or a solvate thereof;

wherein

X is independently selected from the group consisting of O, N and S;

Y is independently selected from the group consisting of N and O;

as valency permits, is a combination of a single bond and a double bond or is two single bonds;

n is 1 or 2;

$R^0$ is H or $C_1$-$C_3$alkyl;

$R^1$ is

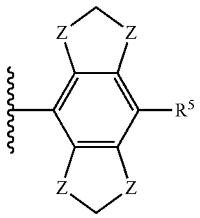

wherein

Z is independently selected from the group consisting of $CH_2$ and O provided that no more than two of Z are O;

$R^5$ is independently selected from the group consisting of hydrogen and halogen;

$R^2$ is independently selected from the group consisting of hydrogen, $C_1$-$C_6$alkyl, $C_3$-$C_6$cycloalkyl; and $R^3$ is independently selected from the group consisting of hetero$C_3$-$C_6$cycloalkyl, aryl or heteroaryl, wherein each of them can be optionally substituted with —$C_1$-$C_6$alkyl, —O—$C_1$-$C_6$alkyl, -Hal, or —$C_1$-$C_6$alkyl-OH.

2. The compound according to claim 1, having a formula (I)

(I)

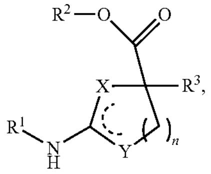

or a stereoisomer, a racemic mixture, a tautomer, a polymorph, a pharmaceutically acceptable salt, a prodrug, a hydrate, or a solvate thereof;

wherein, X, Y, n, $R^1$, $R^2$ and $R^3$ are as defined in claim 1 and wherein $R^0$ is H.

3. The compound according to claim 1, which is a compound of formula (Ic), a compound of formula (Ic'), a compound of formula (Id), or a compound of formula (Id')

(Ic)

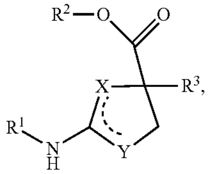

(Ic')

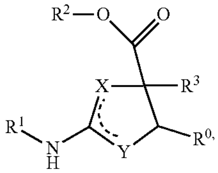

(Id)

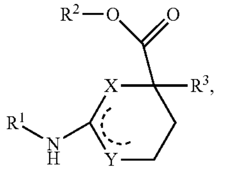

or (Id')

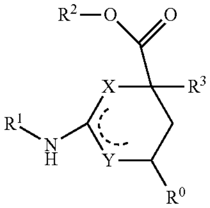

or a stereoisomer, a racemic mixture, a tautomer, a polymorph, a pharmaceutically acceptable salt, a prodrug, a hydrate, or a solvate thereof, wherein , X, Y, $R^1$, $R^2$ and $R^3$ are as defined in claim 1, and wherein $R^0$ is $C_1$-$C_3$alkyl.

4. The compound according to claim 3, which is a compound of formula (Ic)

(Ic)

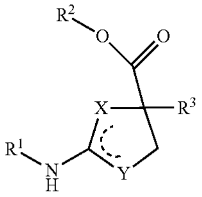

wherein , X, Y, $R^1$, $R^2$ and $R^3$ are as defined in claim 1.

5. The compound according to claim 1, wherein

X is O;

Y is N;

as valency permits, is the combination of a single bond and a double bond;

$R^1$ is
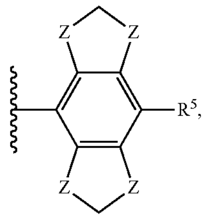
wherein Z is $CH_2$; $R^5$ is hydrogen;
$R^3$ is
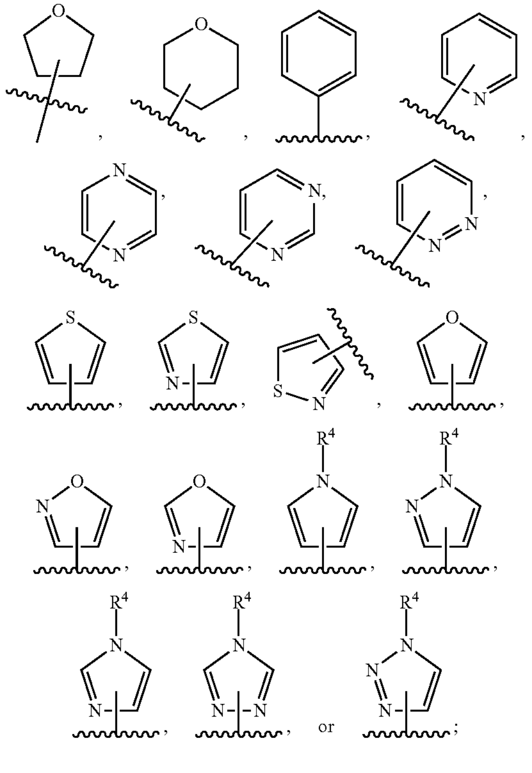
or
each of them can be optionally substituted, and $R^4$ is independently selected from the group consisting of hydrogen, $C_1$-$C_6$alkyl and $C_3$-$C_6$cycloalkyl.
6. The compound according to claim 1, which is selected from
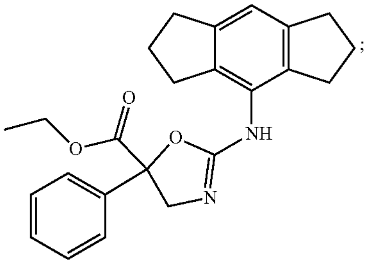 [SMILES: CCOC(=O)C1(c2ccccc2)CN=C(Nc2c3c(cc4c2CCC4)CCC3)O1]
;
-continued
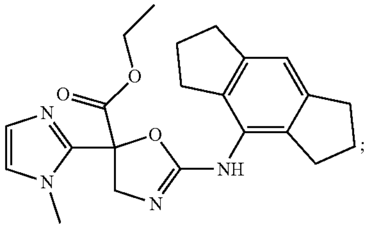 [SMILES: CCOC(=O)C1(c2nccn2C)CN=C(Nc2c3c(cc4c2CCC4)CCC3)O1]
;
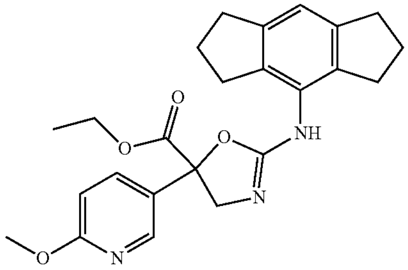
;
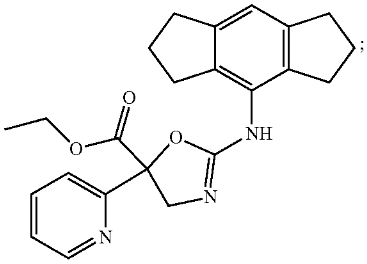 [SMILES: CCOC(=O)C1(c2ccccn2)CN=C(Nc2c3c(cc4c2CCC4)CCC3)O1]
;
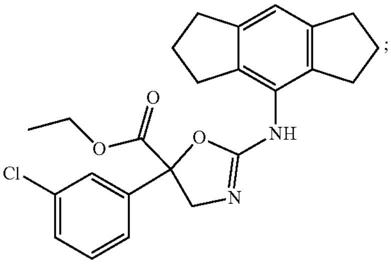 [SMILES: CCOC(=O)C1(c2cccc(Cl)c2)CN=C(Nc2c3c(cc4c2CCC4)CCC3)O1]
;
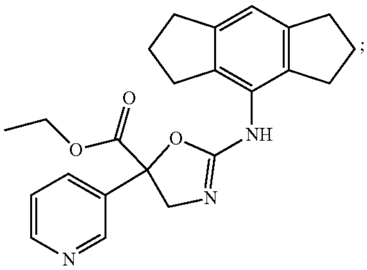 [SMILES: CCOC(=O)C1(c2cccnc2)CN=C(Nc2c3c(cc4c2CCC4)CCC3)O1]
;
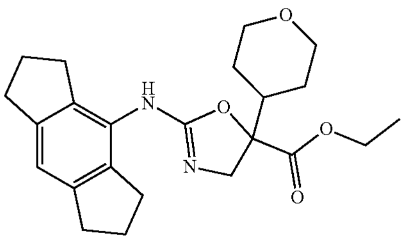
;

-continued
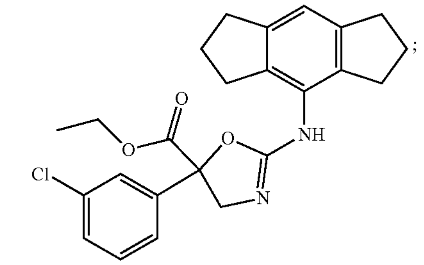 [SMILES: CCOC(=O)C1(c2cccc(Cl)c2)CN=C(Nc2c3c(cc4c2CCC4)CCC3)O1]
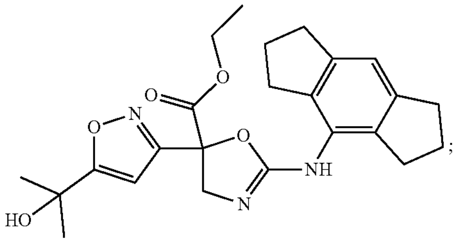 [SMILES: CCOC(=O)C1(c2cc(C(C)(C)O)on2)CN=C(Nc2c3c(cc4c2CCC4)CCC3)O1]
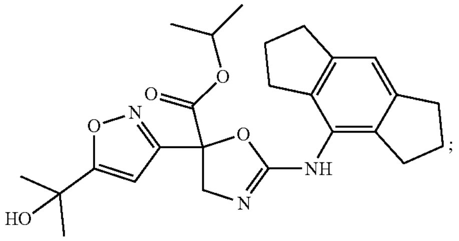 [SMILES: CC(C)OC(=O)C1(c2cc(C(C)(C)O)on2)CN=C(Nc2c3c(cc4c2CCC4)CCC3)O1]
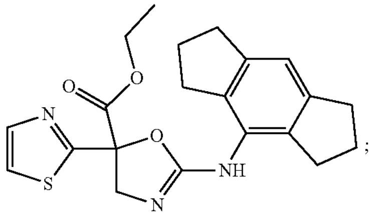 [SMILES: CCOC(=O)C1(c2nccs2)CN=C(Nc2c3c(cc4c2CCC4)CCC3)O1]
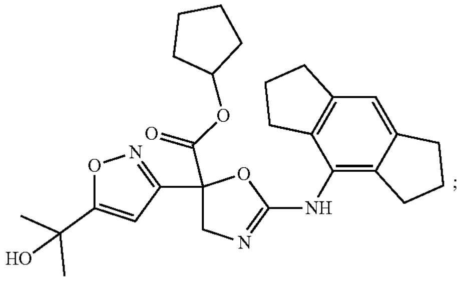 [SMILES: CC(C)(O)c1cc(C2(C(=O)OC3CCCC3)CN=C(Nc3c4c(cc5c3CCC5)CCC4)O2)no1]
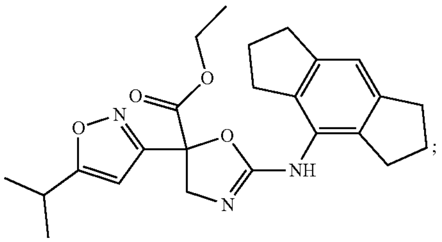 [SMILES: CCOC(=O)C1(c2cc(C(C)C)on2)CN=C(Nc2c3c(cc4c2CCC4)CCC3)O1]
-continued
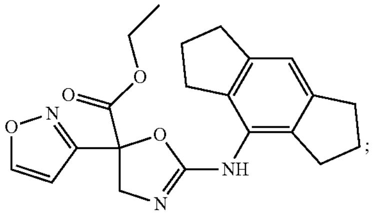 [SMILES: CCOC(=O)C1(c2ccon2)CN=C(Nc2c3c(cc4c2CCC4)CCC3)O1]
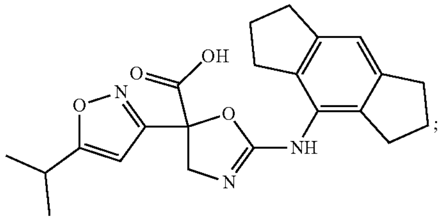 [SMILES: CC(C)c1cc(C2(C(=O)O)CN=C(Nc3c4c(cc5c3CCC5)CCC4)O2)no1]
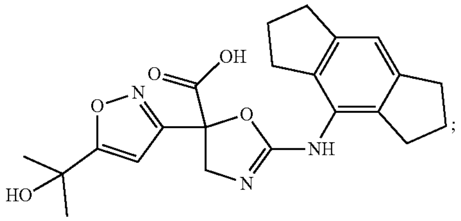 [SMILES: CC(C)(O)c1cc(C2(C(=O)O)CN=C(Nc3c4c(cc5c3CCC5)CCC4)O2)no1]
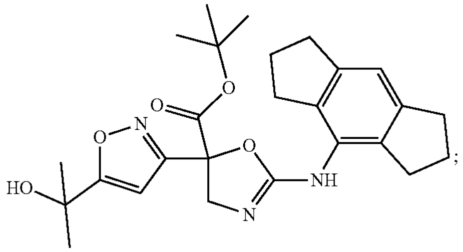 [SMILES: CC(C)(C)OC(=O)C1(c2cc(C(C)(C)O)on2)CN=C(Nc2c3c(cc4c2CCC4)CCC3)O1]
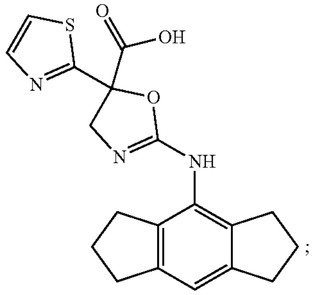
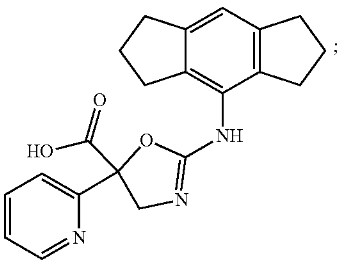 [SMILES: O=C(O)C1(c2ccccn2)CN=C(Nc2c3c(cc4c2CCC4)CCC3)O1]

-continued
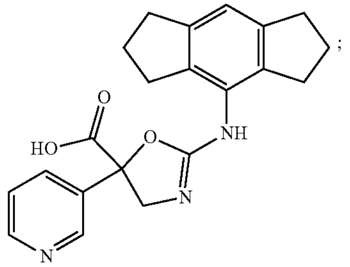 [SMILES: O=C(O)C1(c2cccnc2)CN=C(Nc2c3c(cc4c2CCC4)CCC3)O1]
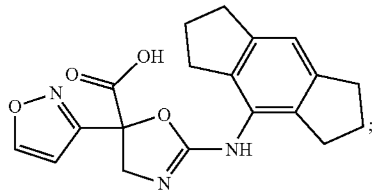 [SMILES: O=C(O)C1(c2ccon2)CN=C(Nc2c3c(cc4c2CCC4)CCC3)O1]
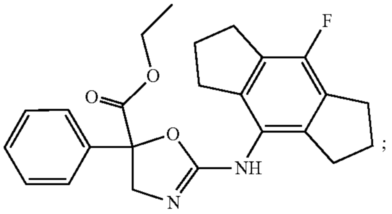 [SMILES: CCOC(=O)C1(c2ccccc2)CN=C(Nc2c3c(c(F)c4c2CCC4)CCC3)O1]
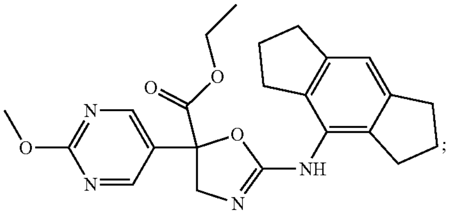 [SMILES: CCOC(=O)C1(c2cnc(OC)nc2)CN=C(Nc2c3c(cc4c2CCC4)CCC3)O1]
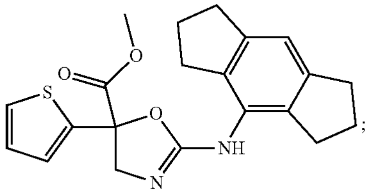 [SMILES: COC(=O)C1(c2cccs2)CN=C(Nc2c3c(cc4c2CCC4)CCC3)O1]
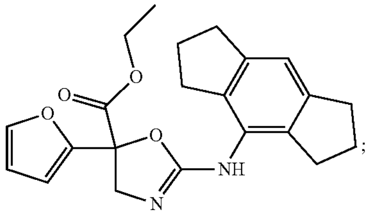 [SMILES: CCOC(=O)C1(c2ccco2)CN=C(Nc2c3c(cc4c2CCC4)CCC3)O1]
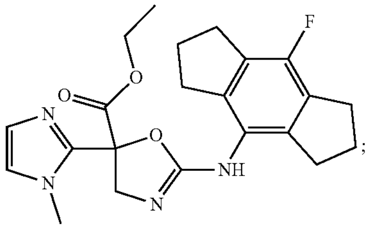 [SMILES: CCOC(=O)C1(c2nccn2C)CN=C(Nc2c3c(c(F)c4c2CCC4)CCC3)O1]
-continued
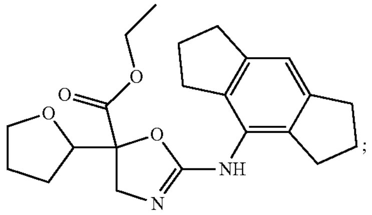 [SMILES: CCOC(=O)C1(C2CCCO2)CN=C(Nc2c3c(cc4c2CCC4)CCC3)O1]
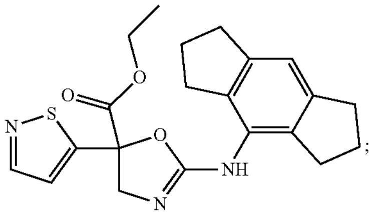 [SMILES: CCOC(=O)C1(c2ccns2)CN=C(Nc2c3c(cc4c2CCC4)CCC3)O1]
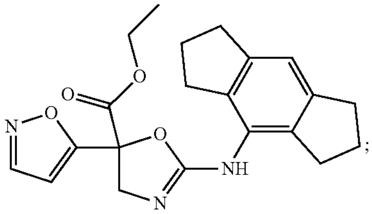 [SMILES: CCOC(=O)C1(c2ccno2)CN=C(Nc2c3c(cc4c2CCC4)CCC3)O1]
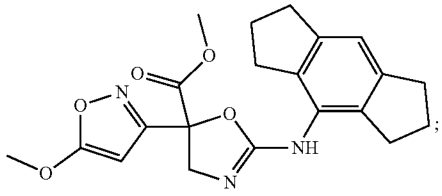 [SMILES: COC(=O)C1(c2cc(OC)on2)CN=C(Nc2c3c(cc4c2CCC4)CCC3)O1]
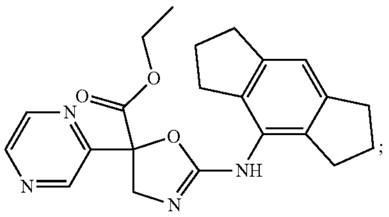 [SMILES: CCOC(=O)C1(c2cnccn2)CN=C(Nc2c3c(cc4c2CCC4)CCC3)O1]
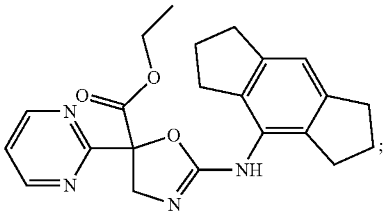
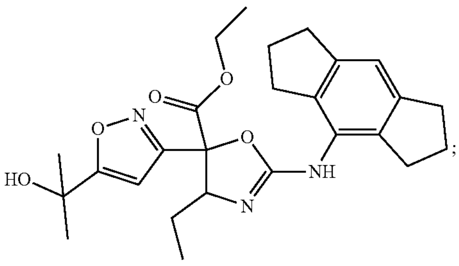 [SMILES: CCOC(=O)C1(c2cc(C(C)(C)O)on2)OC(Nc2c3c(cc4c2CCC4)CCC3)=NC1CC]

-continued
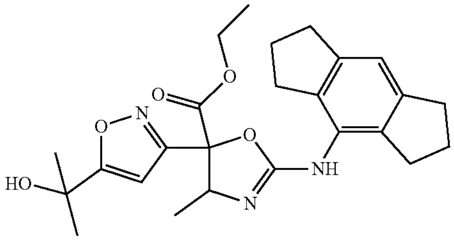
;
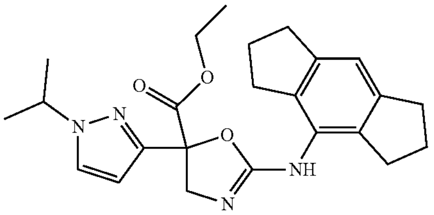
;
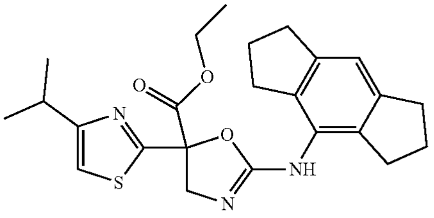
;
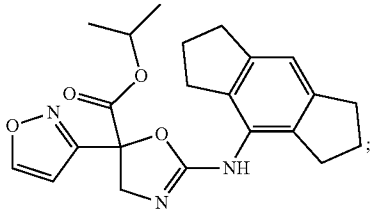 [SMILES: CC(C)OC(=O)C1(c2ccon2)CN=C(Nc2c3c(cc4c2CCC4)CCC3)O1]
;
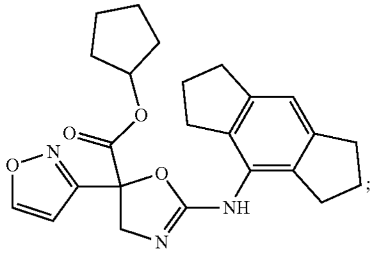 [SMILES: O=C(OC1CCCC1)C1(c2ccon2)CN=C(Nc2c3c(cc4c2CCC4)CCC3)O1]
;
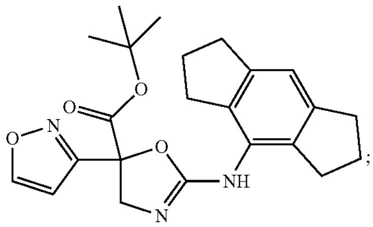 [SMILES: CC(C)(C)OC(=O)C1(c2ccon2)CN=C(Nc2c3c(cc4c2CCC4)CCC3)O1]
;
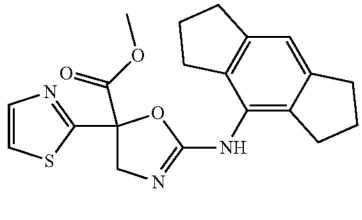
;
-continued
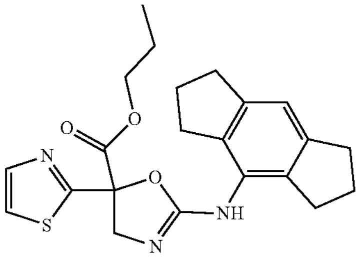
;
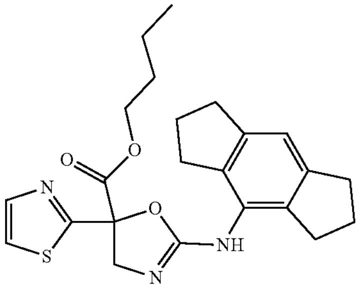
;
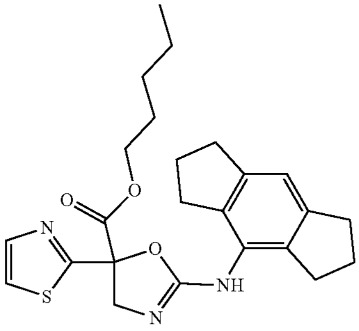
;
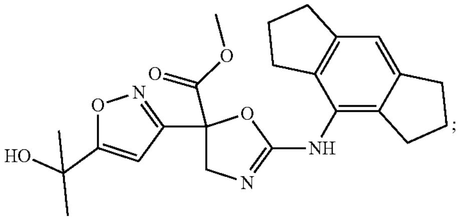 [SMILES: COC(=O)C1(c2cc(C(C)(C)O)on2)CN=C(Nc2c3c(cc4c2CCC4)CCC3)O1]
;
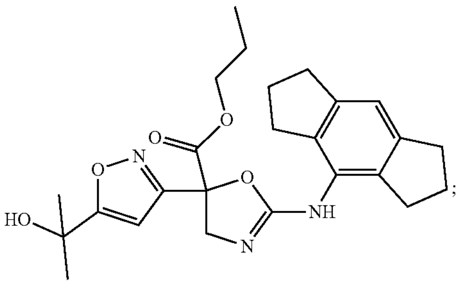 [SMILES: CCCOC(=O)C1(c2cc(C(C)(C)O)on2)CN=C(Nc2c3c(cc4c2CCC4)CCC3)O1]
;

-continued

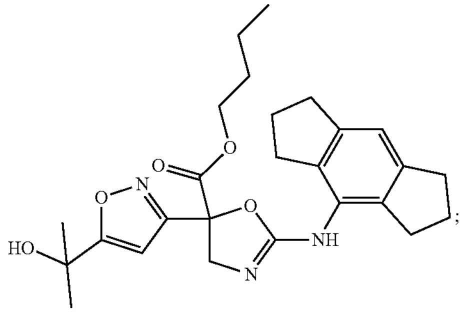 [SMILES: CCCCOC(=O)C1(c2cc(C(C)(C)O)on2)CN=C(Nc2c3c(cc4c2CCC4)CCC3)O1]
;

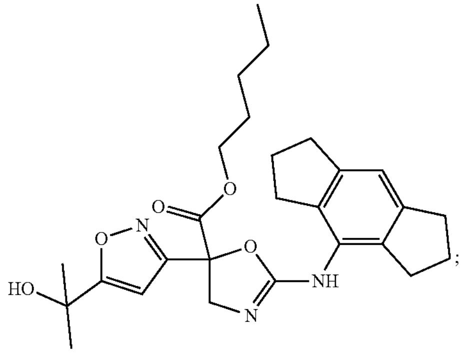 [SMILES: CCCCCOC(=O)C1(c2cc(C(C)(C)O)on2)CN=C(Nc2c3c(cc4c2CCC4)CCC3)O1]
;

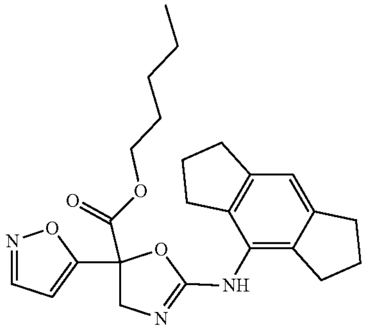
;

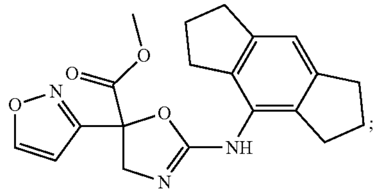 [SMILES: COC(=O)C1(c2ccon2)CN=C(Nc2c3c(cc4c2CCC4)CCC3)O1]
;

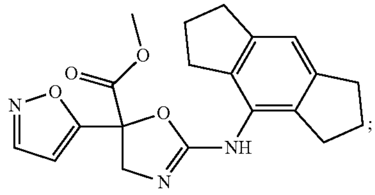 [SMILES: COC(=O)C1(c2ccno2)CN=C(Nc2c3c(cc4c2CCC4)CCC3)O1]
;

-continued

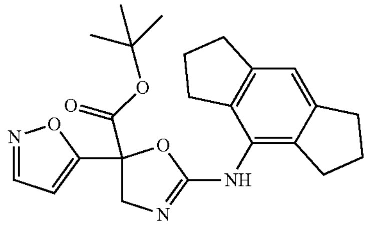
;

or a stereoisomer, a racemic mixture, a tautomer, a polymorph, a pharmaceutically acceptable salt, a prodrug, a hydrate, or a solvate thereof.

7. A pharmaceutical composition comprising a compound as defined in claim 1, or a stereoisomer, a racemic mixture, a tautomer, a polymorph, a pharmaceutically acceptable salt, a prodrug, a hydrate, or a solvate thereof, and optionally comprising at least one pharmaceutically acceptable carrier, diluent, adjuvant or excipient.

8. A method for the treatment, or alleviation of a disease, a disorder, or an abnormality which is responsive to the modulation of a component of the NLRP3 inflammasome pathway and/or which is responsive to the modulation of IL-1 beta and/or IL-18 levels, the method comprising:

administering to a host in need thereof a compound according to claim 1, or a stereoisomer, a racemic mixture, a tautomer, a polymorph, a pharmaceutically acceptable salt, a prodrug, a hydrate, or a solvate thereof, wherein the disease, the disorder or the abnormality is selected from amyotrophic lateral sclerosis, epilepsy, cryopyrin-associated periodic syndromes (CAPS), non-alcoholic fatty liver disease, hypertension, graft-versus host disease, type 2 diabetes, myelodysplastic syndrome, acne, pyogenic arthritis pyoderma gangrenosum and acne (PAPA), psoriasis, chronic obstructive pulmonary disorder (COPD), obesity, chronic kidney disease, osteoarthritis, Coronaviruses, and hidradenitis suppurativa (HS).

9. The method according to claim 8, wherein the modulation is the reduction and/or inhibition of IL-1 beta.

10. The method according to claim 8, wherein the component of the inflammasome pathway is NLRP3 inflammasome.

11. The method according to claim 8, wherein the activation of NLRP3 inflammasome pathway is inhibited.

12. A pharmaceutical composition comprising a compound according to claim 1, or a stereoisomer, a racemic mixture, a tautomer, a polymorph, a pharmaceutically acceptable salt, a prodrug, a hydrate, or a solvate thereof, and at least one further biologically active compound, and optionally comprising at least one pharmaceutically acceptable carrier, diluent, adjuvant or excipient.

* * * * *